US011254972B2

(12) United States Patent
Minev et al.

(10) Patent No.: US 11,254,972 B2
(45) Date of Patent: Feb. 22, 2022

(54) CRISSCROSS COOPERATIVE SELF-ASSEMBLY

(71) Applicants: President and Fellows of Harvard College, Cambridge, MA (US); Dana-Farber Cancer Institute, Inc., Boston, MA (US)

(72) Inventors: Dionis Minev, Cambridge, MA (US); Christopher Wintersinger, Jamaica Plain, MA (US); William M. Shih, Cambridge, MA (US)

(73) Assignees: President and Fellows of Harvard College, Cambridge, MA (US); Dana-Farber Cancer Institute, Inc., Boston, MA (US)

(*) Notice: Subject to any disclaimer, the term of this patent is extended or adjusted under 35 U.S.C. 154(b) by 297 days.

(21) Appl. No.: 16/322,787

(22) PCT Filed: Aug. 2, 2017

(86) PCT No.: PCT/US2017/045013
§ 371 (c)(1),
(2) Date: Feb. 1, 2019

(87) PCT Pub. No.: WO2018/026880
PCT Pub. Date: Feb. 8, 2018

(65) Prior Publication Data

US 2019/0203277 A1 Jul. 4, 2019

Related U.S. Application Data

(60) Provisional application No. 62/370,098, filed on Aug. 2, 2016.

(51) Int. Cl.

| | |
|---|---|
| ***C12Q 1/6837*** | (2018.01) |
| ***B82Y 30/00*** | (2011.01) |
| ***C07H 21/04*** | (2006.01) |
| ***C12Q 1/6811*** | (2018.01) |
| ***C07H 21/00*** | (2006.01) |
| ***C07H 1/00*** | (2006.01) |

(52) U.S. Cl.
CPC ............ *C12Q 1/6837* (2013.01); *B82Y 30/00* (2013.01); *C07H 1/00* (2013.01); *C07H 21/00* (2013.01); *C07H 21/04* (2013.01); *C12Q 1/6811* (2013.01)

(58) Field of Classification Search
None
See application file for complete search history.

(56) References Cited

U.S. PATENT DOCUMENTS

| | | | |
|---|---|---|---|
| 5,591,601 | A | 1/1997 | Wagner et al. |
| 5,846,949 | A | 12/1998 | Wagner et al. |
| 6,355,247 | B1 | 3/2002 | Selby et al. |
| 7,842,793 | B2 | 11/2010 | Rothemund |
| 8,501,923 | B2 | 8/2013 | Rothemund |
| 2005/0112578 | A1 | 5/2005 | Matsuura et al. |
| 2007/0117109 | A1 | 5/2007 | Rothemund |
| 2011/0033706 | A1 | 2/2011 | Krishnan |
| 2011/0243910 | A1 | 10/2011 | Hahn et al. |
| 2011/0293698 | A1 | 12/2011 | Primiano et al. |
| 2012/0263783 | A1 | 10/2012 | Messmer |
| 2013/0136925 | A1 | 5/2013 | Kim et al. |
| 2013/0245102 | A1 | 9/2013 | Ryan et al. |
| 2014/0220655 | A1 | 8/2014 | Sun et al. |
| 2014/0255939 | A1 | 9/2014 | Wong et al. |
| 2016/0271268 | A1 | 9/2016 | Shih et al. |
| 2019/0083522 | A1 | 3/2019 | Shih et al. |
| 2020/0308625 | A1 | 10/2020 | Wong et al. |

FOREIGN PATENT DOCUMENTS

| | | | |
|---|---|---|---|
| JP | 2002-114797 | A | 4/2002 |
| JP | 2003-522524 | A | 7/2003 |
| JP | 2008-504846 | A | 2/2008 |
| JP | 2008-523061 | A | 7/2008 |
| JP | 2009-518008 | A | 5/2009 |
| JP | 2009-213390 | A | 9/2009 |
| JP | 2012-509983 | A | 4/2012 |
| KR | 2011-0014258 | A | 2/2011 |
| WO | WO 2012/058488 | A2 | 5/2012 |
| WO | WO 2012/151328 | A2 | 11/2012 |
| WO | WO 2014/018675 | A1 | 1/2014 |
| WO | WO 2015/070080 | A2 | 5/2015 |
| WO | WO 2015/130805 | A1 | 9/2015 |
| WO | WO 2015/165643 | A1 | 11/2015 |
| WO | WO 2016/144755 | A1 | 9/2016 |
| WO | WO 2017/156252 | A1 | 9/2017 |
| WO | WO 2017/156264 | A1 | 9/2017 |
| WO | WO 2018/026880 | A2 | 2/2018 |

OTHER PUBLICATIONS

Partial European Search Report dated Mar. 20, 2020, for Application No. EP 17837580.4.

Douglas et al., Self-assembly of DNA into nanoscale three-dimensional shapes. Nature. May 21, 2009;459(7245):414-8. doi: 10.1038/nature08016.

Han et al., DNA gridiron nanostructures based on four-arm junctions. Science. Mar. 22, 2013;339(6126):1412-5. doi: 10.1126/science.1232252.

Simmel et al., Wireframe and tensegrity DNA nanostructures. Acc Chem Res. Jun. 17, 2014;47(6):1691-9. doi: 10.1021/ar400319n. Epub Apr. 10, 2014.

U.S. Appl. No. 15/034,566, filed May 5, 2016, Published, 2016-0271268.

U.S. Appl. No. 16/083,712, filed Sep. 10, 2018, Published, 2019-083522.

U.S. Appl. No. 16/083,932, filed Sep. 11, 2018, Pending, WO 2017/156264.

(Continued)

*Primary Examiner* — Robert M Kelly
(74) *Attorney, Agent, or Firm* — Wolf, Greenfield & Sacks, P.C.

(57) ABSTRACT

Provided herein, in some embodiments, are methods, compositions and kits for controlling nucleation and assembly of molecular nanostructures, microstructures and macrostructures.

23 Claims, 34 Drawing Sheets

Specification includes a Sequence Listing.

(56) References Cited

OTHER PUBLICATIONS

EP 17764091, Jul. 15, 2019, Extended European Search Report.
PCT/US2017/021562, May 31, 2017, International Search Report and Written Opinion.
PCT/US2017/021562, Sep. 20, 2018, International Preliminary Report on Patentability.
Bikram et al., Biodegradable Poly(ethylene glycol)-co-poly(1-lysine)-g-histidine Multiblock Copolymers for Nonviral Gene Delivery. Macromolecules. Feb. 11, 2004;37(5):1903-16.
Fujigaya et al., Enhanced cell uptake via non-covalent decollation of a single-walled carbon nanotube-DNA hybrid with polyethylene glycol-grafted poly(l-lysine) labeled with an Alexa-dye and its efficient uptake in a cancer cell. Nanoscale. Oct. 5, 2011;3(10):4352-8. doi: 10.1039/c1nr10635j. Epub Sep. 20, 2011.
Kadlecova et al., Hyperbranched polylysine: a versatile, biodegradable transfection agent for the production of recombinant proteins by transient gene expression and the transfection of primary cells. Macromol Biosci. Jun. 2012;12(6):794-804. doi: 10.1002/mabi.201100519. Epub Apr. 11, 2012.
Rajendran et al., Single-molecule analysis using DNA origami. Angew Chem Int Ed Engl. Jan. 23, 2012;51(4):874-90. doi: 10.1002/anie.201102113. Epub Nov. 25, 2011.
Santos et al., Low-cost fabrication technologies for nanostructures: state-of-the-art and potential. Nanotechnology. Jan. 30, 2015;26(4):042001(1-20). doi: 10.1088/0957-4484/26/4/042001. Epub Jan. 8, 2015.
Schlichthaerle et al., DNA nanotechnology and fluorescence applications. Curr Opin Biotechnol. Jun. 2016;39:41-47. doi: 10.1016/j.copbio.2015.12.014. Epub Jan. 13, 2016.
EP 17837580.4, Mar. 20, 2020, Partial European Search Report.
U.S. Appl. No. 16/083,932, filed Sep. 11, 2018, Published, 2020-0308625.
No Author Listed, Biochemistry Dictionary, 1998, 3rd edition, pp. 886.
Babic et al. Poly L-lysine-modified iron oxide nanoparticle for stem cell labelling. Bioconjug Chem. 2008;19:740-50. Epub Feb. 21, 2008.
Dietz et al., Folding DNA into twisted and curved nanoscale shapes. Science. Aug. 7, 2009;325(5941):725-30.
Ding et al., Gold nanoparticle self-similar chain structure organized by DNA origami. J Am Chem Soc. 2010;132(10):3248-9. Epub Feb. 17, 2010.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Koussa et al., DNA nanoswitches: A quantitative platform for gel-based biomolecular interaction analysis. Nat Methods. Feb. 2015;12(2):123-6. Epub Dec. 8, 2014.
Koussa et al., Protocol for sortase-mediated construction of DNA-protein hybrids and functional nanostructures. Methods. May 2014;67(2):134-41.
Kuzuya et al., Precisely programmed and robust 2D streptavidin nanoarrays by using periodical nanometer-scale wells embedded in DNA origami assembly. Chembiochem. Jul. 2009;10(11):1811-5.
Kuzyk et al., DNA-based self-assembly of chiral plasmonic nanostructures with tailored optical response. Nature. Mar. 15, 2012;483(7389):311-4. doi:10.1038/nature10889.
Kwoh et al., Stablilization of poly-L-lysine/DNA polyplexes for in vivo gene delivery to the liver. Biochimica et Biophysica Acta. 1999;1444:171-90.
Liu et al., Biological properties of poly-L-lysine-DNA complexes generated by cooperative binding of the polycation. J Biol Chem. Sep. 14, 2001;276(37):34379-87. Epub Jul. 3, 2001.
Lu et al., Recent advances in the synthesis and functions of reconfigurable interlocked DNA nanostructures. J Am Chem Soc. 2016;138:5172-85. Epub Mar. 28, 2016.
Maruyama et al., Characterization of interpolyelectrolyte complexes between double-stranded DNA and polylysine comb-type copolymers having hydrophilic side chains. Bioconjugate Chem. 1998;9:292-9. Epub Feb. 24, 1998.
Shih et al., poster. DNA-Based Molecular Containers and NMR Alignment Media. 2006. 1 page.
Steinhauer et al., DNA origami as a nanoscopic ruler for super-resolution microscopy. Angew Chem Int Ed Engl. 2009;48(47):8870-3. doi: 10.1002/anie.200903308.
Valero et al., Interlocked DNA topologies for nanotechnology. Curr Opin Biotechnol. May 12, 2017;48:159-67.
Walsh et al., DNA cage delivery to mammalian cells. ACS Nano. 2011;5(7):5427-32. Epub Jun. 22, 2011.
Weizmann et al., A polycatenated DNA scaffold for the one-step assembly of hierarchical nanostructures. Proc Nat Acad Sci. Apr. 8, 2008;105(14):5289-94.
Yan et al., DNA-templated self-assembly of protein arrays and highly conductive nanowires. Science. Sep. 26, 2003;301(5641):1882-4.
Yang et al., Nanostructures as Programmable Biomolecular Scaffolds. Bioconjug Chem. Aug. 19, 2015;26(8):1381-95. doi:10.1021/acs.bioconjchem.5b00194. Epub May 11, 2015.
Zhang et al., Dynamic DNA nanotechnology using strand-displacement reactions. Nat Chem. Feb. 2011;3(2):103-13. doi: 10.1038/nchem.957.
Zhang et al., Structural DNA nanotechnology: state of the art and future perspective. J Am Chem Soc. Aug. 13, 2014;136(32):11198-211. doi:10.1021/ja505101a. Epub Jul. 16, 2014.
Zhou et al., Lipophilic polylysines mediate efficient DNA transfection in mammalian cells. Biochim Biophys Acta. May 31, 1991;1065(1):8-14.
Zhu et al. Hollow mesoporous silica poly-(l-lysine) particles for codelivery of drug and gene with enzyme-triggered release property. J Phys Chem C. Jun. 2011;115:13630-5. Epub Jun. 15, 2011.
Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.
Douglas et al., Self-assembly of DNA into nanoscale three-dimensional shapes. Nature. May 21, 2009;459(7245):414-8. doi: 10.1038/nature08016. Author Manuscript, 11 pages.

Terminology:
Queen Drone Worker

Short linker drone/worker 1000x drones/workers
With queen 10x drones/workers
With queen Long linker drone/worker 1000x drones/workers
With queen 10x drones/workers
With queen 1x drones/workers
With queen FIG. 23A
FIG. 23B
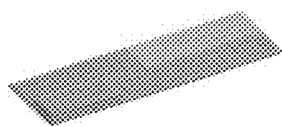
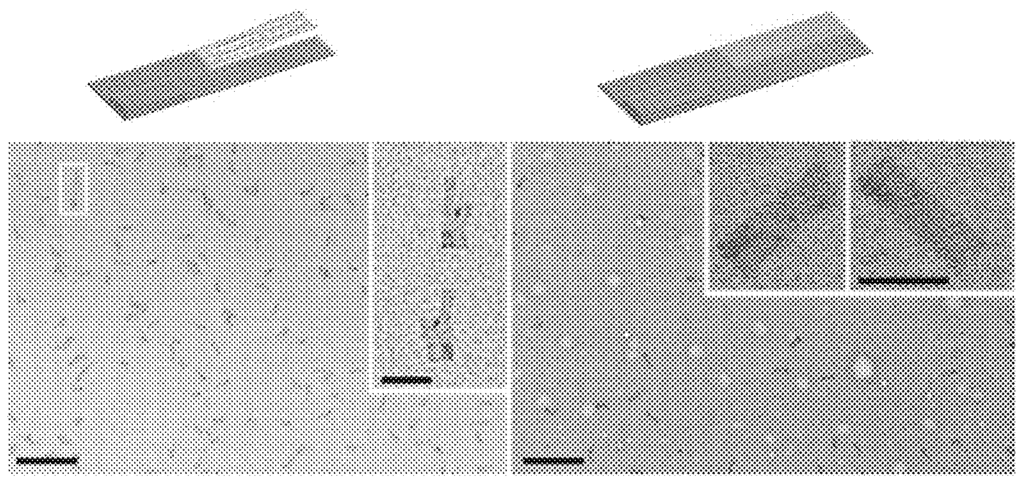
FIG. 24A
FIG. 24B
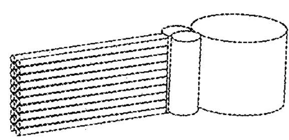
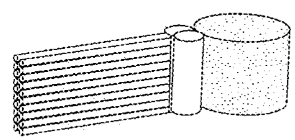
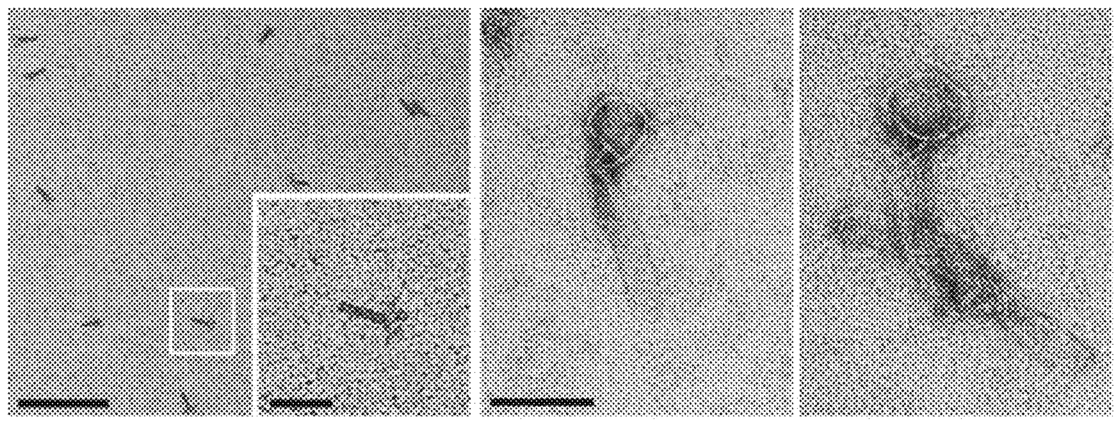

Analyte
No Analyte
1.
2.
3.
Destruction
Ligation of 2 DNA slats

CRISSCROSS COOPERATIVE SELF-ASSEMBLY

RELATED APPLICATIONS

This application is a national stage filing under 35 U.S.C. § 371 of international application number PCT/US2017/045013, filed Aug. 2, 2017, which claims the benefit under 35 U.S.C. § 119(e) of U.S. provisional Application number 62/370,098, filed Aug. 2, 2016, each of which is incorporated by reference herein in its entirety.

FEDERALLY SPONSORED RESEARCH

This invention was made with government support under 1435964 awarded by the Office of Naval Research. The government has certain rights in the invention.

BACKGROUND

In nature, biomolecules assemble into hierarchical structures through intermolecular interactions. In synthetic biology, it is possible to rationally design biosynthetic building blocks, with hierarchical structures arising from built-in functionality at the molecular level controlling intermolecular interactions. Such biosynthetic self-assembling structures have useful applications in the field of nanotechnology, for example.

SUMMARY

Provided herein, in some embodiments, is a technology (including, for example, methods, compositions and kits) for controlling nucleation and hierarchical assembly (programmable self-assembly) of molecular structures, such as nucleic acid (e.g., DNA) and/or protein nanostructures, microstructures, and macrostructures. This technology, referred to herein as 'crisscross cooperative assembly' can be used to program and rapidly assemble structures that only originate from provided macromolecular 'seeds,' thus may be considered a 'zero-background' assembly method. Through the design of cooperative binding sites on individual biomolecular subunits that require simultaneous engagement with a large number of other subunits to achieve stable attachment, the system imposes an intrinsically high energetic barrier against spontaneous nucleation of structures, even in the presence of high concentrations of each individual component. Nucleation can only be triggered by providing a macromolecular 'seed' that resembles a pre-existing structural interface (presents multiple weak binding sites for stable capture of the next subunit). Addition of a seed that can stably capture individual subunits effectively bypasses the activation energy barrier against spontaneous nucleation to drive higher-order assembly of a microscale structure. Components can be continually added to the structures such that their growth in one-dimension, two-dimensions or three-dimensions is potentially as large as for other polymerization or crystallization processes.

Crisscross cooperative assembly, as provided herein, uses molecular (e.g., nucleic acid or protein) building blocks (FIG. 1A) that are programmed to self-assemble into crisscrossed layers (FIG. 1B). A building block, in some embodiments, may be a rod-shaped structure assembled from programmable nucleic acid hybridization interactions. As indicated above, this crisscross cooperative assembly technology uses a 'seed' structure from which programmable nucleic acid self-assembly begins. This seed structure is formed through irreversible interactions between a nucleating structure (FIG. 1A; 'queen') and a subset of building blocks (FIG. 1A; 'drones') that are aligned to form an initial seed layer along the nucleating structure. In the presence of a seed structure, another set of building blocks (FIG. 1A; 'workers') are added to the pre-existing seed layer (FIG. 1B). Binding between a sufficient number of building blocks (drones) and a nucleating structure (queen) to form a seed can trigger the addition of many additional layers of building blocks (workers), with each layer rotated by some degree (e.g., 90°) relative to adjacent layers (above and/or below).

The nucleating structure and the building blocks are engineered to interact with (e.g., bind to) each other based on a set of kinetic/nucleation energy parameters, as follows. An initial subset of building blocks (drones) should bind strongly (irreversibly/stably) to and form an aligned layer along the nucleating structure (queen). The building blocks (drones) of the initial subset should not interact with (bind to) each other. Likewise, building blocks (workers) of a subsequent subset should not interact with (bind to) each other. Further, in the absence of a nucleating structure (queen), any building block (drone) from the initial subset should have only one weak (reversible) interaction with any other building block (worker) from another subset. In the presence of a nucleating structure (queen), a single building block (drone) from an initial subset may interact with more than one building block (worker) from a subsequent subset, and a single building block (worker) from a subsequent subset may interact with more than one building block (drone) from the initial subset or another subset ('workers' of another subset). For example, with reference to FIG. 1B, a single building block (e.g., DNA nanorod) may bind to eight other building blocks DNA nanorods), although the single building block binds to each of the eight building blocks only once to form two layers having a 'crisscross' pattern.

The single interaction between a building block (drone) from the initial subset and a building block from a subsequent subset (worker) should be weak enough such that there is an arbitrarily large entropy penalty against nucleation in the absence of a seed structure (a large number of individual workers would have to come together simultaneously). With these parameters, zero-background and minimal detects can be achieved, even at high concentrations of interacting building blocks, thereby enabling rapid nucleation and assembly of nucleic acid nanostructures.

Thus, provided herein are compositions, comprising (a) a nucleating nucleic acid nanostructure, (b) a first layer of parallel elongated nucleic acid nanostructures stably bound to the nucleating nanostructure of (a), and (c) a second layer of parallel elongated nucleic acid nanostructures stably bound to the elongated nanostructures of (b) and rotated at an angle relative to the parallel elongated nanostructures of (b), wherein a single elongated nanostructure of (b) binds to multiple elongated nanostructures of (c), each through a single cooperative binding site. In some embodiments, a single elongated nanostructure of (c) binds to multiple elongated nanostructures of (b), each through a single cooperative binding site.

Also provided herein, in some aspects, are compositions comprising: (a) nucleating nanostructures; (b) a first subset of elongated nanostructures, wherein less than 10% of the nanostructures of (b) bind to each other, and wherein the nanostructures of (h) irreversibly bind to a nucleating nanostructure of (a); and (c) a second subset of elongated nanostructures, wherein less than 10% of the nanostructures of (c) bind to each other, wherein, in the absence of a nucleating nanostructure, a nanostructure of (b) can reversibly binding to a nanostructure of (a) only at a single position on the nanostructure of (a), and wherein, in the absence of a nucleating nanostructure, a nanostructure of (a) can reversibly binding to a nanostructure of (b) only at a single position on the nanostructure of (b). See, e.g., FIGS. 1A-1B.

Also provided herein, in some embodiments, are crisscross nucleic acid nanostructures, comprising a first nanorod comprising a first plug strand and a second plug strand; a second nanorod comprising a third plug strand and a fourth plug strand, wherein the second nanorod is parallel to the first nanorod; a third nanorod comprising a fifth plug strand complementary to and bound to the first plug strand and a sixth plug strand complementary to and bound to the second plug strand; a fourth nanorod comprising a seventh plug strand complementary to and bound to the third plug strand and an eighth plug strand complementary to and bound to the fourth plug strand, wherein the third nanorod is parallel to the fourth nanorod. See, e.g., FIG. 18. A crisscross nanostructure is not limited to 4 nanorods and, in many embodiments, includes at least 4 (e.g., at least 5, 10, 15, 20, 25, 50, 100 or more) nanorods arranged in a crisscross pattern as described herein.

Thus, in some embodiments, a crisscross nucleic acid nanostructure, comprises a first plurality of nanorods parallel to each other, and a second plurality of nanorods parallel to each other, wherein the nanorods of the first plurality are bound to and perpendicular to (or are non-parallel to) the nanorods of the second plurality. See, e.g., FIG. 18.

In some embodiments, each nanorod is comprised of DNA. For example, a nanorod may be comprised of a 6-helix DNA bundle (see, e.g., Douglas S M I, Chou J J, Shih W M. DNA-nanotube-induced alignment of membrane proteins for NMR structure determination. Proc Natl Acad Sci USA. 104, 6644-6648, 2007, incorporated herein by reference).

Also provided herein, in some aspects, are crisscross nucleic acid slats, comprising: a first plurality of at least four nucleic acid strands parallel to each other, each strand of the first plurality having a length of 20-100 nucleotides (e.g., 20-30, 20-40 or 20-50 nucleotides); and a second plurality of at least four nucleic acid strands parallel to each, each strand of the second plurality having a length of 20-100 nucleotides (e.g., 20-30, 20-40 or 20-50 nucleotides), wherein the at least four nucleic acid strands of the first plurality are bound to and perpendicular to the at least four nucleic acid strands of the second plurality. See, e.g., FIGS. 21A-21B.

Also provided herein, in some aspects are crisscross nucleic acid slats, comprising: a first plurality of at least four nucleic acid strands parallel to each other, each strand of the first plurality having a length of at least 21 nucleotides; and a second plurality of at least four nucleic acid strands parallel to each, each strand of the second plurality having a length of at least 21 nucleotides, wherein the at least four nucleic acid strands of the first plurality are bound to and perpendicular to the at least four nucleic acid strands of the second plurality. See, e.g., FIGS. 21A-21B.

Further provided herein, in some aspects, are nucleic acid nanostructures comprising a nucleic acid scaffold strand folded (e.g., M13 or M13-derived) into repeating loop-like shapes (e.g., 5-15 loops, or 5, 6, 7, 8, 9 or 10 loops) secured by shorter nucleic acid staple strands, wherein the repeating loop structures are bound to at least one (e.g., at least 2, 3, 4, 5, 10, 20, 25, 30, 35, 40, 45, 50, 60, 70, 80, 90, 100 or more) crisscross nucleic acid slat. See. e.g., FIGS. 22, 24A, 25 and 27B.

Further still, provided herein, in some aspects, are nucleic acid nanostructures, comprising a nucleic acid scaffold strand folded into repeating loop-like shapes secured by at least two crisscross nucleic acid slats. See, e.g., FIGS. 27B and 28B.

The present disclosure also provides, in some aspects, methods of producing a crisscross nucleic acid nanostructures, comprising: combining in a reaction mixture (a) a first nanorod comprising a first plug strand and a second plug strand. (b) a second nanorod comprising a third plug strand and a fourth plug strand, wherein the second nanorod is parallel to the first nanorod, (c) a third nanorod comprising a fifth plug strand complementary to and bound to the first plug strand and a sixth plug strand complementary to and bound to the second plug strand, and (d) fourth nanorod comprising a seventh plug strand complementary to and bound to the third plug strand and an eighth plug strand complementary to and bound to the fourth plug strand, wherein the third nanorod is parallel to the fourth nanorod; and incubating the reaction mixture under conditions (e.g., nucleic acid hybridization conditions) that result in assembly of a crisscross nucleic acid nanostructure. See, e.g., FIG. 22.

Biomolecule (analyte) detection methods are also provided herein, in some aspects. In some embodiments, a method, comprises (a) combining in a reaction mixture (i) a sample comprising a biomolecule (ii) a nucleic acid strand capable of self-assembling into a nanostructure that comprise vertically-stacked parallel strands; (iii) a plurality of oligonucleotides, shorter than the nucleic acid strand of (ii), wherein the oligonucleotides of (iii) bind to the strand of (ii) to assemble the vertically-stacked parallel strands; (iv) two crisscross nucleic acid slats, wherein the two slats bind to the strand of (ii), and wherein each of the slats is linked to a biomolecule binding partner that specifically binds to the biomolecule in the sample; (b) incubating the reaction mixture under conditions that permit binding of the biomolecule binding partners to the biomolecule and assembly of the nanostructure into vertically-stacked parallel strands; (c) removing the plurality of oligonucleotides of (iii) from the reaction mixture of (b); (d) incubating the reaction mixture of (c) in the presence of a plurality of crisscross nucleic acid slats of claim 27, wherein the crisscross nucleic acid slats bind to the vertically-stacked parallel strands to form a three-dimensional barrel structure. In some embodiments, the methods further comprise imaging the three-dimensional barrel structure. See, FIGS. 28A-28B.

In some embodiments, the methods may comprise combining in a reaction mixture (e.g., with hybridization buffer) (a) a sample comprising a biomolecule and (b) a nucleic acid nanostructure comprising (i) a nucleic acid scaffold strand capable of folding into repeating loop-like shapes (e.g., 2-15 vertically-stacked loops) and (ii) two crisscross nucleic acid slats, wherein a biomolecule binding partner (e.g., an antibody) that specifically binds to the biomolecule is linked to each of the crisscross nucleic acid slats such that in the presence of the cognate biomolecule the biomolecule binding partner binds to the biomolecule and the nucleic acid nanostructure folds into repeating loop-like shapes. See, e.g., FIGS. 28A-28B.

In some embodiments, the methods further comprise combining the reaction mixture with a plurality (e.g., 2-50 or 2-100) of crisscross nucleic acid slats to form a three-dimensional barrel-like structure. See, e.g., FIG. 24B.

It should be understood that the nucleic acid nanostructures as described herein (e.g., nanorods, slats, barrels, etc.) and variants thereof, as provided herein, may be designed, for example, using the following publicly-available tool described by Douglas S M, Marblestone A H, Teerapittayanon S, Vazquez A, Church G M, Shill W M. Rapid prototyping of 3D DNA-origami shapes with caDNAno. *Nucleic Acids Res.* 37, 5001-5006, 2009, incorporated herein by reference. See, also, Douglas et al. *Nature,* 459(7245): 414-418, 2009, incorporated herein by reference. For example, and as described elsewhere herein, it is known in the art that custom shape (e.g., megadalton-scale) DNA nanostructures may be produced using a long 'scaffold' strand to template the assembly of hundreds of oligonucleotide 'staple' strands into a planar antiparallel array of cross-linked helices. This 'scaffolded DNA origami' method has also been adapted to produce 3D shapes formed as pleated layers of double helices constrained to a honeycomb lattice. caDNAno, an open-source software package with a graphical user interface, may be used to aid in the design of DNA sequences for folding 3D DNA (or other nucleic acid) nanostructures. The caDNAno software is available at cadnano.org, along with example designs and video tutorials demonstrating their construction.

BRIEF DESCRIPTION OF THE DRAWINGS

FIG. 1A indicates the system without a nucleation site and no self-assembly. FIG. 1B indicates the system after the addition of the nucleation site and triggered spontaneous self-assembly. Growth direction is indicated by the arrows and shows a 1D growth in this example. Individual components are referred to as 'queen,' 'drone' and 'worker.'

FIG. 3A shows queen (Q) and drone/worker (DAV) architecture shown in cross-section (caDNAno software downloaded from cadnano.org) and in 3D representation. Each individual cylinder represents a double stranded DNA helix. FIG. 3B is a representation of 1D and 2D growth with the crisscross DNA-origami cooperative assembly. 3D growth can be achieved by creating a design that merges 1D and 2D growth. FIG. 3C shows different pathways for 2D growth.

FIG. 17A shows drone and worker subcomponents constructed from 6-helix bundle scaffolded. DNA origami to form rods that are customizable in length. The 3' ends of staples contain overhanging single strand DNA sequences that act as plug binding handles to interact with other components. Similarly, the lowermost helix contains socket sequences (i.e. single strand DNA scaffold not complemented by a folding staple) that accept plug sequences from other components. The plugs and socket respectively are periodic and can be situated, for example, every 42 bp (~14 nm) along the length of the component. FIG. 17B shows TEM images of test drones folded from two different scaffold sequences. The drone in the top image is ~250 nm in length, versus the drone in the bottom image, which is ~440 nm in length.

FIG. 19A shows two 440 nm drones placed in the middle two queen cells, FIG. 19B shows one 250 nm drone placed in the middle queen cell, and FIG. 19C shows 250 nm located in every cell of the queen. The desired design is shown to the left, versus a TEM image of the assembled structure to the right. FIG. 19D shows bulk analysis of the design from FIG. 19A using agarose gel electrophoresis for one design using a 7 bp plug-socket, and another with a 10 bp plug-socket.

FIG. 21A is an abstraction of the crisscross DNA slats motif (right). Strands weave and are complementary to each other at each junction, indicated by dotted and stripped pattern. The length of each binding site is shown on the right. Each row and column amount to 21 base pairs (bp). The matrix shows the number of base pairs (bp) per binding site at each position of the abstraction and 3D rendering, FIG. 21B is a 3D rendering of the DNA slats. On the left, the top down view shows the weaving of each strand. A cross section (A-A) is shown on the right.

FIG. 23A shows a flat DNA-origami queen without any DNA slats added. FIG. 23B shows a flat DNA-origami queen with the addition of DNA slats and the correct formation of a sheet, by tiling the ssDNA scaffold of the queen with DNA slats, DNA slat tiled region is indicated in light gray. Scale bars on images are 600 nm and on enlarged view 100 nm.

FIG. 24A shows a barrel DNA-origami queen without any DNA slats added. Scale bar on image is 400 nm and on enlarged view 100 nm. FIG. 24B shows a barrel DNA-origami queen with the addition of DNA slats and the correct formation of a barrel, by tiling the ssDNA scaffold of the queen with DNA slats. Scale bar indicates 50 nm. DNA slat tiled region is indicated in light gray.

FIG. 26A shows first generation extensions tiled with a short second generation of DNA slats, resulting in three tooth-like extensions on the queen. FIG. 26B shows first generation extensions tiled with a long second generation of DNA slats, which are terminally tiled with short third generation DNA slats. FIGS. 26C-26E show first, second, and third generations of DNA slats which are complementary to one another, resulting in extensions of linear sheet structures. FIG. 26C contains one extended first generation, FIG. 26D contains two extended first generations, and FIG. 26E contains three extended first generations. Scale bars for FIGS. 26A-26C are 100 nm and for FIGS. 26D-26E, 200 nm.

(FIG. 27A) Formation of eight loops with M13 scaffold through staple strands. Staple ("strands") strands fold stable DNA-Origami base and DNA slats catenate the eight loops, indicated by a dotted pattern. (FIG. 27B) 3D view of barrel queen additionally serving as multi-host-ring catenane system with high yield typical for DNA-Origami. (FIG. 27C) Abstract and 3D view of DNA slats weaving through the ssDNA M13 scaffold loops on the barrel queen. Through ligation of one side a single DNA slat catenates all eight loops. (FIG. 27D) 3D rendering of DNA slat weaving and catenating eight separate ssDNA loops. Top shows a tilted bottom view and bottom a side view. (FIG. 27E) Former technique to achieve a maximum of four-host-ring catenane system with low yield.

FIG. 28A shows that the biomolecule presence is connected to the DNA slats holding the eight loops together. Without the biomolecule, the queen falls apart and no growth can occur, even with DNA slats present in solution. FIG. 28B shows that biomolecule presence in the reaction holds the DNA slats together and provides the close proximity of ssDNA scaffold for the tube structure to nucleate and grow.

FIG. 30A depicts a flat DNA-origami queen without the bottom right hand sheet shown in FIG. 23A. FIG. 30B is a schematic explaining how the DNA slats (moving in a diagonal direction) assemble on the ssDNA scaffold on the flat queen.

Bottom: No biomolecule present. (1) No biomolecule binds to the antibody bridge. (2) Dashed strand is displaced via toehold-mediated strand displacement, leading to no bridge being intact and the subsequent falling apart of the barrel queen (shown in FIG. 28A).

DETAILED DESCRIPTION

Nature achieves rapid and nucleation-limited growth of cytoskeletal filaments such as actin and microtubules. This is achieved by securing each additional subunit by weak interactions to 2-3 already attached subunits at the growing end of the filament. This means that if any two monomers bind to each other in solution, they will rapidly within milliseconds) dissociate from each other, because the single interaction is so weak. It is only after four subunits come together simultaneously—a rare event—that a stable nucleus will be formed. Therefore, untriggered spontaneous nucleation will be rare. Conversely, nucleation can be triggered by providing a macromolecular "seed" that mimics a fully formed filament end.

Rapid and nucleation-limited growth are very useful features for programmable self-assembly, however technological modification of natural filaments such as actin or microtubules has many current drawbacks: (1) there is a limited understanding of how to tune the interaction strength between subunits; (2) the level of cooperativity is relatively low (the weak interactions upon binding are spread only over 2-3 subunits), therefore the suppression of spontaneous nucleation is not as robust as it could be; and (3) growth is limited to one-dimension (filament formation).

Rapid, reversible, zero-background, triggered nucleation and growth, as provided herein, can have useful applications in nanotechnology and biotechnology, such as ultrasensitive detection, and templates for miniaturized materials.

Crisscross Cooperative Assembly

Figure 1A:
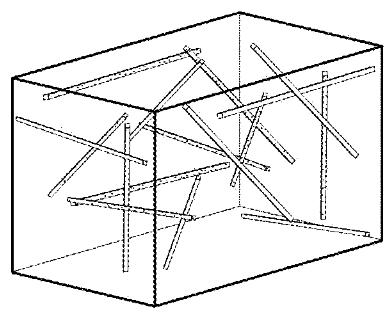
FIGS. 1A-1B show an abstraction of an example of crisscross cooperative assembly, system.
Figure 1A:
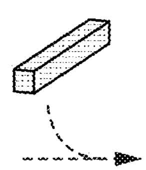

The crisscross cooperative assembly technology as provided herein is based on a concept that may apply to many self-assembling molecules, including nucleic acids and proteins. For simplicity and ease of understanding, however, reference herein primarily will address crisscross cooperative assembly in the context of nucleic acids, such as deoxyribonucleic acid (DNA). A crisscross cooperative assembly system uses three basic components: a nucleating nanostructure, an initial (first) subset of nanostructures programmed to bind to the nucleating nanostructure, and another (second) subset of nanostructures programmed to bind to the nanostructures of the initial. An example of a crisscross cooperative assembly is provided in FIGS. 1A-1B, wherein the nucleating structure is referred to as a 'queen,' nanostructures of the first subset are referred to as 'drones,' and nanostructures of the second (and any subsequent) subset are referred to as 'workers.' The final structure, in this example, includes layers of aligned molecular rods, where each layer is rotated by some amount (e.g., 90 degrees) relative to the layer below and above. For example, one layer may be perpendicular to another adjacent (directly above or below) layer. In some embodiments, one layer is rotated 20, 30, 40, 50, 60, 70, 80 or 90 degrees relative to an adjacent layer (measured alone the length of a drone and/or worker nanorod, for example). Each intersection between rods on adjacent layers adds a small binding energy; any given rod intersects with a large number of rods below and above, and the net binding energy can be tuned (e.g., by adjusting the design of the binding interface, for example, the number of base pairs, or by adjusting subunit concentration, temperature, or salt concentration) to be large enough to achieve stable (irreversible) or slightly favorable (reversible) attachment as desired. Before assembly initiates, any spontaneous crossing between two rods in solution is short-lived, as the net energy is very low because there is only one interaction. Thus, a rod can be stably (or else slightly favorably (reversibly)) added to a pre-existing crisscross structure (many attachment points can immediately be realized), but a structure will not spontaneously assemble in the absence of a pre-existing one. There should be no growth unless a structural mimic of a pre-existing crisscross structure a seed is added to the solution.

An example protocol for a crisscross cooperative assembly system is as follows: (1) Design constitutive building blocks (queen, drones and workers) using DNA CAD tools. See, e.g., Douglas S M, Marblestone A H, Teerapittayanon S, Vazquez A, Church G M, Shih W M. Rapid prototyping of 3D DNA-origami shapes with caDNAno. Nucleic Acids Res. 37, 5001-5006, 2009, incorporated herein by reference in its entirety.

Cooperative binding site sequences and number of sites on queens are tailored to modulate the activation energy of nucleation as required. (2) Construct and purity constitutive building blocks using techniques in DNA synthesis and DNA origami. (3) Mix drones and workers in solution, and add queens to initiate growth of higher order DNA structures.

Nanostructures bind to each other through cooperative binding sites. A "cooperative binding site" is the location at which two nanostructures interact (hybridize/bind). For example, a nucleating nanostructure may be programmed with multiple nucleotide base sequences, each of which is complementary to a nucleotide base sequence of one of the nanostructures of the initial subset of nanostructures. A cooperative binding site may include plug and socket sites that include plug and socket strands. A plug strand is a nucleic acid strand (single-stranded nucleic acid) attached to a nucleic acid nanostructure, such as a nanorod. A plug strand contains a nucleotide sequence that is complementary to (and this binds to) a nucleotide sequence within a cognate socket strand. Thus; a pair of plug and socket strands include nucleotide sequences that are complementary to each other such that the plug and socket strand bind (hybridize) to each other to anchor, for example, a drone to a queen or a worker to a drone (see, e.g., FIG. 17B). In some embodiments, a queen includes multiple plug strands that direct and anchor a drone that includes multiple complementary (cognate) socket strands. Likewise, a drone may include multiple plug strands that direct and anchor a worker that includes multiple complementary socket strands.

Figure 22:
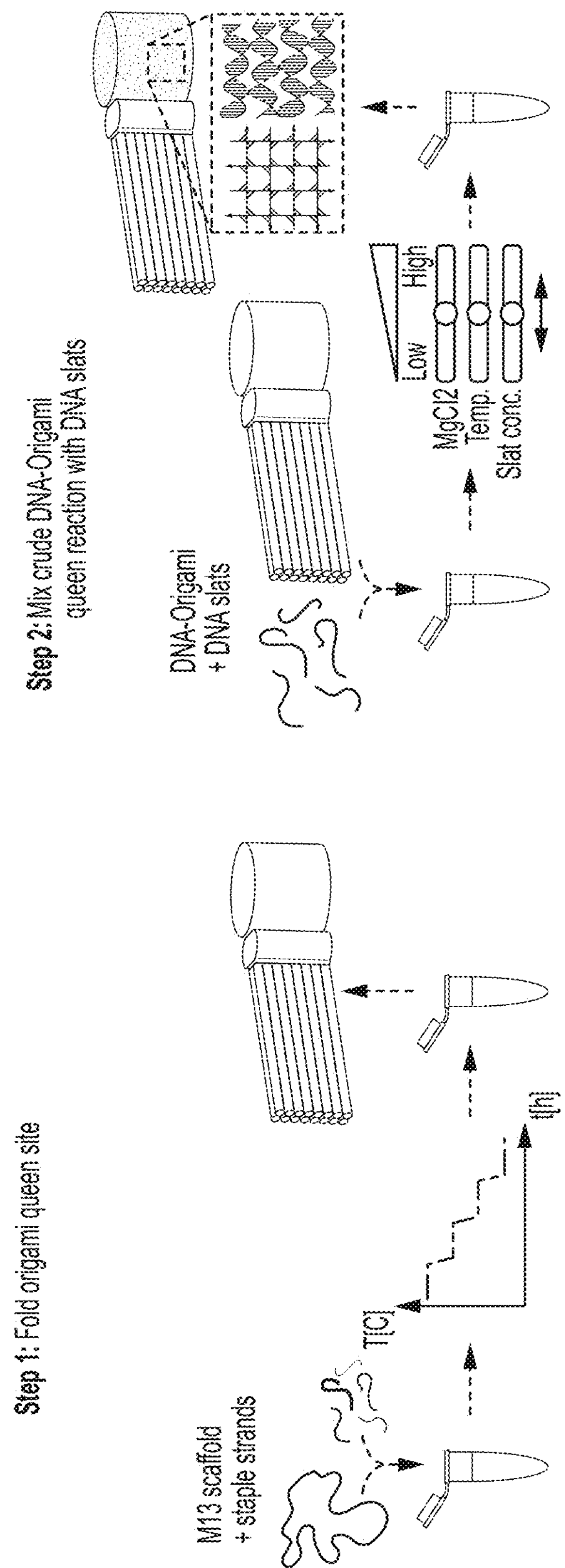
FIG. 22 shows the steps to DNA slats assembly. Step 1 shows DNA-origami folding of an arbitrary DNA-origami queen (a barrel queen shown as an example). Step 2 is the mixing of the crude DNA-origami queen reaction (from step 1) with DNA slats at various salt concentrations, temperatures, and DNA slat concentration.

Cooperative binding sites, e.g., plug and socket strands, may also be used to assemble nucleic acid (e.g., DNA) slats onto another nucleic acid scaffold structure in a similar manner. For example, as shown in FIG. 22, DNA slats may be appended to a nucleic acid scaffold (queen) to secure the two- or three-dimensional shape of the scaffold structure. In the example, shown in FIG. 22, DNA slats are used to secure (hold together) the barrel shape of a larger scaffold nanostructure. "Growth" of these slats along the scaffold through cooperative binding sites results in a barrel-like shape that may be visualized by microscopy, for example.

Cooperative binding sites (e.g., plug and socket sequences) are arranged on a nucleating nanostructure in a spatial configuration that facilitates binding and alignment of the initial e.g., scaffold) nanostructures. The length of a cooperative binding site may vary, depending in part on the desired strength (strong v. weak) of the intended interaction between two molecules having complementary sites. In some embodiments, a cooperative binding site has a length of 5-50 nucleotides. For example, a cooperative binding site may have a length of 5-40, 5-30, 5-20, 5-10, 5-15, 10-50, 10-40, 10-30, 10-20, 30-50, 30-40, or 40-50 nucleotides. In some embodiments, a cooperative binding site has a length of 5, 10, 15, 20, 25, 30, 35, 40, 45, or 50 nucleotides. A single plug strand and/or socket strand may have a length of 5-20 (e.g., 5, 6, 7, 8, 9, 10, 11, 12, 13, 14, 15, 16, 17, 18, 19 or 20) nucleotides, for example.

The number of cooperative binding sites on a nanostructure may also vary. In some embodiments, the number of cooperative binding sites on a nanostructure is 3-1000. For example, the number of cooperative binding sites on a nanostructure may be 3-900, 3-800, 3-700, 3-600, 3-500, 3-400, 3-300, 3-200, or 3-100. In some embodiments, the number of cooperative binding sites on a nanostructure is 3-10, 3-15, 3-20, 3-25, 3-30, 3-35, 3-40, 3-45 or 3-50. In some embodiments, the number of cooperative binding sites on a nanostructure is 3-15, 3-20, 3-25, 3-30, 3-35, 3-40, 3-45 or 3-50. In some embodiments, the number of cooperative binding sites on a nanostructure is 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100.

The distance between cooperative binding sites may also vary. In some embodiments, the distance between two cooperative binding sites on the same nanostructure is 20-1000 angstroms. For example, the distance between two cooperative binding sites on a nanostructures may be 20-900, 20-800, 20-700, 20-600, 20-500, 20-400, 20-300, 20-200, 20-100, 50-1000, 50-900, 50-800, 50-700, 50-600, 50-500, 50-400, 50-300, 50-200, or 50-100 angstroms. In some embodiments, the distance between two cooperative binding sites on a nanostructures is 20, 25, 30, 35, 40, 45, 50, 55, 60, 65, 70, 75, 80, 85, 90, 95, 100, 125, 150, 175, 200, 250, 300, 350, 400, 450 or 500 angstroms.

In some embodiments, the distance between cooperative binding sites, for example, the distance between plug strands (and/or between socket strands) may be 5 to 100 nucleotides (or nucleotide base pairs (bp)). In some embodiments, the distance between plug strands (and/or between socket strands) is 5-20, 5-25, 5-50 or 5-100 nucleotides. In some embodiments, the distance between plug strands (and/or between socket strands) is 5, 10, 15, 20, 25, 30, 35, 40, 45, 50, 55, 60, 65, 70, 75, 80, 85, 90, 95 or 100 nucleotides. In some embodiments, the distance between plug strands (and/or between socket strands) is 5, 6, 7, 8, 9, 10, 11, 12, 13, 14, 15, 16, 17, 18, 19, 20 or 21 nucleotides. In some embodiments, the distance between plug strands (and/or between socket strands) is 42+/−21 nucleotides. For example, the distance between plug strands (and/or between socket strands) may be 21, 42 or 63 nucleotides. In some embodiments, the distance between plug strands (and/or between socket strands) is 42 nucleotides.

One nucleotide unit measures 0.33 nm. Thus, in some embodiments, the distance between cooperative binding sites, for example, the distance between plug strands (and/or between socket strands) may be 5 to 35 nanometers (nm). In some embodiments, the distance between plug strands (and/or between socket strands) is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 ran. In some embodiments, the distance between plug strands (and/or between socket strands) is 14+/−7 nm. For example, the distance between plug strands (and/or between socket strands) may be 7, 14 or 21 nm. In some embodiments, the distance between plug strands (and/or between socket strands) is 14 nucleotides.

In some embodiments, the distance between two cooperative binding sites on a nanostructure is evenly spaced, while in other embodiments, the distances may vary. For example, the distance between a first cooperative binding site and a second cooperative binding site may be 30 angstroms, while the distance between the second cooperative binding site and a third may be 30 angstroms, 40 angstroms or 50 angstroms.

Figure 3A:
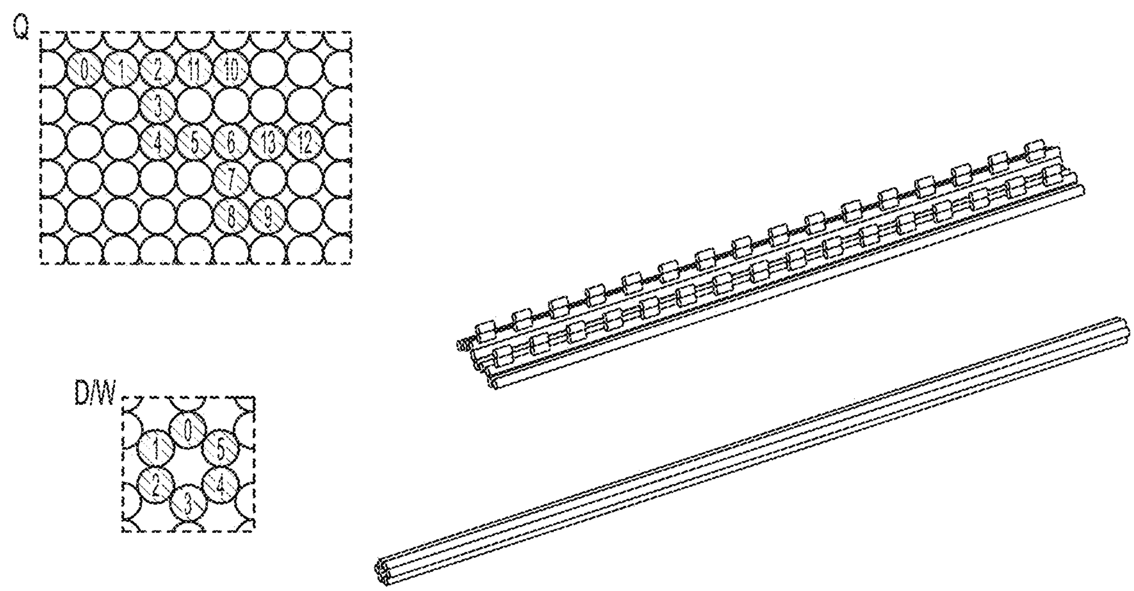
FIGS. 3A-3C show examples of DNA-origami crisscross assembly.
Figure 3B:
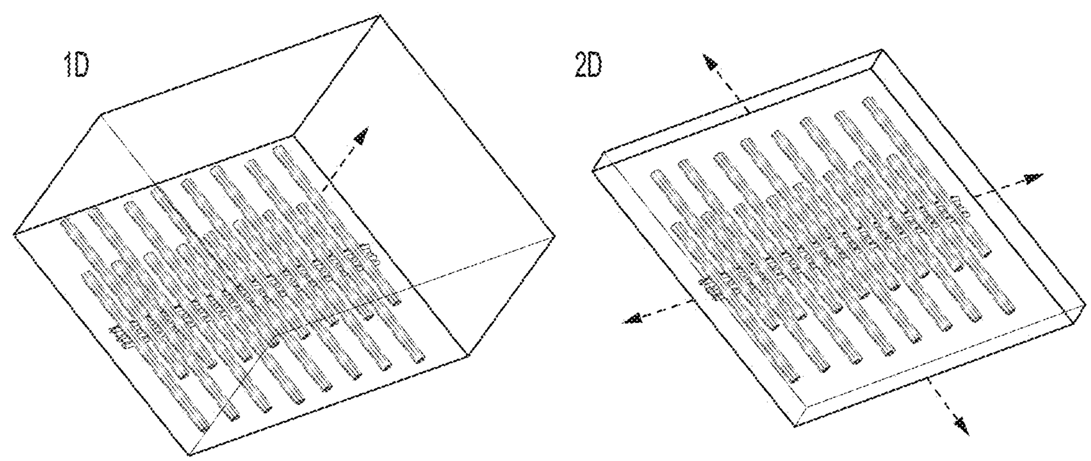
Figure 3C:
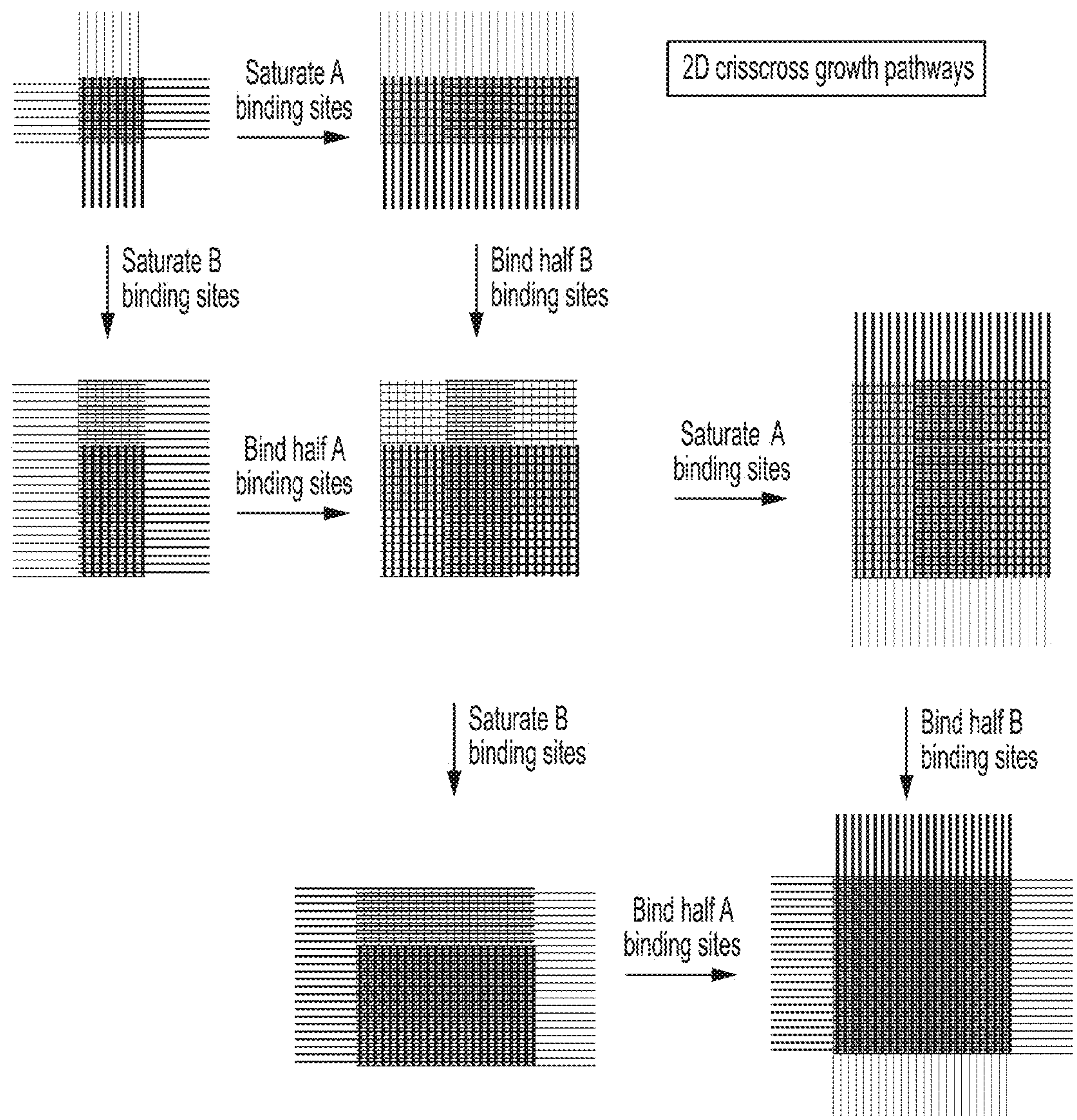

Two or more nanostructures are considered "aligned" if they are oriented in the same direction relative to one another. For example, the 5' ends (or 3' ends) of the nanostructures may be facing the same direction along its y axis. The top layer of the structure shown in FIG. 3B shows aligned nanorods bound to a nucleating nanostructure. The nanorods, in this example, are perpendicular to the nucleating nanostructure.

A nucleating nanostructure is required to initiate assembly of the first (initial) and second (and, thus, subsequent, e.g., third, fourth, fifth, etc.) subsets of nanostructures, and binding of the nanostructures in the first subset to the nucleating structure is required to initiate assembly of the nanostructures of the second subset. A "nucleating nanostructure" is any nanostructure programmed with binding sites that interacts strongly (irreversibly) with binding sites on each member of drone nanostructures of the initial subset, and aligns them for recruitment of subsequent subsets of worker nanostructures. That is, the binding sites between a nucleating nanostructure and nanostructures of the initial subset should be strong enough that the initial nanostructures bind to and align along the nucleating nanostructures and do not dissociate from the nucleating nanostructure under reaction conditions (e.g., isothermal, physiological conditions). A nucleating nanostructure may have a two-dimensional or a three-dimensional shape, for example.

Additional subsets of nanostructures may be added to the crisscross cooperative assembly system to propagate growth of the end structure (e.g., nanostructure, microstructure or macrostructure). For example, third, fourth and fifth subsets of nanostructures may be added. Binding of the nanostructures of the second subset to the first subset is required to initiate assembly of the nanostructures of the third subset; binding of the nanostructures of the third subset to the second subset is required to initiate assembly of the nanostructures of the fourth subset; and so on. The user-defined end structure may be assembled in one dimension, two dimensions (see, e.g., FIG. 3B) or three-dimensions.

Each subset of nanostructures nanorods) should follow a specific set of binding energy parameters. More specifically, the initial subset of nanostructures nanorods) should bind strongly (irreversibly) to and form an aligned layer (where each nanostructure is oriented in the same direction relative to one another) along the nucleating nanostructure. The nanostructures (e.g., nanorods) of the initial subset should not interact with (bind to) each other. Likewise, nanostructures nanorods) of a subsequent subset should not interact with (bind to) each other. Further, in the absence of a nucleating structure, any nanostructure nanorod) from the initial subset should have only one weak (reversible) interaction with any other nanostructure (e.g., nanorod) from a subsequent subset. In the presence of a nucleating structure, a single nanostructure nanorod) from an initial subset may interact with more than one nanostructure (e.g., nanorod) from a subsequent subset, and a single nanostructure (e.g., nanorod) from a subsequent subset may interact with more than one nanostructure (e.g., nanorod) from the initial subset. For example, with reference to FIG. 1B, a single nanostructure (e.g, nanorod) may bind to eight other nanostructure (e.g., nanorod), although the single nanostructure (e.g., nanorod) binds to each of the eight nanostructure (e.g., nanorod) only once to form two layers having a 'crisscross' pattern.

A "strong interaction" refers to binding that is engaged more than 50% (e.g.; more than 60%, 70%, 80% or 90%) of the time that the binding nanostructures are in a reaction together (the dissociation constant is lower than the concentration of the species/nanostructures in excess).

A "weak interaction"—refers to binding that is engaged less than 1% of the time that the binding nanostructures are in a reaction together (the dissociation constant is at least 100 times higher than the concentration of the species/nanostructures in excess).

A nucleating nanostructure may bind to two or more other nanostructures. In some embodiments, a nucleating nanostructure binds to 5-1000 nanostructures (e.g., DNA nanorods). For example, a nucleating nanostructure may bind to 3-900, 3-800, 3-700, 3-600, 3-500, 3-400, 3-300, 3-200, or 3-100 nanostructures. In some embodiments, a nucleating nanostructure binds to 3-10, 3-15, 3-20, 3-25, 3-30, 3-35, 3-40, 3-45 or 3-50 nanostructures. In some embodiments, a nucleating nanostructure binds to 10-15, 10-20, 10-25, 10-30, 10-35, 10-40, 10-45 or 10-50 nanostructures. In some embodiments, a nucleating nanostructure binds to 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100 nanostructures (e.g., DNA nanorods).

Thus, a single subset of nanostructures (nanostructures programmed to interact with a single nucleating nanostructure) may comprise 3-900, 3-800, 3-700, 3-600, 3-500, 3-400, 3-300, 3-200, or 3-100 nanostructures. In some embodiments, a single subset of nanostructures comprises 3-10, 3-15, 3-20, 3-25, 3-30, 3-35, 3-40, 3-45 or 3-50 nanostructures. In some embodiments, a single subset of nanostructures comprises 10-15, 10-20, 10-25, 10-30, 10-35, 10-40, 10-45 or 10-50 nanostructures. In some embodiments, a single subset of nanostructures comprises 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90.95 or 100 nanostructures (e.g., DNA nanorods).

A "subset of nanostructures" refers to a specific group of nanostructures that are similar in size (have similar dimensions) and structure/shape and are programmed to hind to either the nucleating nanostructure (the initial subset) or to a pre-existing layer formed by alignment and binding of other nanostructures that have already aligned and bound to the nucleating structure or nanostructures of another pre-existing layer.

Nanostructures within a defined subset are programmed not bind to each other. Thus, in some embodiments, less than 10% of the nanostructures of a subset bind to another nanostructure of the same subset. In some embodiments, less than 9%, less than 8%, less than 7%, less than 6%, less than 5%, less than 4%, less than 3%, less than 2%, less than 1%, less than 0.5%, less than 0.2%, or less than 0.1% of the nanostructures of a subset bind to another nanostructure of the same subset. In some embodiments, none of the nanostructures of a subset bind to another nanostructure of the same subset.

Figure 1B:
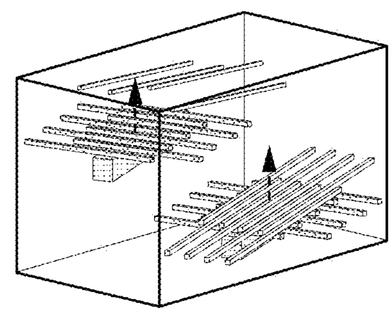
Figure 2:
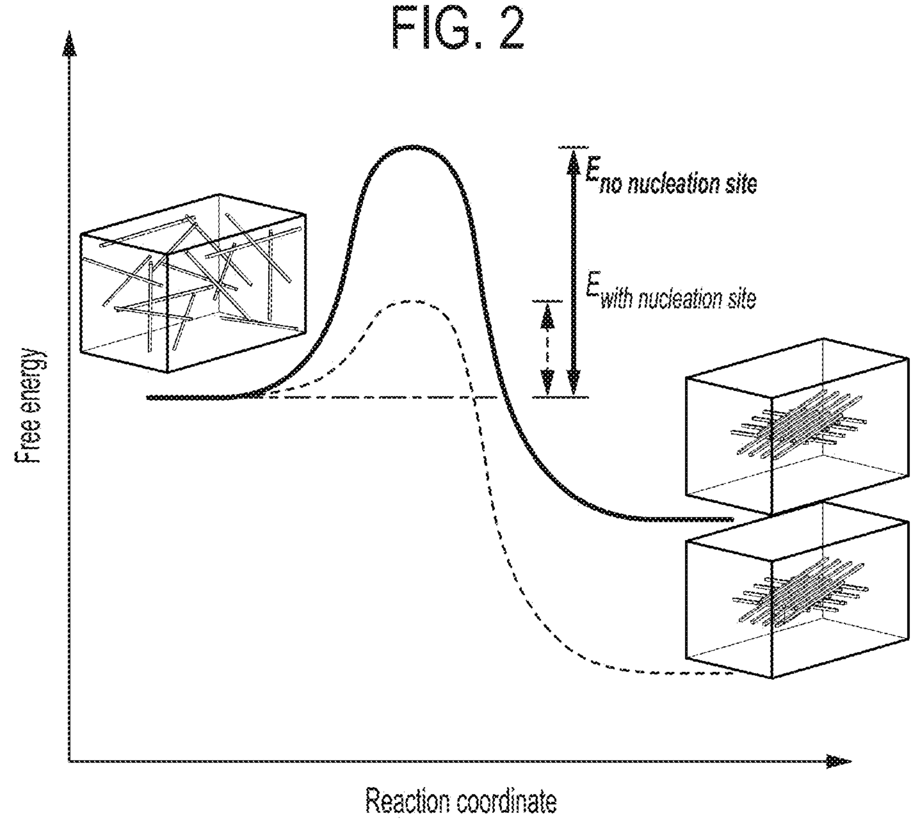
FIG. 2 shows a graph depicting the principle by which the nucleation site (queen) structure initiates higher-order structures with drones and workers by lowering the activation energy for assembly.

With crisscross cooperative assembly, nanostructures are aligned to form multiple layers, each layer rotated by some degree relative to adjacent layers (above and below). An example of two layers rotated relative to one another is shown in FIG. 1B. The top layer of aligned nanorods is rotated 90 degrees relative to the bottom layer of aligned nanorods. The degree of rotation between two adjacent layers may vary. In some embodiments, one layer is rotated 10-90 degrees, 20-90 degrees, 30-90 degrees, 40-90 degrees, 50-90 degrees, 60-90 degrees, 70-90 degrees, or 80-90 degrees relative to an adjacent layer. In some embodiments, one layer is rotated 10, 15, 20, 25, 30, 35, 40, 45, 50, 55, 60, 65, 70, 75, 80, 85, or 90 degrees relative to an adjacent layer.

Nucleic Acid Nanostructures

A "nucleic acid nanostructure," including a "DNA nanostructure," refers to a nanostructure (e.g., a structure that is between 0.1 nm and 1 μm (e.g., 0.1 nm and 100 nm) in each spatial dimension, e.g., 1D, 2D or 3D) that is rationally designed to self-assemble (is programmed) into a predetermined, defined shape that would not otherwise assemble in nature. The use of nucleic acids to build nanostructures is enabled by strict nucleotide base pairing rules (e.g., A binds to T, G binds to C, A does not bind to G or C, T does not bind to G or C), which result in portions of strands with complementary base sequences binding together to form strong, rigid structures. This allows for the rational design of nucleotide base sequences that will selectively assemble (self-assemble) to form nanostructures.

Examples of nucleic acid (e.g., DNA) nanostructures include, but are not limited to, DNA origami structures, in which a long scaffold strand (e.g., at least 500 nucleotides in length) is folded by hundreds (e.g., 100, 200, 200, 400, 500 or more) of short (e.g., less than 200, less than 100 nucleotides in length) auxiliary strands into a complex shape (Rothemund, P. W. K. *Nature* 440, 297-302 (2006); Douglas, S. M. et al. *Nature* 459, 414-418 (2009); Andersen, E. S. et al. *Nature* 459, 73-76 (2009); Dietz, H. et al. *Science* 325, 725-730 (2009); Han, D. et al. *Science* 332, 342-346 (2011); Liu. W et al. *Angew. Chem. Int. Ed.* 50, 264-267 (2011); Zhao, Z. et al. *Nano Lett.* 11, 2997-3002 (2011); Woo, S. & Rothemund, P. *Nat. Chem*, 3, 620-627 (2011); Torring, T. et al. *Chem. Soc. Rev.* 40, 5636-5646 (2011)). Other more modular strategies have also been used to assemble DNA tiles (Fu, T. J. & Seeman, N. C. *Biochemistry* 32, 3211-3220 (1993); Winfree, E. et al. *Nature* 394, 539-544 (1998); Yan, H. et al. *Science* 301, 1882-1884 (2003); Rothemund, P. W. K. et al. *PLoS Biol.* 2, e424 (2004); Park, S. H. et al. *Angew. Chem. Int. Ed.* 45, 735-739 (2006); Schulman, R. & Winfree, E. *Proc. Natl Acad. Sci. USA* 104, 15236-15241 (2007); He, Y. et al. *Nature* 452, 198-201 (2008); Yin, P. et al. *Science* 321, 824-826 (2008); Sharma, J. et al. *Science* 323, 112-116 (2009); Zheng, J P. et al. *Nature* 461, 74-77 (2009): Lin, C. et al. *ChemPhysChem* 7, 1641-1647 (2006)) or RNA tiles (Chworos, A. et al. *Science* 306, 2068-2072 (2004); Delebecque, C. J. et al. *Science* 333, 470-474 (2011)) into periodic (Winfree, E. et al., *Nature* 394, 539-544 (1998); Yan, H. et al. *Science* 301, 1882-1884 (2003); Chworos, A. et al., *Science* 306, 2068-2072 (2004); Delebecque, C. J. et al., *Science* 333, 470-474 (2011)) and algorithmic Rothemund, P. W. K. et al. *PLoS Biol.* 2, e424 (2004)) two-dimensional lattices (Seeman, N. C. *J. Theor. Biol.* 99, 237-247 (1982); Park, S. H. et al. *Angew. Chem. Int. Ed,* 45, 735-739 (2006)), extended ribbons (Schulman, R. & Winfree, E. *Proc. Natl Acad. Sci. USA* 104, 15236-15241 (2007); Yin, P. et al. *Science* 321, 824-826 (2008)) and tubes (Yan, H. et al. *Science* 301, 1882-1884 (2003); Yin; P. et al. *Science* 321, 824-826 (2008); Sharma, J. et al. *Science* 323, 112-116 (2009)), three-dimensional crystals (Zheng, J. P. et al. *Nature* 461, 74-77 (2009)), polyhedral (He, Y. et al. *Nature* 452, 198-201 (2008)) and simple finite two-dimensional shapes (Chworos, A. et al. *Science* 306, 2068-2072 (2004); Park, S. H. et al. *Angew. Chem. Int. Ed.* 45, 735-739 (2006)).

Thus, crisscross cooperative assembly building blocks (e.g., nucleating nanostructures and subsets of nanostructures) may be one of a number of nucleic acid nanostructure shapes, including, but not limited to, rods/tubes, sheets, ribbons, lattices, cubes, spheres, polyhedral, or another two-dimensional or three-dimensional shape. In some embodiments, a nanostructure has junction(s), branch(es), crossovers, and/or double-crossovers formed by nucleotide base pairing of two or more nucleic acid strands (see, e.g., Mao, C. *PLoS Biology,* 2(12), 2036-2038, 2004).

In some embodiments, a nucleic acid nanostructure has a handle and barrel shape, similar to that depicted in FIG. 22.

The versatile and stable nature of DNA origami enables the construction of various individual architectures that can be designed in a particular way, to facilitate to cooperative assembly of larger structures. In one example, each component is a separately folded DNA-origami structure. FIG. 3A shows an example of a DNA origami queen, drone and worker, whereby the drone and worker are of identical architecture (six helix bundle DNA nanotubes). Queen, drones and workers can then assemble in a cooperative manner to form higher order 1D, 2D and 3D structures (FIG. 3B). 3D structures are contemplated by merging 1D and 2D design principles. For example, FIG. 22 depicts a 3D queen nanostructure assembling with 2D drone/worker slats to form a barrel shape.

A nucleic acid (e.g., DNA) slat is a slat-shaped nanostructure that is composed of DNA. A slat may be an antiparallel-crossover single-stranded slat (AXSSS) comprising single strands that cross a partnering single strand only once. Also provided herein are paranemic crossover slats that include a pair of strands that cross another pair of strands.

Figure 4:
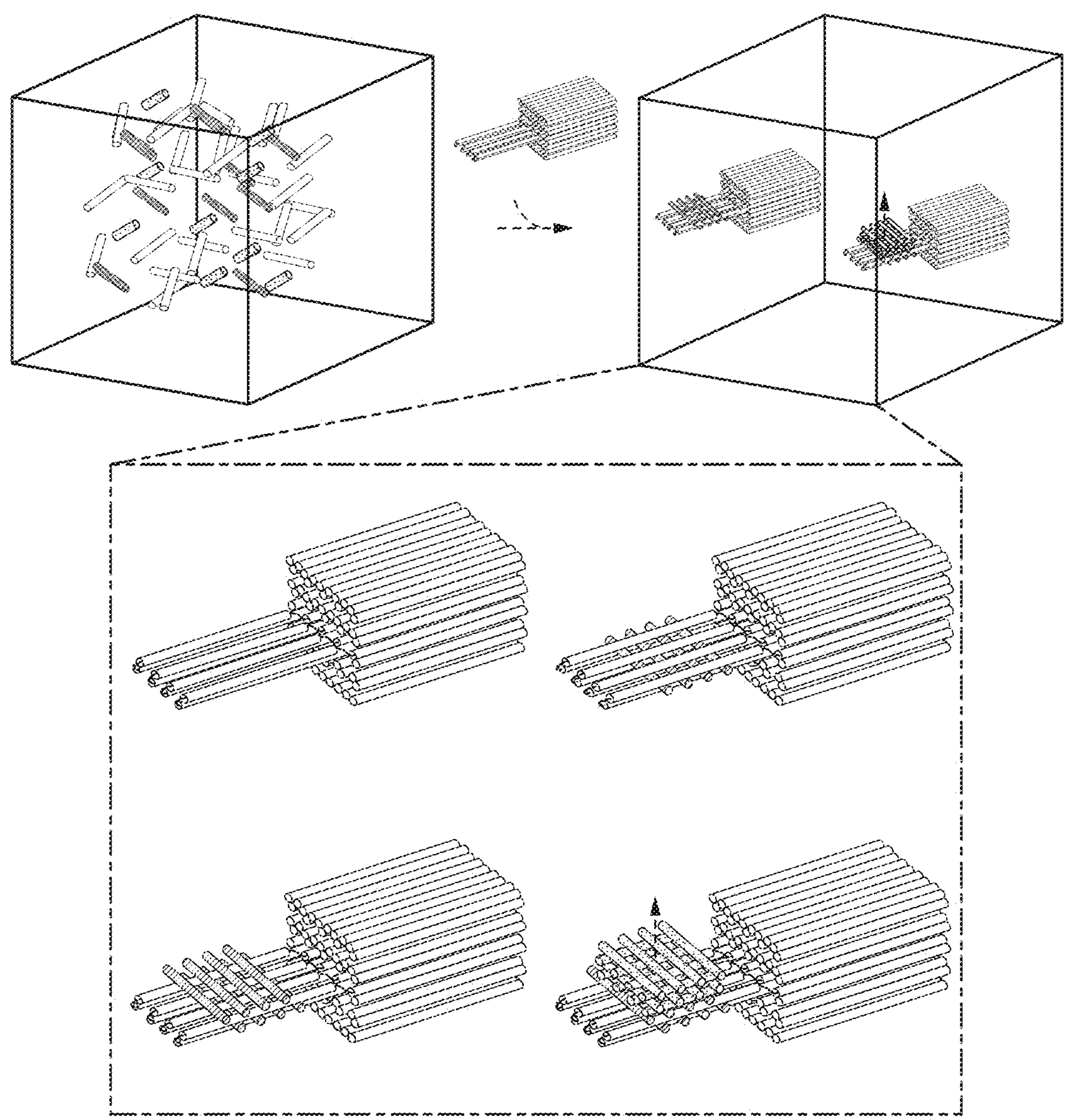
FIG. 4 shows an example of single-stranded DNA crisscross cooperative assembly. Oligonucleotides comprising the workers and drones of the system (shown as cylinders) are nucleated by the addition of a cubic DNA-Origami queen structure with a nucleation site. Stepwise assembly is shown in illustrated magnification.
Figure 5:
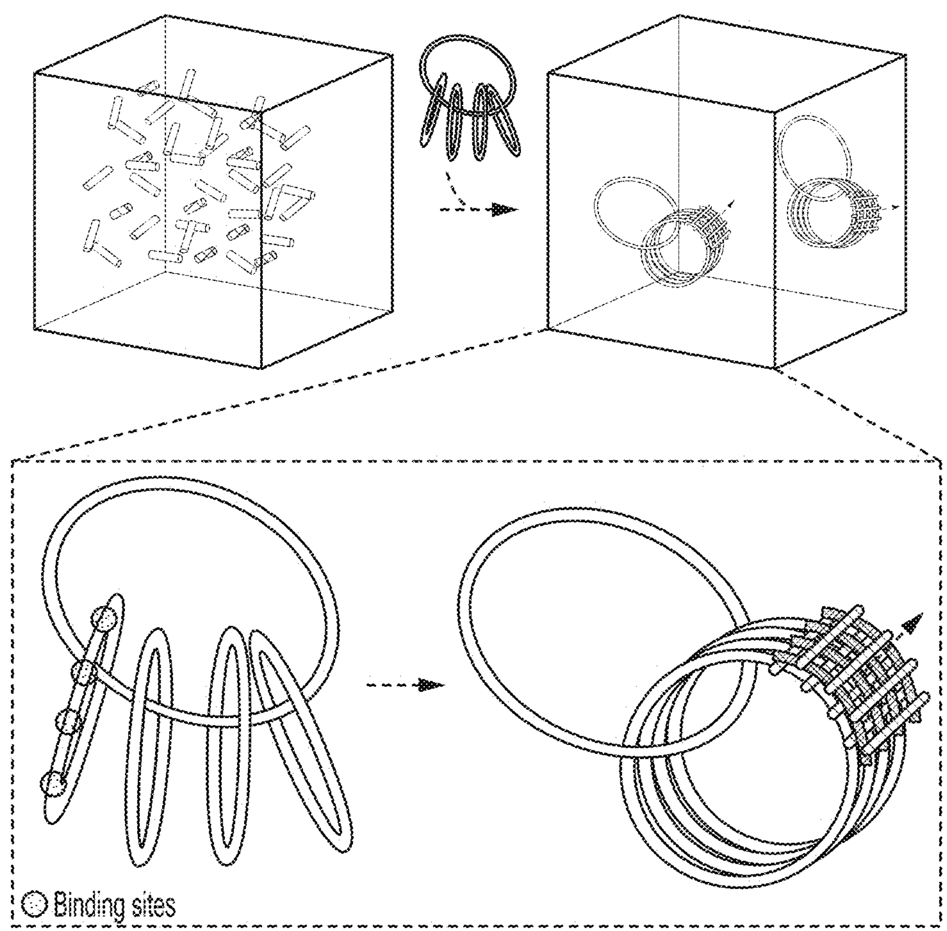
FIG. 5 shows an example of catenane crisscross cooperative assembly queen (catenane queen), useful for ultrasensitive detection. Oligonucleotides comprising the workers and drones of the system (shown as cylinders) are nucleated by the addition of a single-stranded catenane queen structure with a nucleation site. Binding sites on the structure shown to the left of the illustrated magnification indicate the nucleation fix the workers/drones. Each host ring has multiple binding sites, collectively functioning as a cooperative binding site.

Similar to the larger scale DNA-origami crisscross cooperative assembly, single-stranded DNA can be used to achieve cooperative assembly of higher order structures. In order to achieve this, drones and workers are replaced with oligonucleotides of various lengths (depending on the proposed architecture) that can assemble onto a DNA-origami queen nucleation site (shown in FIG. 4) or onto a single stranded DNA catenane structure shown in FIG. 5, FIG. 22 and FIGS. 24A-24B. The ring structures depicted in FIG. 5 are comprised of single-stranded DNA that has exposed binding sites for drone and worker oligonucleotides. In another example, the components are folded into a DNA origami barrel queen (FIGS. 24A-24B). The scaffold can be tiled with extended DNA slats (slats) capable of seeding further DNA slats, leading to growth of the structure. Generally, the DNA slats work in two steps: first, folding the origami queen site (for example, mixing M13 scaffold and staple strands), and second, mixing the crude DNA origami queen reaction with DNA slats, leading to growth of the structure. Varying salt concentrations, temperatures, and DNA slat concentration can alter the binding energy of the various sub-components, leading to reversible or irreversible binding, for example.

Typically, nucleic acid nanostructures do not contain coding sequences (sequences that code for a full length mRNA or protein), thus, nucleic acid nanostructures do not contain a promoter or other genetic elements that control gene/protein expression. An individual single-stranded nucleic acid (e.g., DNA strand or RNA strand without secondary structure), or an individual double-stranded nucleic acid (e.g., without secondary structure), for example, double helices found in nature or produced synthetically or recombinantly (e.g., such as a plasmid or other expression vector), are specifically excluded from the definition of a nucleic acid nanostructure.

Nanostructures, in some embodiments, have a void volume, which is the combine volume of space between nucleic acids that form a nanostructures. It should be understood that "space" includes fluid-filled space. Thus, a nanostructure in solution, have a void volume of 25% may include 75% nucleic acids and 25% reaction buffer (filling the 25% void volume of the nanostructure). In some embodiments, a nanostructure in solution, e.g., in reaction buffer, may have a void volume of at least 10% (e.g., 10-90%, 10-80%, 10-70%, 10-60%, 10-50%, 10-40%, or 10-30%), at least 20% (e.g., 20-90%, 20-80%, 20-70%, 20-60%, 20-50%, 20-40%, or 20-30%), at least 30%, (e.g., 30-90%, 30-80%, 30-70%, 30-60%, 30-50%, or 30-40%), at least 40% (e.g., 40-90%, 40-80%, 40-70%, 40-60%, or 40-50%), at least 50% (e.g., 50-90%, 50-80%, 50-70%, or 50-60%), at least 60% (e.g., 60-90%, 60-80%, or 60-70%), at least 70% (e.g., 70-90% or 70-80%), or at least 80% (e.g., 80-90%). In some embodiments, a nanostructure has a void volume of 10%, 15%, 20%, 25%, 30%, 35%, 40%, 45%, 50%, 55%, 60%, 65%, 70%, 75%, 80%, 85%, or 90%.

A "nucleic acid nanorod," including a "DNA nanorod" is a nucleic acid (e.g., DNA) nanostructure in the shape of a rod. A nanorod is a three-dimensional cylindrical shape having a length longer than its diameter. Examples of nanorods are depicted in FIGS. 1A-1B and FIGS. 3A-3B. In some embodiments, a nucleic acid nanorod comprises six helix bundles. For example, six DNA double helices may be connected to each other at two crossover sites. DNA double helices with 10.5 nucleotide pairs per turn facilitate the programming of DNA double crossover molecules to form hexagonally symmetric arrangements when the crossover points are separated by seven or fourteen nucleotide pairs (see, e.g., Mathieu F. et al. *Nano Lett.* 5(4), 661-664 (2005)). Other methods of assembling nucleic acid nanorods (also referred to as nanotubes) may be used (see, e.g., Feldkamp. U. et al. *Angew. Chem. Int. Ed* 45(12), 1856-1876 (2006); Hariri A. et al. *Nature Chemistry,* 7, 295-300 (2015)).

The length and diameter of a nanorod (or other nanostructure) may vary. In some embodiments, a nanorod (or other nanostructure) has a length of 10-100 nm, or 10-500 nm. For example, a nanorod may have a length of 10-500 nm, 10-400 nm, 10-300 nm, 10-200 nm, 10-100 nm, 10-90 nm, 10-80 nm, 10-70 nm, 10-60 nm, 10-50 nm, 10-30 nm, or 10-20 nm. In some embodiments, a nanorod has a length of 100-500 nm, 200-500 nm, or 300-500 nm. In some embodiments, a nanorod has a length of 100 nm, 150 nm, 200 nm, 250 nm, 300 nm, 350 nm, 400 nm, 450 nm or 500 nm. In some embodiments, a nanorod has a length of 10, 15, 20, 25, 30, 35, 40, 45, 50, 55, 60, 65, 70, 75, 80, 85, 90, 95 or 100 nm. In some embodiments, the length of a nanorod (or other nanostructure) is longer than 100 nm (e.g., 100-1000 nm), or shorter than 10 nm (e.g., 1-10 nm). In some embodiments, a nanorod (or other nanostructure) has a diameter of 5-90 nm. For example, a nanorod may have a diameter of 5-80 nm, 5-70 nm, 5-60 nm, 5-50 nm, 5-30 nm, 5-20 or 5-10 nm. In some embodiments, a nanorod has a diameter of 5, 10, 15, 20, 25, 30, 35, 40, 45, 50, 55, 60, 65, 70, 75, 80, 85 or 90 nm. In some embodiments, the diameter of a nanorod is longer than 9 nm, or shorter than 5 nm. Thus, in some embodiments, a nanorod (or other nanostructure) has a circumference of 15-300 nm ($C \approx 3.14 \times d$).

A nucleic acid nanostructure, such as a nanorod, is considered "elongated," if the length of the nanostructure is longer than its width/diameter (e.g., by at least 10%, 20%, 25%, 50%, 100%, or 200%).

Nucleic acid nanostructures are typically nanometer-scale structures (e.g., having lengths of 1 to 1000 nanometers). In some embodiments, however, the term "nanostructure" herein may include micrometer-scale structures (e.g., assembled from more than one nanometer-scale or micrometer-scale structure). In some embodiments, a nanostructure has a dimension (e.g., length or width/diameter) of greater than 500 mu or greater than 1000 nm. In some embodiments, a nanostructure has a dimension of 1 micrometer to 2 micrometers. In some embodiments, a nanostructure has a dimension of 10 to 500 nm, 10 to 450 nm, 10 to 400 nm, 10 to 350 nm, 10 to 300 nm, 10 to 250 nm, 10 to 200 nm, 10 to 150 nm, 10 to 100 nm, 10 to 50 nm, or 10 to 25 nm. In some embodiments, the nanostructure has a dimension of 500 to 450 nm, 500 to 400 nm, 500 to 350 nm, 500 to 300 nm, 500 to 250 nm, 500 to 200 nm, 500 to 150 nm, 500 to 100 nm, 500 to 50 nm, or 500 to 25 nm. In some embodiments, the nanostructure has a dimension of 10, 25, 50, 75, 100, 150, 200, 250, 300, 350, 400, 450, or 500 nm.

A nucleic acid nanostructure is considered to "self-assemble." Bottom up, self-assembly refers to the process by which molecules adopt a defined arrangement without guidance or management from an outside source. Although, it should be understood that with synthetic nucleic acid self-assembly, as provided herein, the nucleotide base sequences that guide assembly of nucleic acids are artificially designed, and the corresponding nucleic acids are accordingly synthesized by an outside source, such as one of skill in the art (using, for example, standard nucleic acid synthesis techniques). That is, one of ordinary skill in the art can 'program' nucleotide base sequences within a single nucleic acid strand or between two difference nucleic acid strands to selectively bind to each other in solution based on a strict set of nucleotide base pairing rules (e.g., A binds to T, G binds to C, A does not bind to G or C, T does not bind to G or C). Self-assembly may be intramolecular (folding) or intermolecular.

The nanostructures and, thus, nanostructures, microstructures and macrostructures assembled from smaller nanostructures, are "rationally designed." A nanostructure, as discussed above, does not assemble in nature. Nucleic acid strands for use in crisscross cooperative assembly are 'programmed' such that among a specific population of strands, complementary nucleotide base sequences within the same strand or between two different strands bind selectively to each other to form a complex, user-defined structure, such as a rod/tube, ribbon, lattice, sheet, polyhedral, cube, sphere, or other two-dimensional or three-dimensional shape. A nanostructure may have a regular shape (sides that are all equal and interior angles that are all equal) or an irregular shape (sides and angles of any length and degree).

Methods of Crisscross Cooperative Assembly

Self-assembly of a nucleating nanostructure and subsets of nanostructures occurs, in some embodiments, in a 'one-pot' reaction, whereby all nucleic acid nanostructures of a crisscross cooperative assembly system are combined in a reaction buffer, and then the reaction buffer is incubated under conditions that result in self-assembly of all of the nucleic acid nanostructures.

Conditions that result in self-assembly of nucleic acid nanostructures of a crisscross cooperative assembly reaction may vary depending on the size, shape, composition and number of nucleic acid nanostructures in a particular reaction. Such conditions may be determined by one of ordinary skill in the art, for example, one who rationally designs/programs the nanostructures to self-assemble.

A crisscross cooperative assembly method may be performed at a variety of tetnperatures. In some embodiments, a crisscross cooperative assembly method is performed at room temperature (~25° C.) or 37° C., A crisscross cooperative assembly method may be performed at a temperature lower than 25° C. or higher than 37° C.

The salt concentration of the reaction buffer in which a crisscross cooperative assembly reaction is performed may also vary. In some embodiments, the reaction buffer comprises $MgCl_2$ salt at a concentration of 1 mM-10 mM (e.g., 1 mM, 2 mM, 3 mM, 4 mM, 5 mM, 6 mM, 7 mM, 8 mM, 9 mM or 10 mM). In some embodiments, the reaction buffer comprises NaCl at a concentration of 100 mM-500 mM (e.g., 100 mM, 200 mM, 300 mM, 400 mM or 500 mM). In some embodiments, a crisscross cooperative assembly method is performed under high-salt conditions. Thus, in some embodiments, the reaction buffer comprises $MgCl_2$ salt at a concentration of at least 20 mM (e.g., 20-500 mM, or 20-200 mM). In some embodiments, the reaction buffer comprises NaCl at a concentration of at least 1 M (e.g., 1-2 M, 1-3 M, 1-4 M, or 1-5 M).

In any given reaction, the number of initial nanostructures (drones) exceeds the number of nucleating nanostructures (queens). Thus, in some embodiments, the ratio of nucleating nanostructure to non-nucleating nanostructure (e.g., a drone from an initial subset, or a worker from a subsequent subset) is 1:10-1:$10^{12}$ (trillion). For example, the ratio of nucleating nanostructure to non-nucleating nanostructure may be 1:10-1:1000, 1:10-1:500, 1:10-1:100, 1:10-1:75, 1:10-1:50, or 1:10-1:25. In some embodiments, the ratio of nucleating nanostructure to non-nucleating nanostructure is 1:1000, 1:500, 1:100, 1:90, 1:80, 1:70, 1:60, 1:50, 1:40, 1:30, 1:20 or 1:10.

In some embodiments, a crisscross cooperative assembly reaction is incubated for 2-96 hours. For example, a crisscross cooperative assembly reaction may be incubated for 2-24 hours, 2-30 hours, 2-36 hours, 2-42 hours, 2-48 hours, 2-54 hours, 2-60 hours, 2-66 hours, 2-72 hours, 2-78 hours, 2-84 hours, 2-90 hours, or 2-96 hours. In some embodiments, a crisscross cooperative assembly reaction is incubated for 3, 6, 9, 12, 15, 18, 21, 24, 27, 30, 33, 36, 39, 42, 45, 48, 51, 54, 57, 60, 63, 66, 69, or 72 hours. In some embodiments, a crisscross cooperative assembly reaction is incubated for 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70 or 72 hours.

Biosensors

In some embodiments, the crisscross assembly products may be used as biosensors that are capable of detecting a selected biomolecule (analyte) using a variety of different mechanisms and the systems described herein. For example, in such systems, the presence of a biomolecule can be used to trigger crisscross assembly, which can then be detected (visualized), indicating the presence of the biomolecule.

Figure 6:
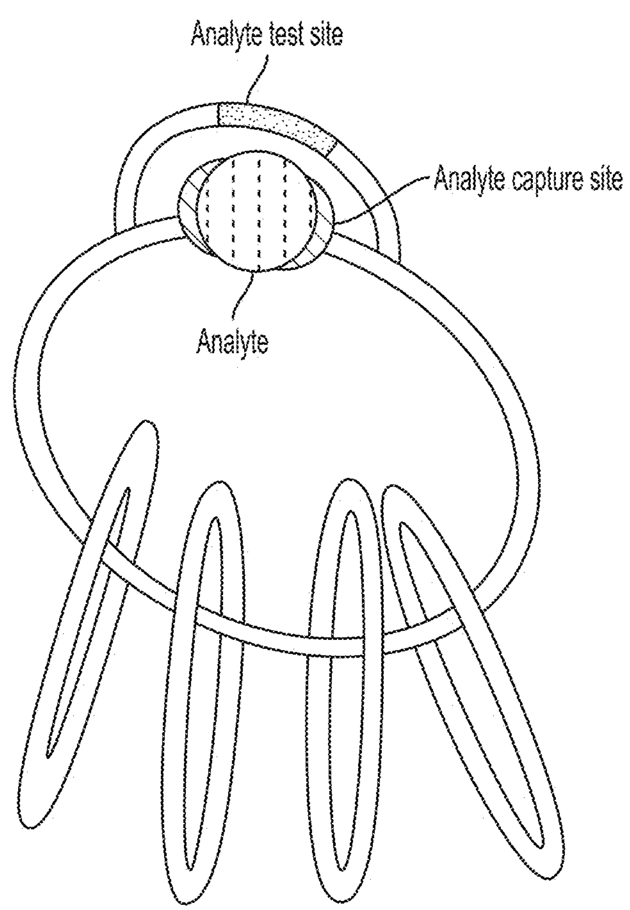
FIG. 6 shows a catenane queen from FIG. 5 that has been modified to serve as a biosensor. The large DNA ring has been split to incorporate and biomolecule capture site to bind a biomolecule (e.g., macromolecule) in biological samples. The presence of the biomolecule, in some embodiments may be detected in mixtures as follows: (1) A biological sample is mixed with a high concentration of the catenane queen and a biomolecule of interest binds the biomolecule capture site. (2) A chemical reaction is used to reversibly cleave the biomolecule capture site. (3) Catenane queens not bound to the target biomolecule fall apart more quickly compared to those held together by the target biomolecule. (4) Remaining catenane queens in the test mixture are re-ligated at the biomolecule capture site. (5) Drones and workers are added to the test mixture to amplify remaining queens using readily observable micrometer-scale DNA structures. This system is modular, as the biomolecule capture site may be customized to bind disease markers, including proteins or nucleic acid sequences.
Figure 7:
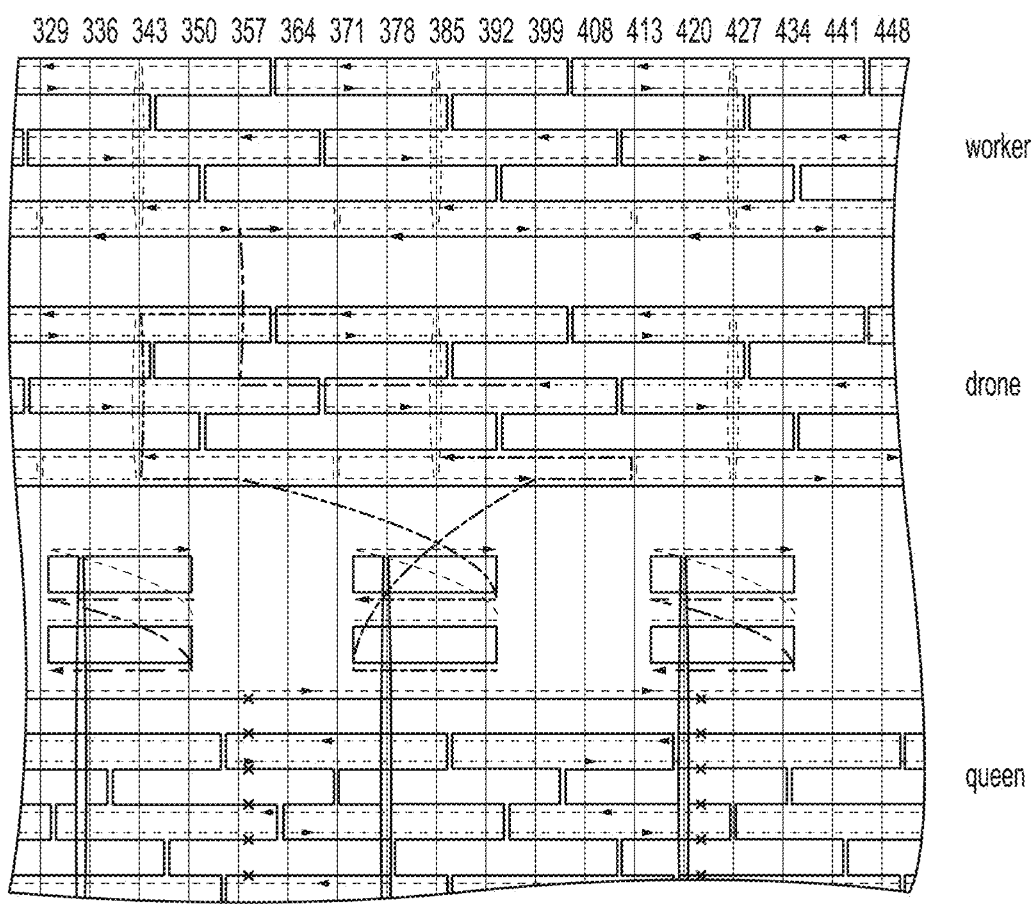
FIG. 7 shows a. CAD schematic of an example of base-pairing linkages between a 6 helix bundle worker and a 6 helix bundle drone to queen. A plug socket linkage design may also be used, as shown in FIGS. 18-20. The following CAD tool was used to design the structures: Douglas S M, Marblestone A H, Teerapittayanon S, Vazquez A, Church G M, Shih W M. Rapid prototyping of 3D DNA-origami shapes with caDNAno. Nucleic Acids Res. 37; 5001-5006, 2009.
Figure 8A:
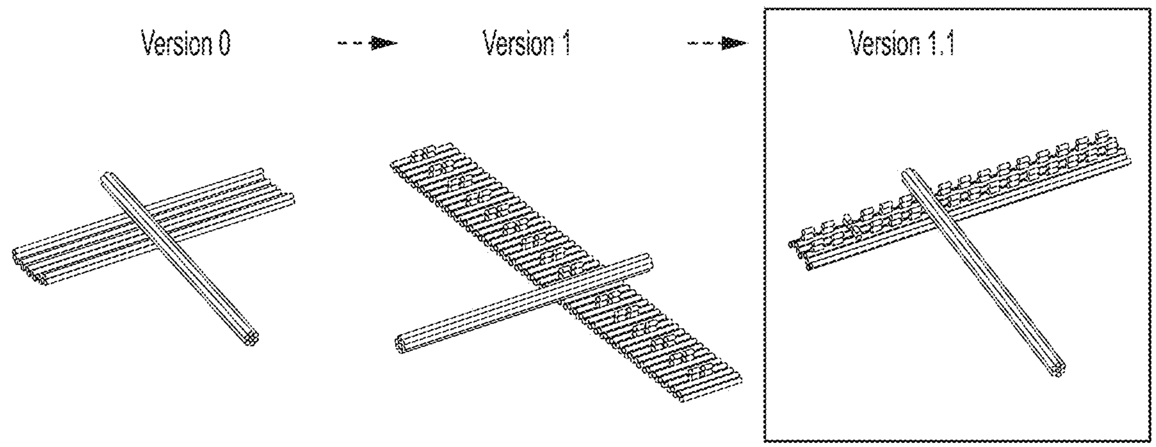
FIGS. 8A-8D are schematics depicting different example 'seed' designs (a 6-helix bundle nanorod bound to a nucleating nanostructure) with different cooperative bind site configurations. Additional example 'seed' designs are shown in FIGS. 16A-16C.
Figure 8B:
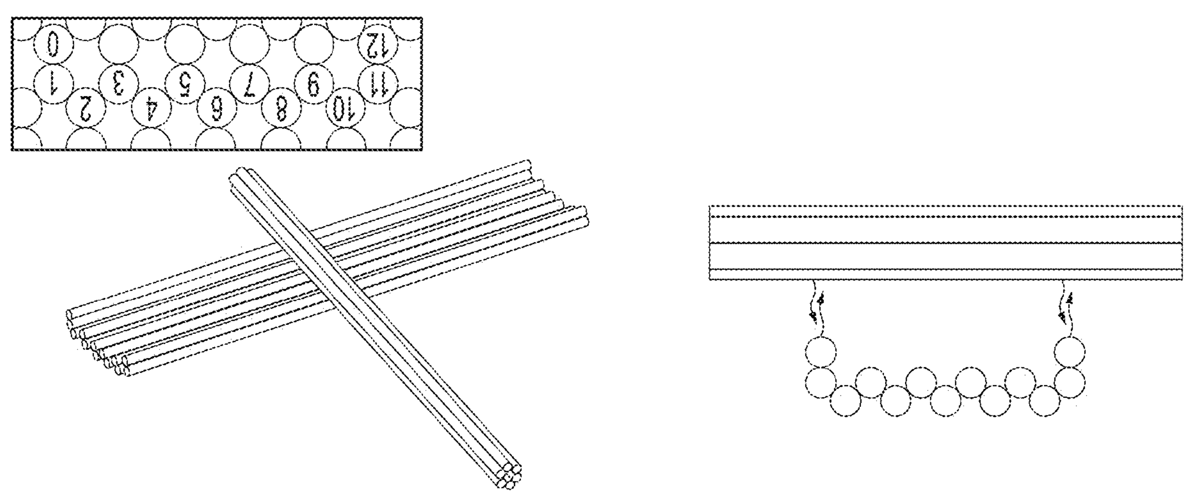
Figure 8C:
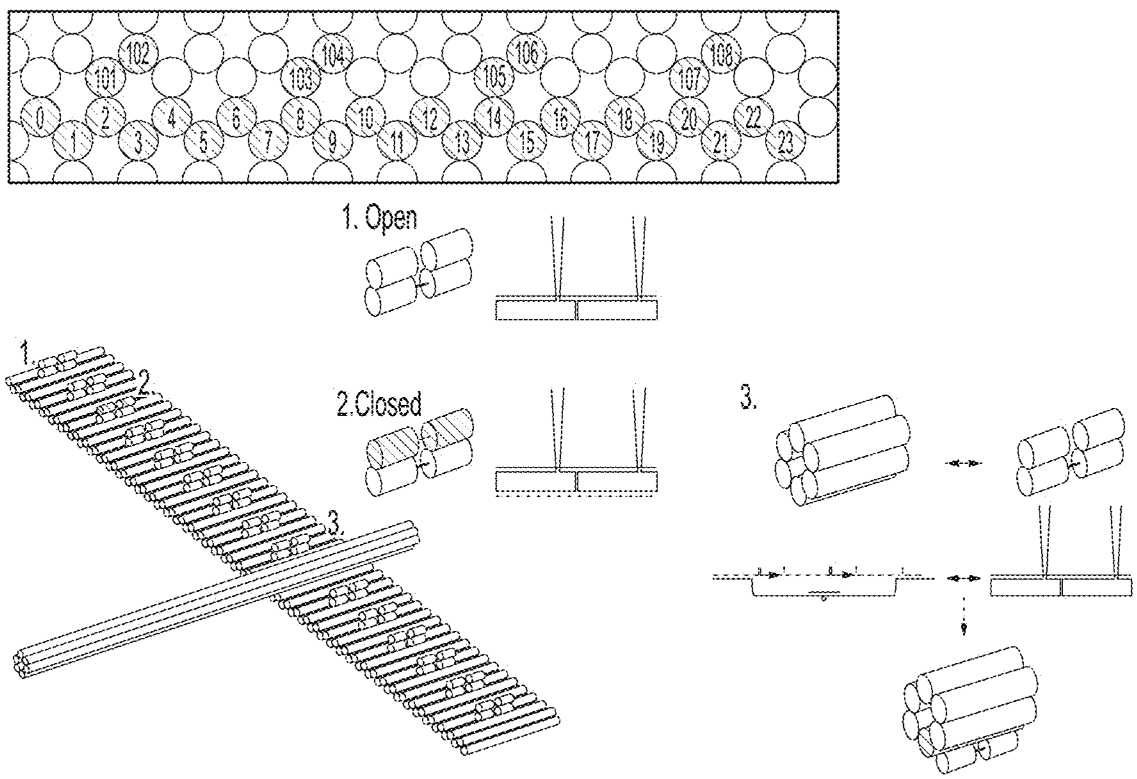
Figure 8D:
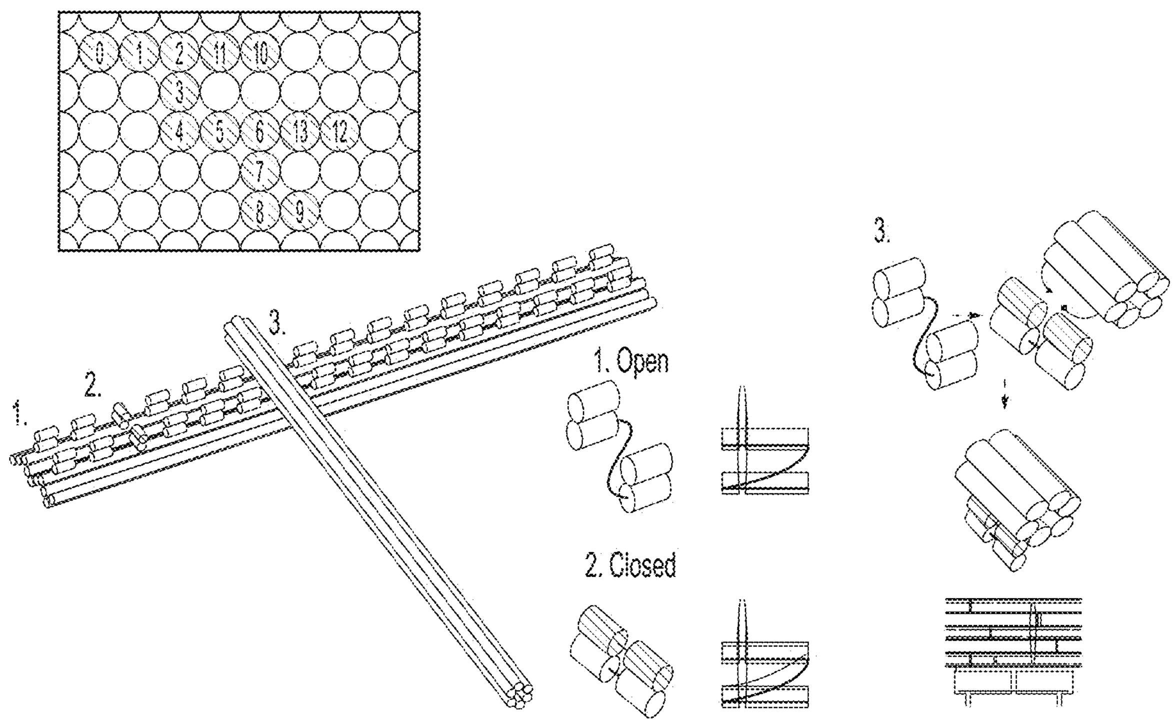

The biomolecule may be detected using a ring system. As depicted in FIG. 6, the large DNA ring ("host ring"), single-stranded DNA, may be split to incorporate a biomolecule capture site (analyte test site) to bind macromolecules in biological samples. The DNA ring loops through and encloses a number of discrete, separate "guest" rings, which are single-stranded DNA and function as catenane queens, so that the guest rings are catenated on the host ring, similar to individual beads on a bracelet. In some embodiments, the guest rings are independently formed from separate single-stranded nucleic acids (see, e.g., FIGS. 5 and 6), while in other embodiments, the guest rings are formed from a long single nucleic acid strand assembled into multiple (e.g., vertically stacked) rings (see, e.g., FIGS. 27A and 27B). The number of guest rings can be 2, 3, 4, or 5 or more. In embodiments, each guest ring (catenane queen) comprises binding sites for drone and worker oligonucleotides and is therefore capable of crisscross assembly. In embodiments, the plurality of catenated guest rings when in close proximity forms a catenane queen comprising binding sites (e.g., plug strands) for drone and worker nucleic acids and/or structures and is thus capable of crisscross assembly. The number of binding sites per guest ring can vary, and may be 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95 or 100. A biomolecule test site, located near the biomolecule capture site may also formed.

The presence of the biomolecule, in some embodiments may be detected in mixtures, such as biological samples, as follows. First, a biological sample is mixed with a high concentration of the catenane queen, allowing macromolecules of interest bind the biomolecule capture site. Then, a chemical reaction is used to reversibly cleave the biomolecule capture site. Catenane queens not bound to the target biomolecule will fall apart more quickly compared to those held together by the target biomolecule. The remaining catenane queens in the test mixture are re-ligated at the biomolecule test site. Subsequently, drones and workers are added to the test mixture to amplify remaining intact queens using readily observable micrometer-scale DNA structures. This system is modular, and the biomolecule capture site may be customized to bind disease markers, including proteins or nucleic acid sequences.

Ultraspecific biosensors can also be created by adding a biomolecule detection system to the multiple guest-ring (e.g., guest-loop) catenane systems with DNA slats, as depicted in FIGS. 27-28. In this example; a barrel queen is used; however, other 3-dimensional shapes are also possible (e.g., sheets, blocks and dendrimers). An example of the production of a barrel queen (a rolled sheet) is described above.

Figure 21A:
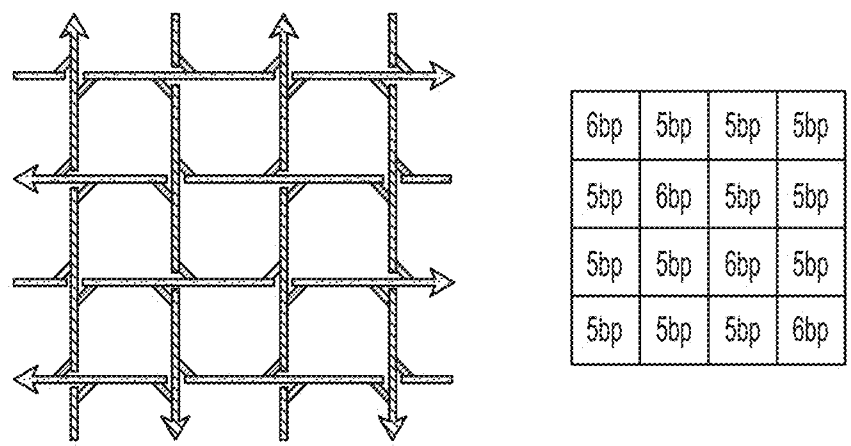
FIGS. 21A-21B show an example of a crisscross DNA slat-based architecture.
Figure 21B:
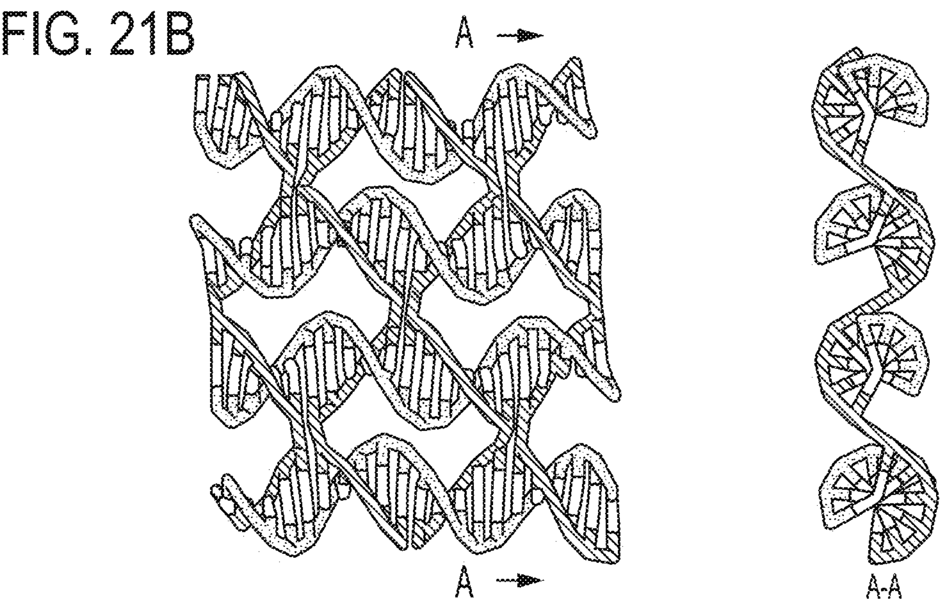

An example of a DNA slat is depicted in FIGS. 21A and 21B.

Figure 27A:
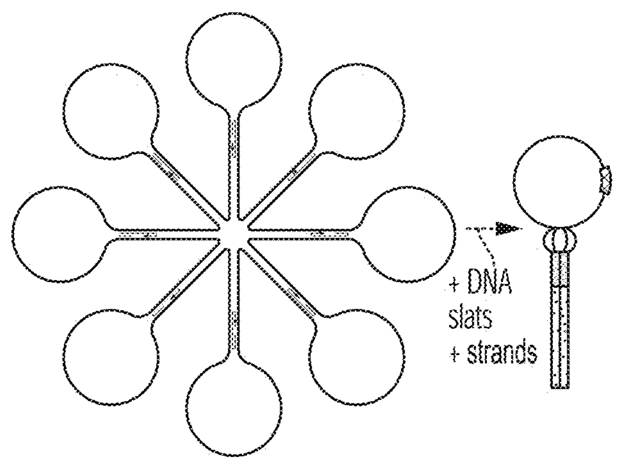
FIGS. 27A-27E show formation of multi-host-ring catenane systems with DNA slats in a one-pot reaction.
Figure 27B:
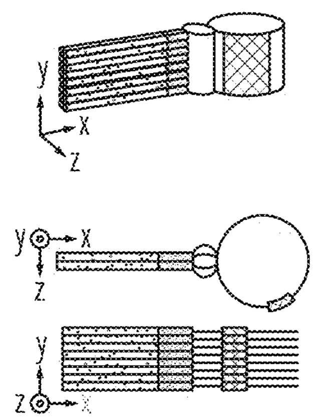
Figure 27C:
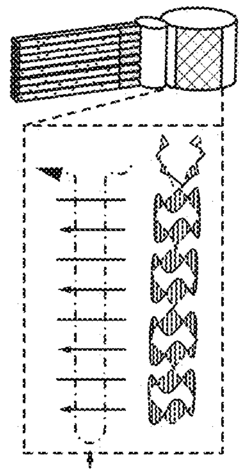
Figure 27D:
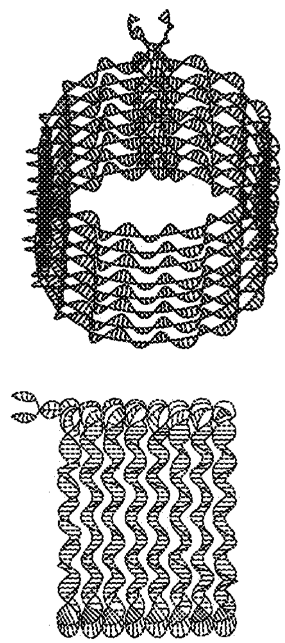
Figure 27E:
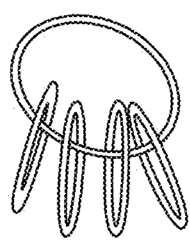
Figure 28A:
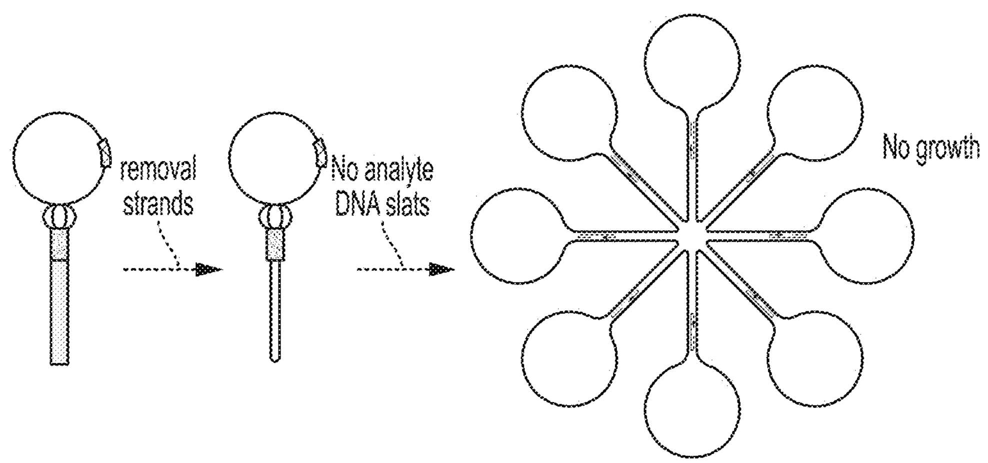
FIGS. 28A-28B show a barrel queen used for ultrasensitive detection.
Figure 28B:
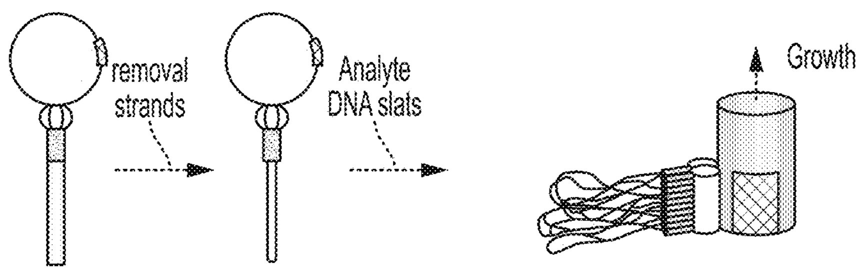
Figure 29:
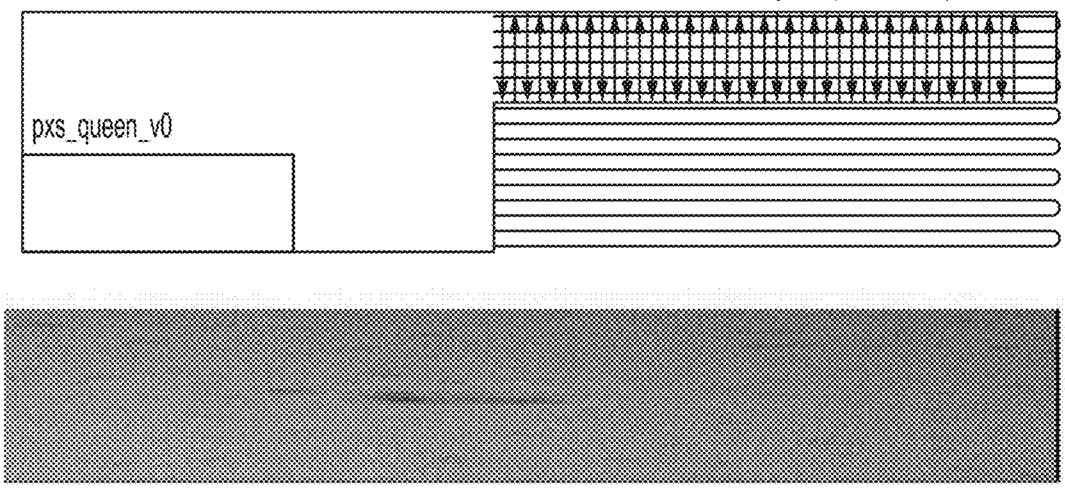
FIG. 29 shows a schematic (upper panel) of a queen with six binding sites per slat and a transmission electron microscope (TEM) image (lower panel) of the queen.

Using a scaffold for DNA origami, fir example an M13 scaffold and staple strands; a multiple guest-ring catenane system can be formed. For example, in FIG. 27, an eight-loop system is formed in a one-pot reaction. The number of loops (rings) can be varied, depending on the design of the system, and may be 2; 3, 4, 5, 6, 7, 8, 9, 10, 11, 12, 13, 14, 15, 16, 17, 18, 19, or 21) loops. Additional loops may be used. Unlike the system described above, the handles (elongated structures) and loops (rings) are all part of the same single-stranded DNA (e.g., M13 DNA); the handle structures are programmed to link together by specific staple strands (slats). The system is designed around the specific staple strands/slats; in the presence of biomolecule, they hold the structure together and growth can occur from the parallel loops when drones and workers are added (FIG. 28B). In the absence of biomolecule, the staple strands/slats release the structure, and no growth can occur as the queen falls apart and the binding sites are not close enough for nucleation and growth even in the presence of drones and workers (FIG. 28A). The presence of the structures can be detected using any one of the methods described above, or with any method known in the art.

DNA slats or other nucleic acids of a biosensor may be modified with one or more switchable bridges. A "switchable bridge" is a link between functional groups that forms or breaks in the presence of a particular agent (e.g., reaction agent or dissociation agent). Examples of switchable bridges include bonds formed via a "click chemistry" reaction (e.g., a between an azide and an alkyne), protein-protein binding (e.g., one or more antibodies binding to a target protein/antigen), a disulfide bond (between two thiols).

Thus, some aspects of the present disclosure provide a biosensor comprising (i) a first DNA slat comprising a first functional group (e.g., ran azide or alkyne), a first binding partner (e.g., an antibody, aptamer or nanobody), and a second functional group (e.g., a thiol or nucleic acid), and (ii) a second DNA slat comprising a third functional group (e.g., a thiol or nucleic acid), a second binding partner (e.g., an antibody, aptamer or nanobody), and a fourth functional group (e.g., an azide or alkyne), wherein the first and fourth functional groups react in the presence of a reaction agent to form a link (e.g., a covalent link), wherein the first and fourth binding partners bind specifically to a biomolecule of interest to form a link (e.g., non-covalent link), and wherein the second and third functional groups form a link (e.g., a covalent link) that breaks in the presence of a dissociation agent.

In some embodiments, a biosensor comprises a first DNA slat comprising an azide, an antibody, and a thiol group, and a second DNA slat comprising an alkyne, an antibody, and a thiol group, wherein antibody of (i) and the antibody of (ii) bind specifically to a biomolecule of interest.

A "first biomolecule binding partner" and a "second biomolecule binding partner" are any molecules that bind to the same target biomolecule to form a switchable bridge linking DNA slats to each other (via a non-covalent link). In some embodiments, the first and second biomolecule binding partners are proteins or peptides. For example, the first and second biomolecule binding partners may be antibodies that bind to different epitopes of the same antigen. Thus, in some embodiments, the first and second biomolecule binding partners are antibodies (e.g., monoclonal, polyclonal, human, humanized or chimeric). In some embodiments, the first and second biomolecule binding partners are antibody fragments (e.g., Fab. F(ab')2, Fc, scFv, or vhh). The biomolecule binding partners may also be nanobodies or aptamers. Other protein-protein binding partners may be used.

A "first functional group" and a "fourth functional group" are functional groups that react with each other to form a link (bond, such as a covalent bond or a non-covalent bond), which forms a switchable bridge linking the DNA slats to each other. In some embodiments, this bridge is formed through a click chemistry azide-alkyne cycloaddition) reaction (e.g., V. V. Rostovtsev, et al., *Angew. Chem. Int Ed.,* 2002, 41, 2596-2599; and F. Himo, et al, *J. Am. Chem. Soc.,* 2005, 127, 210-216, each of which is incorporated herein by reference). Thus, in some embodiments, one of the first or fourth functional group is an azide, while the other of the first or fourth functional groups is an alkyne. For example, the first functional group may be azide, and the fourth functional group may be trans-cyclooctene (TCO). Other click chemistry functional groups may be used.

A "second functional group" and a "third functional group" are functional groups that react with each other to form a link (bond, such as a covalent bond or a non-covalent bond), which forms yet another switchable bridge linking the DNA slats to each other. This bridge breaks (dissociates) in the presence of a dissociation agent. A "dissociation agent" is an agent (e.g., chemical) that breaks the bond (e.g., covalent bond) between the second and third functional groups. In some embodiments, the second and third functional groups are thiol groups that react with each other to form a disulfide bridge. Thus, in some embodiments, the dissociation agent is dithiothreitol (DTT). In some embodiments, the concentration of DTT is 50 mM-200 For example, the concentration of DTT may be 100 mM. Other functional groups may be used.

Additional Embodiments

1. A composition, comprising:

(a) nucleating nanostructures;

(b) a first subset of elongated nanostructures, wherein less than 10% of the nanostructures of (b) bind to each other, and wherein the nanostructures of (b) irreversibly bind to a nucleating nanostructure of (a); and (c) a second subset of elongated nanostructures, wherein less than 10% of the nanostructures of (c) bind to each other, wherein, in the absence of a nucleating nanostructure, a nanostructure of (b) can reversibly binding to a nanostructure of (a) only at a single position on the nanostructure of (a), and wherein, in the absence of a nucleating nanostructure, a nanostructure of (a) can reversibly binding to a nanostructure of (b) only at a single position on the nanostructure of (b), 2. The composition of embodiment 1 further comprising (d) a third subset of elongated nanostructures, wherein less than 10% of the nanostructures of (d) bind to each other.

3. The composition of embodiment 1 or 2, wherein the nanostructures of (b) are aligned in one direction and irreversibly bound to a nucleating nanostructure of (a) to form a first layer.

4. The composition of embodiment 3, wherein the nanostructures of (c) are aligned in one direction and hound to nanostructures of the first layer to form a second layer, wherein first layer is rotated by 10 degrees to 170 degrees relative to the second layer.

5. The composition of embodiment 4, wherein the first layer is rotated by 90 degrees relative to the second layer.

6. The composition of embodiment 4 or 5, wherein the nanostructures of (d) are aligned in one direction and bound to nanostructures of the second layer to form a third layer, wherein second layer is rotated by 10 degrees to 170 degrees relative to the third layer.

7. The composition of embodiment 6, wherein the first layer is rotated by 90 degrees relative to the second layer.

8. The composition of any one of embodiments 1-7, wherein the nucleating nanostructures of (a), the nanostructures of (b), the nanostructures of (c), and/or the nanostructures of (d) are nucleic acid nanostructures.

9. The composition of embodiment 8, wherein the nucleating nanostructures of (a), the nanostructures of (b), the nanostructures of (c), and/or the nanostructures of (d) are DNA nanostructures.

10. The composition of embodiment 8 or 9, wherein the nucleating nanostructures of (a), the nanostructures of (b), the nanostructures of (c), and/or the nanostructures of (d) comprise a long nucleic acid strand bound to multiple nucleic acid strands that are shorter than the long nucleic acid strand, 11. The composition of embodiment 8 or 9, wherein the nucleating nanostructures of (a), the nanostructures of (b), the nanostructures of (c), and/or the nanostructures of (d) comprise multiple nucleic acid strands, each having a length of less than 200 nm.

12. The composition of any one of embodiments 1-6, wherein the nucleating nanostructures of (a), the nanostructures of (b), the nanostructures of (c), and/or the nanostructures of (d) are protein nanostructures.

13. The composition of any one of embodiments 1-12, wherein the nucleating nanostructures of (a), the nanostructures of (b), the nanostructures of (c), and/or the nanostructures of (d) are rod-shaped.

14. A method, comprising:

combining in reaction buffer (a) nucleating nanostructures, (b) a first subset of elongated nanostructures, wherein less than 10% of the nanostructures of (b) bind to each other, and wherein the nanostructures of (b) irreversibly bind to a nucleating nanostructure of (a), and (c) a second subset of elongated nanostructures, wherein less than 10% of the nanostructures of (c) bind to each other, wherein, in the absence of a nucleating nanostructure, a nanostructure of (b) can reversibly binding to a nanostructure of (a) only at a single position on the nanostructure of (a), and wherein, in the absence of a nucleating nanostructure, a nanostructure of (a) can reversibly binding to a nanostructure of (b) only at a single position on the nanostructure of (b); and incubating the reaction buffer comprising (a), (b) and (c) under conditions that result in binding of the nanostructures of (b) to the nucleating nanostructures of (a) and result in binding of the nanostructures of (c) to the nanostructures of (b) to form a hierarchical structure, 15. The method of embodiment 14, wherein the reaction buffer further comprises (d) a third subset of elongated nanostructures, wherein less than 10% of the nanostructures of (d) bind to each other.

16. The method of embodiment 14 or 15, wherein the nucleating nanostructures of (a), the nanostructures of (b), the nanostructures of (c), and/or the nanostructures of (d) are nucleic acid nanostructures.

17. The method of embodiment 16, wherein the nucleating nanostructures of (a), the nanostructures of (b), the nanostructures of (c), and/or the nanostructures of (d) are DNA nanostructures.

18. The method of embodiment 16 or 17, wherein the nucleating nanostructures of (a), the nanostructures of (b), the nanostructures of (c), and/or the nanostructures of (d) comprise a long nucleic acid strand bound to multiple nucleic acid strands that are shorter than the long nucleic acid strand.

19. The method of embodiment 16 or 17, wherein the nucleating nanostructures of (a), the nanostructures of (b), the nanostructures of (c), and/or the nanostructures of (d) comprise multiple nucleic acid strands, each having a length of less than 200 nm.

20. The method of any one of embodiments 14-16, wherein the nucleating nanostructures of (a), the nanostructures of (b), the nanostructures of (c), and/or the nanostructures of (d) are protein nanostructures.

21. The method of any one of embodiments 14-20, wherein the nucleating nanostructures of (a), the nanostructures of (b), the nanostructures of (c), and/or the nanostructures of (d) are rod-shaped.

22. A composition, comprising:

(a) nucleating DNA nanostructures;

(b) a first subset of elongated DNA nanorods, wherein less than 10% of the nanostructures of (b) bind to each other, and wherein the DNA nanorods of (b) irreversibly bind to a nucleating DNA nanostructure of (a); and (c) a second subset of elongated DNA nanorods, wherein less than 10% of the DNA nanorods of (c) bind to each other, wherein, in the absence of a nucleating DNA nanostructure, a DNA nanorod of (b) can reversibly binding to a DNA nanorod of (a) only at a single position on the DNA nanorod of (a), and wherein, in the absence of a nucleating DNA nanostructure, a DNA nanorod of (a) can reversibly binding to a DNA nanorod of (b) only at a single position on the DNA nanorod of (b).

EXAMPLES

Example 1

Figure 9A:
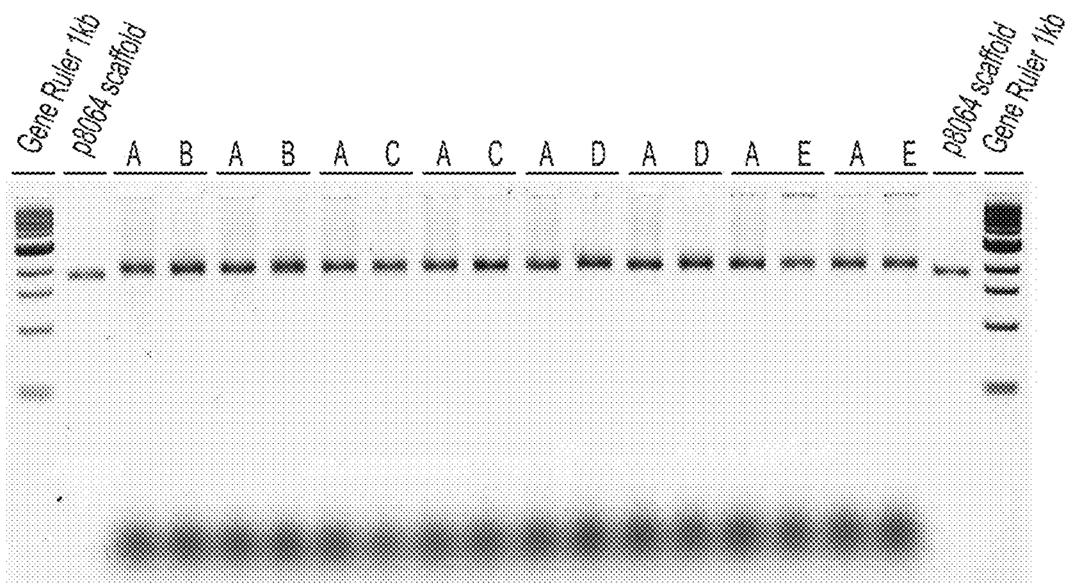
FIG. 9A-9B show results from a seesaw experiment with an example of a nucleating nanostructure (queen) folded at different temperatures (A: 65-60° C.; B: 60-55° C.; C: 65-55° C.; D: 60-50° C.) at a $MgCl_2$ concentration of 6 mM.
Figure 9B:
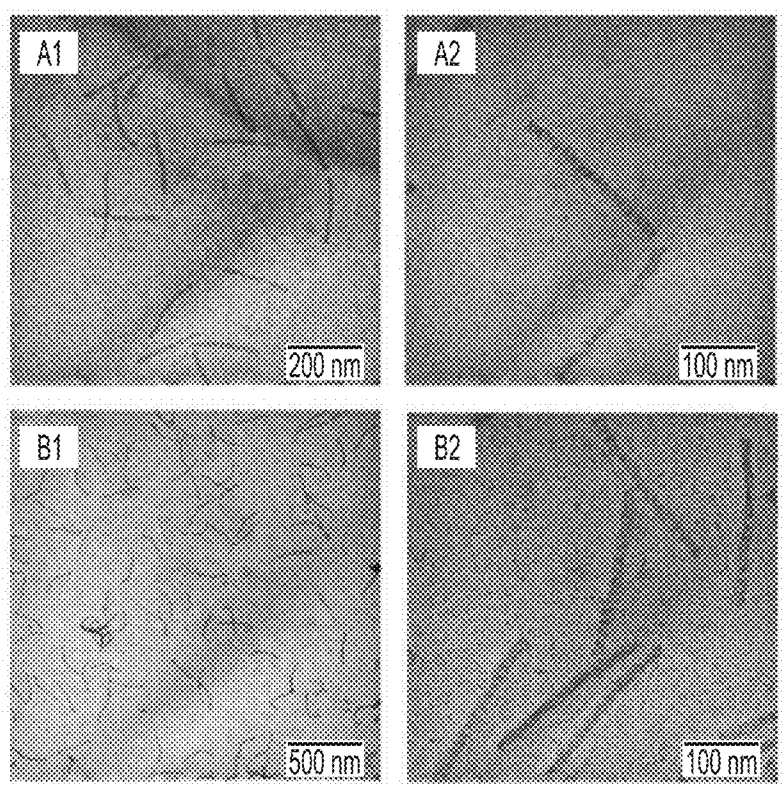

The examples demonstrates assembly of a nucleating nanostructures (queen). The sharpest bands from a screen of nucleic acid self-assembly reactions were selected and subjected to a 2 minute incubation at 90° C. for denaturing and then an 18 hour ramp. The gel (FIG. 9A) was 2% agarose (10 μL ethidium bromide, c=10 mg/mL), and run at 60V for 240 minutes in 0.5× TBE and 11 mM $MgCl_2$. A seesaw experiment was performed, whereby the temperature was varied between 65-60° C. (A), 60-55° C. (B), 65-55° C. (C), and 60-50° C. (D). The structures were purified using band excision of the gel, followed by 15 minutes at 16k×g FreezeNSqueeze and then stained with 2% UF following a 2 minute $ddH_2O$ post-wash. The queen folded well, and no noticeable difference was observed between conditions A through D on the seesaw experiment (FIG. 9B).

Figure 10A:
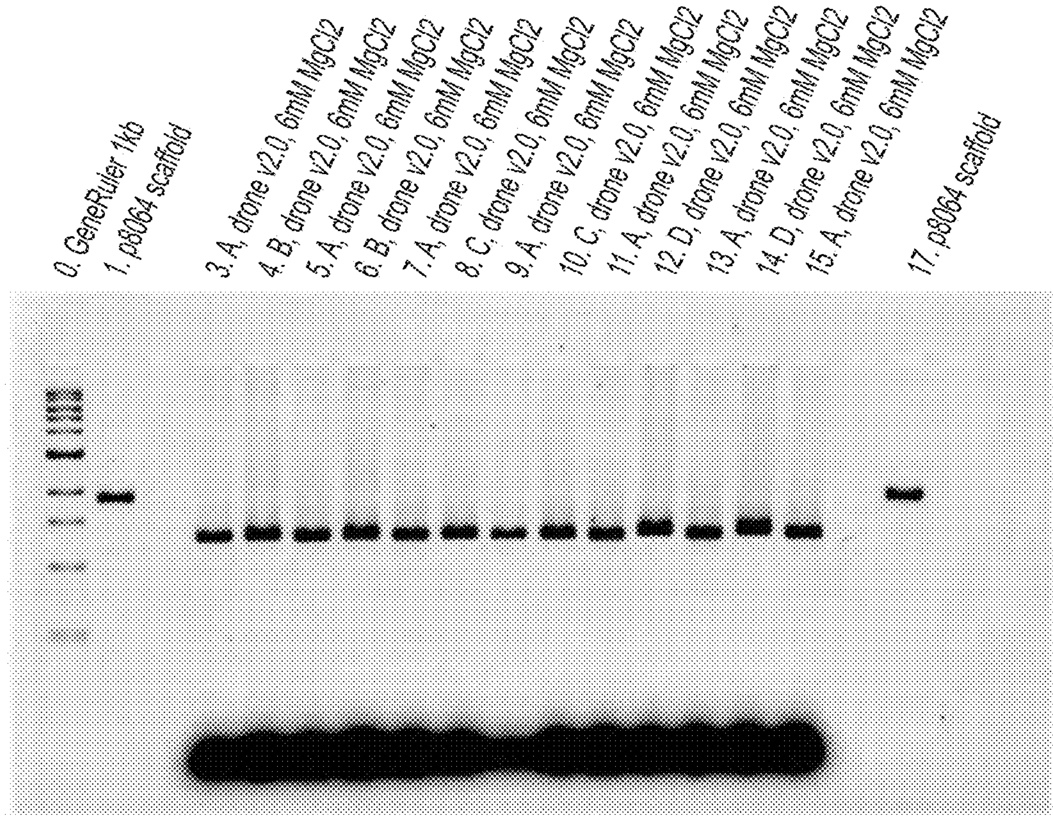
FIGS. 10A-10B show results from a seesaw experiment with an example of a nanostructure (drone) folded at different temperatures (A: 70-60° C.; B: 65-55° C.; C: 65-60° C.; D: 60-55° C.) at a $MgCl_2$ concentration of 6 mM.
Figure 10B:
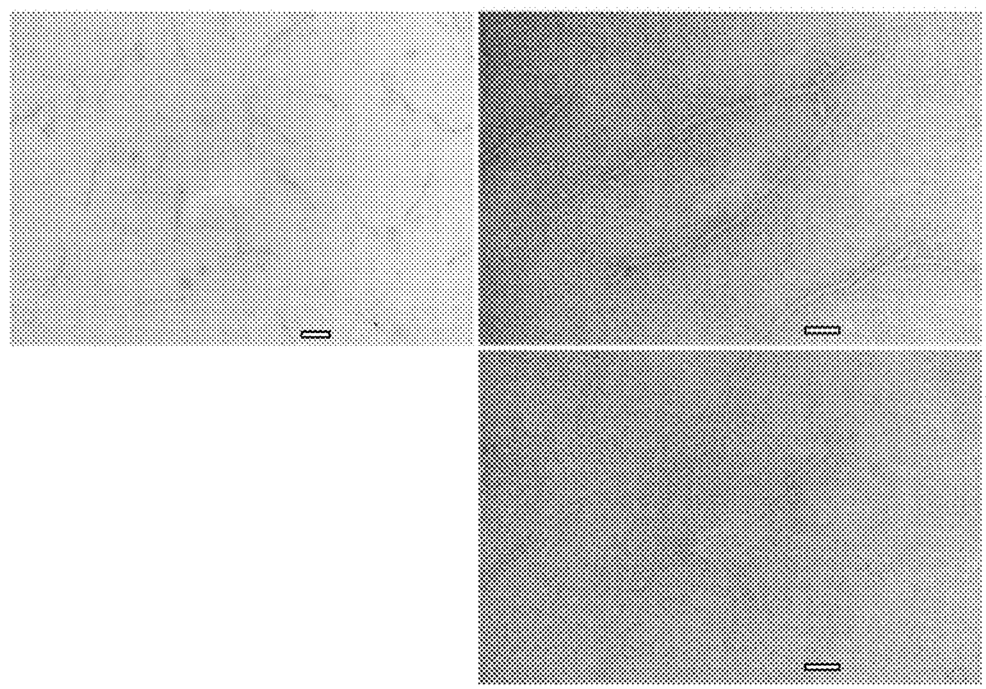

The experiment was repeated with different nanostructures that function as 'drones'. The sharpest bands from a large screen were selected and subjected to 2 minute incubation at 90° C. for denaturing and then an 18 hour ramp. The gel (FIG. 10A) was 2% agarose (10 μL ethidium bromide, c=10 mg/mL), and run at 60 V for 240 minutes in 0.5× TBE and 11 mM $MgCl_2$. In this experiment, the temperature was varied between 70-60° C. (A), 65.55° C. (B), 65-60° C. (C), and 60-55° C. (D). The structures were purified using band excision of the gel, followed by 15 minutes at 16k×g FreezeNSqueeze and then stained with 1% UF. The drone folded well, and there was no noticeable difference between conditions A through D on the seesaw experiment (FIG. 10B).

Figure 11:
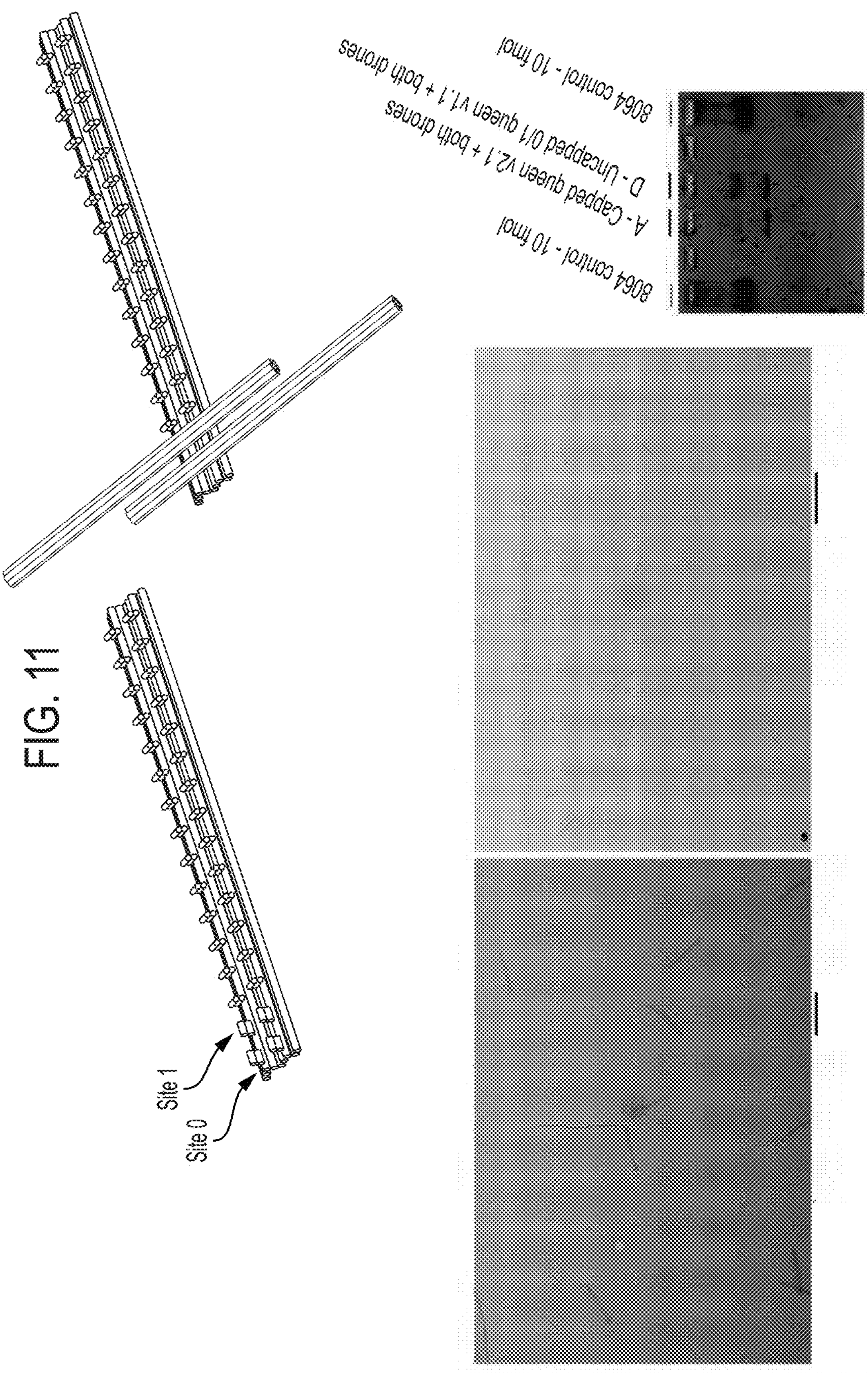
FIG. 11 shows a schematic depicting the assembly of an example seed structure (queen+drones). Images of the structures are also shown. Nanostructure assembly may also be carried out as shown in FIGS. 19A-19D.

Next, the assembly of a queen together with a drone was examined (FIG. 11). The following conditions were tested (with a 1:1:1 ratio): queen—all sites closed and both drones; queen—site 0 exposed and both drones; queen—site 1 exposed and both drones; queen—site 0/1 exposed and both drones; and queen—all sites exposed and both drones. Assembly was achieved through a 72 hour incubation period at 25° C., and the structures were purified by band excision of the gel, followed by 15 minutes at 16k×g FreezeNSqueeze followed by 2% UF staining. The samples were run on a 2% agarose gel (10 μL ethidium bromide, c=10 mg/mL), and run art 60V for 240 minutes in 0.5× TBE and 11 mM $MgCl_2$. Approximately 10-1.5 ng of each structure were observed.

Example 2

Figure 12A:
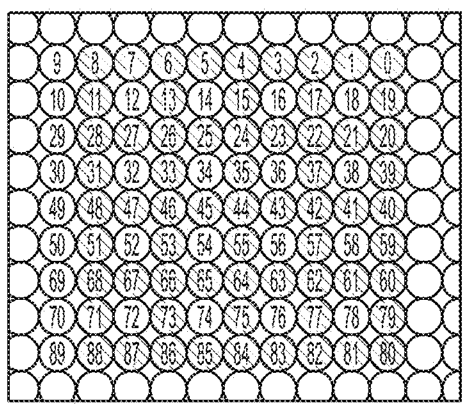
FIGS. 12A-12G show a seed structure forming from the assembly of a single-stranded DNA and additional nanostructures (drones).
Figure 12A:
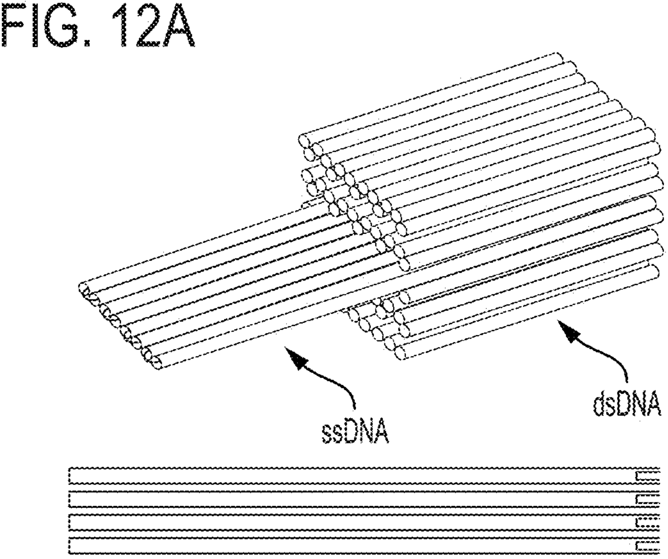
Figure 12B:
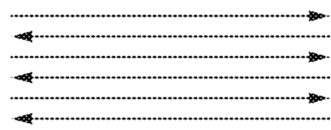
Figure 12B:
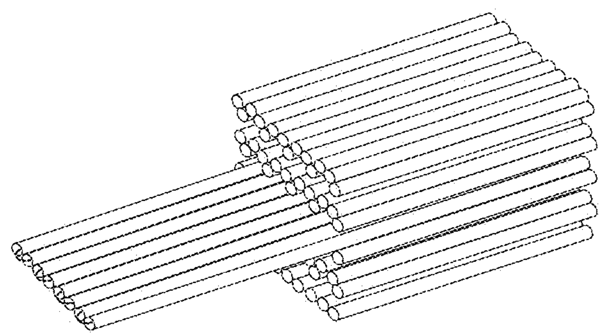
Figure 12C:
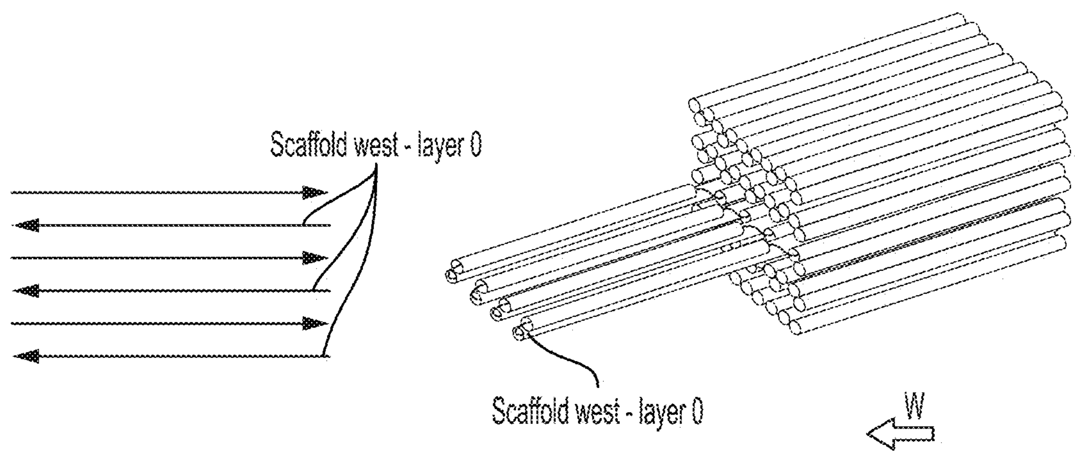
Figure 12D:
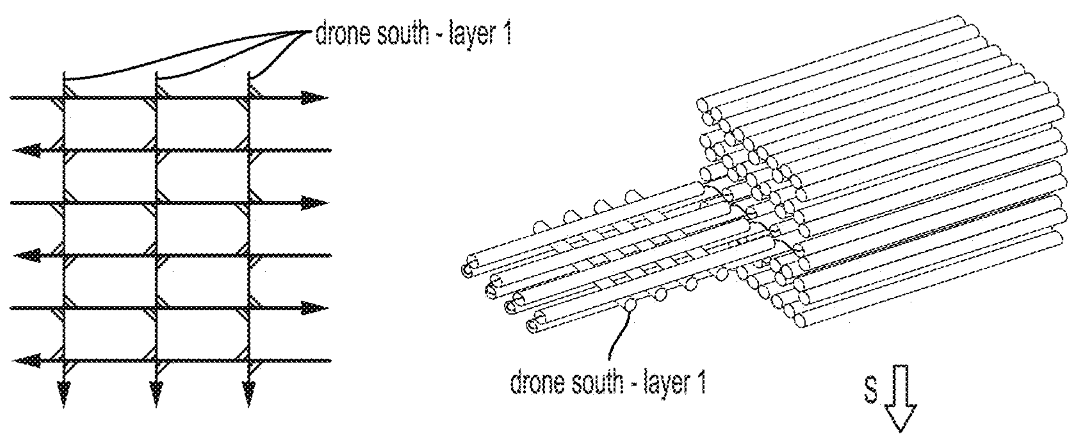
Figure 12E:
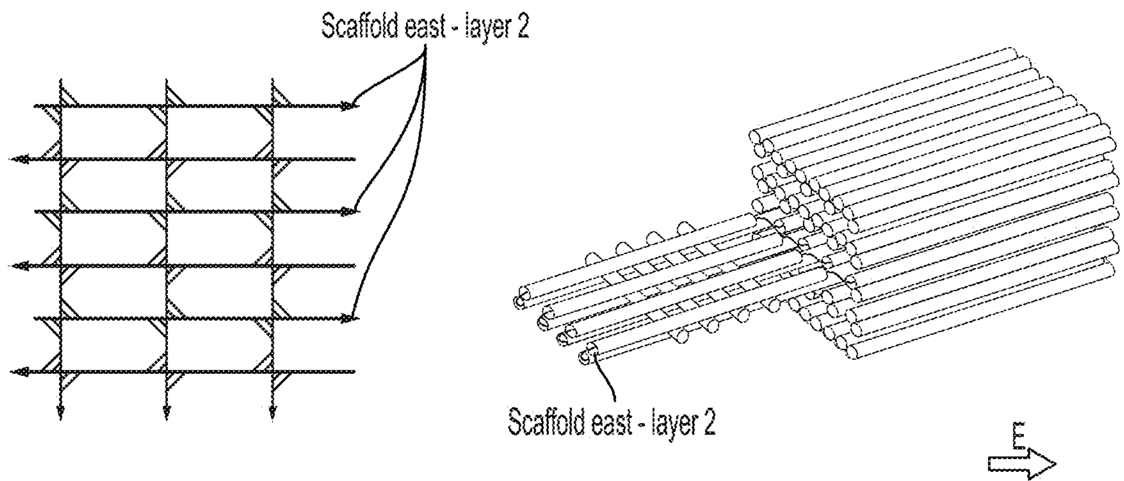
Figure 12F:
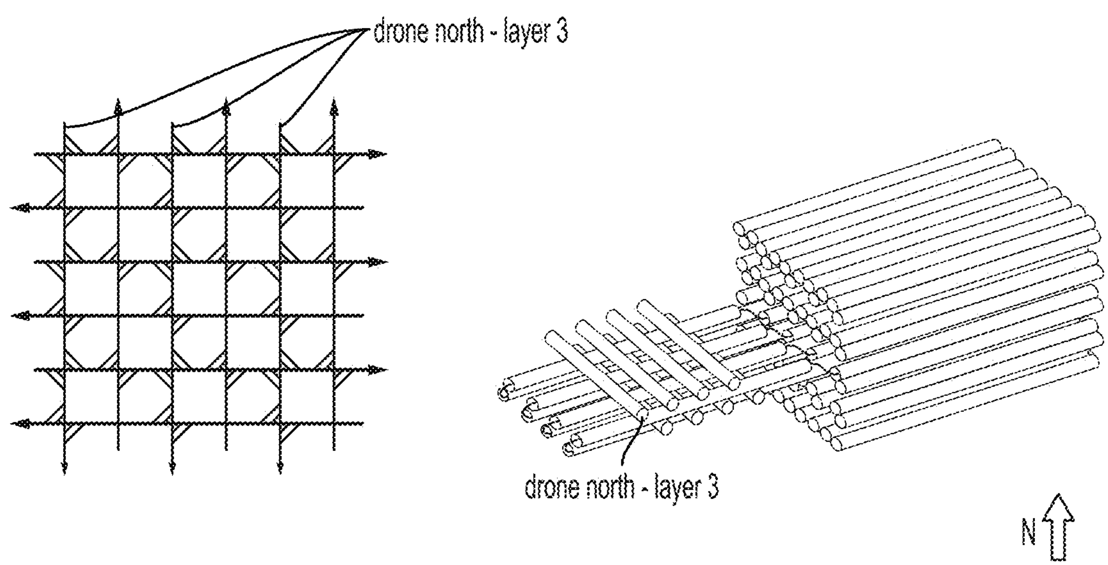
Figure 12G:
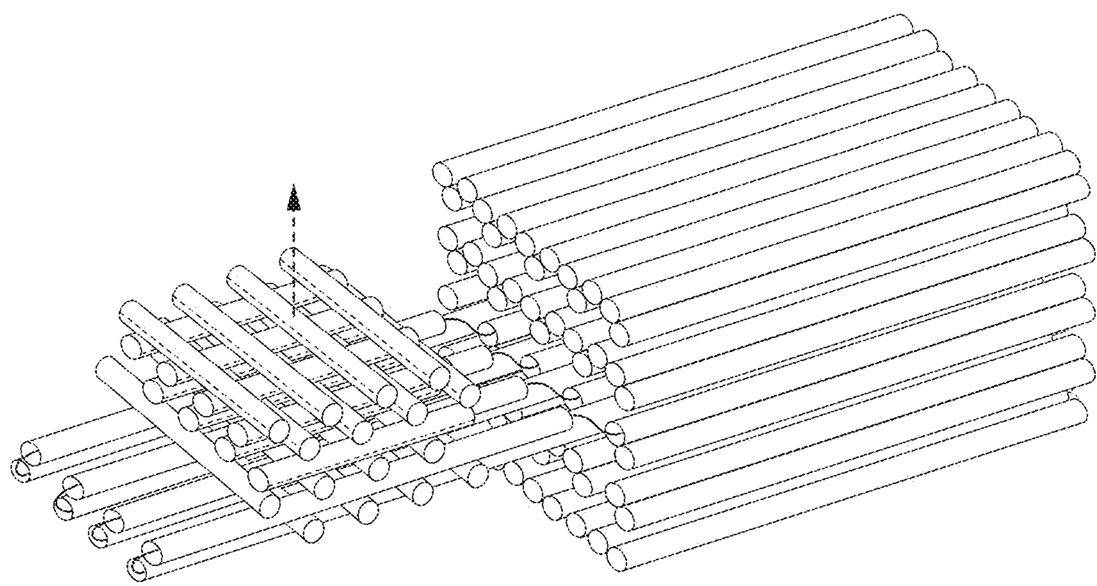

A similar system was built using single-stranded DNA instead of 6 helix bundles. A schematic of the nucleating nanostructure architecture is shown in FIG. 12A. The single strands each contain binding and linker regions, including a 5 bp binding region and 3 and 5 nucleotide linker (poly T) regions. An exemplary 5 bp, 2 nucleotide linker is shown below:

```
62 mer
                                       (SEQ ID NO: 683)
TGCAATTTAATTCTTTTAGCATTTCAATATTTGTAGATTTGAGAATTT
CGTTTTTTTATTCA.
```

Figure 13A:
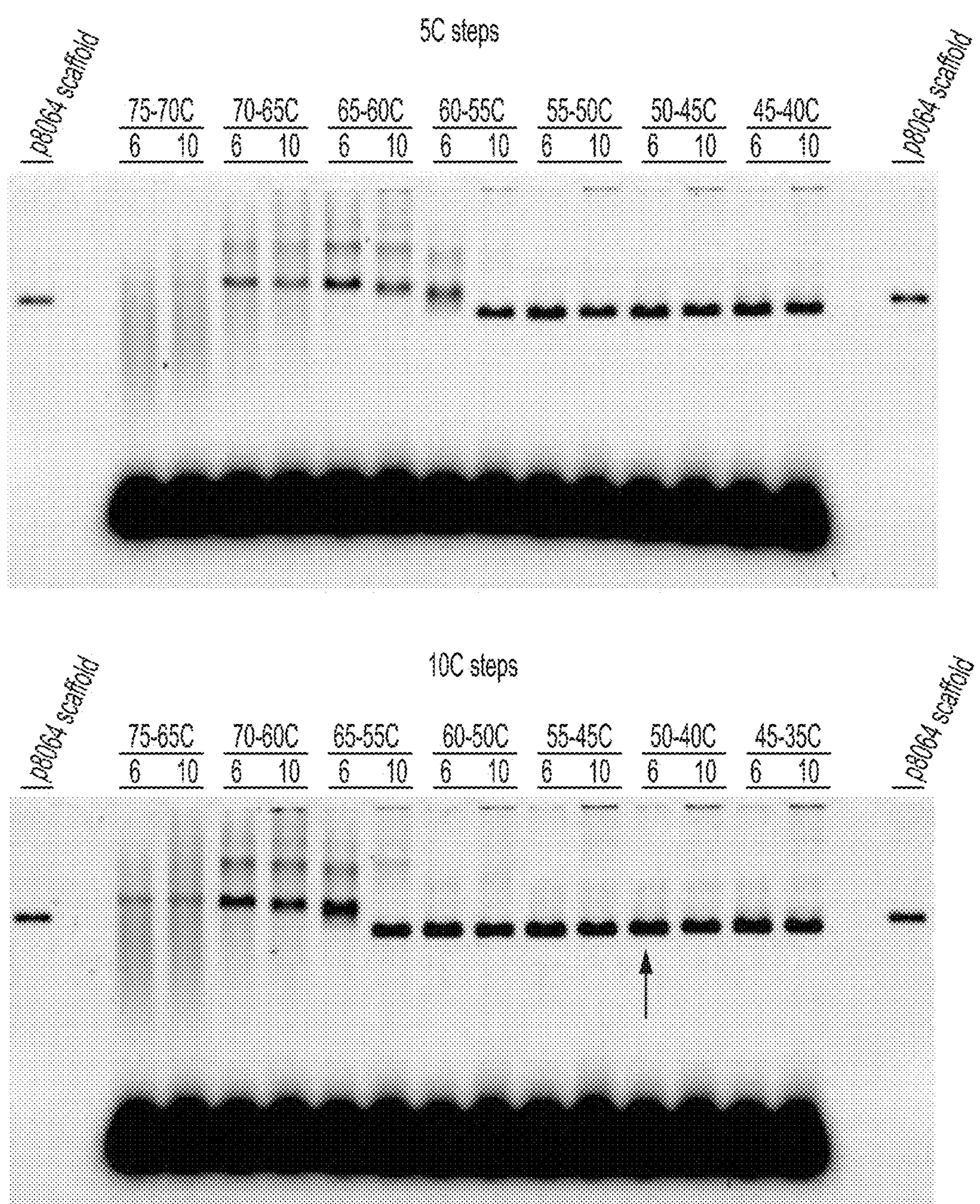
FIGS. 13A-13B show results from seesaw experiments with a single-stranded nucleating nanostructure (queen) at various temperatures and steps.
Figure 13B:
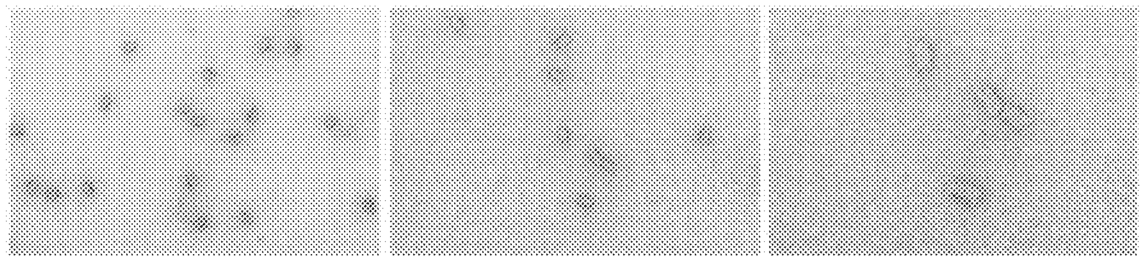
Figure 14A:
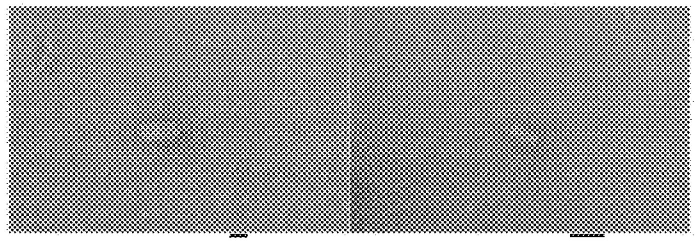
FIGS. 14A-14C show results demonstrating that nanostructures (workers) assemble in the presence of a nucleating nanostructure (queen) but not in the absence of a nucleating nanostructure.
Figure 14A:
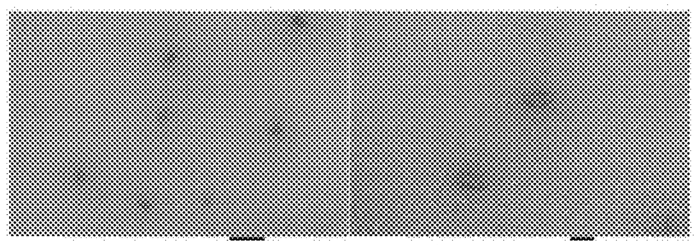
Figure 14B:
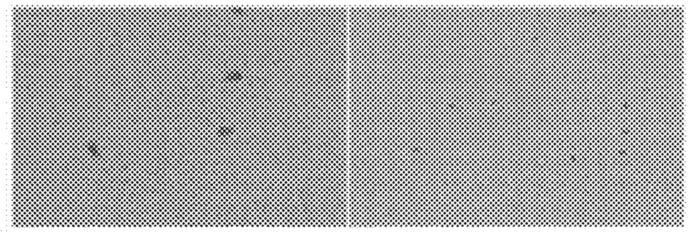
Figure 14B:
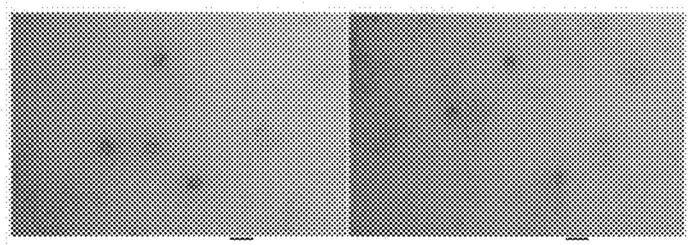
Figure 14B:
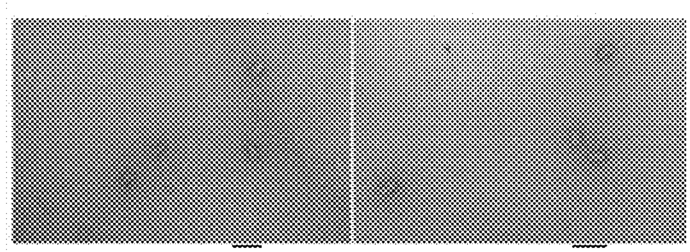
Figure 14C:
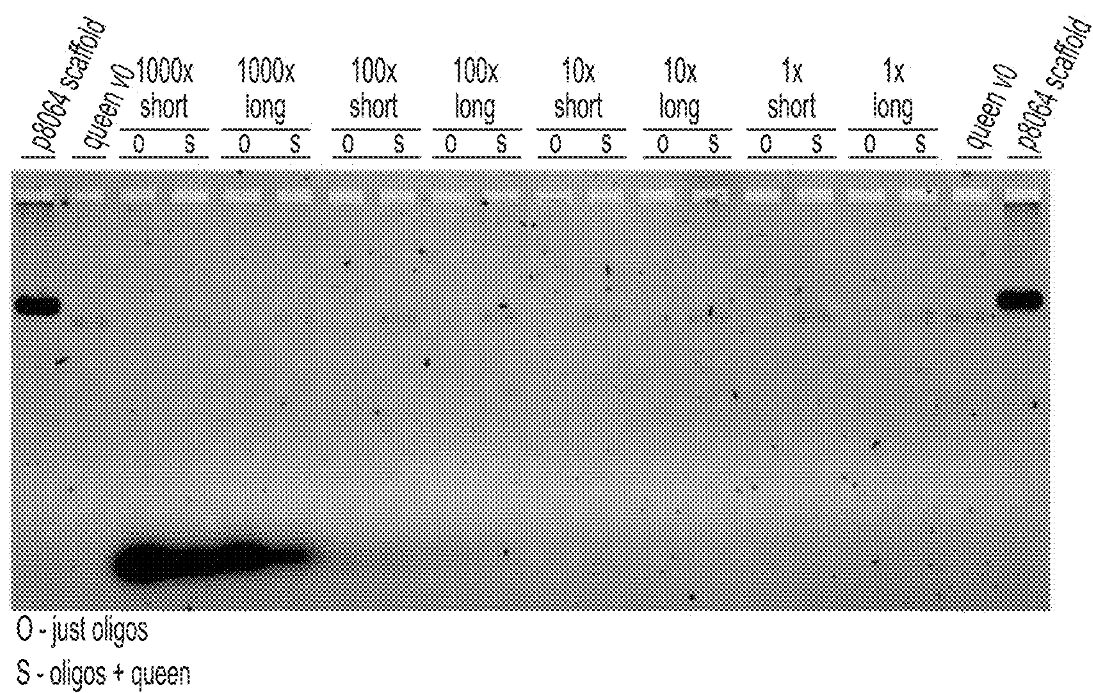

The workers stack on top of drones in layers (FIGS. 12B-12G). The queen was shown to fold in both 5C or 10C steps (FIG. 12A). Folding occurred after a2 minute 90° C. denaturing period and then an 18 hour ramp. The samples were run on a 2% agarose gel (10 μL ethidium bromide, c=10 mg/mL), and run at 60V for 240 minutes in 0.5× TBE and 11 mM $MgCl_2$. The queen was incubated under a 50-40° C. thermal ramp, with 6 mM $MgCl_2$. The resulting structure is shown in FIG. 13B.

Example 3

Assembly without the queen and only the workers (both short and long linkers) was examined. In this example, workers did not assemble under conditions with high salt concentration (1M NaCl, up to 15 mM $MgCl_2$), low temperature (4° C.), and a high concentration of workers (3.125 μM). Other conditions, including 10-20 mM PEG and high salt and a high concentration of oligonucleotides were also tested. No assembly occurred. FIGS. 4A-14B show drone/workers at different concentrations successfully assembling with queens. The structures were purified with band excision, 15 minutes at 16k×g FreezeNSqueeze and 2% UF staining. Without the queens, there was no sign of assembly (FIG. 4C).

Figure 15A:
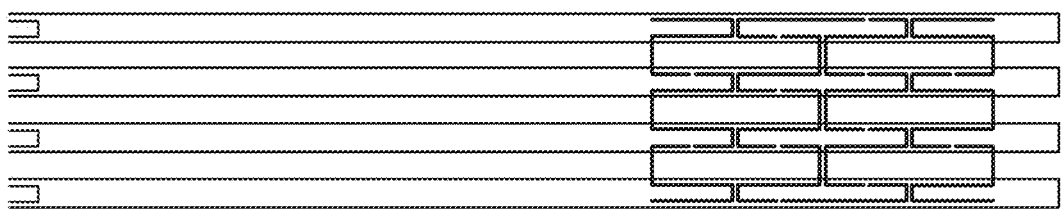
FIGS. 15A-15B show results an example of nanostructures not assembling in the absence of a nucleating nanostructure (queen).
Figure 15B:
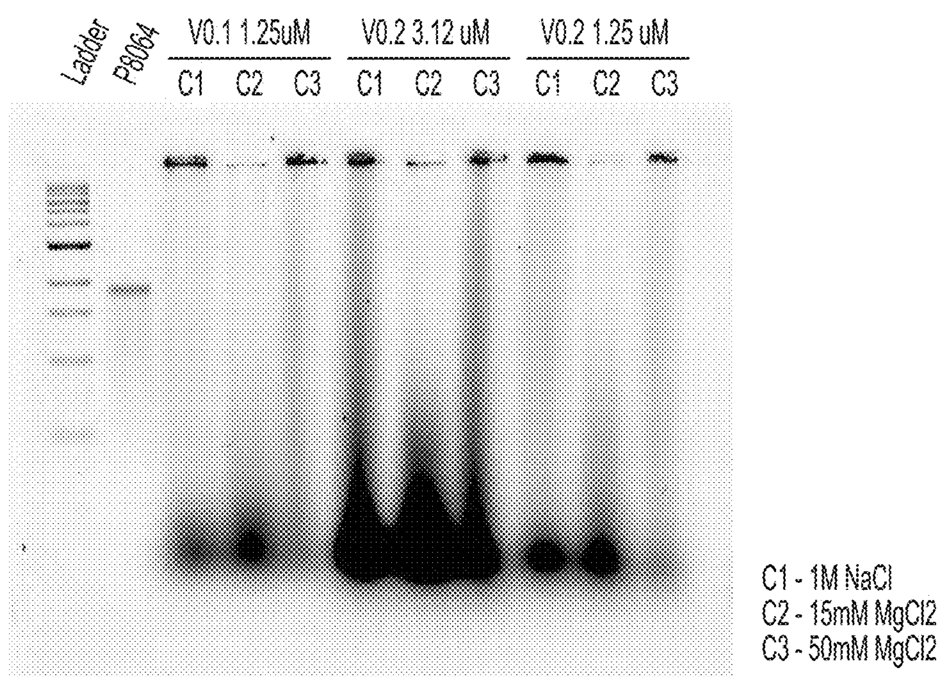

The duplex length was then increased to 8 bp and linker regions of 2 nt (v0.1) and 3 nt (v0.2) were tested. Weaving was introduced into the structure and staple strands were added to constrain the end of the scaffold loops (FIG. 15A). As seen in FIG. 16B, there was no assembly without the queen in any of the groups and under any of the salt concentration conditions.

Example 4

Figure 18:
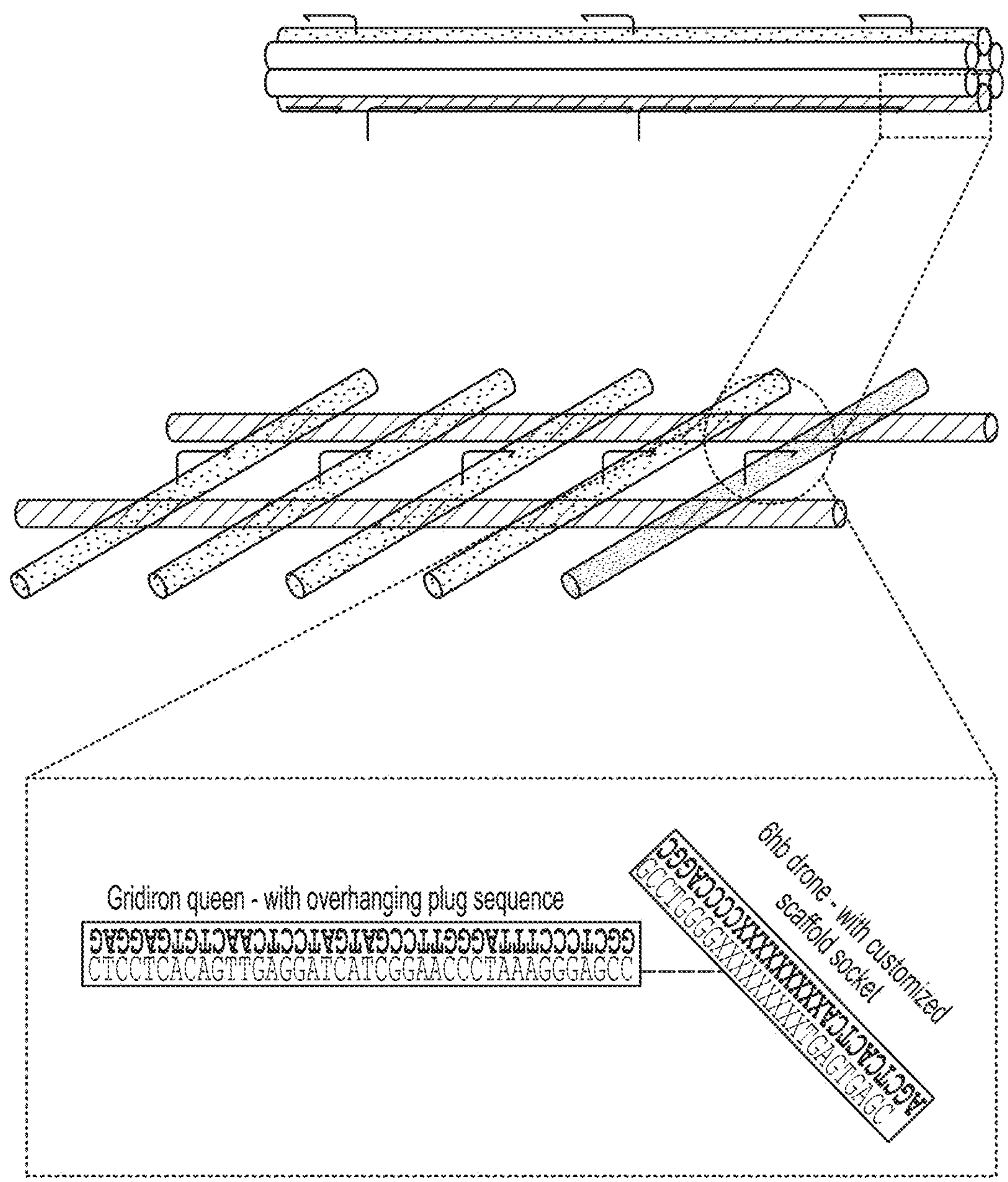
FIG. 18 shows a detailed view of the plug-socket binding system. The case shown in the upper panel shows the full set of 5 single-stranded plug sequences extending from the queen (the small arrow) with matching socket sites in a six-helix bundle drone. In the lower pane, the binding sequence is drawn as a series of 'X' to indicate that both the length and sequence of the plug and socket may be varied. The scaffold sequences are drawn in bold text. Note that this design (shown for a drone-queen assembly) is also used to bind drones to workers. The gridiron queen sequences, from top to bottom, correspond to SEQ ID NOs: 685 and 686. The 6 helix bundle (hb) drone sequences, from left to right, correspond to SEQ ID NOs: 687 and 688.
Figure 19A:
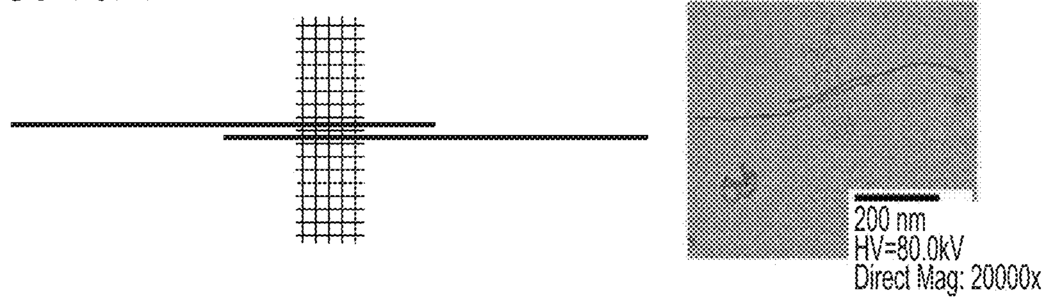
FIGS. 19A-19D shows how the plug-socket binding system can be used to program drones to bind to desired sites on the queen.
Figure 19B:
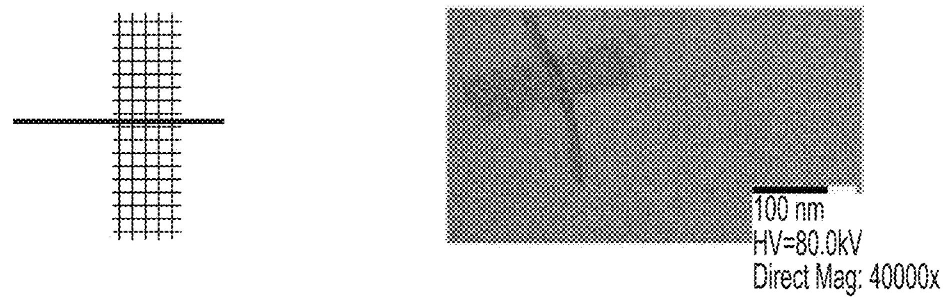
Figure 19C:
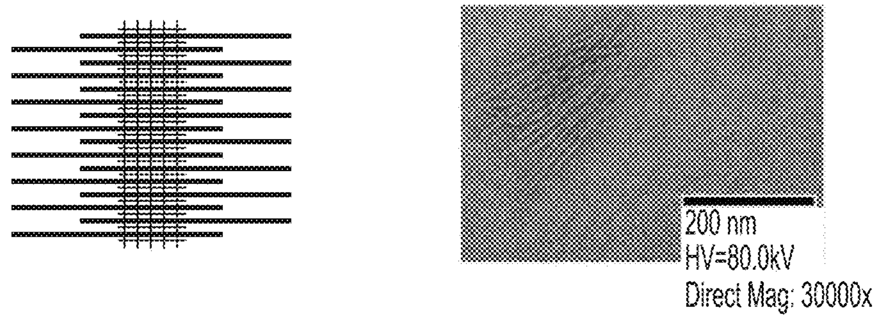
Figure 19D:
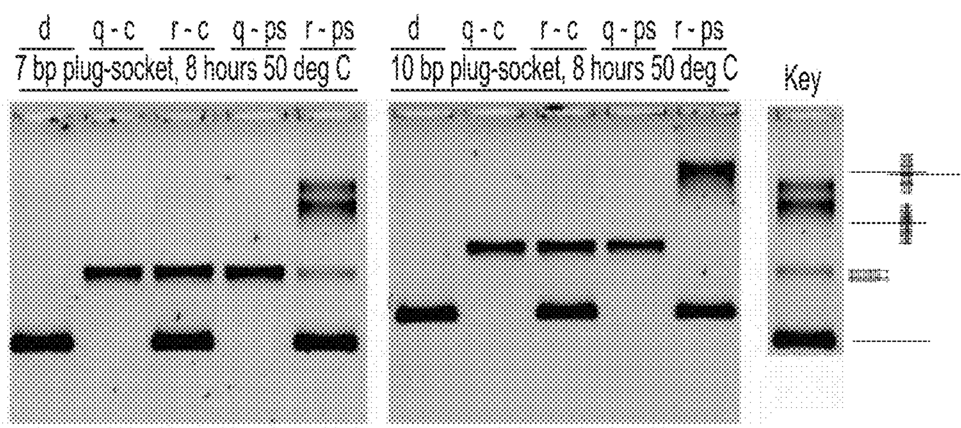

This Example demonstrates assembly of 6-helix bundle DNA nanorod drones into a crisscross structure via nucleation by a gridiron queen (FIGS. 19A-19D). The gridiron queen has 16 cells, each to which may bind a drone using 5 cooperative plug-socket binding sites. Shown here is site-specific binding of two 440 nm long drones (FIG. 19A), one 250 nm long drone (FIG. 19B), and sixteen 250 nm long drones (FIG. 19C). This example shows binding of drones to the gridiron queen using a 10 bp plug-socket. The agarose gel image in FIG. 19D shows that the queen in the reaction is completely bound by drones, when stoichiometric excess of drones is present. Additionally, functionality of the plug-socket binding system (FIG. 18) is shown with the TEM micrographs of these assemblies and kinetics data (FIGS. 19A-D and FIG. 20).

Figure 16A:
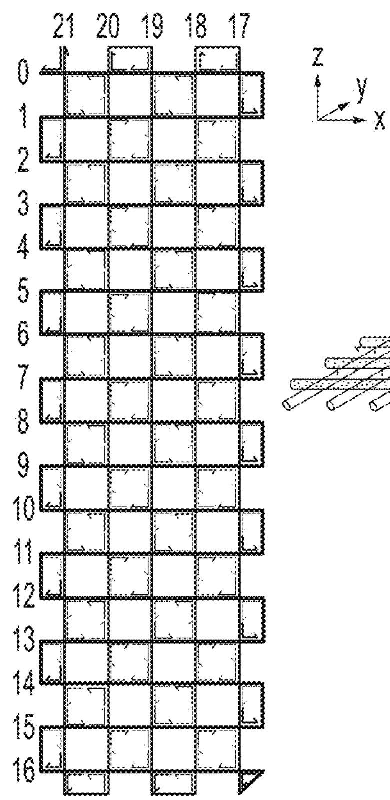
FIG. 16A shows a two-dimensional view of the gridiron queen that can bind 16 drones simultaneously in a horizontal (coordinate x ire FIG. 16B) across the queen. Staples necessary to fold the scaffold into the queen are shown, and the 3' ends of the staples may be appended with overhanging single-stranded sequences to bind drones. A three-dimensional view (FIG. 16B) shows the queen with binding sites in each drone-docking cell. A transmission electron microscope (TEM) image of the queen is shown in FIG. 16C. Lateral dimensions of the structure are approximately 72 nm×240 nm.
Figure 16B:
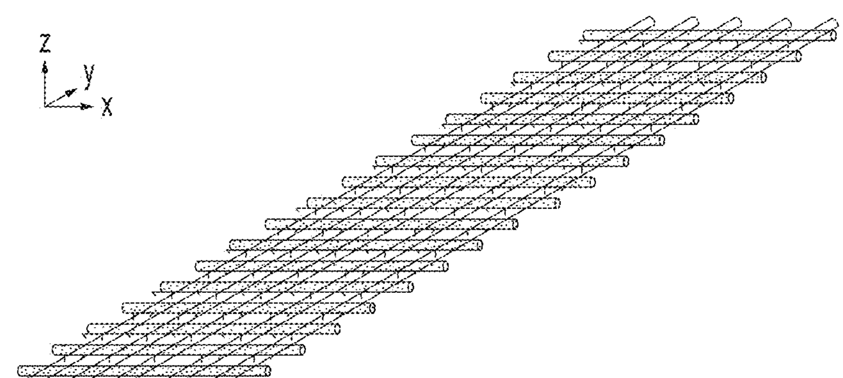
Figure 16C:
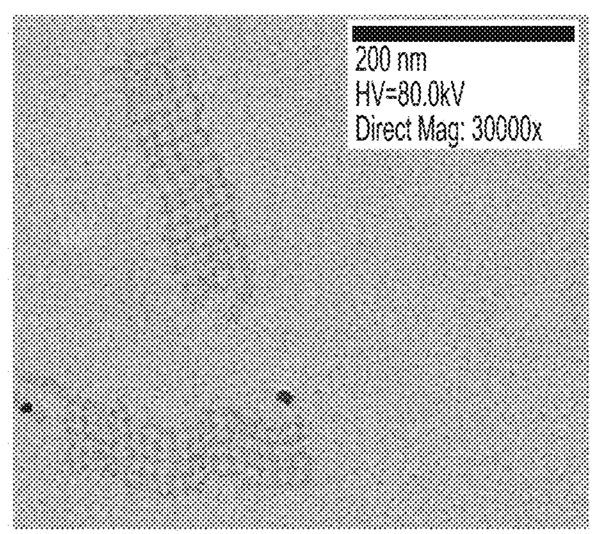
Figure 17A:
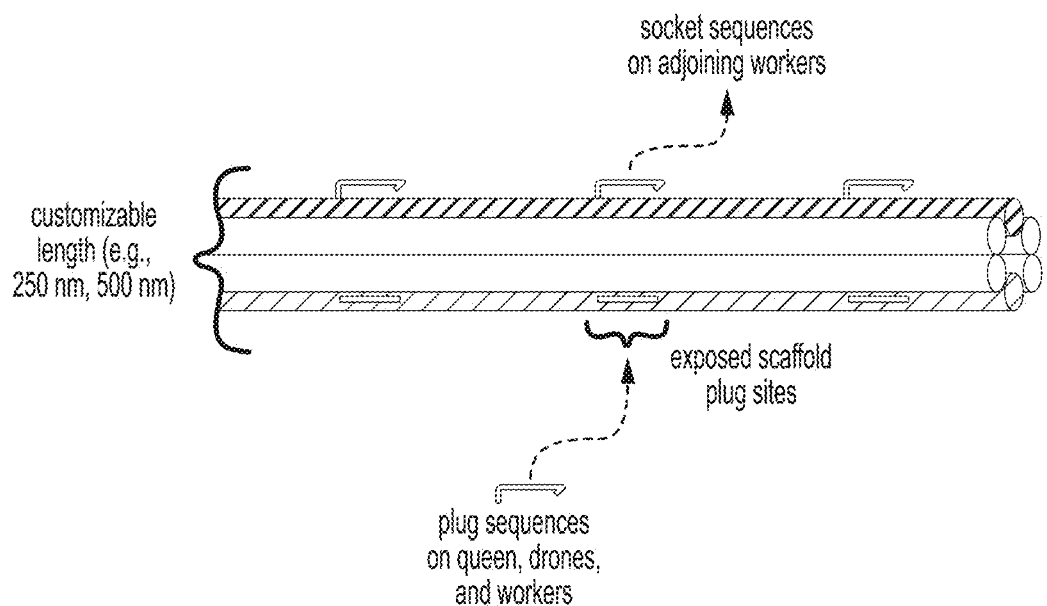
FIGS. 17A-17B depict drone and worker subcomponents.
Figure 17B:
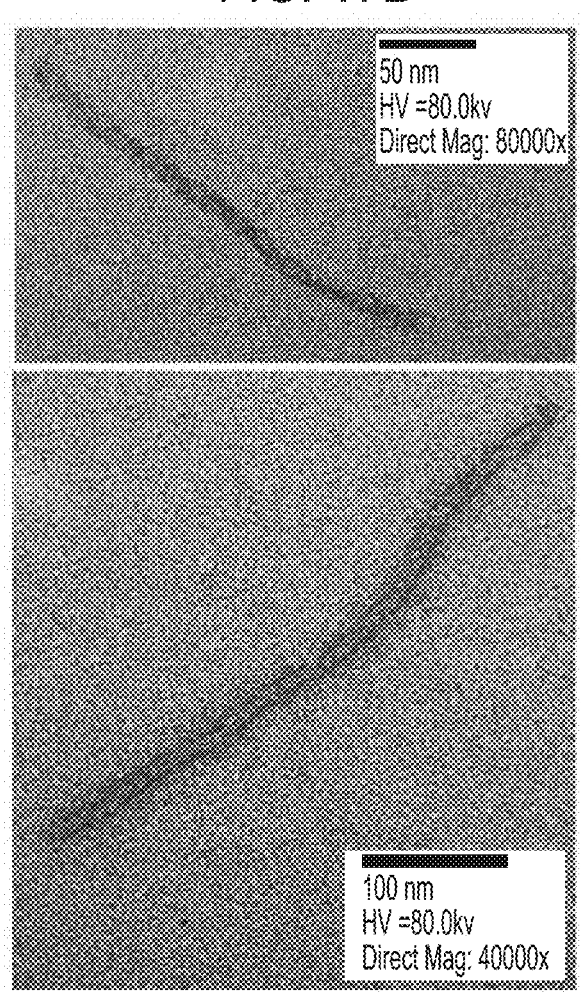

The gridiron queen and 6-helix bundle drones were conceptualized and then designed using the caDNAno design tool (see FIGS. 16A-16C (and data not shown) for the queen, FIGS. 17A-17B (and data not shown) for the drones). Staple sequences designed in caDNAno were ordered commercially and folded with M13 phage scaffold DNA over the following conditions: drones in 6 mM $MgCl_2$, (90° C./2 mins, 60-50° C./18 hrs); queen in 8 mM $MgCl_2$ ({(94° C.-86° C.) in 4° C./5 min steps}; {(85° C.-70° C.) in 1° C./5 minute steps}; {(70° C. to 40° C.) in 1° C./ 15 minutes steps}; {(40° C. to 25° C.) in 1° C./10 minute steps}). The scaffold for the gridiron queen was comprised of a 8634 base genome from M13 phage, and staple DNA sequences were determined by caDNAno. Binding sequences for drones were manually appended to the 3' ends of the staple DNA to bind drones in the desired orientation. The 250 nm and 440 nm 6 hb drones were also designed in caDNAno. The scaffold DNA was comprised of either the 8064 base genome from M13 phage (for the 440 nm drone), or a custom 3825 base sequence derived from M13 phage (for the 250 nm drone). Staple DNA sequences were determined by caDNAno and purchased commercially. Scaffold sections for the sockets and plug sequences were customized to determine the orientation and final location of sub-components in assembled structures. The 5' ends of a subset of the staples are truncated to free scaffold so that it could act as a socket to bind plugs. The 3' ends of another subset of staples were appended with plug DNA sequences so that they could interact with other worker subcomponents.

The folded structures were separated from excess folding staples using agarose gel electrophoresis and bands containing the structure of interest were purified from the agarose gel matrix. The purified structures were placed onto carbon grids, stained with 2% uranyl formate, and analyzed by TEM to validate assembly of the correct structure (see FIG. 16C for the queen and FIG. 17B for the drones).

Figure 20:
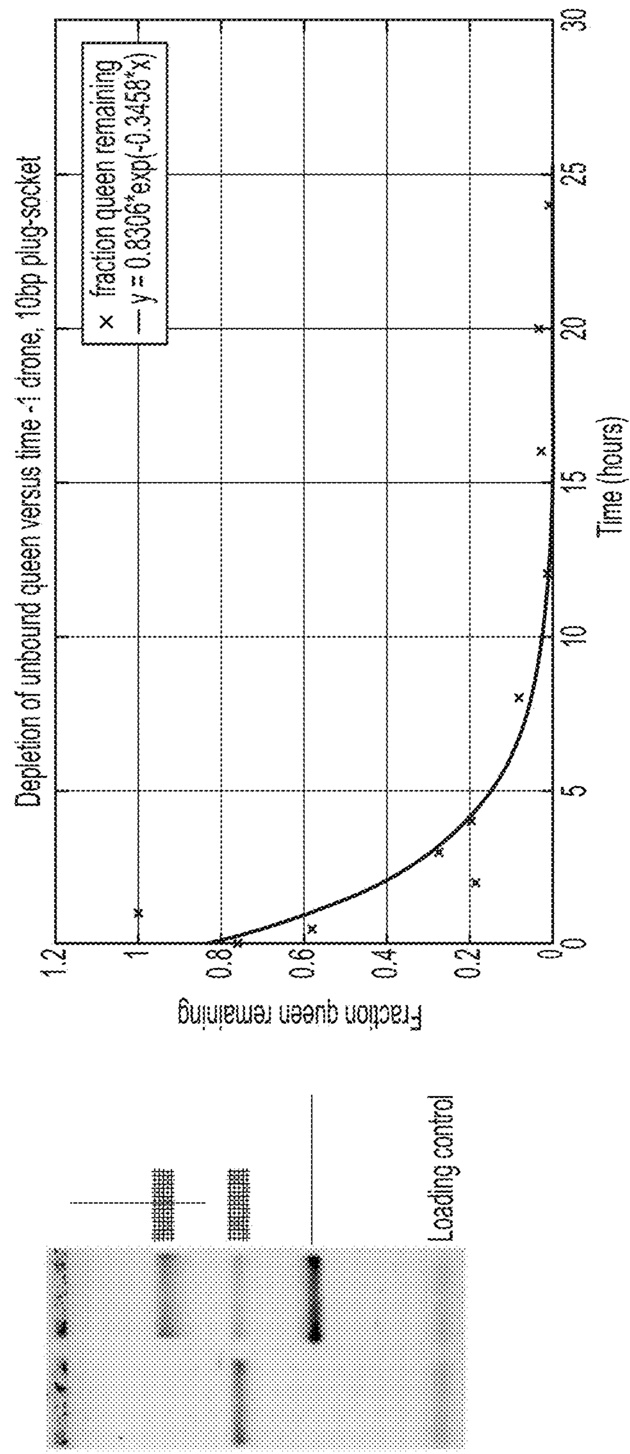
FIG. 20 shows the extent of free queen remaining over time as it becomes bound to a single 440 nm drone.

The purified sub-components were assembled into criss-cross formation using the following conditions: 0.1 or 0.01 nM queen, 1 nM drones, 30 mM $MgCl_2$, 45 mM Tris-borate, 1 mM EDTA, and 0.01% Tween-20; incubation at 50° Celsius for 8-24 hours. Assembly reactions were analyzed using gel electrophoresis and TEM, as shown in FIGS. 19A-19D. Kinetics of binding between the drone and queen are shown in FIG. 20.

Example 5

A similar system was built using single-stranded DNA (ssDNA) instead of 6 helix bundles, referred to as "criss-cross DNA slats" (short: "DNA slats"). A schematic of the base unit is shown in FIGS. 21A-21B. The 21 nucleotide (nt) long oligonucleotide per DNA slat shown in FIGS. 21A-21B allows the 4 by 4 DNA slats array to retains the correct 10.5 bases/turn. The length of the DNA slats can be expanded by repeats of 21 nt, for example, achieving larger structures. FIG. 21A shows an abstraction of the DNA slats architecture and a matrix with the number of base pairs (bp) per binding site at each position. The alternation of 6 bp and 5 bp is used to retain the correct helicity and approximately same binding energy per DNA slat. An exemplary DNA slat strand with 16 binding sites (84 nt) is shown below:

```
                                        (SEQ ID NO: 684)
TGGTTCTGGAGTTTTACTCGGGACACTTCAGCGTAATATCGGAAGCAG
GCACTTTGAAACCTATAAGTCCTGACTATTAATAAC.
```

FIG. 21B shows a 3D rendering from the front and cross-section of the DNA slats architecture. The strands weave over and under each other. The DNA slats can reliably tile the ssDNA overhangs (from the M13 scaffold) of different DNA-Origami queens. FIGS. 23A-24B both show examples of ssDNA scaffold being tiled upon and the addition of DNA slats. The flat DNA-Origami queen shown in FIG. 23A is folded through a 2 minute 90° C. denaturing period following an 18-hour ramp from 55° C.-50° C. with 6 mM $MgCl_2$. The barrel DNA-Origami queen shown in FIG. 24A is folded by a 15 minute 80° C. denaturing period following an 18-hour ramp from 60° C.-25° C. with 8 mM $MgCl_2$. The assembly process of DNA slats with the queen is shown in FIG. 22. Once the queen is folded the crude reaction queen is mixed with the DNA slats, assembly conditions can be tuned by varying the concentrations of DNA slats (100 nM-1000 nM), salt (5 mM-30 mM $MgCl_2$ and 0-1 M NaCl), and the temperature of assembly (4° C.-55° C.). By altering the assembly conditions such as $MgCl_2$ and the DNA slat concentration the kinetics of the assembly process can be influenced.

Example 6

Figure 25:
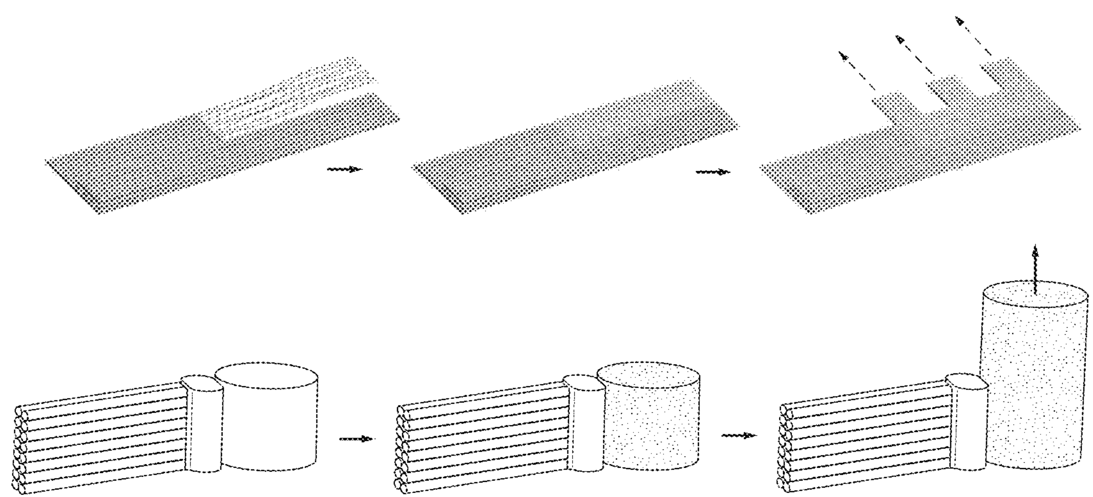
FIG. 25 depicts a growth mechanism of DNA slats seeded on a queen structure. The DNA-origami queen is mixed with DNA slats to tile the ssDNA scaffold of the queen and then later extend and polymerize the growth of micron-sized structures solely through DNA slats (DNA slats may be joined end-to-end, within the same plane, through nucleotide base pairing of adjacent slats). The upper design shows a flat DNA-origami queen with the growth of three linear sheets in the horizontal direction. The lower design shows a barrel DNA-origami queen with tubular growth in the vertical direction.
Figures 26A, 26B:
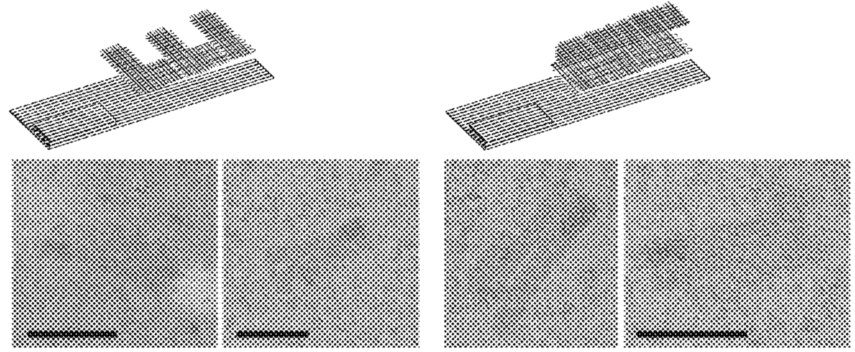
FIGS. 26A-26E show three extensions of the first generation of DNA slats binding to the flat DNA-origami queen.
Figures 26C, 26D, 26E:
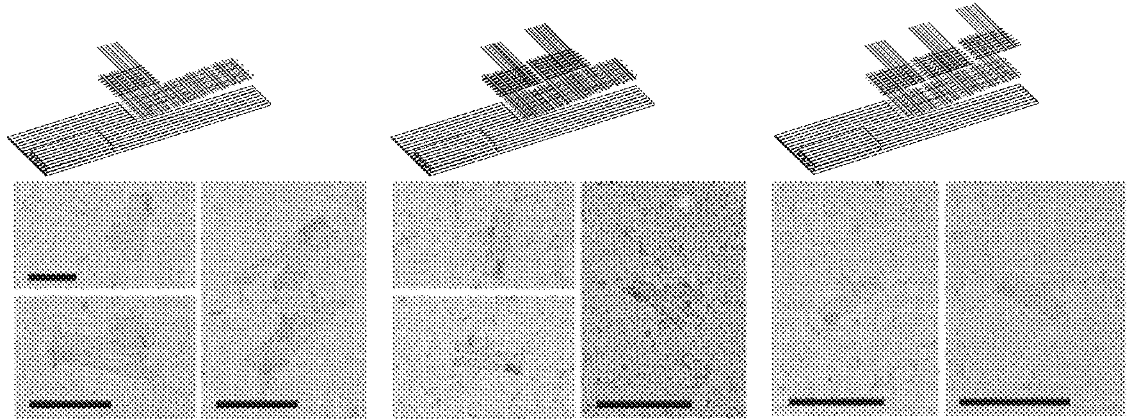
Figure 30A:
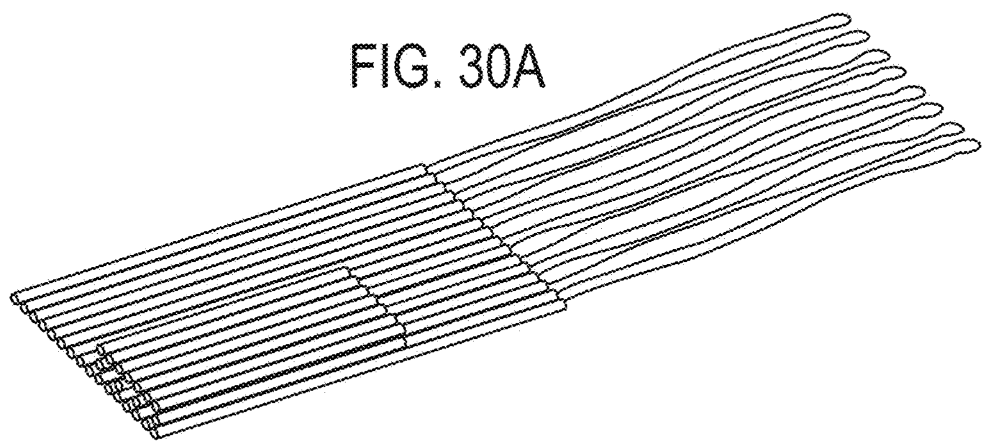
FIGS. 30A-30B show a flat DNA-origami queen nucleating a staggered DNA slats ribbon.
Figure 30B:
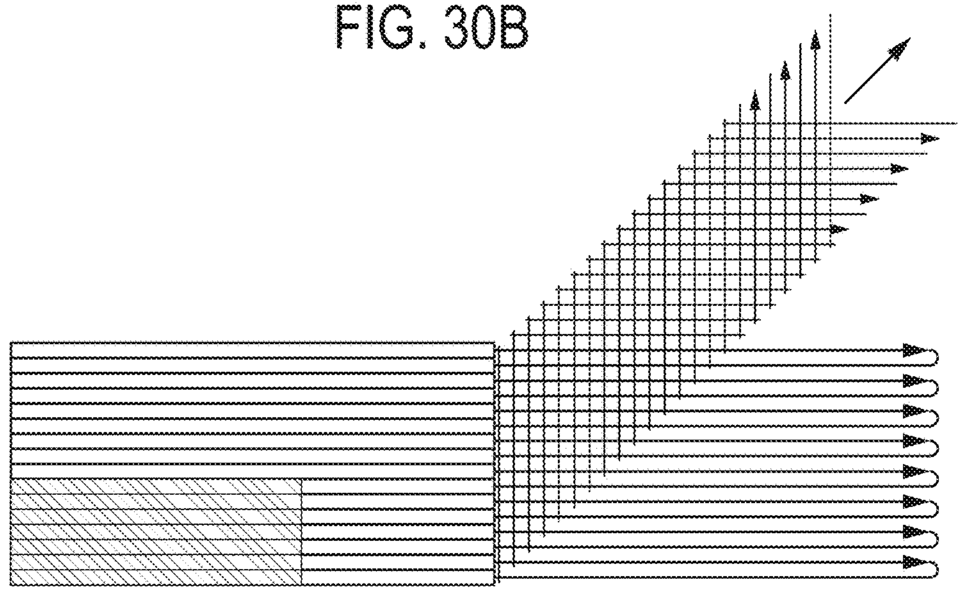
Figure 31:
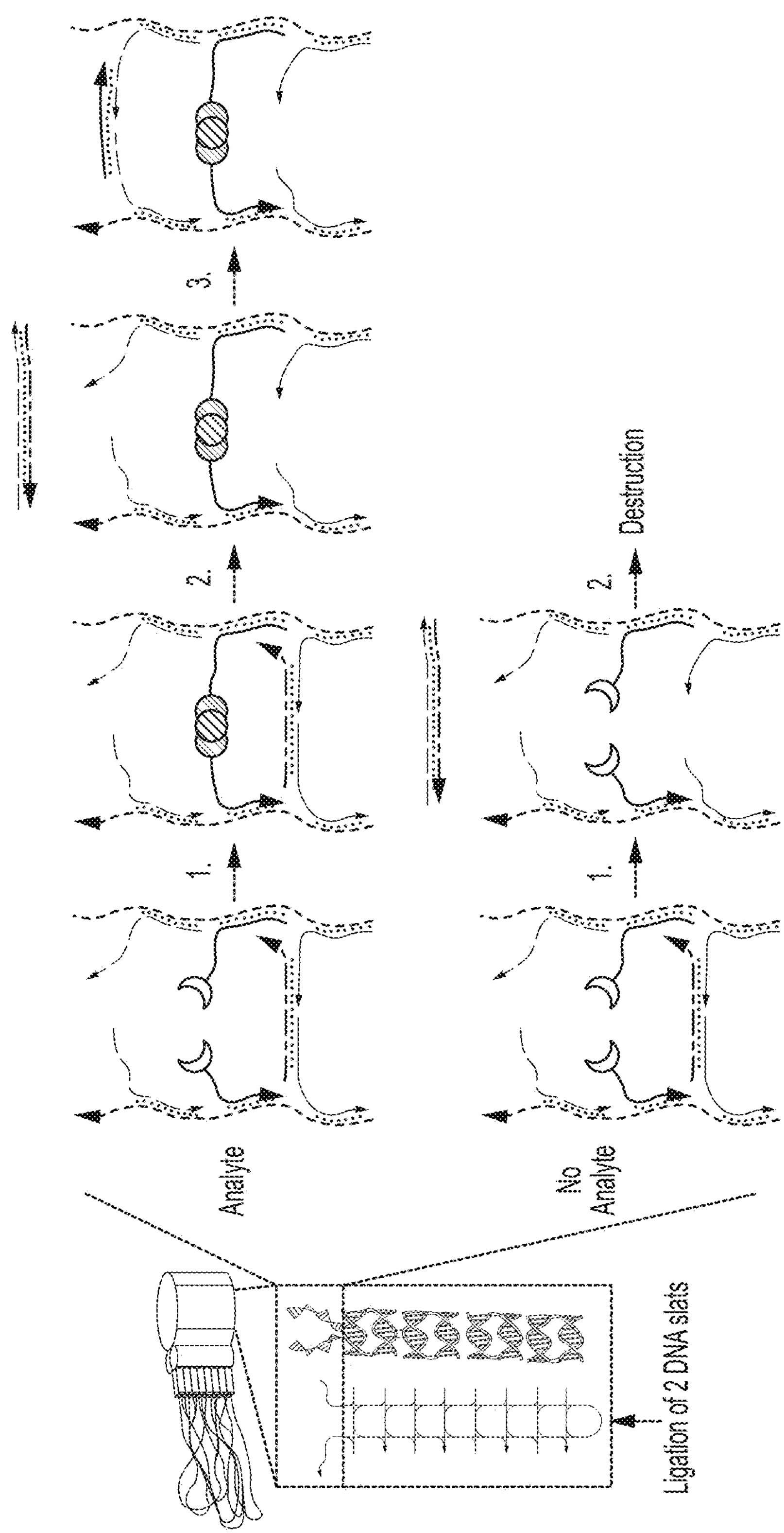
FIG. 31 shows an example of a biomolecule sensing and proofreading mechanism on DNA-Origami barrel queen. Top: Biomolecule present. (1) Biomolecule binds to antibody bridge. (2) The strand is displaced via toehold-mediated strand displacement, indicated by a bold, dashed line. (3) The dotted strand binds to dashed strands, sealing bridge.

This Example shows how extending the DNA slats to create more binding sites facilitates polymerization seeded on the queen. FIG. 25 shows both flat and barrel queen first tiled (as shown in FIGS. 23A-23B and FIGS. 24A-24B) and with extended DNA slats seeding the next generation of DNA slats to bind and eventually grow into micron sized structures. The queen nucleating site determines the shape of the subsequently grown structure. FIGS. 26A and 26B show the flat queen assembled in two types of terminal extensions. FIGS. 26C-26E show the flat queen with one, two, and three domain extensions. Samples shown in FIGS. 26A-26E were prepared using crude flat queen reaction (~1 nM), DNA slats (1000 nM/strand), and 15 mM $MgCl_2$ at 50° C. for 2 hours. FIGS. 30A-30B show a staggered design of DNA slats that bind to the flat queen, growing a ribbon like sheet. The subsequent formation of ribbons is shown in FIG. 31. Control reactions, without the flat queen, showed no assembly of the DNA slats after 18 hours of running the reaction. Samples shown in FIG. 31 were prepared using crude flat queen reaction (~9 nM), DNA slats (7500 nM/strand), and 14 mM $MgCl_2$ at 50° C. for ~66 hours.

Example 7

Through the use of the barrel DNA-Origami queen multiple guest-ring catenane systems can be produced in a one-pot reaction. FIGS. 27A-27C show that by folding the barrel queen, a multiple guest-ring catenane system can be achieved through the addition of DNA slats. In order to catenate the loops two DNA slats are needed. A close up view of the DNA slats weaving and catenating the ssDNA M13 scaffold loops is shown in FIG. 27C. By ligating the two DNA slats on one end, a single DNA slat is created that captures all eight loops. A 3D rendering of the purple DNA slat capturing eight loops is shown in FIG. 27D. FIG. 24 shows the addition of 64 slats, which can simply be reduced, depending on size of the size and number of guest rings. Using the barrel queen with the DNA slats achieves a high yield in a one-pot reaction. The barrel queen can subsequently be transformed into an ultrasensitive biosensor, by coupling a biomolecule detection system to the DNA slats (see, e.g., FIG. 31). Through the integration of proofreading steps, the analyte presence can be transferred into the open or closed state of the purple DNA slat. FIGS. 28A-28B show that without a biomolecule present, the queen falls apart (open DNA slats) and no nucleation of DNA slat mediated growth can occur. The presence of a biomolecule, however, keeps the DNA slats intact and holds the queen structure together, which can then trigger the growth of micron sized tubes, for example, that can subsequently be detected using low-cost optical instruments.

TABLE 1

Exemplary Gridiron Queen Staple Sequences

| Sequence | Comment | SEQ ID NO: |
|---|---|---|
| ATCTGAACTCGCTACGGCGGGGGGAGCCCC CGATTTAGAGCT | 20170216_cc6hb_v3_queen, c0, h21, p0, control, cyan, start 0[94], end 21[94], 42 mer | 1 |
| CATTGCTGATACCGTTTAGCTAACAAACATC AAGAAAACAAA | 20170216_cc6hb_v3_queen, c0, h20, p1, control, cyan, start 1[95], end 20[95], 42 mer | 2 |
| GATACTTGCCCTCTCTGTACATAATTAATTT TCCCTTAGAAT | 20170216_cc6hb_v3_queen, c0, h19, p2, control, cyan, start 0[178], end 19[94], 42 mer | 3 |
| GATTGGGCGTTATCAATGTTGTTTTGTCACA ATCAATAGAAA | 20170216_cc6hb_v3_queen, c0, h18, p3, control, cyan, start 1[179], end 18[95], 42 mer | 4 |
| TCTAATGAAGACAAATCCCCACGTCACCGA CTTGAGCCATTT | 20170216_cc6hb_v3_queen, c0, h17, p4, control, cyan, start 0[262], end 17[94], 42 mer | 5 |
| AAACATCGGGTTGAGTATTATGTGGCGAGA AAGGAAGGGAAG | 20170216_cc6hb_v3_queen, c1, h21, p4, control, cyan, start 1[53], end 21[136], 42 mer | 6 |
| CGCTGGCATTCGCATCAAAGGCGAATTATT CATTTCAATTAC | 20170216_cc6hb_v3_queen, c1, h20, p3, control, cyan, start 2[136], end 20[137], 42 mer | 7 |
| AGTTTATAAATGAGTATCAATTTAGATTAAG ACGCTGAGAAG | 20170216_cc6hb_v3_queen, c1, h19, p2, control, cyan, start 1[137], end 19[136], 42 mer | 8 |
| TATCGACATCATTACGCATCGCAACATATA AAAGAAACGCAA | 20170216_cc6hb_v3_queen, c1, h18, p1, control, cyan, start 2[220], end 18[137], 42 mer | 9 |
| CCATGCAGACATCACGAAGGTCACCAGTAG CACCATTACCAT | 20170216_cc6hb_v3_queen, c1, h17, p0, control, cyan, start 1[221], end 17[136], 42 mer | 10 |
| AAGATAACGCTTGTGAAAATGAGGGCGCTG GCAAGTGTAGCG | 20170216_cc6hb_v3_queen, c2, h21, p0, control, cyan, start 2[94], end 21[178], 42 mer | 11 |
| GCTAACAGTAGGGAAACTGCGGCCTGATTG CTTTGAATACCA | 20170216_cc6hb_v3_queen, c2, h20, p1, control, cyan, start 3[95], end 20[179], 42 mer | 12 |
| ATGGGTTCAGGATGCAGGTGAAATCATAGG TCTGAGAGACTA | 20170216_cc6hb_v3_queen, c2, h19, p2, control, cyan, start 2[178], end 19[178], 42 mer | 13 |
| CTCGGATGGGAGTAAGCGTATGCAGTATGT TAGCAAACGTAG | 20170216_cc6hb_v3_queen, c2, h18, p3, control, cyan, start 3[179], end 18[179], 42 mer | 14 |
| AGAGTTTCTGCGGCAGTTAATCAATGAAAC CATCGATAGCAG | 20170216_cc6hb_v3_queen, c2, h17, p4, control, cyan, start 2[262], end 17[178], 42 mer | 15 |
| GCAATACATCAAACGCCGCGAACACCCGCC GCGCTTAATGCG | 20170216_cc6hb_v3_queen, c3, h21, p4, control, cyan, start 3[53], end 21[220], 42 mer | 16 |
| TCAGGCACTGCGTGAAGCGGCAGTAACAGT ACCTTTTACATC | 20170216_cc6hb_v3_queen, c3, h20, p3, control, cyan, start 4[136], end 20[221], 42 mer | 17 |
| ATCAAAACTCAACGAGCAGCGGTTGGGTTA TATAACTATATG | 20170216_cc6hb_v3_queen, c3, h19, p2, control, cyan, start 3[137], end 19[220], 42 mer | 18 |
| AGGGTTGTCGGACTTGTGCAAGGAATACCC AAAAGAACTGGC | 20170216_cc6hb_v3_queen, c3, h18, p1, control, cyan, start 4[220], end 18[221], 42 mer | 19 |
| AGTCCGTGAAGACGGAAACCAAATCAAGTT TGCCTTTAGCGT | 20170216_cc6hb_v3_queen, c3, h17, p0, control, cyan, start 3[221], end 17[220], 42 mer | 20 |
| CTGGGGATTTGACGCAGACCTGGTTGCTTTG ACGAGCACGTA | 20170216_cc6hb_v3_queen, c4, h21, p0, control, cyan, start 4[94], end 21[262], 42 mer | 21 |
| TTTTCCCAGTCACGACGTTGTGAAATTGCGT AGATTTTCAGG | 20170216_cc6hb_v3_queen, c4, h20, p1, control, cyan, start 5[95], end 20[263], 42 mer | 22 |
| TTATCAGTAAACAGAGAGGTTTCGCAAGAC AAAGAACGCGAG | 20170216_cc6hb_v3_queen, c4, h19, p2, control, cyan, start 4[178], end 19[262], 42 mer | 23 |
| TCAGGGATTAATGAAAGATGGAACAAAGTT ACCAGAAGGAAA | 20170216_cc6hb_v3_queen, c4, h18, p3, control, cyan, start 5[179], end 18[263], 42 mer | 24 |
| AGTGTGGCGATCCGATAGATGCGGCATTTT CGGTCATAGCCC | 20170216_cc6hb_v3_queen, c4, h17, p4, control, cyan, start 4[262], end 17[262], 42 mer | 25 |

TABLE 1-continued

| Sequence | Comment | SEQ ID NO: |
|---|---|---|
| Exemplary Gridiron Queen Staple Sequences | | |
| GGGGGATGTGCTGCAAGGCGAATCAGAGCG GGAGCTAAACAG | 20170216_cc6hb_v3_queen, c5, h21, p4, control, cyan, start 5[53], end 21[304], 42 mer | 26 |
| AGCCAGCTTTCCGGCACCGCTACCTACCATA TCAAAATTATT | 20170216_cc6hb_v3_queen, c5, h20, p3, control, cyan, start 6[136], end 20[305], 42 mer | 27 |
| CTTTATTATTCGCATTCACCCTAGTTAATTTC ATCTTCTGAC | 20170216_cc6hb_v3_queen, c5, h19, p2, control, cyan, start 5[137], end 19[304], 42 mer | 28 |
| TTGGTGTAGATGGGCGCATCGATCTTACCG AAGCCCTTTTTA | 20170216_cc6hb_v3_queen, c5, h18, p1, control, cyan, start 6[220], end 18[305], 42 mer | 29 |
| CAGAAATAGAAGAATTACAGCTTTCATAAT CAAAATCACCGG | 20170216_cc6hb_v3_queen, c5, h17, p0, control, cyan, start 5[221], end 17[304], 42 mer | 30 |
| AAGCGCCATTCGCCATTCAGGAGACAGGAA CGGTACGCCAGA | 20170216_cc6hb_v3_queen, c6, h21, p0, control, cyan, start 6[94], end 21[346], 42 mer | 31 |
| TCAGAAAAGCCCCAAAAACAGCTGATTGTT TGGATTATACTT | 20170216_cc6hb_v3_queen, c6, h20, p1, control, cyan, start 7[95], end 20[347], 42 mer | 32 |
| GAGGGGACGACGACAGTATCGACCGACCGT GTGATAAATAAG | 20170216_cc6hb_v3_queen, c6, h19, p2, control, cyan, start 6[178], end 19[346], 42 mer | 33 |
| TTTTTGTTAAATCAGCTCATTAGCCCAATAA TAAGAGCAAGA | 20170216_cc6hb_v3_queen, c6, h18, p3, control, cyan, start 7[179], end 18[347], 42 mer | 34 |
| GTGGGAACAAACGGCGGATTGCGCCTCCCT CAGAGCCGCCAC | 20170216_cc6hb_v3_queen, c6, h17, p4, control, cyan, start 6[262], end 17[346], 42 mer | 35 |
| TCGTAAAACTAGCATGTCAATATCAGTGAG GCCACCGAGTAA | 20170216_cc6hb_v3_queen, c7, h21, p4, control, cyan, start 7[53], end 21[388], 42 mer | 36 |
| ATGATATTCAACCGTTCTAGCATATTCCTGA TTATCAGATGA | 20170216_cc6hb_v3_queen, c7, h20, p3, control, cyan, start 8[136], end 20[389], 42 mer | 37 |
| TTAAATTGTAAACGTTAATATCGGAATCATA ATTACTAGAAA | 20170216_cc6hb_v3_queen, c7, h19, p2, control, cyan, start 7[137], end 19[388], 42 mer | 38 |
| TATTTTAAATGCAATGCCTGATGAGCGCTAA TATCAGAGAGA | 20170216_cc6hb_v3_queen, c7, h18, p1, control, cyan, start 8[220], end 18[389], 42 mer | 39 |
| TCAAAAATAATTCGCGTCTGGAGCCACCAC CCTCAGAGCCGC | 20170216_cc6hb_v3_queen, c7, h17, p0, control, cyan, start 7[221], end 17[388], 42 mer | 40 |
| GGTAGCTATTTTTGAGAGATCATTAACCGTT GTAGCAATACT | 20170216_cc6hb_v3_queen, c8, h21, p0, control, cyan, start 8[94], end 21[430], 42 mer | 41 |
| ATGGTCAATAACCTGTTTAGCTTGCGGAAC AAAGAAACCACC | 20170216_cc6hb_v3_queen, c8, h20, p1, control, cyan, start 9[95], end 20[431], 42 mer | 42 |
| AAAAGGGTGAGAAAGGCCGGACGTTATACA AATTCTTACCAG | 20170216_cc6hb_v3_queen, c8, h19, p2, control, cyan, start 8[178], end 19[430], 42 mer | 43 |
| AACATCCAATAAATCATACAGGGGAGAATT AACTGAACACCC | 20170216_cc6hb_v3_queen, c8, h18, p3, control, cyan, start 9[179], end 18[431], 42 mer | 44 |
| CTTTATTTCAACGCAAGGATACGCCGCCAG CATTGACAGGAG | 20170216_cc6hb_v3_queen, c8, h17, p4, control, cyan, start 8[262], end 17[430], 42 mer | 45 |
| CGAACGAGTAGATTTAGTTTGACTTGCCTGA GTAGAAGAACT | 20170216_cc6hb_v3_queen, c9, h21, p4, control, cyan, start 9[53], end 21[472], 42 mer | 46 |
| CATTTTTGCGGATGGCTTAGACCGAACGTTA TTAATTTTAAA | 20170216_cc6hb_v3_queen, c9, h20, p3, control, cyan, start 10[136], end 20[473], 42 mer | 47 |
| AGCTGAAAAGGTGGCATCAATTAGGGCTTA ATTGAGAATCGC | 20170216_cc6hb_v3_queen, c9, h19, p2, control, cyan, start 9[137], end 19[472], 42 mer | 48 |
| AGCTTCAAAGCGAACCAGACCTTTACAGAG AGAATAACATAA | 20170216_cc6hb_v3_queen, c9, h18, p1, control, cyan, start 10[220], end 18[473], 42 mer | 49 |

TABLE 1-continued

Exemplary Gridiron Queen Staple Sequences

| Sequence | Comment | SEQ ID NO: |
|---|---|---|
| ATTAAGCAATAAAGCCTCAGAGGCCTTGAT ATTCACAAACAA | 20170216_cc6hb_v3_queen, c9, h17, p0, control, cyan, start 9[221], end 17[472], 42 mer | 50 |
| CTGTAGCTCAACATGTTTAAAATATCCAGA ACAATATTACC | 20170216_cc6hb_v3_queen, c10, h21, p0, control, cyan, start 10[94], end 21[514], 42 mer | 51 |
| GGCTTTTGCAAAAGAAGTTTTAGACTTTACA AACAATTCGAC | 20170216_cc6hb_v3_queen, c10, h20, p1, control, cyan, start 11[95], end 20[515], 42 mer | 52 |
| AGGATTAGAGAGTACCTTTAAGTAATTTAG GCAGAGGCATTT | 20170216_cc6hb_v3_queen, c10, h19, p2, control, cyan, start 10[178], end 19[514], 42 mer | 53 |
| AATATTCATTGAATCCCCCTCGAAACGATTT TTTGTTTAACG | 20170216_cc6hb_v3_queen, c10, h18, p3, control, cyan, start 11[179], end 18[515], 42 mer | 54 |
| AAGAGGAAGCCCGAAAGACTTAATGGAAA GCGCAGTCTCTGA | 20170216_cc6hb_v3_queen, c10, h17, p4, control, cyan, start 10[262], end 17[514], 42 mer | 55 |
| ACCCTCGTTTACCAGACGACGAACGCTCAT GGAAATACCTAC | 20170216_cc6hb_v3_queen, c11, h21, p4, control, cyan, start 11[53], end 21[556], 42 mer | 56 |
| TAACGGAACAACATTATTACAAGAGCCGTC AATAGATAATAC | 20170216_cc6hb_v3_queen, c11, h20, p3, control, cyan, start 12[136], end 20[557], 42 mer | 57 |
| ATGTTTAGACTGGATAGCGTCATAAAGTAC CGACAAAAGGTA | 20170216_cc6hb_v3_queen, c11, h19, p2, control, cyan, start 11[137], end 19[556], 42 mer | 58 |
| TGAATTACCTTATGCGATTTTTTACAAAATA AACAGCCATAT | 20170216_cc6hb_v3_queen, c11, h18, p1, control, cyan, start 12[220], end 18[557], 42 mer | 59 |
| AAACGAGAATGACCATAAATCCATACATGG CTTTTGATGATA | 20170216_cc6hb_v3_queen, c11, h17, p0, control, cyan, start 11[221], end 17[556], 42 mer | 60 |
| AGATTTAGGAATACCACATTCAAATGGATT ATTTACATTGGC | 20170216_cc6hb_v3_queen, c12, h21, p0, control, cyan, start 12[94], end 21[598], 42 mer | 61 |
| CGAGGCGCAGACGGTCAATCAGTTATCTAA AATATCTTTAGG | 20170216_cc6hb_v3_queen, c12, h20, p1, control, cyan, start 13[95], end 20[599], 42 mer | 62 |
| GTCAGGACGTTGGGAAGAAAAGACAATAA ACAACATGTTCAG | 20170216_cc6hb_v3_queen, c12, h19, p2, control, cyan, start 12[178], end 19[598], 42 mer | 63 |
| AGGCTGGCTGACCTTCATCAATACCAACGC TAACGAGCGTCT | 20170216_cc6hb_v3_queen, c12, h18, p3, control, cyan, start 13[179], end 18[599], 42 mer | 64 |
| TAAATTGGGCTTGAGATGGTTTTTTAACGGG GTCAGTGCCTT | 20170216_cc6hb_v3_queen, c12, h17, p4, control, cyan, start 12[262], end 17[598], 42 mer | 65 |
| TGTGTCGAAATCCGCGACCTGAGTAATAAA AGGGACATTCTG | 20170216_cc6hb_v3_queen, c13, h21, p4, control, cyan, start 13[53], end 21[640], 42 mer | 66 |
| TACGAAGGCACCAACCTAAAACTGGTCAGT TGGCAAATCAAC | 20170216_cc6hb_v3_queen, c13, h20, p3, control, cyan, start 14[136], end 20[641], 42 mer | 67 |
| CTTTGAAAGAGGACAGATGAATATCAACAA TAGATAAGTCCT | 20170216_cc6hb_v3_queen, c13, h19, p2, control, cyan, start 13[137], end 19[640], 42 mer | 68 |
| GTAGCAACGGCTACAGAGGCTTAGTTGCTA TTTTGCACCCAG | 20170216_cc6hb_v3_queen, c13, h18, p1, control, cyan, start 14[220], end 18[641], 42 mer | 69 |
| GATATTCATTACCCAAATCAACAGTTAATGC CCCCTGCCTAT | 20170216_cc6hb_v3_queen, c13, h17, p0, control, cyan, start 13[221], end 17[640], 42 mer | 70 |
| CTAAAACACTCATCTTTGACCCTGACCTGAA AGCGTAAGAAT | 20170216_cc6hb_v3_queen, c14, h21, p0, control, cyan, start 14[94], end 21[682], 42 mer | 71 |
| CGAATAATAATTTTTTCACGTATCACCTTGC TGAACCTCAAA | 20170216_cc6hb_v3_queen, c14, h20, p1, control, cyan, start 15[95], end 20[683], 42 mer | 72 |
| ATGAGGAAGTTTCCATTAAACATCCTAATTT ACGAGCATGTA | 20170216_cc6hb_v3_queen, c14, h19, p2, control, cyan, start 14[178], end 19[682], 42 mer | 73 |

TABLE 1-continued

Exemplary Gridiron Queen Staple Sequences

| Sequence | Comment | SEQ ID NO: |
|---|---|---|
| TTCGAGGTGAATTTCTTAAACACCTCCCGAC TTGCGGGAGGT | 20170216_cc6hb_v3_queen, c14, h18, p3, control, cyan, start 15[179], end 18[683], 42 mer | 74 |
| GGATCGTCACCCTCAGCAGCGACATGAAAG TATTAAGAGGCT | 20170216_cc6hb_v3_queen, c14, h17, p4, control, cyan, start 14[262], end 17[682], 42 mer | 75 |
| TTTCAGCGGAGTGAGAATAGATGAATGGCT ATTAGTCTTTAA | 20170216_cc6hb_v3_queen, c15, h21, p4, control, cyan, start 15[53], end 21[724], 42 mer | 76 |
| CTACAACGCCTGTAGCATTCCAGTGCCACG CTGAGAGCCAGC | 20170216_cc6hb_v3_queen, c15, h20, p3, control, cyan, start 16[136], end 20[725], 42 mer | 77 |
| CTCCAAAAGGAGCCTTTAATTGTCTTTCCTT ATCATTCCAAG | 20170216_cc6hb_v3_queen, c15, h19, p2, control, cyan, start 15[137], end 19[724], 42 mer | 78 |
| CAGAGCCACCACCCTCATTTTAAGGCTTATC CGGTATTCTAA | 20170216_cc6hb_v3_queen, c15, h18, p1, control, cyan, start 16[220], end 18[725], 42 mer | 79 |
| CCGACAATGACAACAACCATCTAGGATTAG CGGGGTTTTGCT | 20170216_cc6hb_v3_queen, c15, h17, p0, control, cyan, start 15[221], end 17[724], 42 mer | 80 |
| TCGTAAAACTAGCATGTCAATATCAGTGAG GCCACCGAGTAAGAAAAAC | 20170216_cc6hb_v3_queen, c7, h21, p4, 7 bp plug, cyan, start 7[53], end 21[388], 49 mer | 81 |
| ATGATATTCAACCGTTCTAGCATATTCCTGA TTATCAGATGAAGAGTCC | 20170216_cc6hb_v3_queen, c7, h20, p3, 7 bp plug, cyan, start 8[136], end 20[389], 49 mer | 82 |
| TTAAATTGTAAACGTTAATATCGGAATCATA ATTACTAGAAAAATAGCC | 20170216_cc6hb_v3_queen, c7, h19, p2, 7 bp plug, cyan, start 7[137], end 19[388], 49 mer | 83 |
| TATTTTAAATGCAATGCCTGATGAGCGCTAA TATCAGAGAGAATGGTGG | 20170216_cc6hb_v3_queen, c7, h18, p1, 7 bp plug, cyan, start 8[220], end 18[389], 49 mer | 84 |
| TCAAAAATAATTCGCGTCTGGAGCCACCAC CCTCAGAGCCGCCGGTCCA | 20170216_cc6hb_v3_queen, c7, h17, p0, 7 bp plug, cyan, start 7[221], end 17[388], 49 mer | 85 |
| GGTAGCTATTTTTGAGAGATCATTAACCGTT GTAGCAATACTCGGTCCA | 20170216_cc6hb_v3_queen, c8, h21, p0, 7 bp plug, cyan, start 8[94], end 21[430], 49 mer | 86 |
| ATGGTCAATAACCTGTTTAGCTTGCGGAAC AAAGAAACCACCATGGTGG | 20170216_cc6hb_v3_queen, c8, h20, p1, 7 bp plug, cyan, start 9[95], end 20[431], 49 mer | 87 |
| AAAAGGGTGAGAAAGGCCGGACGTTATACA AATTCTTACCAGAATAGCC | 20170216_cc6hb_v3_queen, c8, h19, p2, 7 bp plug, cyan, start 8[178], end 19[430], 49 mer | 88 |
| AACATCCAATAAATCATACAGGGGAGAATT AACTGAACACCCAGAGTCC | 20170216_cc6hb_v3_queen, c8, h18, p3, 7 bp plug, cyan, start 9[179], end 18[431], 49 mer | 89 |
| CTTTATTTCAACGCAAGGATACGCCGCCAG CATTGACAGGAGGAAAAAC | 20170216_cc6hb_v3_queen, c8, h17, p4, 7 bp plug, cyan, start 8[262], end 17[430], 49 mer | 90 |
| TCGTAAAACTAGCATGTCAATATCAGTGAG GCCACCGAGTAAGAAAAACCGT | 20170216_cc6hb_v3_queen, c7, h21, p4, 10 bp plug, cyan, start 7[53], end 21[388], 52 mer | 91 |
| ATGATATTCAACCGTTCTAGCATATTCCTGA TTATCAGATGAAGAGTCCACT | 20170216_cc6hb_v3_queen, c7, h20, p3, 10 bp plug, cyan, start 8[136], end 20[389], 52 mer | 92 |
| TTAAATTGTAAACGTTAATATCGGAATCATA ATTACTAGAAAAATAGCCCGA | 20170216_cc6hb_v3_queen, c7, h19, p2, 10 bp plug, cyan, start 7[137], end 19[388], 52 mer | 93 |
| TATTTTAAATGCAATGCCTGATGAGCGCTAA TATCAGAGAGAATGGTGGTTC | 20170216_cc6hb_v3_queen, c7, h18, p1, 10 bp plug, cyan, start 8[220], end 18[389], 52 mer | 94 |
| TCAAAAATAATTCGCGTCTGGAGCCACCAC CCTCAGAGCCGCCGGTCCACGC | 20170216_cc6hb_v3_queen, c7, h17, p0, 10 bp plug, cyan, start 7[221], end 17[388], 52 mer | 95 |
| GGTAGCTATTTTTGAGAGATCATTAACCGTT GTAGCAATACTCGGTCCACGC | 20170216_cc6hb_v3_queen, c8, h21, p0, 10 bp plug, cyan, start 8[94], end 21[430], 52 mer | 96 |
| ATGGTCAATAACCTGTTTAGCTTGCGGAAC AAAGAAACCACCATGGTGGTTC | 20170216_cc6hb_v3_queen, c8, h20, p1, 10 bp plug, cyan, start 9[95], end 20[431], 52 mer | 97 |

TABLE 1-continued

Exemplary Gridiron Queen Staple Sequences

| Sequence | Comment | SEQ ID NO: |
|---|---|---|
| AAAAGGGTGAGAAAGGCCGGACGTTATACA AATTCTTACCAGAATAGCCCGA | 20170216_cc6hb_v3_queen, c8, h19, p2, 10 bp plug, cyan, start 8[178], end 19[430], 52 mer | 98 |
| AACATCCAATAAATCATACAGGGGAGAATT AACTGAACACCCAGAGTCCACT | 20170216_cc6hb_v3_queen, c8, h18, p3, 10 bp plug, cyan, start 9[179], end 18[431], 52 mer | 99 |
| CTTTATTTCAACGCAAGGATACGCCGCCAG CATTGACAGGAGGAAAAACCGT | 20170216_cc6hb_v3_queen, c8, h17, p4, 10 bp plug, cyan, start 8[262], end 17[430], 52 mer | 100 |
| CAATATTACATAACAATCCTCCATTTGAATT ACCTTTTTTAA | 20170216_cc6hb_v3_queen, edge, na, na, na, black, start 0[136], end 20[53], 42 mer | 101 |
| ACTGATACCGTGCAAAATTATCAAAGACAA AAGGGCGACATT | 20170216_cc6hb_v3_queen, edge, na, na, na, black, start 0[220], end 18[53], 42 mer | 102 |
| CGTAACGATCTAAAGTTTTGTAACATCGCCA TTAAAAATACC | 20170216_cc6hb_v3_queen, edge, na, na, na, black, start 16[94], end 21[766], 42 mer | 103 |
| GAACCCATGTACCGTAACACTCGCACTCAT CGAGAACAAGCA | 20170216_cc6hb_v3_queen, edge, na, na, na, black, start 16[178], end 19[766], 42 mer | 104 |
| TACCGCCACCCTCAGAACCGCCGTCGAGAG GGTTGATATAAG | 20170216_cc6hb_v3_queen, edge, na, na, na, black, start 16[262], end 17[766], 42 mer | 105 |
| TCATTAAAGGTGAATTATCACTTCTGCAATG TGCGAGAAATG | 20170216_cc6hb_v3_queen, edge, na, na, na, black, start 17[53], end 0[221], 42 mer | 106 |
| GGGAATTAGAGCCAGCAAAATGTTTATGTA GATGAAGGTATA | 20170216_cc6hb_v3_queen, edge, na, na, na, black, start 17[95], end 1[262], 42 mer | 107 |
| CACCGTAATCAGTAGCGACAGGTTTCTTGTT GTTCGCCATCC | 20170216_cc6hb_v3_queen, edge, na, na, na, black, start 17[179], end 3[262], 42 mer | 108 |
| CCTTATTAGCGTTTGCCATCTGCAACACAGC AATAAAAATGC | 20170216_cc6hb_v3_queen, edge, na, na, na, black, start 17[263], end 5[262], 42 mer | 109 |
| CCTCAGAACCGCCACCCTCAGCCTTCCTGTA GCCAGCTTTCA | 20170216_cc6hb_v3_queen, edge, na, na, na, black, start 17[347], end 7[262], 42 mer | 110 |
| GTTGAGGCAGGTCAGACGATTGCATAAAGC TAAATCGGTTGT | 20170216_cc6hb_v3_queen, edge, na, na, na, black, start 17[431], end 9[262], 42 mer | 111 |
| ATTTACCGTTCCAGTAAGCGTAAAAATCAG GTCTTTACCCTG | 20170216_cc6hb_v3_queen, edge, na, na, na, black, start 17[515], end 11[262], 42 mer | 112 |
| GAGTAACAGTGCCCGTATAAACGTAACAAA GCTGCTCATTCA | 20170216_cc6hb_v3_queen, edge, na, na, na, black, start 17[599], end 13[262], 42 mer | 113 |
| GAGACTCCTCAAGAGAAGGATGCCCACGCA TAACCGATATAT | 20170216_cc6hb_v3_queen, edge, na, na, na, black, start 17[683], end 15[262], 42 mer | 114 |
| TAGCAAGCAAATCAGATATAGCAGGGATAG CAAGCCCAATAG | 20170216_cc6hb_v3_queen, edge, na, na, na, black, start 18[766], end 16[179], 42 mer | 115 |
| GCTTCTGTAAATCGTCGCTATAAACATATAG ATGATTAAACC | 20170216_cc6hb_v3_queen, edge, na, na, na, black, start 19[53], end 0[137], 42 mer | 116 |
| AGTATTAACACCGCCTGCAACACAGACAGC CCTCATAGTTAG | 20170216_cc6hb_v3_queen, edge, na, na, na, black, start 20[766], end 16[95], 42 mer | 117 |
| GCACTAAATCGGAACCCTAAATTTTGTTTTA TGGAGATGATA | 20170216_cc6hb_v3_queen, edge, na, na, na, black, start 21[53], end 0[53], 42 mer | 118 |
| AAAGCGAAAGGAGCGGGCGCTCTGAATTTC GCGTCGTCTTCA | 20170216_cc6hb_v3_queen, edge, na, na, na, black, start 21[137], end 2[53], 42 mer | 119 |
| CCGCTACAGGGCGCGTACTATTTTCCATGAA TTGGTAACACC | 20170216_cc6hb_v3_queen, edge, na, na, na, black, start 21[221], end 4[53], 42 mer | 120 |
| GAGGCCGATTAAAGGGATTTTCTGCGCAAC TGTTGGGAAGGG | 20170216_cc6hb_v3_queen, edge, na, na, na, black, start 21[305], end 6[53], 42 mer | 121 |

TABLE 1-continued

| Exemplary Gridiron Queen Staple Sequences | | |
|---|---|---|
| Sequence | Comment | SEQ ID NO: |
| AAGAGTCTGTCCATCACGCAATACAAAGGC TATCAGGTCATT | 20170216_cc6hb_v3_queen, edge, na, na, na, black, start 21[389], end 8[53], 42 mer | 122 |
| CAAACTATCGGCCTTGCTGGTATATGCAACT AAAGTACGGTG | 20170216_cc6hb_v3_queen, edge, na, na, na, black, start 21[473], end 10[53], 42 mer | 123 |
| ATTTTGACGCTCAATCGTCTGAACTAATGCA GATACATAACG | 20170216_cc6hb_v3_queen, edge, na, na, na, black, start 21[557], end 12[53], 42 mer | 124 |
| GCCAACAGAGATAGAACCCTTCCCAGCGAT TATACCAAGCGC | 20170216_cc6hb_v3_queen, edge, na, na, na, black, start 21[641], end 14[53], 42 mer | 125 |
| TGCGCGAACTGATAGCCCTAACGTCTTTCCA GACGTTAGTAA | 20170216_cc6hb_v3_queen, edge, na, na, na, black, start 21[725], end 16[53], 42 mer | 126 |
| CAAAGGGCGAAAAACCAACAGCTGATTGCC CTGCGCCAGG | 20170216_cc6hb_v3_queen, reference sheet, na, na, na, puke green, start 22[79], end 24[72], 40 mer | 127 |
| AGTCCACTATTAAAGAAGAGAGTTGCAGCA AGCAACGCGC | 20170216_cc6hb_v3_queen, reference sheet, na, na, na, puke green, start 22[111], end 24[104], 40 mer | 128 |
| TAGGGTTGAGTGTTGTGCCCCAGCAGGCGA AAACCTGTCG | 20170216_cc6hb_v3_queen, reference sheet, na, na, na, puke green, start 22[143], end 24[136], 40 mer | 129 |
| AATCCCTTATAAATCAGTTCCGAAATCGGC AA | 20170216_cc6hb_v3_queen, reference sheet, na, na, na, puke green, start 22[175], end 23[175], 32 mer | 130 |
| GTGAGACGGGCGTCTATCA | 20170216_cc6hb_v3_queen, reference sheet, na, na, na, puke green, start 23[53], end 22[56], 19 mer | 131 |
| GTGGTTTTTGTTTCCTGTGTGAAA | 20170216_cc6hb_v3_queen, reference sheet, na, na, na, puke green, start 24[71], end 25[79], 24 mer | 132 |
| CGTATTGGTCACCGCCTGGCCCTGACGTGG ACTCCAACGT | 20170216_cc6hb_v3_queen, reference sheet, na, na, na, puke green, start 24[87], end 22[80], 40 mer | 133 |
| GGGGAGAGATTCCACACAACATAC | 20170216_cc6hb_v3_queen, reference sheet, na, na, na, puke green, start 24[103], end 25[111], 24 mer | 134 |
| GAATCGGCCGGTCCACGCTGGTTTTCCAGTT TGGAACAAG | 20170216_cc6hb_v3_queen, reference sheet, na, na, na, puke green, start 24[119], end 22[112], 40 mer | 135 |
| TGCCAGCTGTGTAAAGCCTGGGGT | 20170216_cc6hb_v3_queen, reference sheet, na, na, na, puke green, start 24[135], end 25[143], 24 mer | 136 |
| GTCGGGAAATCCTGTTTGATGGTGAAAGAA TAGCCCGAGA | 20170216_cc6hb_v3_queen, reference sheet, na, na, na, puke green, start 24[151], end 22[144], 40 mer | 137 |
| GTTGCGCTCACTGCCCAACTCACATTAATTG C | 20170216_cc6hb_v3_queen, reference sheet, na, na, na, puke green, start 24[175], end 25[175], 32 mer | 138 |
| GTCATAGCTCTTTTCACCA | 20170216_cc6hb_v3_queen, reference sheet, na, na, na, puke green, start 25[56], end 24[53], 19 mer | 139 |
| TTGTTATCCGCTCACAGCGGTTTG | 20170216_cc6hb_v3_queen, reference sheet, na, na, na, puke green, start 25[80], end 24[88], 24 mer | 140 |
| GAGCCGGAAGCATAAAGCATTAAT | 20170216_cc6hb_v3_queen, reference sheet, na, na, na, puke green, start 25[112], end 24[120], 24 mer | 141 |
| GCCTAATGAGTGAGCTGCTTTCCA | 20170216_cc6hb_v3_queen, reference sheet, na, na, na, puke green, start 25[144], end 24[152], 24 mer | 142 |
| AAAATACATACATAAAGGTGGCTATTACGG GGTTGGAGGTCA | 20170216_cc6hb_v3_queen, cell not used, na, na, na, red, start 18[178], end 2[179], 42 mer | 143 |
| TAGCAAGGCCGGAAACGTCACCGAACAAGA CCCGTTAGTAAC | 20170216_cc6hb_v3_queen, cell not used, na, na, na, red, start 17[137], end 2[221], 42 mer | 144 |
| CAGACTGTAGCGCGTTTTCATAACGAAGAC GCCTGGTCGTTC | 20170216_cc6hb_v3_queen, cell not used, na, na, na, red, start 17[221], end 4[221], 42 mer | 145 |

TABLE 1-continued

| Exemplary Gridiron Queen Staple Sequences | | |
|---|---|---|
| Sequence | Comment | SEQ ID NO: |
| AACCAGAGCCACCACCGGAACACCGTAATG GGATAGGTCACG | 20170216_cc6hb_v3_queen, cell not used, na, na, na, red, start 17[305], end 6[221], 42 mer | 146 |
| CACCAGAACCACCACCAGAGCAAAATTTTT AGAACCCTCATA | 20170216_cc6hb_v3_queen, cell not used, na, na, na, red, start 17[389], end 8[221], 42 mer | 147 |
| ATAAATCCTCATTAAAGCCAGCAAATATCG CGTTTTAATTCG | 20170216_cc6hb_v3_queen, cell not used, na, na, na, red, start 17[473], end 10[221], 42 mer | 148 |
| CAGGAGTGTACTGGTAATAAGTAATTTCAA CTTTAATCATTG | 20170216_cc6hb_v3_queen, cell not used, na, na, na, red, start 17[557], end 12[221], 42 mer | 149 |
| TTCGGAACCTATTATTCTGAAAAAGACAGC ATCGGAACGAGG | 20170216_cc6hb_v3_queen, cell not used, na, na, na, red, start 17[641], end 14[221], 42 mer | 150 |
| CAGTACCAGGCGGATAAGTGCCACCCTCAG AACCGCCACCCT | 20170216_cc6hb_v3_queen, cell not used, na, na, na, red, start 17[725], end 16[221], 42 mer | 151 |
| ATTCATATGGTTTACCAGCGCTATCACGAGT ACGGTGGAAAC | 20170216_cc6hb_v3_queen, cell not used, na, na, na, red, start 18[94], end 0[179], 42 mer | 152 |
| AGACACCACGGAATAAGTTTATGCAGATCC GGTGTCTTGTCT | 20170216_cc6hb_v3_queen, cell not used, na, na, na, red, start 18[136], end 1[220], 42 mer | 153 |
| ATGATTAAGACTCCTTATTACTGCTAAACTG GAAAGCAACGA | 20170216_cc6hb_v3_queen, cell not used, na, na, na, red, start 18[220], end 3[220], 42 mer | 154 |
| CCGAGGAAACGCAATAATAACGTTGCCAGG AGGATCTGGAAC | 20170216_cc6hb_v3_queen, cell not used, na, na, na, red, start 18[262], end 4[179], 42 mer | 155 |
| AGAAAAGTAAGCAGATAGCCGCAGACATCA TTGATTCAGCAT | 20170216_cc6hb_v3_queen, cell not used, na, na, na, red, start 18[304], end 5[220], 42 mer | 156 |
| AACAATGAAATAGCAATAGCTTAACCGTGC ATCTGCCAGTTT | 20170216_cc6hb_v3_queen, cell not used, na, na, na, red, start 18[346], end 6[179], 42 mer | 157 |
| TAACCCACAAGAATTGAGTTATTTTAACCA ATAGGAACGCCA | 20170216_cc6hb_v3_queen, cell not used, na, na, na, red, start 18[388], end 7[220], 42 mer | 158 |
| TGAACAAAGTCAGAGGGTAATGTAATGTGT AGGTAAAGATTC | 20170216_cc6hb_v3_queen, cell not used, na, na, na, red, start 18[430], end 8[179], 42 mer | 159 |
| AAACAGGGAAGCGCATTAGACGCAAGGCA AAGAATTAGCAAA | 20170216_cc6hb_v3_queen, cell not used, na, na, na, red, start 18[472], end 9[220], 42 mer | 160 |
| TCAAAAATGAAAATAGCAGCCGGAAGCAA ACTCCAACAGGTC | 20170216_cc6hb_v3_queen, cell not used, na, na, na, red, start 18[514], end 10[179], 42 mer | 161 |
| TATTTATCCCAATCCAAATAAAAATGCTTTA AACAGTTCAGA | 20170216_cc6hb_v3_queen, cell not used, na, na, na, red, start 18[556], end 11[220], 42 mer | 162 |
| TTCCAGAGCCTAATTTGCCAGAAGAACTGG CTCATTATACCA | 20170216_cc6hb_v3_queen, cell not used, na, na, na, red, start 18[598], end 12[179], 42 mer | 163 |
| CTACAATTTTATCCTGAATCTGAGTAATCTT GACAAGAACCG | 20170216_cc6hb_v3_queen, cell not used, na, na, na, red, start 18[640], end 13[220], 42 mer | 164 |
| TTTGAAGCCTTAAATCAAGATTTGAGGACT AAAGACTTTTTC | 20170216_cc6hb_v3_queen, cell not used, na, na, na, red, start 18[682], end 14[179], 42 mer | 165 |
| GAACGCGAGGCGTTTTAGCGAAGCTTGATA CCGATAGTTGCG | 20170216_cc6hb_v3_queen, cell not used, na, na, na, red, start 18[724], end 15[220], 42 mer | 166 |
| CCTTGAAAACATAGCGATAGCGAGTTAGAG TCTGAGCAAAAA | 20170216_cc6hb_v3_queen, cell not used, na, na, na, red, start 19[95], end 1[178], 42 mer | 167 |
| AGTCAATAGTGAATTTATCAAGTATCTGCAT ATGATGTCTGA | 20170216_cc6hb_v3_queen, cell not used, na, na, na, red, start 19[137], end 2[137], 42 mer | 168 |
| CCTTTTTAACCTCCGGCTTAGTGAGTATTAC GAAGGTGTTAT | 20170216_cc6hb_v3_queen, cell not used, na, na, na, red, start 19[179], end 3[178], 42 mer | 169 |

TABLE 1-continued

Exemplary Gridiron Queen Staple Sequences

| Sequence | Comment | SEQ ID NO: |
|---|---|---|
| TAAATGCTGATGCAAATCCAACGAAGTGAG CGAAATTAACTC | 20170216_cc6hb_v3_queen, cell not used, na, na, na, red, start 19[221], end 4[137], 42 mer | 170 |
| AAAACTTTTTCAAATATATTTTCATGCGTAT TAACCAACAGT | 20170216_cc6hb_v3_queen, cell not used, na, na, na, red, start 19[263], end 5[178], 42 mer | 171 |
| CTAAATTTAATGGTTTGAAATGCCTCAGGA AGATCGCACTCC | 20170216_cc6hb_v3_queen, cell not used, na, na, na, red, start 19[305], end 6[137], 42 mer | 172 |
| GCGTTAAATAAGAATAAACACTTTGTTAAA ATTCGCATTAAA | 20170216_cc6hb_v3_queen, cell not used, na, na, na, red, start 19[347], end 7[178], 42 mer | 173 |
| AAGCCTGTTTAGTATCATATGGACAGTCAA ATCACCATCAAT | 20170216_cc6hb_v3_queen, cell not used, na, na, na, red, start 19[389], end 8[137], 42 mer | 174 |
| TATAAAGCCAACGCTCAACAGTCTACTAAT AGTAGTAGCATT | 20170216_cc6hb_v3_queen, cell not used, na, na, na, red, start 19[431], end 9[178], 42 mer | 175 |
| CATATTTAACAACGCCAACATTTGCTCCTTT TGATAAGAGGT | 20170216_cc6hb_v3_queen, cell not used, na, na, na, red, start 19[473], end 10[137], 42 mer | 176 |
| TCGAGCCAGTAATAAGAGAATCAATACTGC GGAATCGTCATA | 20170216_cc6hb_v3_queen, cell not used, na, na, na, red, start 19[515], end 11[178], 42 mer | 177 |
| AAGTAATTCTGTCCAGACGACATCTACGTTA ATAAAACGAAC | 20170216_cc6hb_v3_queen, cell not used, na, na, na, red, start 19[557], end 12[137], 42 mer | 178 |
| CTAATGCAGAACGCGCCTGTTCGGTGTACA GACCAGGCGCAT | 20170216_cc6hb_v3_queen, cell not used, na, na, na, red, start 19[599], end 13[178], 42 mer | 179 |
| GAACAAGAAAAATAATATCCCGGGTAAAAT ACGTAATGCCAC | 20170216_cc6hb_v3_queen, cell not used, na, na, na, red, start 19[641], end 14[137], 42 mer | 180 |
| GAAACCAATCAATAATCGGCTGTATCGGTT TATCAGCTTGCT | 20170216_cc6hb_v3_queen, cell not used, na, na, na, red, start 19[683], end 15[178], 42 mer | 181 |
| AACGGGTATTAAACCAAGTACGAGTTTCGT CACCAGTACAAA | 20170216_cc6hb_v3_queen, cell not used, na, na, na, red, start 19[725], end 16[137], 42 mer | 182 |
| ATTAATTACATTTAACAATTTGCACTCGCGG GGATTTATTTT | 20170216_cc6hb_v3_queen, cell not used, na, na, na, red, start 20[94], end 0[95], 42 mer | 183 |
| CTGAGCAAAAGAAGATGATGAGAAACGAC ATACATTGCAAGG | 20170216_cc6hb_v3_queen, cell not used, na, na, na, red, start 20[136], end 1[136], 42 mer | 184 |
| AGTTACAAAATCGCGCAGAGGAGAGTGAGA TCGGTTTTGTAA | 20170216_cc6hb_v3_queen, cell not used, na, na, na, red, start 20[178], end 2[95], 42 mer | 185 |
| GGGAGAAACAATAACGGATTCTGTTGAGCT TGAAACAGCAAA | 20170216_cc6hb_v3_queen, cell not used, na, na, na, red, start 20[220], end 3[136], 42 mer | 186 |
| TTTAACGTCAGATGAATATACAGAGCAGGC AATGCATGACGA | 20170216_cc6hb_v3_queen, cell not used, na, na, na, red, start 20[262], end 4[95], 42 mer | 187 |
| TGCACGTAAAACAGAAATAAAAAAACGAC GGCCAGTGCCAAG | 20170216_cc6hb_v3_queen, cell not used, na, na, na, red, start 20[304], end 5[136], 42 mer | 188 |
| CTGAATAATGGAAGGGTTAGATCTGGTGCC GGAAACCAGGCA | 20170216_cc6hb_v3_queen, cell not used, na, na, na, red, start 20[346], end 6[95], 42 mer | 189 |
| TGGCAATTCATCAATATAATCGAAGATTGT ATAAGCAAATAT | 20170216_cc6hb_v3_queen, cell not used, na, na, na, red, start 20[388], end 7[136], 42 mer | 190 |
| AGAAGGAGCGGAATTATCATCTGATAAATT AATGCCGGAGAG | 20170216_cc6hb_v3_queen, cell not used, na, na, na, red, start 20[430], end 8[95], 42 mer | 191 |
| AGTTTGAGTAACATTATCATTTATATTTTCA TTTGGGGCGCG | 20170216_cc6hb_v3_queen, cell not used, na, na, na, red, start 20[472], end 9[136], 42 mer | 192 |
| AACTCGTATTAAATCCTTTGCGCTTAATTGC TGAATATAATG | 20170216_cc6hb_v3_queen, cell not used, na, na, na, red, start 20[514], end 10[95], 42 mer | 193 |

TABLE 1-continued

| Exemplary Gridiron Queen Staple Sequences | | |
|---|---|---|
| Sequence | Comment | SEQ ID NO: |
| ATTTGAGGATTTAGAAGTATTGCCAGAGGG GGTAATAGTAAA | 20170216_cc6hb_v3_queen, cell not used, na, na, na, red, start 20[556], end 11[136], 42 mer | 194 |
| AGCACTAACAACTAATAGATTGGTAGAAAG ATTCATCAGTTG | 20170216_cc6hb_v3_queen, cell not used, na, na, na, red, start 20[598], end 12[95], 42 mer | 195 |
| AGTTGAAAGGAATTGAGGAAGTAAGGGAA CCGAACTGACCAA | 20170216_cc6hb_v3_queen, cell not used, na, na, na, red, start 20[640], end 13[136], 42 mer | 196 |
| TATCAAACCCTCAATCAATATCGAAAGAGG CAAAAGAATACA | 20170216_cc6hb_v3_queen, cell not used, na, na, na, red, start 20[682], end 14[95], 42 mer | 197 |
| AGCAAATGAAAAATCTAAAGCTGAAAATCT CCAAAAAAAAGG | 20170216_cc6hb_v3_queen, cell not used, na, na, na, red, start 20[724], end 15[136], 42 mer | 198 |
| TGACGGGGAAAGCCGGCGAACCTTACTGTT TCTTTACATAAA | 20170216_cc6hb_v3_queen, cell not used, na, na, na, red, start 21[95], end 1[94], 42 mer | 199 |
| GTCACGCTGCGCGTAACCACCCCAGGAGAA CGAGGATATTGC | 20170216_cc6hb_v3_queen, cell not used, na, na, na, red, start 21[179], end 3[94], 42 mer | 200 |
| TAACGTGCTTTCCTCGTTAGATTAAGTTGGG TAACGCCAGGG | 20170216_cc6hb_v3_queen, cell not used, na, na, na, red, start 21[263], end 5[94], 42 mer | 201 |
| ATCCTGAGAAGTGTTTTTATACATATGTACC CCGGTTGATAA | 20170216_cc6hb_v3_queen, cell not used, na, na, na, red, start 21[347], end 7[94], 42 mer | 202 |
| TCTTTGATTAGTAATAACATCACCATTAGAT ACATTTCGCAA | 20170216_cc6hb_v3_queen, cell not used, na, na, na, red, start 21[431], end 9[94], 42 mer | 203 |
| GCCAGCCATTGCAACAGGAAAATAAAAACC AAAATAGCGAGA | 20170216_cc6hb_v3_queen, cell not used, na, na, na, red, start 21[515], end 11[94], 42 mer | 204 |
| AGATTCACCAGTCACACGACCCTCCATGTTA CTTAGCCGGAA | 20170216_cc6hb_v3_queen, cell not used, na, na, na, red, start 21[599], end 13[94], 42 mer | 205 |
| ACGTGGCACAGACAATATTTTAAGGAACAA CTAAAGGAATTG | 20170216_cc6hb_v3_queen, cell not used, na, na, na, red, start 21[683], end 15[94], 42 mer | 206 |
| ATCTGAACTCGCTACGGCGGGGGGAGCCCC CGATTTAGAGCTCGGTCCA | 20170407_cc6hb_v3-1_queen, c0, h21, p0, 7 bp plug, cyan, start 0[94], end 21[94], 49 mer | 207 |
| CATTGCTGATACCGTTTAGCTAACAAACATC AAGAAAACAAAATGGTGG | 20170407_cc6hb_v3-1_queen, c0, h20, p1, 7 bp plug, cyan, start 1[95], end 20[95], 49 mer | 208 |
| GATACTTGCCCTCTCTGTACATAATTAATTT TCCCTTAGAATAATAGCC | 20170407_cc6hb_v3-1_queen, c0, h19, p2, 7 bp plug, cyan, start 0[178], end 19[94], 49 mer | 209 |
| GATTGGGCGTTATCAATGTTGTTTTGTCACA ATCAATAGAAAAGAGTCC | 20170407_cc6hb_v3-1_queen, c0, h18, p3, 7 bp plug, cyan, start 1[179], end 18[95], 49 mer | 210 |
| TCTAATGAAGACAAATCCCCACGTCACCGA CTTGAGCCATTTGAAAAAC | 20170407_cc6hb_v3-1_queen, c0, h17, p4, 7 bp plug, cyan, start 0[262], end 17[94], 49 mer | 211 |
| AAACATCGGGTTGAGTATTATGTGGCGAGA AAGGAAGGGAAGGAAAAAC | 20170407_cc6hb_v3-1_queen, c1, h21, p4, 7 bp plug, cyan, start 1[53], end 21[136], 49 mer | 212 |
| CGCTGGCATTCGCATCAAAGGCGAATTATT CATTTCAATTACAGAGTCC | 20170407_cc6hb_v3-1_queen, c1, h20, p3, 7 bp plug, cyan, start 2[136], end 20[137], 49 mer | 213 |
| AGTTTATAAATGAGTATCAATTTAGATTAAG ACGCTGAGAAGAATAGCC | 20170407_cc6hb_v3-1_queen, c1, h19, p2, 7 bp plug, cyan, start 1[137], end 19[136], 49 mer | 214 |
| TATCGACATCATTACGCATCGCAACATATA AAAGAAACGCAAATGGTGG | 20170407_cc6hb_v3-1_queen, c1, h18, p1, 7 bp plug, cyan, start 2[220], end 18[137], 49 mer | 215 |
| CCATGCAGACATCACGAAGGTCACCAGTAG CACCATTACCATCGGTCCA | 20170407_cc6hb_v3-1_queen, c1, h17, p0, 7 bp plug, cyan, start 1[221], end 17[136], 49 mer | 216 |
| AAGATAACGCTTGTGAAAATGAGGGCGCTG GCAAGTGTAGCGCGGTCCA | 20170407_cc6hb_v3-1_queen, c2, h21, p0, 7 bp plug, cyan, start 2[94], end 21[178], 49 mer | 217 |

TABLE 1-continued

| Exemplary Gridiron Queen Staple Sequences | | |
|---|---|---|
| Sequence | Comment | SEQ ID NO: |
| GCTAACAGTAGGGAAACTGCGGCCTGATTG CTTTGAATACCAATGGTGG | 20170407_cc6hb_v3-1_queen, c2, h20, p1, 7 bp plug, cyan, start 3[95], end 20[179], 49 mer | 218 |
| ATGGGTTCAGGATGCAGGTGAAATCATAGG TCTGAGAGACTAAATAGCC | 20170407_cc6hb_v3-1_queen, c2, h19, p2, 7 bp plug, cyan, start 2[178], end 19[178], 49 mer | 219 |
| CTCGGATGGGAGTAAGCGTATGCAGTATGT TAGCAAACGTAGAGAGTCC | 20170407_cc6hb_v3-1_queen, c2, h18, p3, 7 bp plug, cyan, start 3[179], end 18[179], 49 mer | 220 |
| AGAGTTTCTGCGGCAGTTAATCAATGAAAC CATCGATAGCAGGAAAAAC | 20170407_cc6hb_v3-1_queen, c2, h17, p4, 7 bp plug, cyan, start 2[262], end 17[178], 49 mer | 221 |
| GCAATACATCAAACGCCGCGAACACCCGCC GCGCTTAATGCGGAAAAAC | 20170407_cc6hb_v3-1_queen, c3, h21, p4, 7 bp plug, cyan, start 3[53], end 21[220], 49 mer | 222 |
| TCAGGCACTGCGTGAAGCGGCAGTAACAGT ACCTTTTACATCAGAGTCC | 20170407_cc6hb_v3-1_queen, c3, h20, p3, 7 bp plug, cyan, start 4[136], end 20[221], 49 mer | 223 |
| ATCAAAACTCAACGAGCAGCGGTTGGGTTA TATAACTATATGAATAGCC | 20170407_cc6hb_v3-1_queen, c3, h19, p2, 7 bp plug, cyan, start 3[137], end 19[220], 49 mer | 224 |
| AGGGTTGTCGGACTTGTGCAAGGAATACCC AAAAGAACTGGCATGGTGG | 20170407_cc6hb_v3-1_queen, c3, h18, p1, 7 bp plug, cyan, start 4[220], end 18[221], 49 mer | 225 |
| AGTCCGTGAAGACGGAAACCAAATCAAGTT TGCCTTTAGCGTCGGTCCA | 20170407_cc6hb_v3-1_queen, c3, h17, p0, 7 bp plug, cyan, start 3[221], end 17[220], 49 mer | 226 |
| CTGGGGATTTGACGCAGACCTGGTTGCTTTG ACGAGCACGTACGGTCCA | 20170407_cc6hb_v3-1_queen, c4, h21, p0, 7 bp plug, cyan, start 4[94], end 21[262], 49 mer | 227 |
| TTTTCCCAGTCACGACGTTGTGAAATTGCGT AGATTTTCAGGATGGTGG | 20170407_cc6hb_v3-1_queen, c4, h20, p1, 7 bp plug, cyan, start 5[95], end 20[263], 49 mer | 228 |
| TTATCAGTAAACAGAGAGGTTTCGCAAGAC AAAGAACGCGAGAATAGCC | 20170407_cc6hb_v3-1_queen, c4, h19, p2, 7 bp plug, cyan, start 4[178], end 19[262], 49 mer | 229 |
| TCAGGGATTAATGAAAGATGGAACAAAGTT ACCAGAAGGAAAAGAGTCC | 20170407_cc6hb_v3-1_queen, c4, h18, p3, 7 bp plug, cyan, start 5[179], end 18[263], 49 mer | 230 |
| AGTGTGGCGATCCGATAGATGCGGCATTTT CGGTCATAGCCCGAAAAAC | 20170407_cc6hb_v3-1_queen, c4, h17, p4, 7 bp plug, cyan, start 4[262], end 17[262], 49 mer | 231 |
| GGGGGATGTGCTGCAAGGCGAATCAGAGCG GGAGCTAAACAGGAAAAAC | 20170407_cc6hb_v3-1_queen, c5, h21, p4, 7 bp plug, cyan, start 5[53], end 21[304], 49 mer | 232 |
| AGCCAGCTTTCCGGCACCGCTACCTACCATA TCAAAATTATTAGAGTCC | 20170407_cc6hb_v3-1_queen, c5, h20, p3, 7 bp plug, cyan, start 6[136], end 20[305], 49 mer | 233 |
| CTTTATTATTCGCATTCACCCTAGTTAATTTC ATCTTCTGACAATAGCC | 20170407_cc6hb_v3-1_queen, c5, h19, p2, 7 bp plug, cyan, start 5[137], end 19[304], 49 mer | 234 |
| TTGGTGTAGATGGGCGCATCGATCTTACCG AAGCCCTTTTTAATGGTGG | 20170407_cc6hb_v3-1_queen, c5, h18, p1, 7 bp plug, cyan, start 6[220], end 18[305], 49 mer | 235 |
| CAGAAATAGAAGAATTACAGCTTTCATAAT CAAAATCACCGGCGGTCCA | 20170407_cc6hb_v3-1_queen, c5, h17, p0, 7 bp plug, cyan, start 5[221], end 17[304], 49 mer | 236 |
| AAGCGCCATTCGCCATTCAGGAGACAGGAA CGGTACGCCAGACGGTCCA | 20170407_cc6hb_v3-1_queen, c6, h21, p0, 7 bp plug, cyan, start 6[94], end 21[346], 49 mer | 237 |
| TCAGAAAAGCCCCAAAAACAGCTGATTGTT TGGATTATACTTATGGTGG | 20170407_cc6hb_v3-1_queen, c6, h20, p1, 7 bp plug, cyan, start 7[95], end 20[347], 49 mer | 238 |
| GAGGGGACGACGACAGTATCGACCGACCGT GTGATAAATAAGAATAGCC | 20170407_cc6hb_v3-1_queen, c6, h19, p2, 7 bp plug, cyan, start 6[178], end 19[346], 49 mer | 239 |
| TTTTTGTTAAATCAGCTCATTAGCCCAATAA TAAGAGCAAGAAGAGTCC | 20170407_cc6hb_v3-1_queen, c6, h18, p3, 7 bp plug, cyan, start 7[179], end 18[347], 49 mer | 240 |
| GTGGGAACAAACGGCGGATTGCGCCTCCCT CAGAGCCGCCACGAAAAAC | 20170407_cc6hb_v3-1_queen, c6, h17, p4, 7 bp plug, cyan, start 6[262], end 17[346], 49 mer | 241 |

TABLE 1-continued

Exemplary Gridiron Queen Staple Sequences

| Sequence | Comment | SEQ ID NO: |
|---|---|---|
| CGAACGAGTAGATTTAGTTTGACTTGCCTGA GTAGAAGAACTGAAAAAC | 20170407_cc6hb_v3-1_queen, c9, h21, p4, 7 bp plug, cyan, start 9[53], end 21[472], 49 mer | 242 |
| CATTTTTGCGGATGGCTTAGACCGAACGTTA TTAATTTTAAAAGAGTCC | 20170407_cc6hb_v3-1_queen, c9, h20, p3, 7 bp plug, cyan, start 10[136], end 20[473], 49 mer | 243 |
| AGCTGAAAAGGTGGCATCAATTAGGGCTTA ATTGAGAATCGCAATAGCC | 20170407_cc6hb_v3-1_queen, c9, h19, p2, 7 bp plug, cyan, start 9[137], end 19[472], 49 mer | 244 |
| AGCTTCAAAGCGAACCAGACCTTTACAGAG AGAATAACATAAATGGTGG | 20170407_cc6hb_v3-1_queen, c9, h18, p1, 7 bp plug, cyan, start 10[220], end 18[473], 49 mer | 245 |
| ATTAAGCAATAAAGCCTCAGAGGCCTTGAT ATTCACAAACAACGGTCCA | 20170407_cc6hb_v3-1_queen, c9, h17, p0, 7 bp plug, cyan, start 9[221], end 17[472], 49 mer | 246 |
| CTGTAGCTCAACATGTTTTAAAATATCCAGA ACAATATTACCCGGTCCA | 20170407_cc6hb_v3-1_queen, c10, h21, p0, 7 bp plug, cyan, start 10[94], end 21[514], 49 mer | 247 |
| GGCTTTTGCAAAAGAAGTTTTAGACTTTACA AACAATTCGACATGGTGG | 20170407_cc6hb_v3-1_queen, c10, h20, p1, 7 bp plug, cyan, start 11[95], end 20[515], 49 mer | 248 |
| AGGATTAGAGAGTACCTTTAAGTAATTTAG GCAGAGGCATTTAATAGCC | 20170407_cc6hb_v3-1_queen, c10, h19, p2, 7 bp plug, cyan, start 10[178], end 19[514], 49 mer | 249 |
| AATATTCATTGAATCCCCCTCGAAACGATTT TTTGTTTAACGAGAGTCC | 20170407_cc6hb_v3-1_queen, c10, h18, p3, 7 bp plug, cyan, start 11[179], end 18[515], 49 mer | 250 |
| AAGAGGAAGCCCGAAAGACTTAATGGAAA GCGCAGTCTCTGAGAAAAAC | 20170407_cc6hb_v3-1_queen, c10, h17, p4, 7 bp plug, cyan, start 10[262], end 17[514], 49 mer | 251 |
| ACCCTCGTTTACCAGACGACGAACGCTCAT GGAAATACCTACGAAAAAC | 20170407_cc6hb_v3-1_queen, c11, h21, p4, 7 bp plug, cyan, start 11[53], end 21[556], 49 mer | 252 |
| TAACGGAACAACATTATTACAAGAGCCGTC AATAGATAATACAGAGTCC | 20170407_cc6hb_v3-1_queen, c11, h20, p3, 7 bp plug, cyan, start 12[136], end 20[557], 49 mer | 253 |
| ATGTTTAGACTGGATAGCGTCATAAAGTAC CGACAAAAGGTAAATAGCC | 20170407_cc6hb_v3-1_queen, c11, h19, p2, 7 bp plug, cyan, start 11[137], end 19[556], 49 mer | 254 |
| TGAATTACCTTATGCGATTTTTTACAAAATA AACAGCCATATATGGTGG | 20170407_cc6hb_v3-1_queen, c11, h18, p1, 7 bp plug, cyan, start 12[220], end 18[557], 49 mer | 255 |
| AAACGAGAATGACCATAAATCCATACATGG CTTTTGATGATACGGTCCA | 20170407_cc6hb_v3-1_queen, c11, h17, p0, 7 bp plug, cyan, start 11[221], end 17[556], 49 mer | 256 |
| AGATTTAGGAATACCACATTCAAATGGATT ATTTACATTGGCCGGTCCA | 20170407_cc6hb_v3-1_queen, c12, h21, p0, 7 bp plug, cyan, start 12[94], end 21[598], 49 mer | 257 |
| CGAGGCGCAGACGGTCAATCAGTTATCTAA AATATCTTTAGGATGGTGG | 20170407_cc6hb_v3-1_queen, c12, h20, p1, 7 bp plug, cyan, start 13[95], end 20[599], 49 mer | 258 |
| GTCAGGACGTTGGGAAGAAAAGACAATAA ACAACATGTTCAGAATAGCC | 20170407_cc6hb_v3-1_queen, c12, h19, p2, 7 bp plug, cyan, start 12[178], end 19[598], 49 mer | 259 |
| AGGCTGGCTGACCTTCATCAATACCAACGC TAACGAGCGTCTAGAGTCC | 20170407_cc6hb_v3-1_queen, c12, h18, p3, 7 bp plug, cyan, start 13[179], end 18[599], 49 mer | 260 |
| TAAATTGGGCTTGAGATGGTTTTTTAACGGG GTCAGTGCCTTGAAAAAC | 20170407_cc6hb_v3-1_queen, c12, h17, p4, 7 bp plug, cyan, start 12[262], end 17[598], 49 mer | 261 |
| TGTGTCGAAATCCGCGACCTGAGTAATAAA AGGGACATTCTGGAAAAAC | 20170407_cc6hb_v3-1_queen, c13, h21, p4, 7 bp plug, cyan, start 13[53], end 21[640], 49 mer | 262 |
| TACGAAGGCACCAACCTAAAACTGGTCAGT TGGCAAATCAACAGAGTCC | 20170407_cc6hb_v3-1_queen, c13, h20, p3, 7 bp plug, cyan, start 14[136], end 20[641], 49 mer | 263 |
| CTTTGAAAGAGGACAGATGAATATCAACAA TAGATAAGTCCTAATAGCC | 20170407_cc6hb_v3-1_queen, c13, h19, p2, 7 bp plug, cyan, start 13[137], end 19[640], 49 mer | 264 |
| GTAGCAACGGCTACAGAGGCTTAGTTGCTA TTTTGCACCCAGATGGTGG | 20170407_cc6hb_v3-1_queen, c13, h18, p1, 7 bp plug, cyan, start 14[220], end 18[641], 49 mer | 265 |

TABLE 1-continued

Exemplary Gridiron Queen Staple Sequences

| Sequence | Comment | SEQ ID NO: |
|---|---|---|
| GATATTCATTACCCAAATCAACAGTTAATGC CCCCTGCCTATCGGTCCA | 20170407_cc6hb_v3-1_queen, c13, h17, p0, 7 bp plug, cyan, start 13[221], end 17[640], 49 mer | 266 |
| CTAAAACACTCATCTTTGACCCTGACCTGAA AGCGTAAGAATCGGTCCA | 20170407_cc6hb_v3-1_queen, c14, h21, p0, 7 bp plug, cyan, start 14[94], end 21[682], 49 mer | 267 |
| CGAATAATAATTTTTTCACGTATCACCTTGC TGAACCTCAAAATGGTGG | 20170407_cc6hb_v3-1_queen, c14, h20, p1, 7 bp plug, cyan, start 15[95], end 20[683], 49 mer | 268 |
| ATGAGGAAGTTTCCATTAAACATCCTAATTT ACGAGCATGTAAATAGCC | 20170407_cc6hb_v3-1_queen, c14, h19, p2, 7 bp plug, cyan, start 14[178], end 19[682], 49 mer | 269 |
| TTCGAGGTGAATTTCTTAAACACCTCCCGAC TTGCGGGAGGTAGAGTCC | 20170407_cc6hb_v3-1_queen, c14, h18, p3, 7 bp plug, cyan, start 15[179], end 18[683], 49 mer | 270 |
| GGATCGTCACCCTCAGCAGCGACATGAAAG TATTAAGAGGCTGAAAAAC | 20170407_cc6hb_v3-1_queen, c14, h17, p4, 7 bp plug, cyan, start 14[262], end 17[682], 49 mer | 271 |
| TTTCAGCGGAGTGAGAATAGATGAATGGCT ATTAGTCTTTAAGAAAAAC | 20170407_cc6hb_v3-1_queen, c15, h21, p4, 7 bp plug, cyan, start 15[53], end 21[724], 49 mer | 272 |
| CTACAACGCCTGTAGCATTCCAGTGCCACG CTGAGAGCCAGCAGAGTCC | 20170407_cc6hb_v3-1_queen, c15, h20, p3, 7 bp plug, cyan, start 16[136], end 20[725], 49 mer | 273 |
| CTCCAAAAGGAGCCTTTAATTGTCTTTCCTT ATCATTCCAAGAATAGCC | 20170407_cc6hb_v3-1_queen, c15, h19, p2, 7 bp plug, cyan, start 15[137], end 19[724], 49 mer | 274 |
| CAGAGCCACCACCCTCATTTTAAGGCTTATC CGGTATTCTAAATGGTGG | 20170407_cc6hb_v3-1_queen, c15, h18, p1, 7 bp plug, cyan, start 16[220], end 18[725], 49 mer | 275 |
| CCGACAATGACAACAACCATCTAGGATTAG CGGGGTTTTGCTCGGTCCA | 20170407_cc6hb_v3-1_queen, c15, h17, p0, 7 bp plug, cyan, start 15[221], end 17[724], 49 mer | 276 |
| ATCTGAACTCGCTACGGCGGGGGGAGCCCC CGATTTAGAGCTCGGTCCACGC | 20170407_cc6hb_v3-1_queen, c0, h21, p0, 10 bp plug, cyan, start 0[94], end 21[94], 52 mer | 277 |
| CATTGCTGATACCGTTTAGCTAACAAACATC AAGAAAACAAAATGGTGGTTC | 20170407_cc6hb_v3-1_queen, c0, h20, p1, 10 bp plug, cyan, start 1[95], end 20[95], 52 mer | 278 |
| GATACTTGCCCTCTCTGTACATAATTAATTT TCCCTTAGAATAATAGCCCGA | 20170407_cc6hb_v3-1_queen, c0, h19, p2, 10 bp plug, cyan, start 0[178], end 19[94], 52 mer | 279 |
| GATTGGGCGTTATCAATGTTGTTTTGTCACA ATCAATAGAAAAGAGTCCACT | 20170407_cc6hb_v3-1_queen, c0, h18, p3, 10 bp plug, cyan, start 1[179], end 18[95], 52 mer | 280 |
| TCTAATGAAGACAAATCCCCACGTCACCGA CTTGAGCCATTTGAAAAACCGT | 20170407_cc6hb_v3-1_queen, c0, h17, p4, 10 bp plug, cyan, start 0[262], end 17[94], 52 mer | 281 |
| AAACATCGGGTTGAGTATTATGTGGCGAGA AAGGAAGGGAAGGAAAAACCGT | 20170407_cc6hb_v3-1_queen, c1, h21, p4, 10 bp plug, cyan, start 1[53], end 21[136], 52 mer | 282 |
| CGCTGGCATTCGCATCAAAGGCGAATTATT CATTTCAATTACAGAGTCCACT | 20170407_cc6hb_v3-1_queen, c1, h20, p3, 10 bp plug, cyan, start 2[136], end 20[137], 52 mer | 283 |
| AGTTTATAAATGAGTATCAATTTAGATTAAG ACGCTGAGAAGAATAGCCCGA | 20170407_cc6hb_v3-1_queen, c1, h19, p2, 10 bp plug, cyan, start 1[137], end 19[136], 52 mer | 284 |
| TATCGACATCATTACGCATCGCAACATATA AAAGAAACGCAAATGGTGGTTC | 20170407_cc6hb_v3-1_queen, c1, h18, p1, 10 bp plug, cyan, start 2[220], end 18[137], 52 mer | 285 |
| CCATGCAGACATCACGAAGGTCACCAGTAG CACCATTACCATCGGTCCACGC | 20170407_cc6hb_v3-1_queen, c1, h17, p0, 10 bp plug, cyan, start 1[221], end 17[136], 52 mer | 286 |
| AAGATAACGCTTGTGAAAATGAGGGCGCTG GCAAGTGTAGCGCGGTCCACGC | 20170407_cc6hb_v3-1_queen, c2, h21, p0, 10 bp plug, cyan, start 2[94], end 21[178], 52 mer | 287 |
| GCTAACAGTAGGGAAACTGCGGCCTGATTG CTTTGAATACCAATGGTGGTTC | 20170407_cc6hb_v3-1_queen, c2, h20, p1, 10 bp plug, cyan, start 3[95], end 20[179], 52 mer | 288 |
| ATGGGTTCAGGATGCAGGTGAAATCATAGG TCTGAGAGACTAAATAGCCCGA | 20170407_cc6hb_v3-1_queen, c2, h19, p2, 10 bp plug, cyan, start 2[178], end 19[178], 52 mer | 289 |

TABLE 1-continued

Exemplary Gridiron Queen Staple Sequences

| Sequence | Comment | SEQ ID NO: |
|---|---|---|
| CTCGGATGGGAGTAAGCGTATGCAGTATGT TAGCAAACGTAGAGAGTCCACT | 20170407_cc6hb_v3-1_queen, c2, h18, p3, 10 bp plug, cyan, start 3[179], end 18[179], 52 mer | 290 |
| AGAGTTTCTGCGGCAGTTAATCAATGAAAC CATCGATAGCAGGAAAAACCGT | 20170407_cc6hb_v3-1_queen, c2, h17, p4, 10 bp plug, cyan, start 2[262], end 17[178], 52 mer | 291 |
| GCAATACATCAAACGCCGCGAACACCCGCC GCGCTTAATGCGGAAAAACCGT | 20170407_cc6hb_v3-1_queen, c3, h21, p4, 10 bp plug, cyan, start 3[53], end 21[220], 52 mer | 292 |
| TCAGGCACTGCGTGAAGCGGCAGTAACAGT ACCTTTTACATCAGAGTCCACT | 20170407_cc6hb_v3-1_queen, c3, h20, p3, 10 bp plug, cyan, start 4[136], end 20[221], 52 mer | 293 |
| ATCAAAACTCAACGAGCAGCGGTTGGGTTA TATAACTATATGAATAGCCCGA | 20170407_cc6hb_v3-1_queen, c3, h19, p2, 10 bp plug, cyan, start 3[137], end 19[220], 52 mer | 294 |
| AGGGTTGTCGGACTTGTGCAAGGAATACCC AAAAGAACTGGCATGGTGGTTC | 20170407_cc6hb_v3-1_queen, c3, h18, p1, 10 bp plug, cyan, start 4[220], end 18[221], 52 mer | 295 |
| AGTCCGTGAAGACGGAAACCAAATCAAGTT TGCCTTTAGCGTCGGTCCACGC | 20170407_cc6hb_v3-1_queen, c3, h17, p0, 10 bp plug, cyan, start 3[221], end 17[220], 52 mer | 296 |
| CTGGGGATTTGACGCAGACCTGGTTGCTTTG ACGAGCACGTACGGTCCACGC | 20170407_cc6hb_v3-1_queen, c4, h21, p0, 10 bp plug, cyan, start 4[94], end 21[262], 52 mer | 297 |
| TTTTCCCAGTCACGACGTTGTGAAATTGCGT AGATTTTCAGGATGGTGGTTC | 20170407_cc6hb_v3-1_queen, c4, h20, p1, 10 bp plug, cyan, start 5[95], end 20[263], 52 mer | 298 |
| TTATCAGTAAACAGAGAGGTTTCGCAAGAC AAAGAACGCGAGAATAGCCCGA | 20170407_cc6hb_v3-1_queen, c4, h19, p2, 10 bp plug, cyan, start 4[178], end 19[262], 52 mer | 299 |
| TCAGGGATTAATGAAAGATGGAACAAAGTT ACCAGAAGGAAAAGAGTCCACT | 20170407_cc6hb_v3-1_queen, c4, h18, p3, 10 bp plug, cyan, start 5[179], end 18[263], 52 mer | 300 |
| AGTGTGGCGATCCGATAGATGCGGCATTTT CGGTCATAGCCCGAAAAACCGT | 20170407_cc6hb_v3-1_queen, c4, h17, p4, 10 bp plug, cyan, start 4[262], end 17[262], 52 mer | 301 |
| GGGGGATGTGCTGCAAGGCGAATCAGAGCG GGAGCTAAACAGGAAAAACCGT | 20170407_cc6hb_v3-1_queen, c5, h21, p4, 10 bp plug, cyan, start 5[53], end 21[304], 52 mer | 302 |
| AGCCAGCTTTCCGGCACCGCTACCTACCATA TCAAAATTATTAGAGTCCACT | 20170407_cc6hb_v3-1_queen, c5, h20, p3, 10 bp plug, cyan, start 6[136], end 20[305], 52 mer | 303 |
| CTTTATTATTCGCATTCACCCTAGTTAATTTC ATCTTCTGACAATAGCCCGA | 20170407_cc6hb_v3-1_queen, c5, h19, p2, 10 bp plug, cyan, start 5[137], end 19[304], 52 mer | 304 |
| TTGGTGTAGATGGGCGCATCGATCTTACCG AAGCCCTTTTTAATGGTGGTTC | 20170407_cc6hb_v3-1_queen, c5, h18, p1, 10 bp plug, cyan, start 6[220], end 18[305], 52 mer | 305 |
| CAGAAATAGAAGAATTACAGCTTTCATAAT CAAAATCACCGGCGGTCCACGC | 20170407_cc6hb_v3-1_queen, c5, h17, p0, 10 bp plug, cyan, start 5[221], end 17[304], 52 mer | 306 |
| AAGCGCCATTCGCCATTCAGGAGACAGGAA CGGTACGCCAGACGGTCCACGC | 20170407_cc6hb_v3-1_queen, c6, h21, p0, 10 bp plug, cyan, start 6[94], end 21[346], 52 mer | 307 |
| TCAGAAAAGCCCCAAAAACAGCTGATTGTT TGGATTATACTTATGGTGGTTC | 20170407_cc6hb_v3-1_queen, c6, h20, p1, 10 bp plug, cyan, start 7[95], end 20[347], 52 mer | 308 |
| GAGGGGACGACGACAGTATCGACCGACCGT GTGATAAATAAGAATAGCCCGA | 20170407_cc6hb_v3-1_queen, c6, h19, p2, 10 bp plug, cyan, start 6[178], end 19[346], 52 mer | 309 |
| TTTTTGTTAAATCAGCTCATTAGCCCAATAA TAAGAGCAAGAAGAGTCCACT | 20170407_cc6hb_v3-1_queen, c6, h18, p3, 10 bp plug, cyan, start 7[179], end 18[347], 52 mer | 310 |
| GTGGGAACAAACGGCGGATTGCGCCTCCCT CAGAGCCGCCACGAAAAACCGT | 20170407_cc6hb_v3-1_queen, c6, h17, p4, 10 bp plug, cyan, start 6[262], end 17[346], 52 mer | 311 |
| CGAACGAGTAGATTTAGTTTGACTTGCCTGA GTAGAAGAACTGAAAAACCGT | 20170407_cc6hb_v3-1_queen, c9, h21, p4, 10 bp plug, cyan, start 9[53], end 21[472], 52 mer | 312 |
| CATTTTTGCGGATGGCTTAGACCGAACGTTA TTAATTTTAAAAGAGTCCACT | 20170407_cc6hb_v3-1_queen, c9, h20, p3, 10 bp plug, cyan, start 10[136], end 20[473], 52 mer | 313 |

TABLE 1-continued

| Exemplary Gridiron Queen Staple Sequences | | |
|---|---|---|
| Sequence | Comment | SEQ ID NO: |
| AGCTGAAAAGGTGGCATCAATTAGGGCTTA ATTGAGAATCGCAATAGCCCGA | 20170407_cc6hb_v3-1_queen, c9, h19, p2, 10 bp plug, cyan, start 9[137], end 19[472], 52 mer | 314 |
| AGCTTCAAAGCGAACCAGACCTTTACAGAG AGAATAACATAAATGGTGGTTC | 20170407_cc6hb_v3-1_queen, c9, h18, p1, 10 bp plug, cyan, start 10[220], end 18[473], 52 mer | 315 |
| ATTAAGCAATAAAGCCTCAGAGGCCTTGAT ATTCACAAACAACGGTCCACGC | 20170407_cc6hb_v3-1_queen, c9, h17, p0, 10 bp plug, cyan, start 9[221], end 17[472], 52 mer | 316 |
| CTGTAGCTCAACATGTTTTAAAATATCCAGA ACAATATTACCCGGTCCACGC | 20170407_cc6hb_v3-1_queen, c10, h21, p0, 10 bp plug, cyan, start 10[94], end 21[514], 52 mer | 317 |
| GGCTTTTGCAAAAGAAGTTTTAGACTTTACA AACAATTCGACATGGTGGTTC | 20170407_cc6hb_v3-1_queen, c10, h20, p1, 10 bp plug, cyan, start 11[95], end 20[515], 52 mer | 318 |
| AGGATTAGAGAGTACCTTTAAGTAATTTAG GCAGAGGCATTTAATAGCCCGA | 20170407_cc6hb_v3-1_queen, c10, h19, p2, 10 bp plug, cyan, start 10[178], end 19[514], 52 mer | 319 |
| AATATTCATTGAATCCCCCTCGAAACGATTT TTTGTTTAACGAGAGTCCACT | 20170407_cc6hb_v3-1_queen, c10, h18, p3, 10 bp plug, cyan, start 11[179], end 18[515], 52 mer | 320 |
| AAGAGGAAGCCCGAAAGACTTAATGGAAA GCGCAGTCTCTGAGAAAAACCGT | 20170407_cc6hb_v3-1_queen, c10, h17, p4, 10 bp plug, cyan, start 10[262], end 17[514], 52 mer | 321 |
| ACCCTCGTTTACCAGACGACGAACGCTCAT GGAAATACCTACGAAAAACCGT | 20170407_cc6hb_v3-1_queen, c11, h21, p4, 10 bp plug, cyan, start 11[53], end 21[556], 52 mer | 322 |
| TAACGGAACAACATTATTACAAGAGCCGTC AATAGATAATACAGAGTCCACT | 20170407_cc6hb_v3-1_queen, c11, h20, p3, 10 bp plug, cyan, start 12[136], end 20[557], 52 mer | 323 |
| ATGTTTAGACTGGATAGCGTCATAAAGTAC CGACAAAAGGTAAATAGCCCGA | 20170407_cc6hb_v3-1_queen, c11, h19, p2, 10 bp plug, cyan, start 11[137], end 19[556], 52 mer | 324 |
| TGAATTACCTTATGCGATTTTTTACAAAATA AACAGCCATATATGGTGGTTC | 20170407_cc6hb_v3-1_queen, c11, h18, p1, 10 bp plug, cyan, start 12[220], end 18[557], 52 mer | 325 |
| AAACGAGAATGACCATAAATCCATACATGG CTTTTGATGATACGGTCCACGC | 20170407_cc6hb_v3-1_queen, c11, h17, p0, 10 bp plug, cyan, start 11[221], end 17[556], 52 mer | 326 |
| AGATTTAGGAATACCACATTCAAATGGATT ATTTACATTGGCCGGTCCACGC | 20170407_cc6hb_v3-1_queen, c12, h21, p0, 10 bp plug, cyan, start 12[94], end 21[598], 52 mer | 327 |
| CGAGGCGCAGACGGTCAATCAGTTATCTAA AATATCTTTAGGATGGTGGTTC | 20170407_cc6hb_v3-1_queen, c12, h20, p1, 10 bp plug, cyan, start 13[95], end 20[599], 52 mer | 328 |
| GTCAGGACGTTGGGAAGAAAAGACAATAA ACAACATGTTCAGAATAGCCCGA | 20170407_cc6hb_v3-1_queen, c12, h19, p2, 10 bp plug, cyan, start 12[178], end 19[598], 52 mer | 329 |
| AGGCTGGCTGACCTTCATCAATACCAACGC TAACGAGCGTCTAGAGTCCACT | 20170407_cc6hb_v3-1_queen, c12, h18, p3, 10 bp plug, cyan, start 13[179], end 18[599], 52 mer | 330 |
| TAAATTGGGCTTGAGATGGTTTTTAACGGG GTCAGTGCCTTGAAAAACCGT | 20170407_cc6hb_v3-1_queen, c12, h17, p4, 10 bp plug, cyan, start 12[262], end 17[598], 52 mer | 331 |
| TGTGTCGAAATCCGCGACCTGAGTAATAAA AGGGACATTCTGGAAAAACCGT | 20170407_cc6hb_v3-1_queen, c13, h21, p4, 10 bp plug, cyan, start 13[53], end 21[640], 52 mer | 332 |
| TACGAAGGCACCAACCTAAAACTGGTCAGT TGGCAAATCAACAGAGTCCACT | 20170407_cc6hb_v3-1_queen, c13, h20, p3, 10 bp plug, cyan, start 14[136], end 20[641], 52 mer | 333 |
| CTTTGAAAGAGGACAGATGAATATCAACAA TAGATAAGTCCTAATAGCCCGA | 20170407_cc6hb_v3-1_queen, c13, h19, p2, 10 bp plug, cyan, start 13[137], end 19[640], 52 mer | 334 |
| GTAGCAACGGCTACAGAGGCTTAGTTGCTA TTTTGCACCCAGATGGTGGTTC | 20170407_cc6hb_v3-1_queen, c13, h18, p1, 10 bp plug, cyan, start 14[220], end 18[641], 52 mer | 335 |
| GATATTCATTACCCAAATCAACAGTTAATGC CCCCTGCCTATCGGTCCACGC | 20170407_cc6hb_v3-1_queen, c13, h17, p0, 10 bp plug, cyan, start 13[221], end 17[640], 52 mer | 336 |
| CTAAAACACTCATCTTTGACCCTGACCTGAA AGCGTAAGAATCGGTCCACGC | 20170407_cc6hb_v3-1_queen, c14, h21, p0, 10 bp plug, cyan, start 14[94], end 21[682], 52 mer | 337 |

TABLE 1-continued

Exemplary Gridiron Queen Staple Sequences

| Sequence | Comment | SEQ ID NO: |
|---|---|---|
| CGAATAATAATTTTTTCACGTATCACCTTGC TGAACCTCAAAATGGTGGTTC | 20170407_cc6hb_v3-1_queen, c14, h20, p1, 10 bp plug, cyan, start 15[95], end 20[683], 52 mer | 338 |
| ATGAGGAAGTTTCCATTAAACATCCTAATTT ACGAGCATGTAAATAGCCCGA | 20170407_cc6hb_v3-1_queen, c14, h19, p2, 10 bp plug, cyan, start 14[178], end 19[682], 52 mer | 339 |
| TTCGAGGTGAATTTCTTAAACACCTCCCGAC TTGCGGGAGGTAGAGTCCACT | 20170407_cc6hb_v3-1_queen, c14, h18, p3, 10 bp plug, cyan, start 15[179], end 18[683], 52 mer | 340 |
| GGATCGTCACCCTCAGCAGCGACATGAAAG TATTAAGAGGCTGAAAAACCGT | 20170407_cc6hb_v3-1_queen, c14, h17, p4, 10 bp plug, cyan, start 14[262], end 17[682], 52 mer | 341 |
| TTTCAGCGGAGTGAGAATAGATGAATGGCT ATTAGTCTTTAAGAAAAACCGT | 20170407_cc6hb_v3-1_queen, c15, h21, p4, 10 bp plug, cyan, start 15[53], end 21[724], 52 mer | 342 |
| CTACAACGCCTGTAGCATTCCAGTGCCACG CTGAGAGCCAGCAGAGTCCACT | 20170407_cc6hb_v3-1_queen, c15, h20, p3, 10 bp plug, cyan, start 16[136], end 20[725], 52 mer | 343 |
| CTCCAAAAGGAGCCTTTAATTGTCTTTCCTT ATCATTCCAAGAATAGCCCGA | 20170407_cc6hb_v3-1_queen, c15, h19, p2, 10 bp plug, cyan, start 15[137], end 19[724], 52 mer | 344 |
| CAGAGCCACCACCCTCATTTTAAGGCTTATC CGGTATTCTAAATGGTGGTTC | 20170407_cc6hb_v3-1_queen, c15, h18, p1, 10 bp plug, cyan, start 16[220], end 18[725], 52 mer | 345 |
| CCGACAATGACAACAACCATCTAGGATTAG CGGGGTTTTGCTCGGTCCACGC | 20170407_cc6hb_v3-1_queen, c15, h17, p0, 10 bp plug, cyan, start 15[221], end 17[724], 52 mer | 346 |

TABLE 2

Exemplary 250 nm Six-helix Bundle Sequences

| Sequence | Comment | SEQ ID NO: |
|---|---|---|
| TCATCAACATTAAAAGAACGCGAGAAAATT GTTAAATCAGACCGTGCAT | 20170608 cc6hb v4-base 250 nm 6hb, grey standard seq, start 0[41], end 4[21], 49 mer | 347 |
| TAATCGTAAAACTAATCTTCTGACCTAAAGC TATTTTTGATA | 20170608 cc6hb v4-base 250 nm 6hb, grey standard seq, start 0[83], end 4[70], 42 mer | 348 |
| ATATATTTTAAATGGATAAATAAGGCGTAA AAACATTATGTC | 20170608 cc6hb v4-base 250 nm 6hb, grey standard seq, start 0[125], end 4[112], 42 mer | 349 |
| GCGAGCTGAAAAGGTTACTAGAAAAAGCAC GAGTAGATTTCT | 20170608 cc6hb v4-base 250 nm 6hb, grey standard seq, start 0[167], end 4[154], 42 mer | 350 |
| GGTCATTTTTGCGGTTCTTACCAGTATATTC AAAGCGAACCC | 20170608 cc6hb v4-base 250 nm 6hb, grey standard seq, start 0[209], end 4[196], 42 mer | 351 |
| AGAAAACGAGAATGTGAGAATCGCCATATT TAGACTGGATAG | 20170608 cc6hb v4-base 250 nm 6hb, grey standard seq, start 0[251], end 4[238], 42 mer | 352 |
| ACGCCAAAAGGAATAGAGGCATTTTCGACG GAACAACATTAG | 20170608 cc6hb v4-base 250 nm 6hb, grey standard seq, start 0[293], end 4[280], 42 mer | 353 |
| TAGTAAATTGGGCTACAAAAGGTAAAGTAT TCATTACCCAAG | 20170608 cc6hb v4-base 250 nm 6hb, grey standard seq, start 0[335], end 4[322], 42 mer | 354 |
| GAACGAGGCGCAGAACATGTTCAGCTAAAC AAAGTACAACCA | 20170608 cc6hb v4-base 250 nm 6hb, grey standard seq, start 0[377], end 4[364], 42 mer | 355 |
| TTCATGAGGAAGTTGATAAGTCCTGAACTC GTCACCCTCATT | 20170608 cc6hb v4-base 250 nm 6hb, grey standard seq, start 0[419], end 4[406], 42 mer | 356 |
| GCTTTCGAGGTGAACGAGCATGTAGAAAAT AATAATTTTTTG | 20170608 cc6hb v4-base 250 nm 6hb, grey standard seq, start 0[461], end 4[448], 42 mer | 357 |
| TAGCGTAACGATCTTCATTCCAAGAACGCC CATGTACCGTAA | 20170608 cc6hb v4-base 250 nm 6hb, grey standard seq, start 0[503], end 4[490], 42 mer | 358 |

TABLE 2-continued

Exemplary 250 nm Six-helix Bundle Sequences

| Sequence | Comment | SEQ ID NO: |
|---|---|---|
| AAGTATAGCCCGGAAGAACAAGCAAGCCAC TCCTCAAGAGCA | 20170608 cc6hb v4-base 250 nm 6hb, grey standard seq, start 0[545], end 4[532], 42 mer | 359 |
| ATACAGGAGTGTACCCGCGCCCAATAGCAA TCCTCATTAATC | 20170608 cc6hb v4-base 250 nm 6hb, grey standard seq, start 0[587], end 4[574], 42 mer | 360 |
| CACCCTCAGAACCGGGTATTCTAAGAACTA TTAGCGTTTGAC | 20170608 cc6hb v4-base 250 nm 6hb, grey standard seq, start 0[629], end 4[616], 42 mer | 361 |
| CATTAGCAAGGCCGTGCGGGAGGTTTTGTT AAAGGTGAATTT | 20170608 cc6hb v4-base 250 nm 6hb, grey standard seq, start 0[671], end 4[658], 42 mer | 362 |
| CAAAGACACCACGGTTGCACCCAGCTACAT TAAGACTCCTGG | 20170608 cc6hb v4-base 250 nm 6hb, grey standard seq, start 0[713], end 4[700], 42 mer | 363 |
| AGAAACAATGAAATACGAGCGTCTTTCCGA ATTAACTGAAAA | 20170608 cc6hb v4-base 250 nm 6hb, grey standard seq, start 0[755], end 4[742], 42 mer | 364 |
| GAACAAACGGCGGATTGACAATAATTCG | 20170608 cc6hb v4-base 250 nm 6hb, grey standard seq, start 1[7], end 1[34], 28 mer | 365 |
| CGTCTGGCCTTCCTGTCCCGGTTGATAATCA GAAGAGTCTGG | 20170608 cc6hb v4-base 250 nm 6hb, grey standard seq, start 1[35], end 1[76], 42 mer | 366 |
| AGCAAACAAGAGAATCAGGTAAAGATTCAA AAGTTTCAACGC | 20170608 cc6hb v4-base 250 nm 6hb, grey standard seq, start 1[77], end 1[118], 42 mer | 367 |
| AAGGATAAAAATTTTTAGTAGTAGCATTAA CATCAATAACCT | 20170608 cc6hb v4-base 250 nm 6hb, grey standard seq, start 1[119], end 1[160], 42 mer | 368 |
| GTTTAGCTATATTTTCCTGAATATAATGCTG TATAGAGAGTA | 20170608 cc6hb v4-base 250 nm 6hb, grey standard seq, start 1[161], end 1[202], 42 mer | 369 |
| CCTTTAATTGCTCCTTGTCTTTACCCTGACTA TTCATTGAAT | 20170608 cc6hb v4-base 250 nm 6hb, grey standard seq, start 1[203], end 1[244], 42 mer | 370 |
| CCCCCTCAAATGCTTTAACACTATCATAACC CTTAGGAATAC | 20170608 cc6hb v4-base 250 nm 6hb, grey standard seq, start 1[245], end 1[286], 42 mer | 371 |
| CACATTCAACTAATGCCTTTAATCATTGTGA ATTAAGGCTTG | 20170608 cc6hb v4-base 250 nm 6hb, grey standard seq, start 1[287], end 1[328], 42 mer | 372 |
| CCCTGACGAGAAACACCGAACTGACCAACT TTGCGAAATCCG | 20170608 cc6hb v4-base 250 nm 6hb, grey standard seq, start 1[329], end 1[370], 42 mer | 373 |
| CGACCTGCTCCATGTTACGTAATGCCACTAC GAAACGGCTAC | 20170608 cc6hb v4-base 250 nm 6hb, grey standard seq, start 1[371], end 1[412], 42 mer | 374 |
| AGAGGCTTTGAGGACTCCGATAGTTGCGCC GACAAAGGAGCC | 20170608 cc6hb v4-base 250 nm 6hb, grey standard seq, start 1[413], end 1[454], 42 mer | 375 |
| TTTAATTGTATCGGTTAGACGTTAGTAAATG AAACGCCTGTA | 20170608 cc6hb v4-base 250 nm 6hb, grey standard seq, start 1[455], end 1[496], 42 mer | 376 |
| GCATTCCACAGACAGCCAGGAGGTTTAGTA CCGCCAGGCGGA | 20170608 cc6hb v4-base 250 nm 6hb, grey standard seq, start 1[497], end 1[538], 42 mer | 377 |
| TAAGTGCCGTCGAGAGGGTCAGTGCCTTGA GTACCGTTCCAG | 20170608 cc6hb v4-base 250 nm 6hb, grey standard seq, start 1[539], end 1[580], 42 mer | 378 |
| TAAGCGTCATACATGGCCTCAGAGCCGCCA CCAGAGCCACCA | 20170608 cc6hb v4-base 250 nm 6hb, grey standard seq, start 1[581], end 1[622], 42 mer | 379 |
| CCGGAACCGCCTCCCTCATCGATAGCAGCA CCGTTAGAGCCA | 20170608 cc6hb v4-base 250 nm 6hb, grey standard seq, start 1[623], end 1[664], 42 mer | 380 |
| GCAAAATCACCAGTAGAATCAATAGAAAAT TCAACATACATA | 20170608 cc6hb v4-base 250 nm 6hb, grey standard seq, start 1[665], end 1[706], 42 mer | 381 |
| AAGGTGGCAACATATAAAGCCCTTTTTAAG AAAAGAATTGAGTTAAGCC | 20170608 cc6hb v4-base 250 nm 6hb, grey standard seq, start 1[707], end 1[755], 49 mer | 382 |

TABLE 2-continued

Exemplary 250 nm Six-helix Bundle Sequences

| Sequence | Comment | SEQ ID NO: |
|---|---|---|
| ACAGGAAGATTGAATAGGAACGCCATCAAA CGTAATGGGATA | 20170608 cc6hb v4-base 250 nm 6hb, grey standard seq, start 2[55], end 2[14], 42 mer | 383 |
| AGATGGGCGCATCGTACTCATTTTTTAACCT ATAA | 20170608 cc6hb v4-base 250 nm 6hb, grey standard seq, start 3[14], end 3[48], 35 mer | 384 |
| GCAAATATTTAAATTGTAAACGTGAGATCT ACAAAGGAATCA | 20170608 cc6hb v4-base 250 nm 6hb, grey standard seq, start 3[49], end 3[90], 42 mer | 385 |
| CCATCAATATGATATTCAACCGTACCCTGTA ATACTTAAGAA | 20170608 cc6hb v4-base 250 nm 6hb, grey standard seq, start 3[91], end 3[132], 42 mer | 386 |
| TTAGCAAAATTAAGCAATAAAGCAGTTTGA CCATTAGCTAAA | 20170608 cc6hb v4-base 250 nm 6hb, grey standard seq, start 3[133], end 3[174], 42 mer | 387 |
| GTACGGTGTCTGGAAGTTTCATTCAGACCGG AAGCAACATCA | 20170608 cc6hb v4-base 250 nm 6hb, grey standard seq, start 3[175], end 3[216], 42 mer | 388 |
| AAAAGATTAAGAGGAAGCCCGAAAGCGTCC AATACTGCAAAA | 20170608 cc6hb v4-base 250 nm 6hb, grey standard seq, start 3[217], end 3[258], 42 mer | 389 |
| TAGCGAGAGGCTTTTGCAAAAGAATTACAG GTAGAAAGCTCA | 20170608 cc6hb v4-base 250 nm 6hb, grey standard seq, start 3[259], end 3[300], 42 mer | 390 |
| TTATACCAGTCAGGACGTTGGGAAATCAAC GTAACAAAGACC | 20170608 cc6hb v4-base 250 nm 6hb, grey standard seq, start 3[301], end 3[342], 42 mer | 391 |
| AGGCGCATAGGCTGGCTGACCTTGGAGATT TGTATCAGCAAA | 20170608 cc6hb v4-base 250 nm 6hb, grey standard seq, start 3[343], end 3[384], 42 mer | 392 |
| AGAATACACTAAAACACTCATCTGCAGCGA AAGACAGATAAC | 20170608 cc6hb v4-base 250 nm 6hb, grey standard seq, start 3[385], end 3[426], 42 mer | 393 |
| CGATATATTCGGTCGCTGAGGCTTCACGTTG AAAATCCAACT | 20170608 cc6hb v4-base 250 nm 6hb, grey standard seq, start 3[427], end 3[468], 42 mer | 394 |
| TTCAACAGTTTCAGCGGAGTGAGAACACTG AGTTTCGGAACC | 20170608 cc6hb v4-base 250 nm 6hb, grey standard seq, start 3[469], end 3[510], 42 mer | 395 |
| GCCACCCTCAGAGCCACCACCCTAAGGATT AGGATTAGCCCC | 20170608 cc6hb v4-base 250 nm 6hb, grey standard seq, start 3[511], end 3[552], 42 mer | 396 |
| CTGCCTATTTCGGAACCTATTATAGCCAGAA TGGAAAGCATT | 20170608 cc6hb v4-base 250 nm 6hb, grey standard seq, start 3[553], end 3[594], 42 mer | 397 |
| GACAGGAGGTTGAGGCAGGTCAGCCATCTT TTCATAATTGCC | 20170608 cc6hb v4-base 250 nm 6hb, grey standard seq, start 3[595], end 3[636], 42 mer | 398 |
| TTTAGCGTCAGACTGTAGCGCGTTATCACCG TCACCGAAAGG | 20170608 cc6hb v4-base 250 nm 6hb, grey standard seq, start 3[637], end 3[678], 42 mer | 399 |
| GCGACATTCAACCGATTGAGGGATATTACG CAGTATGTACCA | 20170608 cc6hb v4-base 250 nm 6hb, grey standard seq, start 3[679], end 3[720], 42 mer | 400 |
| GAAGGAAACCGAGGAAACGCAATCACCCTG AACAAAGTCAGATAATATC | 20170608 cc6hb v4-base 250 nm 6hb, grey standard seq, start 3[721], end 2[756], 49 mer | 401 |
| ATATTTTGTTAAAATTCGCATTAAATTTCTTT TTCAAATATA | 20170608 cc6hb v4-base 250 nm 6hb, grey standard seq, start 4[69], end 5[55], 42 mer | 402 |
| TAGCTGATAAATTAATGCCGGAGAGGGTAT TTAATGGTTTGA | 20170608 cc6hb v4-base 250 nm 6hb, grey standard seq, start 4[111], end 5[97], 42 mer | 403 |
| CAGAGCATAAAGCTAAATCGGTTGTACCTA AATAAGAATAAA | 20170608 cc6hb v4-base 250 nm 6hb, grey standard seq, start 4[153], end 5[139], 42 mer | 404 |
| ATATAACAGTTGATTCCCAATTCTGCGACTG TTTAGTATCAT | 20170608 cc6hb v4-base 250 nm 6hb, grey standard seq, start 4[195], end 5[181], 42 mer | 405 |
| ACTTCAAATATCGCGTTTTAATTCGAGCAAG CCAACGCTCAA | 20170608 cc6hb v4-base 250 nm 6hb, grey standard seq, start 4[237], end 5[223], 42 mer | 406 |

TABLE 2-continued

Exemplary 250 nm Six-helix Bundle Sequences

| Sequence | Comment | SEQ ID NO: |
|---|---|---|
| TTTTGCCAGAGGGGGTAATAGTAAAATGTTTAACAACGCCAA | 20170608 cc6hb v4-base 250 nm 6hb, grey standard seq, start 4[279], end 5[265], 42 mer | 407 |
| AAAAATCTACGTTAATAAAACGAACTAAGCCAGTAATAAGAG | 20170608 cc6hb v4-base 250 nm 6hb, grey standard seq, start 4[321], end 5[307], 42 mer | 408 |
| TCAAGAGTAATCTTGACAAGAACCGGATAATTCTGTCCAGAC | 20170608 cc6hb v4-base 250 nm 6hb, grey standard seq, start 4[363], end 5[349], 42 mer | 409 |
| GACCCCCAGCGATTATACCAAGCGCGAATGCAGAACGCGCCT | 20170608 cc6hb v4-base 250 nm 6hb, grey standard seq, start 4[405], end 5[391], 42 mer | 410 |
| CAGGGAGTTAAAGGCCGCTTTTGCGGGAAAGAAAAATAATAT | 20170608 cc6hb v4-base 250 nm 6hb, grey standard seq, start 4[447], end 5[433], 42 mer | 411 |
| TAGAAAGGAACAACTAAAGGAATTGCGACCAATCAATAATCG | 20170608 cc6hb v4-base 250 nm 6hb, grey standard seq, start 4[489], end 5[475], 42 mer | 412 |
| TTTTCAGGGATAGCAAGCCCAATAGGAAGGTATTAAACCAAG | 20170608 cc6hb v4-base 250 nm 6hb, grey standard seq, start 4[531], end 5[517], 42 mer | 413 |
| TGAAACATGAAAGTATTAAGAGGCTGAGGTTTTTATTTTCAT | 20170608 cc6hb v4-base 250 nm 6hb, grey standard seq, start 4[573], end 5[559], 42 mer | 414 |
| GATTGGCCTTGATATTCACAAACAAATAAAGCAAATCAGATA | 20170608 cc6hb v4-base 250 nm 6hb, grey standard seq, start 4[615], end 5[601], 42 mer | 415 |
| TCATCGGCATTTTCGGTCATAGCCCCCTGCGAGGCGTTTTAG | 20170608 cc6hb v4-base 250 nm 6hb, grey standard seq, start 4[657], end 5[643], 42 mer | 416 |
| GAAGGTAAATATTGACGGAAATTATTCAAAGCCTTAAATCAA | 20170608 cc6hb v4-base 250 nm 6hb, grey standard seq, start 4[699], end 5[685], 42 mer | 417 |
| TAACGGAATACCCAAAAGAACTGGCATGAATTTTATCCTGAA | 20170608 cc6hb v4-base 250 nm 6hb, grey standard seq, start 4[741], end 5[727], 42 mer | 418 |
| CGCATTAGACGGGAAGAGCCT | 20170608 cc6hb v4-base 250 nm 6hb, grey standard seq, start 4[769], end 5[762], 21 mer | 419 |
| AAGACAATGTGAGCGAGTAACAACCCGT | 20170608 cc6hb v4-base 250 nm 6hb, grey standard seq, start 5[21], end 0[7], 28 mer | 420 |
| TTTTAGTTAATTTCGCATGTCAATCATATGTACAGCCAGCTT | 20170608 cc6hb v4-base 250 nm 6hb, yellow standard seq, start 5[56], end 0[42], 42 mer | 421 |
| AATACCGACCGTGTCAATGCCTGAGTAATGTGTGATGAACGG | 20170608 cc6hb v4-base 250 nm 6hb, yellow standard seq, start 5[98], end 0[84], 42 mer | 422 |
| CACCGGAATCATAATGGCATCAATTCTACTAATAGAACCCTC | 20170608 cc6hb v4-base 250 nm 6hb, yellow standard seq, start 5[140], end 0[126], 42 mer | 423 |
| ATGCGTTATACAAAATGGCTTAGAGCTTAATTGATTTGGGGC | 20170608 cc6hb v4-base 250 nm 6hb, yellow standard seq, start 5[182], end 0[168], 42 mer | 424 |
| CAGTAGGGCTTAATACCATAAATCAAAAATCAGTTGATAAGA | 20170608 cc6hb v4-base 250 nm 6hb, yellow standard seq, start 5[224], end 0[210], 42 mer | 425 |
| CATGTAATTTAGGCTACGAGGCATAGTAAGAGCAAACAGTTC | 20170608 cc6hb v4-base 250 nm 6hb, yellow standard seq, start 5[266], end 0[252], 42 mer | 426 |
| AATATAAAGTACCGTGAGATGGTTTAATTTCAAAGATACATA | 20170608 cc6hb v4-base 250 nm 6hb, yellow standard seq, start 5[308], end 0[294], 42 mer | 427 |
| GACGACAATAAACACGGTCAATCATAAGGGAACCAGAACGAG | 20170608 cc6hb v4-base 250 nm 6hb, yellow standard seq, start 5[350], end 0[336], 42 mer | 428 |
| GTTTATCAACAATATCCATTAAACGGGTAAAATACTTAGCCG | 20170608 cc6hb v4-base 250 nm 6hb, yellow standard seq, start 5[392], end 0[378], 42 mer | 429 |
| CCCATCCTAATTTATTTCTTAAACAGCTTGATAAAAGACTTT | 20170608 cc6hb v4-base 250 nm 6hb, yellow standard seq, start 5[434], end 0[420], 42 mer | 430 |

TABLE 2-continued

Exemplary 250 nm Six-helix Bundle Sequences

| Sequence | Comment | SEQ ID NO: |
|---|---|---|
| GCTGTCTTTCCTTAAAAGTTTTGTCGTCTTTC CTATCAGCTT | 20170608 cc6hb v4-base 250 nm 6hb, yellow standard seq, start 5[476], end 0[462], 42 mer | 431 |
| TACCGCACTCATCGATAGGTGTATCACCGTA CTCCTCATAGT | 20170608 cc6hb v4-base 250 nm 6hb, yellow standard seq, start 5[518], end 0[504], 42 mer | 432 |
| CGTAGGAATCATTATGGTAATAAGTTTTAAC GGGGTTGATAT | 20170608 cc6hb v4-base 250 nm 6hb, yellow standard seq, start 5[560], end 0[546], 42 mer | 433 |
| TAGAAGGCTTATCCCCACCCTCAGAGCCAC CACCTTTTGATG | 20170608 cc6hb v4-base 250 nm 6hb, yellow standard seq, start 5[602], end 0[588], 42 mer | 434 |
| CGAACCTCCCGACTGAAACGTCACCAATGA AACCAGAGCCGC | 20170608 cc6hb v4-base 250 nm 6hb, yellow standard seq, start 5[644], end 0[630], 42 mer | 435 |
| GATTAGTTGCTATTAATAAGTTTATTTTGTC ACCACCATTAC | 20170608 cc6hb v4-base 250 nm 6hb, yellow standard seq, start 5[686], end 0[672], 42 mer | 436 |
| TCTTACCAACGCTAAGCAATAGCTATCTTAC CGAAAGAAACG | 20170608 cc6hb v4-base 250 nm 6hb, yellow standard seq, start 5[728], end 0[714], 42 mer | 437 |
| CGGAGACAGTCACTATCAGGTCATTGCCTG AAAGCCCCAAAA | 20170608 cc6hb v4-base 250 nm 6hb, magenta standard seq, start 2[97], end 2[56], 42 mer | 438 |
| ACAGGCAAGGCATTGCGGGAGAAGCCTTTA GGTGAGAAAGGC | 20170608 cc6hb v4-base 250 nm 6hb, magenta standard seq, start 2[139], end 2[98], 42 mer | 439 |
| TTAAATATGCAAATACATTTCGCAAATGGTC CAATAAATCAT | 20170608 cc6hb v4-base 250 nm 6hb, magenta standard seq, start 2[181], end 2[140], 42 mer | 440 |
| CAAAGCGGATTGACTCCAACAGGTCAGGAT GCTCAACATGTT | 20170608 cc6hb v4-base 250 nm 6hb, magenta standard seq, start 2[223], end 2[182], 42 mer | 441 |
| GACGATAAAAACCGGAATCGTCATAAATAT TATAGTCAGAAG | 20170608 cc6hb v4-base 250 nm 6hb, magenta standard seq, start 2[265], end 2[224], 42 mer | 442 |
| TTTTAAGAACTGGATTCATCAGTTGAGATTC GTTTACCAGAC | 20170608 cc6hb v4-base 250 nm 6hb, magenta standard seq, start 2[307], end 2[266], 42 mer | 443 |
| TGAACGGTGTACAGCTGCTCATTCAGTGAAT ACCTTATGCGA | 20170608 cc6hb v4-base 250 nm 6hb, magenta standard seq, start 2[349], end 2[308], 42 mer | 444 |
| AAAACGAAAGAGTCGCCTGATAAATTGTGT AAAGAGGACAGA | 20170608 cc6hb v4-base 250 nm 6hb, magenta standard seq, start 2[391], end 2[350], 42 mer | 445 |
| CATCGCCCACGCCATCGGAACGAGGGTAGC AGGCACCAACCT | 20170608 cc6hb v4-base 250 nm 6hb, magenta standard seq, start 2[433], end 2[392], 42 mer | 446 |
| GATTTTGCTAAATCCAAAAAAAAGGCTCCA AATGACAACAAC | 20170608 cc6hb v4-base 250 nm 6hb, magenta standard seq, start 2[475], end 2[434], 42 mer | 447 |
| CCGCCACCCTCATCACCAGTACAAACTACA TTTTCTGTATGG | 20170608 cc6hb v4-base 250 nm 6hb, magenta standard seq, start 2[517], end 2[476], 42 mer | 448 |
| TAAACAGTTAATGCGGGGTTTTGCTCAGTAC CACCCTCAGAA | 20170608 cc6hb v4-base 250 nm 6hb, magenta standard seq, start 2[559], end 2[518], 42 mer | 449 |
| GAGCCGCCGCCAGCGCAGTCTCTGAATTTA ACAGTGCCCGTA | 20170608 cc6hb v4-base 250 nm 6hb, magenta standard seq, start 2[601], end 2[560], 42 mer | 450 |
| ACAGAATCAAGTTCAAAATCACCGGAACCA GAACCACCACCA | 20170608 cc6hb v4-base 250 nm 6hb, magenta standard seq, start 2[643], end 2[602], 42 mer | 451 |
| GCGCCAAAGACAACTTGAGCCATTTGGGAA TAATCAGTAGCG | 20170608 cc6hb v4-base 250 nm 6hb, magenta standard seq, start 2[685], end 2[644], 42 mer | 452 |
| CCGAACAAAGTTTAGCAAACGTAGAAAATT ATGGTTTACCA | 20170608 cc6hb v4-base 250 nm 6hb, magenta standard seq, start 2[726], end 2[686], 41 mer | 453 |
| AGAGAGATAACCCACAAGTAAGCAGATAG | 20170608 cc6hb v4-base 250 nm 6hb, magenta standard seq, start 2[755], end 2[727], 29 mer | 454 |

TABLE 2-continued

Exemplary 250 nm Six-helix Bundle Sequences

| Sequence | Comment | SEQ ID NO: |
|---|---|---|
| AGAAGATGAAATTAACTAAAATATATTTGAAA AAGTTTTCTCGCGTTCTTTGTCTTGCGATTG | 20170608, cc6hb v4-250 nm 16 component square, default 6hb, miniscaf, node-0 | 455 |
| ATTTATCACACGGTCGGTATTTCAAACCATT AAATTTAGGTC | 20170608, cc6hb v4-250 nm 16 component square, default 6hb, miniscaf, node-1 | 456 |
| CTAGTAATTATGATTCCGGTGTTTATTCTTA TTTAACGCCTT | 20170608, cc6hb v4-250 nm 16 component square, default 6hb, miniscaf, node-2 | 457 |
| GTAAGAATTTGTATAACGCATATGATACTA AACAGGCTTTTT | 20170608, cc6hb v4-250 nm 16 component square, default 6hb, miniscaf, node-3 | 458 |
| ATTCTCAATTAAGCCCTACTGTTGAGCGTTG GCTTTATACTG | 20170608, cc6hb v4-250 nm 16 component square, default 6hb, miniscaf, node-4 | 459 |
| TGCCTCTGCCTAAATTACATGTTGGCGTTGT TAAATATGGCG | 20170608, cc6hb v4-250 nm 16 component square, default 6hb, miniscaf, node-5 | 460 |
| CTTTTGTCGGTACTTTATATTCTCTTATTACT GGCTCGAAAA | 20170608, cc6hb v4-250 nm 16 component square, default 6hb, miniscaf, node-6 | 461 |
| AACATGTTGTTTATTGTCGTCGTCTGGACAG AATTACTTTAC | 20170608, cc6hb v4-250 nm 16 component square, default 6hb, miniscaf, node-7 | 462 |
| ACTTATCTATTGTTGATAAACAGGCGCGTTC TGCATTAGCTG | 20170608, cc6hb v4-250 nm 16 component square, default 6hb, miniscaf, node-8 | 463 |
| ATGCTCGTAAATTAGGATGGGATATTATTTT TCTTGTTCAGG | 20170608, cc6hb v4-250 nm 16 component square, default 6hb, miniscaf, node-9 | 464 |
| GGAATGATAAGGAAAGACAGCCGATTATTG ATTGGTTTCTAC | 20170608, cc6hb v4-250 nm 16 component square, default 6hb, miniscaf, node-10 | 465 |
| TTGTTCTCGATGAGTGCGGTACTTGGTTTAA TACCCGTTCTT | 20170608, cc6hb v4-250 nm 16 component square, default 6hb, miniscaf, node-11 | 466 |
| GGCGCGGTAATGATTCCTACGATGAAAATA AAAACGGCTTGC | 20170608, cc6hb v4-250 nm 16 component square, default 6hb, miniscaf, node-12 | 467 |
| GAATACCGGATAAGCCTTCTATATCTGATTT GCTTGCTATTG | 20170608, cc6hb v4-250 nm 16 component square, default 6hb, miniscaf, node-13 | 468 |
| TCCCGCAAGTCGGGAGGTTCGCTAAAACGC CTCGCGTTCTTA | 20170608, cc6hb v4-250 nm 16 component square, default 6hb, miniscaf, node-14 | 469 |
| GGTGCAAAATAGCAACTAATCTTGATTTAA GGCTTCAAAACC | 20170608, cc6hb v4-250 nm 16 component square, default 6hb, miniscaf, node-15 | 470 |
| GCAAATTAGGCTCTGGAAAGACGCTCGTTAGC GTTGGTAAGATTCAGGATAAAATTGTAGCTG | 20170608, cc6hb v4-250 nm 16 component square, default 6hb, miniscaf, node-16 | 471 |
| ATTCTCAATTAGCGTGGACCGTTGAGCGTTG GCTTTATACTG | cc6hbv3_miniscaf_10s_n4 | 472 |
| TGCCTCTGCCTGAACCACCATTTGGCGTTGT TAAATATGGCG | cc6hbv3_miniscaf_10s_n5 | 473 |
| CTTTTGTCGGTTCGGCTATTCTCTTATTACT GGCTCGAAAA | cc6hbv3_miniscaf_10s_n6 | 474 |
| AACATGTTGTTAGTGGACTCTGTCTGGACAG AATTACTTTAC | cc6hbv3_miniscaf_10s_n7 | 475 |
| ACTTATCTATTACGGTTTTTCAGGCGCGTTC TGCATTAGCTG | cc6hbv3_miniscaf_10s_n8 | 476 |
| TAATACCATAAATCAAAAATCAGTTGATAA GA | cc6hbv3_yellow_term_10s_n4 | 477 |
| AGGCTACGAGGCATAGTAAGAGCAAACAGT TC | cc6hbv3_yellow_term_10s_n5 | 478 |

TABLE 2-continued

| Exemplary 250 nm Six-helix Bundle Sequences | | |
|---|---|---|
| Sequence | Comment | SEQ ID NO: |
| ACCGTGAGATGGTTTAATTTCAAAGATACAT A | cc6hbv3_yellow_term_10s_n6 | 479 |
| AACACGGTCAATCATAAGGGAACCAGAACG AG | cc6hbv3_yellow_term_10s_n7 | 480 |
| AATATCCATTAAACGGGTAAAATACTTAGC CG | cc6hbv3_yellow_term_10s_n8 | 481 |

TABLE 3

| Exemplary 440 nm Six-helix Bundle | | |
|---|---|---|
| Sequence | Comment | SEQ ID NO: |
| AACGGCATCTCCGTGAGCCTCCTCACAGAG CCTGGGGTGCCT | 6hb_440 nm, start 0[76], end 5[62] | 482 |
| GGCAGCACCCATCCCTTACACTGGTGTGGTT GCGCTCACTGC | 6hb_440 nm, start 0[118], end 5[104] | 483 |
| AAATCCCGTGGTCTGGTCAGCAGCAACCCC AGCTGCATTAAT | 6hb_440 nm, start 0[160], end 5[146] | 484 |
| GAGCCGCCAAGCAGTTGGGCGGTTGTGTTTT GCGTATTGGGC | 6hb_440 nm, start 0[202], end 5[188] | 485 |
| GGCACCGCTAAAACGACGGCCAGTGCCAAG ACGGGCAACAGC | 6hb_440 nm, start 0[244], end 5[230] | 486 |
| CGCGTCTGGGCCTCAGGAAGATCGCACTAG AGTTGCAGCAAG | 6hb_440 nm, start 0[286], end 5[272] | 487 |
| GGAGCAAACTTTTAACCAATAGGAACGCGA AAATCCTGTTTG | 6hb_440 nm, start 0[328], end 5[314] | 488 |
| GCAAGGATATACAAAGGCTATCAGGTCATT ATAAATCAAAAG | 6hb_440 nm, start 0[370], end 5[356] | 489 |
| CTGTTTAGCTAATACTTTTGCGGGAGAATCC AGTTTGGAACA | 6hb_440 nm, start 0[412], end 5[398] | 490 |
| TACCTTTAAACCATTAGATACATTTCGCCAA CGTCAAAGGGC | 6hb_440 nm, start 0[454], end 5[440] | 491 |
| ATCCCCCTCGGAAGCAAACTCCAACAGGAC TACGTGAACCAT | 6hb_440 nm, start 0[496], end 5[482] | 492 |
| ACCACATTCCAATACTGCGGAATCGTCAGT GCCGTAAAGCAC | 6hb_440 nm, start 0[538], end 5[524] | 493 |
| TGCCCTGACGGTAGAAAGATTCATCAGTATT TAGAGCTTGAC | 6hb_440 nm, start 0[580], end 5[566] | 494 |
| CGCGACCTGCGTAACAAAGCTGCTCATTGG AAGGGAAGAAAG | 6hb_440 nm, start 0[622], end 5[608] | 495 |
| ACAGAGGCTTTGTATCATCGCCTGATAAAA GTGTAGCGGTCA | 6hb_440 nm, start 0[664], end 5[650] | 496 |
| CCTTTAATTAAAGACAGCATCGGAACGAGC TTAATGCGCCGC | 6hb_440 nm, start 0[706], end 5[692] | 497 |
| TAGCATTCCTGAAAATCTCCAAAAAAAACG AGCACGTATAAC | 6hb_440 nm, start 0[748], end 5[734] | 498 |
| GATAAGTGCGAGTTTCGTCACCAGTACAAG CTAAACAGGAGG | 6hb_440 nm, start 0[790], end 5[776] | 499 |

TABLE 3-continued

| Exemplary 440 nm Six-helix Bundle | | |
|---|---|---|
| Sequence | Comment | SEQ ID NO: |
| AGTAAGCGTTAGGATTAGCGGGGTTTTGGT ACGCCAGAATCC | 6hb_440 nm, start 0[832], end 5[818] | 500 |
| CACCGGAACAATGGAAAGCGCAGTCTCTCA CCGAGTAAAAGA | 6hb_440 nm, start 0[874], end 5[860] | 501 |
| CAGCAAAATTTTCATAATCAAAATCACCTA GCAATACTTCTT | 6hb_440 nm, start 0[916], end 5[902] | 502 |
| TAAAGGTGGCGTCACCGACTTGAGCCATTA GAAGAACTCAAA | 6hb_440 nm, start 0[958], end 5[944] | 503 |
| ATTGAGTTAGCAGTATGTTAGCAAACGTCA ATATTACCGCCA | 6hb_440 nm, start 0[1000], end 5[986] | 504 |
| ATTTGCCAGTGAGCGCTAATATCAGAGAAA ATACCTACATTT | 6hb_440 nm, start 0[1042], end 5[1028] | 505 |
| TTTCATCGTTACCAACGCTAACGAGCGTTTA CATTGGCAGAT | 6hb_440 nm, start 0[1084], end 5[1070] | 506 |
| CCAGACGACCGCACTCATCGAGAACAAGGG ACATTCTGGCCA | 6hb_440 nm, start 0[1126], end 5[1112] | 507 |
| AATAAACACATAAAGTACCGACAAAAGGGC GTAAGAATACGT | 6hb_440 nm, start 0[1168], end 5[1154] | 508 |
| ATTTATCAAACCGACCGTGTGATAAATATA GTCTTTAATGCG | 6hb_440 nm, start 0[1210], end 5[1196] | 509 |
| AGATGATGATTAGATTAAGACGCTGAGATA AAAATACCGAAC | 6hb_440 nm, start 0[1252], end 5[1238] | 510 |
| AGGGTTAGACGAATTATTCATTTCAATTTGA GGCGGTCAGTA | 6hb_440 nm, start 0[1294], end 5[1280] | 511 |
| AGAAGTATTCTGATTGTTTGGATTATACGAG AGCCAGCAGCA | 6hb_440 nm, start 0[1336], end 5[1322] | 512 |
| TCATGGTCATAGCCGTGCCTGTTCTTCGCGA GATGCCGGGTT | 6hb_440 nm, start 1[38], end 1[79] | 513 |
| ACCTGCAGCCAGCTCTTTGCTCGTCATAAAG TCGGTGGTGCC | 6hb_440 nm, start 1[80], end 1[121] | 514 |
| ATCCCACGCAACCAACGTCAGCGTGGTGCT AAAAAAAGCCGC | 6hb_440 nm, start 1[122], end 1[163] | 515 |
| ACAGGCGGCCTTTTCTGCTCATTTGCCGCCC GGGAACGGATA | 6hb_440 nm, start 1[164], end 1[205] | 516 |
| ACCTCACCGGAAACCCAGTCACGACGTTGT TCTGGTGCCGGA | 6hb_440 nm, start 1[206], end 1[247] | 517 |
| AACCAGGCAAAGCGGACGACGACAGTATCG CCTTCCTGTAGC | 6hb_440 nm, start 1[248], end 1[289] | 518 |
| CAGCTTTCATCAATGTTAAATCAGCTCATTA AGAGAATCGAT | 6hb_440 nm, start 1[290], end 1[331] | 519 |
| GAACGGTAATCGTGCTATTTTTGAGAGATCA AAATTTTTAGA | 6hb_440 nm, start 1[332], end 1[373] | 520 |
| ACCCTCATATATTAAAACATTATGACCCTGT ATATTTTCATT | 6hb_440 nm, start 1[374], end 1[415] | 521 |
| TGGGGCGCGAGCTCGAGTAGATTTAGTTTGT TGCTCCTTTTG | 6hb_440 nm, start 1[416], end 1[457] | 522 |
| ATAAGAGGTCATTTCAAAGCGAACCAGACC AAATGCTTTAAA | 6hb_440 nm, start 1[458], end 1[499] | 523 |

TABLE 3-continued

| Exemplary 440 nm Six-helix Bundle | | |
|---|---|---|
| Sequence | Comment | SEQ ID NO: |
| CAGTTCAGAAAACTTAGACTGGATAGCGTC AACTAATGCAGA | 6hb_440 nm, start 1[500], end 1[541] | 524 |
| TACATAACGCCAAGGAACAACATTATTACA GAGAAACACCAG | 6hb_440 nm, start 1[542], end 1[583] | 525 |
| AACGAGTAGTAAATTCATTACCCAAATCAA CTCCATGTTACT | 6hb_440 nm, start 1[584], end 1[625] | 526 |
| TAGCCGGAACGAGCAAAGTACAACGGAGAT TTGAGGACTAAA | 6hb_440 nm, start 1[626], end 1[667] | 527 |
| GACTTTTTCATGACGTCACCCTCAGCAGCGG TATCGGTTTAT | 6hb_440 nm, start 1[668], end 1[709] | 528 |
| CAGCTTGCTTTCGTAATAATTTTTTCACGTA CAGACAGCCCT | 6hb_440 nm, start 1[710], end 1[751] | 529 |
| CATAGTTAGCGTACCATGTACCGTAACACTC GTCGAGAGGGT | 6hb_440 nm, start 1[752], end 1[793] | 530 |
| TGATATAAGTATACTCCTCAAGAGAAGGAT CATACATGGCTT | 6hb_440 nm, start 1[794], end 1[835] | 531 |
| TTGATGATACAGGATCCTCATTAAAGCCAG CGCCTCCCTCAG | 6hb_440 nm, start 1[836], end 1[877] | 532 |
| AGCCGCCACCCTCATTAGCGTTTGCCATCTC ACCAGTAGCAC | 6hb_440 nm, start 1[878], end 1[919] | 533 |
| CATTACCATTAGCTAAAGGTGAATTATCACC AACATATAAAA | 6hb_440 nm, start 1[920], end 1[961] | 534 |
| GAAACGCAAAGACTTAAGACTCCTTATTAC AGCCCAATAATA | 6hb_440 nm, start 1[962], end 1[1003] | 535 |
| AGAGCAAGAAACACAAAGTCAGAGGGTAA TTTACAAAATAAA | 6hb_440 nm, start 1[1004], end 1[1045] | 536 |
| CAGCCATATTATTAATTTTATCCTGAATCTA GGAATCATTAC | 6hb_440 nm, start 1[1046], end 1[1087] | 537 |
| CGCGCCCAATAGCGGTATTAAACCAAGTAC GACAATAAACAA | 6hb_440 nm, start 1[1088], end 1[1129] | 538 |
| CATGTTCAGCTAAGCCAGTAATAAGAGAAT CGGAATCATAAT | 6hb_440 nm, start 1[1130], end 1[1171] | 539 |
| TACTAGAAAAAGCATTTAATGGTTTGAAAT AATCATAGGTCT | 6hb_440 nm, start 1[1172], end 1[1213] | 540 |
| GAGAGACTACCTTGAAAACATAGCGATAGC AACAAACATCAA | 6hb_440 nm, start 1[1214], end 1[1255] | 541 |
| GAAAACAAAATTAACAAAATCGCGCAGAG GACCTACCATATC | 6hb_440 nm, start 1[1256], end 1[1297] | 542 |
| AAAATTATTTGCAAATTCATCAATATAATCA GACTTTACAAACAAT | 6hb_440 nm, start 1[1298], end 1[1343] | 543 |
| TCGACAACTCTAACAACTAATCGTCAATAG ATAATGAACCTCAAATATC | 6hb_440 nm, start 1[1344], end 5[1364] | 544 |
| TCTGCCAGCACGTGTTTCCTGTGTGCCGCTC AC | 6hb_440 nm, start 2[62], end 3[45] | 545 |
| TGGGTAAAGGTTGGTGCCGGTGCCCCCTGC ATACCGGGGGTT | 6hb_440 nm, start 2[104], end 2[63] | 546 |
| CCGGACTTGTAGAGCTTACGGCTGGAGGTG TGCGGCTGGTAA | 6hb_440 nm, start 2[146], end 2[105] | 547 |

TABLE 3-continued

| Exemplary 440 nm Six-helix Bundle | | |
|---|---|---|
| Sequence | Comment | SEQ ID NO: |
| CAAACTTAAATTAGTGATGAAGGGTAAAGT TAACGGAACGTG | 6hb_440 nm, start 2[188], end 2[147] | 548 |
| CGCCAGGGTTTTCAATCGGCGAAACGTACA GAAACAGCGGAT | 6hb_440 nm, start 2[230], end 2[189] | 549 |
| GCCAGTTTGAGGGCCATTCGCCATTCAGGCT AAGTTGGGTAA | 6hb_440 nm, start 2[272], end 2[231] | 550 |
| GCATTAAATTTTCATTAAATGTGAGCGAGTA ACCGTGCATCT | 6hb_440 nm, start 2[314], end 2[273] | 551 |
| CCGGAGAGGGTAAAAACTAGCATGTCAATC TTGTTAAAATTC | 6hb_440 nm, start 2[356], end 2[315] | 552 |
| TCGGTTGTACCATTAAATGCAATGCCTGAGG ATAAATTAATG | 6hb_440 nm, start 2[398], end 2[357] | 553 |
| CAATTCTGCGAAGAAAAGGTGGCATCAATT CATAAAGCTAAA | 6hb_440 nm, start 2[440], end 2[399] | 554 |
| TTAATTCGAGCTTTTGCGGATGGCTTAGAGA CAGTTGATTCC | 6hb_440 nm, start 2[482], end 2[441] | 555 |
| ATAGTAAAATGTGAGAATGACCATAAATCA AAATATCGCGTT | 6hb_440 nm, start 2[524], end 2[483] | 556 |
| AAACGAACTAACAAGGAATTACGAGGCATA CCAGAGGGGGTA | 6hb_440 nm, start 2[566], end 2[525] | 557 |
| AAGAACCGGATATTGGGCTTGAGATGGTTT TCTACGTTAATA | 6hb_440 nm, start 2[608], end 2[567] | 558 |
| CCAAGCGCGAAAGCGCAGACGGTCAATCAT AGTAATCTTGAC | 6hb_440 nm, start 2[650], end 2[609] | 559 |
| CTTTTGCGGGATGGAAGTTTCCATTAAACGC CAGCGATTATA | 6hb_440 nm, start 2[692], end 2[651] | 560 |
| AGGAATTGCGAAAGGTGAATTTCTTAAACA AGTTAAAGGCCG | 6hb_440 nm, start 2[734], end 2[693] | 561 |
| CCCAATAGGAACACGATCTAAAGTTTTGTC AGGAACAACTAA | 6hb_440 nm, start 2[776], end 2[735] | 562 |
| AAGAGGCTGAGAGCCCGGAATAGGTGTATC AGGGATAGCAAG | 6hb_440 nm, start 2[818], end 2[777] | 563 |
| ACAAACAAATAAAGTGTACTGGTAATAAGT CATGAAAGTATT | 6hb_440 nm, start 2[860], end 2[819] | 564 |
| CATAGCCCCCTTAGAACCGCCACCCTCAGA GCCTTGATATTC | 6hb_440 nm, start 2[902], end 2[861] | 565 |
| GAAATTATTCATAAGGCCGGAAACGTCACC GGCATTTTCGGT | 6hb_440 nm, start 2[944], end 2[903] | 566 |
| GAACTGGCATGAACCACGGAATAAGTTTAT TAAATATTGACG | 6hb_440 nm, start 2[986], end 2[945] | 567 |
| GAACACCCTGAAATGAAATAGCAATAGCTA GAATACCCAAAA | 6hb_440 nm, start 2[1028], end 2[987] | 568 |
| GCACCCAGCTACTATCCCAATCCAAATAAG GGAGAATTAACT | 6hb_440 nm, start 2[1070], end 2[1029] | 569 |
| ATTCCAAGAACGAAGCAAATCAGATATAGA AGTTGCTATTTT | 6hb_440 nm, start 2[1112], end 2[1071] | 570 |
| AGGCATTTTCGATGCAGAACGCGCCTGTTTT CTTTCCTTATC | 6hb_440 nm, start 2[1154], end 2[1113] | 571 |

TABLE 3-continued

| Exemplary 440 nm Six-helix Bundle | | |
|---|---|---|
| Sequence | Comment | SEQ ID NO: |
| CTTCTGACCTAACTGTTTAGTATCATATGCT AATTTAGGCAG | 6hb_440 nm, start 2[1196], end 2[1155] | 572 |
| CTTAGAATCCTTTTTAACCTCCGGCTTAGGA GTTAATTTCAT | 6hb_440 nm, start 2[1238], end 2[1197] | 573 |
| GAATACCAAGTTATTACATTTAACAATTTCA ATTAATTTTCC | 6hb_440 nm, start 2[1280], end 2[1239] | 574 |
| TCAGATGATGGCCGTAAAACAGAAATAAAG CCTGATTGCTTT | 6hb_440 nm, start 2[1322], end 2[1281] | 575 |
| TCTTTAGGAGCACGTATTAAATCCTTTGCCT ATTCCTGATTA | 6hb_440 nm, start 2[1364], end 2[1323] | 576 |
| AATTCCACACAAGGGCCGTTTTCACGGTCAT CAGACGATCCA | 6hb_440 nm, start 3[46], end 3[87] | 577 |
| GCGCAGTGTCACCCGGGTCACTGTTGCCCTC CAGCATCAGCG | 6hb_440 nm, start 3[88], end 3[129] | 578 |
| GGGTCATTGCAGGCCAGAGCACATCCTCAT AAACGATGCTGA | 6hb_440 nm, start 3[130], end 3[171] | 579 |
| TTGCCGTTCCGGACGGAAAAAGAGACGCAG CGCCATGTTTAC | 6hb_440 nm, start 3[172], end 3[213] | 580 |
| CAGTCCCGGAATATGTGCTGCAAGGCGATT GCGCAACTGTTG | 6hb_440 nm, start 3[214], end 3[255] | 581 |
| GGAAGGGCGATCGTAGATGGGCGCATCGTA ACAACCCGTCGG | 6hb_440 nm, start 3[256], end 3[297] | 582 |
| ATTCTCCGTGGGTTGTAAACGTTAATATTAT ATGTACCCCGG | 6hb_440 nm, start 3[298], end 3[339] | 583 |
| TTGATAATCAGAATTCAACCGTTCTAGCTTA ATGTGTAGGTA | 6hb_440 nm, start 3[340], end 3[381] | 584 |
| AAGATTCAAAAGGCAATAAAGCCTCAGAGC TACTAATAGTAG | 6hb_440 nm, start 3[382], end 3[423] | 585 |
| TAGCATTAACATAAGTTTCATTCCATATACT TAATTGCTGAA | 6hb_440 nm, start 3[424], end 3[465] | 586 |
| TATAATGCTGTAGAAGCCCGAAAGACTTCA AAATCAGGTCTT | 6hb_440 nm, start 3[466], end 3[507] | 587 |
| TACCCTGACTATTTGCAAAAGAAGTTTTGGT AAGAGCAACAC | 6hb_440 nm, start 3[508], end 3[549] | 588 |
| TATCATAACCCTGACGTTGGGAAGAAAAAA ATTTCAACTTTA | 6hb_440 nm, start 3[550], end 3[591] | 589 |
| ATCATTGTGAATGGCTGACCTTCATCAAGAA GGGAACCGAAC | 6hb_440 nm, start 3[592], end 3[633] | 590 |
| TGACCAACTTTGACACTCATCTTTGACCCGG TAAAATACGTA | 6hb_440 nm, start 3[634], end 3[675] | 591 |
| ATGCCACTACGACGCTGAGGCTTGCAGGGG CTTGATACCGAT | 6hb_440 nm, start 3[676], end 3[717] | 592 |
| AGTTGCGCCGACGCGGAGTGAGAATAGAAG TCTTTCCAGACG | 6hb_440 nm, start 3[718], end 3[759] | 593 |
| TTAGTAAATGAACCACCACCCTCATTTTCAC CGTACTCAGGA | 6hb_440 nm, start 3[760], end 3[801] | 594 |
| GGTTTAGTACCGAACCTATTATTCTGAAATT TAACGGGGTCA | 6hb_440 nm, start 3[802], end 3[843] | 595 |

TABLE 3-continued

Exemplary 440 nm Six-helix Bundle

| Sequence | Comment | SEQ ID NO: |
|---|---|---|
| GTGCCTTGAGTAGGCAGGTCAGACGATTGG CCACCACCCTCA | 6hb_440 nm, start 3[844], end 3[885] | 596 |
| GAGCCGCCACCATGTAGCGCGTTTTCATCA ATGAAACCATCG | 6hb_440 nm, start 3[886], end 3[927] | 597 |
| ATAGCAGCACCGGATTGAGGGAGGGAAGGT TTGTCACAATCA | 6hb_440 nm, start 3[928], end 3[969] | 598 |
| ATAGAAAATTCAGAAACGCAATAATAACGT CTTACCGAAGCC | 6hb_440 nm, start 3[970], end 3[1011] | 599 |
| CTTTTTAAGAAAGGGAAGCGCATTAGACGA AACGATTTTTTG | 6hb_440 nm, start 3[1012], end 3[1053] | 600 |
| TTTAACGTCAAAAGCCTTAAATCAAGATTA GGCTTATCCGGT | 6hb_440 nm, start 3[1054], end 3[1095] | 601 |
| ATTCTAAGAACGCAATCAATAATCGGCTGA TCAACAATAGAT | 6hb_440 nm, start 3[1096], end 3[1137] | 602 |
| AAGTCCTGAACATTAACAACGCCAACATGG TTATACAAATTC | 6hb_440 nm, start 3[1138], end 3[1179] | 603 |
| TTACCAGTATAATTTTTCAAATATATTTTTTG GGTTATATAA | 6hb_440 nm, start 3[1180], end 3[1221] | 604 |
| CTATATGTAAATTGTAAATCGTCGCTATTAT TTGAATTACCT | 6hb_440 nm, start 3[1222], end 3[1263] | 605 |
| TTTTTAATGGAAAAACAATAACGGATTCGA AATTGCGTAGAT | 6hb_440 nm, start 3[1264], end 3[1305] | 606 |
| TTTCAGGTTTAAGAGCGGAATTATCATCACG AACGTTATTAA | 6hb_440 nm, start 3[1306], end 3[1347] | 607 |
| TTTTAAAAGTTTAAAGGAATTGAGTAAAAT A | 6hb_440 nm, start 3[1348], end 2[1365] | 608 |
| CGGAAGCATAAAGTGTAATTGAGGATCCCC GG | 6hb_440 nm, start 4[48], end 0[35] | 609 |
| GTGCACTCTGTGGTCTCACATTAATTGCTTC AGCAAATCGTT | 6hb_440 nm, start 4[90], end 0[77] | 610 |
| CACTCAATCCGCCGGGAAACCTGTCGTGGC AAGAATGCCAAC | 6hb_440 nm, start 4[132], end 0[119] | 611 |
| TCCGTTTTTTCGTCGCGGGGAGAGGCGGAC ATCGACATAAAA | 6hb_440 nm, start 4[174], end 0[161] | 612 |
| ATAGACTTTCTCCGTCTTTTCACCAGTGAGC TTTCAGAGGTG | 6hb_440 nm, start 4[216], end 0[203] | 613 |
| CTCTTCGCTATTACCGCCTGGCCCTGAGCCA GCCAGCTTTCC | 6hb_440 nm, start 4[258], end 0[245] | 614 |
| CGGATTGACCGTAATTGCCCCAGCAGGCCA TCAAAAATAATT | 6hb_440 nm, start 4[300], end 0[287] | 615 |
| AAAACAGGAAGATTATCGGCAAAATCCCTT GCCTGAGAGTCT | 6hb_440 nm, start 4[342], end 0[329] | 616 |
| GGCCGGAGACAGTCGGGTTGAGTGTTGTGC CTTTATTTCAAC | 6hb_440 nm, start 4[384], end 0[371] | 617 |
| CATACAGGCAAGGCAAGAACGTGGACTCAA ATGGTCAATAAC | 6hb_440 nm, start 4[426], end 0[413] | 618 |
| GTTTTAAATATGCACAGGGCGATGGCCCTC AGGATTAGAGAG | 6hb_440 nm, start 4[468], end 0[455] | 619 |

TABLE 3-continued

| Exemplary 440 nm Six-helix Bundle | | |
|---|---|---|
| Sequence | Comment | SEQ ID NO: |
| AAGCAAAGCGGATTTTTTTGGGGTCGAGTA AATATTCATTGA | 6hb_440 nm, start 4[510], end 0[497] | 620 |
| GACGACGATAAAAAAAAGGGAGCCCCCGT GAGATTTAGGAAT | 6hb_440 nm, start 4[552], end 0[539] | 621 |
| CGATTTTAAGAACTAACGTGGCGAGAAACA GTGAATAAGGCT | 6hb_440 nm, start 4[594], end 0[581] | 622 |
| AGATGAACGGTGTAGCTAGGGCGCTGGCAT TGTGTCGAAATC | 6hb_440 nm, start 4[636], end 0[623] | 623 |
| CCTAAAACGAAAGAACCACACCCGCCGCGG GTAGCAACGGCT | 6hb_440 nm, start 4[678], end 0[665] | 624 |
| AACCATCGCCCACGTATGGTTGCTTTGAGGC TCCAAAAGGAG | 6hb_440 nm, start 4[720], end 0[707] | 625 |
| TGGGATTTTGCTAAAGAATCAGAGCGGGAA CTACAACGCCTG | 6hb_440 nm, start 4[762], end 0[749] | 626 |
| GAACCGCCACCCTCTTTAGACAGGAACGCT CAGTACCAGGCG | 6hb_440 nm, start 4[804], end 0[791] | 627 |
| GTATAAACAGTTAAATAATCAGTGAGGCGA ATTTACCGTTCC | 6hb_440 nm, start 4[846], end 0[833] | 628 |
| CCAGAGCCGCCGCCCAAATTAACCGTTGGG AACCAGAGCCAC | 6hb_440 nm, start 4[888], end 0[875] | 629 |
| GCGACAGAATCAAGATCACTTGCCTGAGTT GGGAATTAGAGC | 6hb_440 nm, start 4[930], end 0[917] | 630 |
| CCAGCGCCAAAGACGGTAATATCCAGAAAG AAAATACATACA | 6hb_440 nm, start 4[972], end 0[959] | 631 |
| ATAGCCGAACAAAGAAAAACGCTCATGGGA TAACCCACAAGA | 6hb_440 nm, start 4[1014], end 0[1001] | 632 |
| AGCAGCCTTTACAGCTGAAATGGATTATCTT TCCAGAGCCTA | 6hb_440 nm, start 4[1056], end 0[1043] | 633 |
| TTAGCGAACCTCCCACCAGTAATAAAAGCA AGCCGTTTTTAT | 6hb_440 nm, start 4[1098], end 0[1085] | 634 |
| ATATCCCATCCTAACTTCTGACCTGAAATAA AGTAATTCTGT | 6hb_440 nm, start 4[1140], end 0[1127] | 635 |
| TCAACAGTAGGGCTTTTTGAATGGCTATAGG CGTTAAATAAG | 6hb_440 nm, start 4[1182], end 0[1169] | 636 |
| AATCCAATCGCAAGTAAAACATCGCCATAG AGTCAATAGTGA | 6hb_440 nm, start 4[1224], end 0[1211] | 637 |
| AAATCAATATATGTAGATAAAACAGAGGAC CTGAGCAAAAGA | 6hb_440 nm, start 4[1266], end 0[1253] | 638 |
| AATATACAGTAACAAACAGTGCCACGCTTT CTGAATAATGGA | 6hb_440 nm, start 4[1308], end 0[1295] | 639 |
| TATCATTTTGCGGAAGCATCACCTTGCTACA TTTGAGGATTT | 6hb_440 nm, start 4[1350], end 0[1337] | 640 |
| AATGAGTGAGCTAAGCTGCGGCCAGAATGC GGCCATACGAGC | 6hb_440 nm, start 5[63], end 4[49] | 641 |
| CCGCTTTCCAGTCGGGCGCGGTTGCGGTATG AGTGCGCGCCT | 6hb_440 nm, start 5[105], end 4[91] | 642 |
| GAATCGGCCAACGCTCGTCGCTGGCAGCCT CCGGCGCTTTCG | 6hb_440 nm, start 5[147], end 4[133] | 643 |

TABLE 3-continued

Exemplary 440 nm Six-helix Bundle

| Sequence | Comment | SEQ ID NO: |
|---|---|---|
| GCCAGGGTGGTTTTTGGTGAAGGGATAGCT CTCCAAACGCGG | 6hb_440 nm, start 5[189], end 4[175] | 644 |
| TGATTGCCCTTCACGCCAGCTGGCGAAAGG GGGTTGTGAGAG | 6hb_440 nm, start 5[231], end 4[217] | 645 |
| CGGTCCACGCTGGTTGGGATAGGTCACGTT GGTGGTGCGGGC | 6hb_440 nm, start 5[273], end 4[259] | 646 |
| ATGGTGGTTCCGAAGTATAAGCAAATATTT AAAAACAAACGG | 6hb_440 nm, start 5[315], end 4[301] | 647 |
| AATAGCCCGAGATAAAATCACCATCAATAT GATAAAGCCCCA | 6hb_440 nm, start 5[357], end 4[343] | 648 |
| AGAGTCCACTATTAAAAGAATTAGCAAAAT TAAGGTGAGAAA | 6hb_440 nm, start 5[399], end 4[385] | 649 |
| GAAAAACCGTCTATACTAAAGTACGGTGTC TGGCCAATAAAT | 6hb_440 nm, start 5[441], end 4[427] | 650 |
| CACCCAAATCAAGTGCATCAAAAAGATTAA GAGGCTCAACAT | 6hb_440 nm, start 5[483], end 4[469] | 651 |
| TAAATCGGAACCCTCCAAAATAGCGAGAGG CTTTATAGTCAG | 6hb_440 nm, start 5[525], end 4[511] | 652 |
| GGGGAAAGCCGGCGGGCTCATTATACCAGT CAGCGTTTACCA | 6hb_440 nm, start 5[567], end 4[553] | 653 |
| CGAAAGGAGCGGGCCAGACCAGGCGCATA GGCTTACCTTATG | 6hb_440 nm, start 5[609], end 4[595] | 654 |
| CGCTGCGCGTAACCGGCAAAAGAATACACT AAAAAAGAGGAC | 6hb_440 nm, start 5[651], end 4[637] | 655 |
| TACAGGGCGCGTACCATAACCGATATATTC GGTAGGCACCAA | 6hb_440 nm, start 5[693], end 4[679] | 656 |
| GTGCTTTCCTCGTTACAACTTTCAACAGTTT CAAATGACAAC | 6hb_440 nm, start 5[735], end 4[721] | 657 |
| CCGATTAAAGGGATAGAACCGCCACCCTCA GAGTTTTCTGTA | 6hb_440 nm, start 5[777], end 4[763] | 658 |
| TGAGAAGTGTTTTTTGCCCCCTGCCTATTTC GGCCACCCTCA | 6hb_440 nm, start 5[819], end 4[805] | 659 |
| GTCTGTCCATCACGAGCATTGACAGGAGGT TGAACAGTGCCC | 6hb_440 nm, start 5[861], end 4[847] | 660 |
| TGATTAGTAATAACTTTGCCTTTAGCGTCAG ACGAACCACCA | 6hb_440 nm, start 5[903], end 4[889] | 661 |
| CTATCGGCCTTGCTAAAAGGGCGACATTCA ACCTAATCAGTA | 6hb_440 nm, start 5[945], end 4[931] | 662 |
| GCCATTGCAACAGGTTACCAGAAGGAAACC GAGTATGGTTTA | 6hb_440 nm, start 5[987], end 4[973] | 663 |
| TGACGCTCAATCGTAGAGAATAACATAAAA ACAAGTAAGCAG | 6hb_440 nm, start 5[1029], end 4[1015] | 664 |
| TCACCAGTCACACGGACTTGCGGGAGGTTT TGAAATGAAAAT | 6hb_440 nm, start 5[1071], end 4[1057] | 665 |
| ACAGAGATAGAACCTTTACGAGCATGTAGA AACCGAGGCGTT | 6hb_440 nm, start 5[1113], end 4[1099] | 666 |
| GGCACAGACAATATTAATTGAGAATCGCCA TATAGAAAAATA | 6hb_440 nm, start 5[1155], end 4[1141] | 667 |

TABLE 3-continued

| Exemplary 440 nm Six-helix Bundle | | |
|---|---|---|
| Sequence | Comment | SEQ ID NO: |
| CGAACTGATAGCCCACAAAGAACGCGAGAA AACAGCCAACGC | 6hb_440 nm, start 5[1197], end 4[1183] | 668 |
| GAACCACCAGCAGAGAGTGAATAACCTTGC TTCGCTGATGCA | 6hb_440 nm, start 5[1239], end 4[1225] | 669 |
| TTAACACCGCCTGCGTACCTTTTACATCGGG AGACAGTACAT | 6hb_440 nm, start 5[1281], end 4[1267] | 670 |
| AATGAAAAATCTAAACAAAGAAACCACCAG AAGCGTCAGATG | 6hb_440 nm, start 5[1323], end 4[1309] | 671 |
| AAACCCTCAATCAAGTTGGCAAATCAACAG TTGGAGTAACAT | 6hb_440 nm, start 5[1365], end 4[1351] | 672 |
| CGCTGGTTGGGATAGGTCACGTTGGTGGTG CGGGC | 6hb_440 nm, 7 bp socket end distal to queen, start 5[280], end 4[259] | 673 |
| TTCCGAAGTATAAGCAAATATTTAAAAACA AACGG | 6hb_440 nm, 7 bp socket end distal to queen, start 5[322], end 4[301] | 674 |
| CGAGATAAAATCACCATCAATATGATAAAG CCCCA | 6hb_440 nm, 7 bp socket end distal to queen, start 5[364], end 4[343] | 675 |
| ACTATTAAAAGAATTAGCAAAATTAAGGTG AGAAA | 6hb_440 nm, 7 bp socket end distal to queen, start 5[406], end 4[385] | 676 |
| CGTCTATACTAAAGTACGGTGTCTGGCCAAT AAAT | 6hb_440 nm, 7 bp socket end distal to queen, start 5[448], end 4[427] | 677 |
| TGGTTGGGATAGGTCACGTTGGTGGTGCGG GC | 6hb_440 nm, 10 bp socket end distal to queen, start 5[283], end 4[259] | 678 |
| CGAAGTATAAGCAAATATTTAAAAACAAAC GG | 6hb_440 nm, 10 bp socket end distal to queen, start 5[325], end 4[301] | 679 |
| GATAAAATCACCATCAATATGATAAAGCCC CA | 6hb_440 nm, 10 bp socket end distal to queen, start 5[367], end 4[343] | 680 |
| ATTAAAAGAATTAGCAAAATTAAGGTGAGA AA | 6hb_440 nm, 10 bp socket end distal to queen, start 5[409], end 4[385] | 681 |
| CTATACTAAAGTACGGTGTCTGGCCAATAA AT | 6hb_440 nm, 10 bp socket end distal to queen, start 5[451], end 4[427] | 682 |

All references, patents and patent applications disclosed herein are incorporated by reference with respect to the subject matter for which each is cited, which in some cases may encompass the entirety of the document.

The indefinite articles “a” and “an,” as used herein in the specification and in the claims, unless clearly indicated to the contrary, should be understood to mean “at least one.”

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising,” “including,” “carrying,” “having,” “containing,” “involving,” “holding,” “composed of,” and the like are to be understood to be open-ended, i.e., to mean including but not limited to. Only the transitional phrases “consisting of” and “consisting essentially of” shall be closed or semi-closed transitional phrases, respectively, as set forth in the United States Patent Office Manual of Patent Examining Procedures, Section 2111.03.

What is claimed is:

1. A crisscross nucleic acid slat, comprising:

(a) a first plurality of at least four single-stranded nucleic acid strands aligned parallel to each other; each strand of the first plurality having a length of at least 21 nucleotides; and (b) a second plurality of at least four single-stranded nucleic acid strands aligned parallel to each, each strand of the second plurality having a length of at least 21 nucleotides, wherein the at least four nucleic acid strands of the first plurality are bound to and rotated at an angle relative to the at least four nucleic acid strands of the second plurality, wherein a single nucleic acid strand of (b) binds to multiple nucleic acid strands of (a), each through a single cooperative binding site, and a single nucleic acid strand of (a) binds to multiple nucleic acid strands of (b), each through a single cooperative binding site.

2. A nucleic acid nanostructure, comprising a nucleic acid scaffold strand folded into multiple stacked parallel loops that are bound to at least one crisscross nucleic acid slat of claim 1.

3. The nucleic acid nanostructure of claim 2, wherein the length of the nucleic acid scaffold strand is longer than 1 kilobase.

4. The nucleic acid nanostructure of claim 2, wherein the nanostructure is a DNA nanostructure.

5. A nucleic acid nanostructure comprising a stack of parallel nucleic acid loops bound to a plurality of nucleic acid slats of claim 1.

6. A method of detecting a biomolecule, comprising (a) combining in a reaction mixture (i) a sample comprising a biomolecule;

(ii) a nucleic acid strand capable of self-assembling into a nanostructure that comprises stacked parallel strands;

(iii) at least two crisscross nucleic acid slats of claim 1, wherein the at least two slats bind to the stacked parallel strands of (ii), and wherein at least one nucleic acid strand of the at least two slats is linked to a biomolecule binding partner that specifically binds to the biomolecule in the sample;

(b) incubating the reaction mixture under conditions that permit binding of the biomolecule binding partners to the biomolecule, assembly of the nanostructure into stacked parallel strands, and binding of the crisscross nucleic acid slats to the stacked parallel strands to form a three-dimensional nanostructure; and (c) visualizing the three-dimensional nanostructure, thereby detecting the biomolecule.

7. The method of claim 6, wherein the sample is a biological sample.

8. The method of claim 6, wherein the biomolecule is a macromolecule.

9. The method of claim 8, wherein the macromolecule is a protein.

10. The method of claim 9, wherein the biomolecule binding partner is selected from antibodies, antibody fragments, and aptamers.

11. The method of claim 10, wherein the biomolecule binding partner is an antibody.

12. The method of claim 10, wherein the biomolecule binding partner is an antibody fragment selected from Fab, F(ab')2, Fe, scFv, and vhh antibody fragments.

13. A method of detecting a biomolecule, comprising:

(a) combining in a reaction mixture (i) a sample comprising a biomolecule, and (ii) nucleic acid nanostructure comprising (i) a nucleic acid scaffold strand and nucleic acid staple strands capable of assembling into multiple stacked parallel loops and (ii) at least two crisscross nucleic acid slats of claim 1 that bind to the loops of (i), wherein a biomolecule binding partner that specifically binds to the biomolecule is linked to at least one nucleic acid strand of the at least two slats such that in the presence of the biomolecule the biomolecule binding partners bind to the biomolecule and the nucleic acid nanostructure folds into multiple stacked parallel loops; and incubating the reaction mixture to assemble multiple stacked parallel loops; and (b) visualizing the three-dimensional nanostructure, thereby detecting the biomolecule.

14. The method of claim 13, wherein the sample is a biological sample.

15. The method of claim 13, wherein the biomolecule is a macromolecule.

16. The method of claim 15, wherein the macromolecule is a protein.

17. The crisscross nucleic acid slat of claim 1, wherein the first plurality and/or the second plurality comprises 4-100 nucleic acid strands.

18. The crisscross nucleic acid slat of claim 1, wherein the nucleic acid strands of (a) and/or (b) are DNA strands.

19. The crisscross nucleic acid slat of claim 1, wherein nucleic acid strands of the first plurality and/or nucleic acid strands of the second plurality have a length of 21-30 nucleotides.

20. The crisscross nucleic acid slat of claim 1, wherein the angle is between 10 and 170 degrees.

21. The crisscross nucleic acid slat of claim 1, wherein the angle is between 60 and 120 degrees.

22. The crisscross nucleic acid slat of claim 1, wherein nucleic acid strands of the first plurality and/or nucleic acid strands of the second plurality have a length of 21, 42, 63, 84, 105 or 126 nucleotides.

23. A method comprising (a) combining in a reaction mixture (i) a sample comprising a biomolecule;

(ii) a nucleic acid strand capable of self-assembling; into a nanostructure that comprises stacked parallel strands;

(iii) at least two crisscross nucleic acid slats of claim 1, wherein the at least two slats bind to the stacked parallel strands of GO, and wherein at least one nucleic acid strand of the at least two slats is linked to a biomolecule binding partner that specifically binds to the biomolecule in the sample; and (b) incubating the reaction mixture under conditions that permit binding of the biomolecule binding partners to the biomolecule, assembly of the nanostructure into stacked parallel strands, and binding of the crisscross nucleic acid slats to the stacked parallel strands to form a three-dimensional nanostructure.

* * * * *

UNITED STATES PATENT AND TRADEMARK OFFICE

CERTIFICATE OF CORRECTION

PATENT NO. : 11,254,972 B2
APPLICATION NO. : 16/322787
DATED : February 22, 2022
INVENTOR(S) : Dionis Minev et al.

It is certified that error appears in the above-identified patent and that said Letters Patent is hereby corrected as shown below:

In the Specification

At Column 1, Lines 15-17, please change the paragraph:
"This invention was made with government support under 1435964 awarded by the Office of Naval Research. The government has certain rights in the invention."
To:
--This invention was made with government support under 1435964 awarded by National Science Foundation (NSF). The government has certain rights in the invention.--

Signed and Sealed this
Thirtieth Day of September, 2025

John A. Squires
*Director of the United States Patent and Trademark Office*

SEQUENCE LISTING

```
<160> NUMBER OF SEQ ID NOS: 688

<210> SEQ ID NO 1
<211> LENGTH: 42
<212> TYPE: DNA
<213> ORGANISM: Artificial Sequence
```

<220> FEATURE:
<223> OTHER INFORMATION: Synthetic Polynucleotide

<400> SEQUENCE: 1
atctgaactc gctacggcgg ggggagcccc cgatttagag ct 42

<210> SEQ ID NO 2
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 2
cattgctgat accgtttagc taacaaacat caagaaaaca aa 42

<210> SEQ ID NO 3
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 3
gatacttgcc ctctctgtac ataattaatt ttcccttaga at 42

<210> SEQ ID NO 4
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 4
gattgggcgt tatcaatgtt gttttgtcac aatcaataga aa 42

<210> SEQ ID NO 5
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 5
tctaatgaag acaaatcccc acgtcaccga cttgagccat tt 42

<210> SEQ ID NO 6
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 6
aaacatcggg ttgagtatta tgtggcgaga aaggaaggga ag 42

<210> SEQ ID NO 7
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 7
cgctggcatt cgcatcaaag gcgaattatt catttcaatt ac 42

<210> SEQ ID NO 8
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 8
agtttataaa tgagtatcaa tttagattaa gacgctgaga ag 42

<210> SEQ ID NO 9
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 9
tatcgacatc attacgcatc gcaacatata aaagaaacgc aa 42

<210> SEQ ID NO 10
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 10
ccatgcagac atcacgaagg tcaccagtag caccattacc at 42

<210> SEQ ID NO 11
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 11
aagataacgc ttgtgaaaat gagggcgctg gcaagtgtag cg 42

<210> SEQ ID NO 12
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 12
gctaacagta gggaaactgc ggcctgattg ctttgaatac ca 42

<210> SEQ ID NO 13
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 13
atgggttcag gatgcaggtg aaatcatagg tctgagagac ta 42

<210> SEQ ID NO 14
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 14
ctcggatggg agtaagcgta tgcagtatgt tagcaaacgt ag 42

<210> SEQ ID NO 15
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 15
agagtttctg cggcagttaa tcaatgaaac catcgatagc ag 42

<210> SEQ ID NO 16
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 16
gcaatacatc aaacgccgcg aacacccgcc gcgcttaatg cg 42

<210> SEQ ID NO 17
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 17
tcaggcactg cgtgaagcgg cagtaacagt accttttaca tc 42

<210> SEQ ID NO 18
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 18
atcaaaactc aacgagcagc ggttgggtta tataactata tg 42

<210> SEQ ID NO 19
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 19
agggttgtcg gacttgtgca aggaataccc aaaagaactg gc 42

<210> SEQ ID NO 20
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 20
agtccgtgaa gacggaaacc aaatcaagtt tgcctttagc gt 42

<210> SEQ ID NO 21

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 21
ctggggattt gacgcagacc tggttgcttt gacgagcacg ta 42

<210> SEQ ID NO 22
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 22
ttttcccagt cacgacgttg tgaaattgcg tagattttca gg 42

<210> SEQ ID NO 23
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 23
ttatcagtaa acagagaggt ttcgcaagac aaagaacgcg ag 42

<210> SEQ ID NO 24
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 24
tcagggatta atgaaagatg gaacaaagtt accagaagga aa 42

<210> SEQ ID NO 25
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 25
agtgtggcga tccgatagat gcggcatttt cggtcatagc cc 42

<210> SEQ ID NO 26
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 26
gggggatgtg ctgcaaggcg aatcagagcg ggagctaaac ag 42

<210> SEQ ID NO 27
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 27
agccagcttt ccggcaccgc tacctaccat atcaaaatta tt 42

<210> SEQ ID NO 28
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 28
ctttattatt cgcattcacc ctagttaatt tcatcttctg ac 42

<210> SEQ ID NO 29
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 29
ttggtgtaga tgggcgcatc gatcttaccg aagccctttt ta 42

<210> SEQ ID NO 30
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 30
cagaaataga agaattacag ctttcataat caaaatcacc gg 42

<210> SEQ ID NO 31
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 31
aagcgccatt cgccattcag gagacaggaa cggtacgcca ga 42

<210> SEQ ID NO 32
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 32
tcagaaaagc cccaaaaaca gctgattgtt tggattatac tt 42

<210> SEQ ID NO 33
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 33
gaggggacga cgacagtatc gaccgaccgt gtgataaata ag 42

<210> SEQ ID NO 34
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 34
tttttgttaa atcagctcat tagcccaata ataagagcaa ga 42

<210> SEQ ID NO 35
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 35
gtgggaacaa acggcggatt gcgcctccct cagagccgcc ac 42

<210> SEQ ID NO 36
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 36
tcgtaaaact agcatgtcaa tatcagtgag gccaccgagt aa 42

<210> SEQ ID NO 37
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 37
atgatattca accgttctag catattcctg attatcagat ga 42

<210> SEQ ID NO 38
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 38
ttaaattgta aacgttaata tcggaatcat aattactaga aa 42

<210> SEQ ID NO 39
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 39
tattttaaat gcaatgcctg atgagcgcta atatcagaga ga 42

<210> SEQ ID NO 40
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 40
tcaaaaataa ttcgcgtctg gagccaccac cctcagagcc gc 42

<210> SEQ ID NO 41
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 41
ggtagctatt tttgagagat cattaaccgt tgtagcaata ct 42

<210> SEQ ID NO 42
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 42
atggtcaata acctgtttag cttgcggaac aaagaaacca cc 42

<210> SEQ ID NO 43
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 43
aaaagggtga gaaaggccgg acgttataca aattcttacc ag 42

<210> SEQ ID NO 44
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 44
aacatccaat aaatcataca ggggagaatt aactgaacac cc 42

<210> SEQ ID NO 45
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 45
ctttatttca acgcaaggat acgccgccag cattgacagg ag 42

<210> SEQ ID NO 46
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 46
cgaacgagta gatttagttt gacttgcctg agtagaagaa ct 42

<210> SEQ ID NO 47
<211> LENGTH: 42
<212> TYPE: DNA
<213> ORGANISM: Artificial Sequence
<220> FEATURE:

<223> OTHER INFORMATION: Synthetic Polynucleotide

<400> SEQUENCE: 47
catttttgcg gatggcttag accgaacgtt attaatttta aa 42

<210> SEQ ID NO 48
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 48
agctgaaaag gtggcatcaa ttagggctta attgagaatc gc 42

<210> SEQ ID NO 49
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 49
agcttcaaag cgaaccagac ctttacagag agaataacat aa 42

<210> SEQ ID NO 50
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 50
attaagcaat aaagcctcag aggccttgat attcacaaac aa 42

<210> SEQ ID NO 51
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 51
ctgtagctca acatgtttta aaatatccag aacaatatta cc 42

<210> SEQ ID NO 52
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 52
ggcttttgca aaagaagttt tagactttac aaacaattcg ac 42

<210> SEQ ID NO 53
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 53
aggattagag agtaccttta agtaatttag gcagaggcat tt 42

<210> SEQ ID NO 54
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 54
aatattcatt gaatccccct cgaaacgatt ttttgtttaa cg 42

<210> SEQ ID NO 55
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 55
aagaggaagc ccgaaagact taatggaaag cgcagtctct ga 42

<210> SEQ ID NO 56
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 56
accctcgttt accagacgac gaacgctcat ggaaatacct ac 42

<210> SEQ ID NO 57
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 57
taacggaaca acattattac aagagccgtc aatagataat ac 42

<210> SEQ ID NO 58
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 58
atgtttagac tggatagcgt cataaagtac cgacaaaagg ta 42

<210> SEQ ID NO 59
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 59
tgaattacct tatgcgattt tttacaaaat aaacagccat at 42

<210> SEQ ID NO 60
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 60
aaacgagaat gaccataaat ccatacatgg cttttgatga ta 42

<210> SEQ ID NO 61
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 61
agatttagga ataccacatt caaatggatt atttacattg gc 42

<210> SEQ ID NO 62
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 62
cgaggcgcag acggtcaatc agttatctaa aatatcttta gg 42

<210> SEQ ID NO 63
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 63
gtcaggacgt tgggaagaaa agacaataaa caacatgttc ag 42

<210> SEQ ID NO 64
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 64
aggctggctg accttcatca ataccaacgc taacgagcgt ct 42

<210> SEQ ID NO 65
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 65
taaattgggc ttgagatggt tttttaacgg ggtcagtgcc tt 42

<210> SEQ ID NO 66
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 66
tgtgtcgaaa tccgcgacct gagtaataaa agggacattc tg 42

<210> SEQ ID NO 67
<211> LENGTH: 42

<212> TYPE: DNA
<213> ORGANISM: Artificial Sequence
<220> FEATURE:
<223> OTHER INFORMATION: Synthetic Polynucleotide

<400> SEQUENCE: 67
tacgaaggca ccaacctaaa actggtcagt tggcaaatca ac 42

<210> SEQ ID NO 68
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 68
ctttgaaaga ggacagatga atatcaacaa tagataagtc ct 42

<210> SEQ ID NO 69
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 69
gtagcaacgg ctacagaggc ttagttgcta ttttgcaccc ag 42

<210> SEQ ID NO 70
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 70
gatattcatt acccaaatca acagttaatg ccccctgcct at 42

<210> SEQ ID NO 71
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 71
ctaaaacact catctttgac cctgacctga aagcgtaaga at 42

<210> SEQ ID NO 72
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 72
cgaataataa ttttttcacg tatcaccttg ctgaacctca aa 42

<210> SEQ ID NO 73
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 73
atgaggaagt ttccattaaa catcctaatt tacgagcatg ta 42

<210> SEQ ID NO 74
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 74
ttcgaggtga atttcttaaa cacctcccga cttgcgggag gt 42

<210> SEQ ID NO 75
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 75
ggatcgtcac cctcagcagc gacatgaaag tattaagagg ct 42

<210> SEQ ID NO 76
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 76
tttcagcgga gtgagaatag atgaatggct attagtcttt aa 42

<210> SEQ ID NO 77
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 77
ctacaacgcc tgtagcattc cagtgccacg ctgagagcca gc 42

<210> SEQ ID NO 78
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 78
ctccaaaagg agcctttaat tgtctttcct tatcattcca ag 42

<210> SEQ ID NO 79
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 79
cagagccacc accctcattt taaggcttat ccggtattct aa 42

<210> SEQ ID NO 80
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 80
ccgacaatga caacaaccat ctaggattag cggggttttg ct 42

<210> SEQ ID NO 81
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 81
tcgtaaaact agcatgtcaa tatcagtgag gccaccgagt aagaaaaac 49

<210> SEQ ID NO 82
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 82
atgatattca accgttctag catattcctg attatcagat gaagagtcc 49

<210> SEQ ID NO 83
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 83
ttaaattgta aacgttaata tcggaatcat aattactaga aaaatagcc 49

<210> SEQ ID NO 84
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 84
tattttaaat gcaatgcctg atgagcgcta atatcagaga gaatggtgg 49

<210> SEQ ID NO 85
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 85
tcaaaaataa ttcgcgtctg gagccaccac cctcagagcc gccggtcca 49

<210> SEQ ID NO 86
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 86
ggtagctatt tttgagagat cattaaccgt tgtagcaata ctcggtcca 49

<210> SEQ ID NO 87
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 87
atggtcaata acctgtttag cttgcggaac aaagaaacca ccatggtgg 49

<210> SEQ ID NO 88
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 88
aaaagggtga gaaaggccgg acgttataca aattcttacc agaatagcc 49

<210> SEQ ID NO 89
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 89
aacatccaat aaatcataca ggggagaatt aactgaacac ccagagtcc 49

<210> SEQ ID NO 90
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 90
ctttatttca acgcaaggat acgccgccag cattgacagg aggaaaaac 49

<210> SEQ ID NO 91
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 91
tcgtaaaact agcatgtcaa tatcagtgag gccaccgagt aagaaaaacc gt 52

<210> SEQ ID NO 92
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 92
atgatattca accgttctag catattcctg attatcagat gaagagtcca ct 52

<210> SEQ ID NO 93
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 93
ttaaattgta aacgttaata tcggaatcat aattactaga aaaatagccc ga 52

<210> SEQ ID NO 94
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 94
tattttaaat gcaatgcctg atgagcgcta atatcagaga gaatggtggt tc 52

<210> SEQ ID NO 95
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 95
tcaaaaataa ttcgcgtctg gagccaccac cctcagagcc gccggtccac gc 52

<210> SEQ ID NO 96
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 96
ggtagctatt tttgagagat cattaaccgt tgtagcaata ctcggtccac gc 52

<210> SEQ ID NO 97
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 97
atggtcaata acctgtttag cttgcggaac aaagaaacca ccatggtggt tc 52

<210> SEQ ID NO 98
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 98
aaaagggtga gaaaggccgg acgttataca aattcttacc agaatagccc ga 52

<210> SEQ ID NO 99
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 99
aacatccaat aaatcataca ggggagaatt aactgaacac ccagagtcca ct 52

<210> SEQ ID NO 100

<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 100
ctttatttca acgcaaggat acgccgccag cattgacagg aggaaaaacc gt 52

<210> SEQ ID NO 101
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 101
caatattaca taacaatcct ccatttgaat tacctttttt aa 42

<210> SEQ ID NO 102
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 102
actgataccg tgcaaaatta tcaaagacaa aagggcgaca tt 42

<210> SEQ ID NO 103
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 103
cgtaacgatc taaagttttg taacatcgcc attaaaaata cc 42

<210> SEQ ID NO 104
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 104
gaacccatgt accgtaacac tcgcactcat cgagaacaag ca 42

<210> SEQ ID NO 105
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 105
taccgccacc ctcagaaccg ccgtcgagag ggttgatata ag 42

<210> SEQ ID NO 106
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 106
tcattaaagg tgaattatca cttctgcaat gtgcgagaaa tg 42

<210> SEQ ID NO 107
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 107
gggaattaga gccagcaaaa tgtttatgta gatgaaggta ta 42

<210> SEQ ID NO 108
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 108
caccgtaatc agtagcgaca ggtttcttgt tgttcgccat cc 42

<210> SEQ ID NO 109
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 109
ccttattagc gtttgccatc tgcaacacag caataaaaat gc 42

<210> SEQ ID NO 110
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 110
cctcagaacc gccaccctca gccttcctgt agccagcttt ca 42

<210> SEQ ID NO 111
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 111
gttgaggcag gtcagacgat tgcataaagc taaatcggtt gt 42

<210> SEQ ID NO 112
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 112
atttaccgtt ccagtaagcg taaaaatcag gtctttaccc tg 42

<210> SEQ ID NO 113
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 113
gagtaacagt gcccgtataa acgtaacaaa gctgctcatt ca 42

<210> SEQ ID NO 114
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 114
gagactcctc aagagaagga tgcccacgca taaccgatat at 42

<210> SEQ ID NO 115
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 115
tagcaagcaa atcagatata gcagggatag caagcccaat ag 42

<210> SEQ ID NO 116
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 116
gcttctgtaa atcgtcgcta taaacatata gatgattaaa cc 42

<210> SEQ ID NO 117
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 117
agtattaaca ccgcctgcaa cacagacagc cctcatagtt ag 42

<210> SEQ ID NO 118
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 118
gcactaaatc ggaaccctaa attttgtttt atggagatga ta 42

<210> SEQ ID NO 119
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 119
aaagcgaaag gagcgggcgc tctgaatttc gcgtcgtctt ca 42

<210> SEQ ID NO 120
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 120
ccgctacagg gcgcgtacta ttttccatga attggtaaca cc 42

<210> SEQ ID NO 121
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 121
gaggccgatt aaagggattt tctgcgcaac tgttgggaag gg 42

<210> SEQ ID NO 122
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 122
aagagtctgt ccatcacgca atacaaaggc tatcaggtca tt 42

<210> SEQ ID NO 123
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 123
caaactatcg gccttgctgg tatatgcaac taaagtacgg tg 42

<210> SEQ ID NO 124
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 124
attttgacgc tcaatcgtct gaactaatgc agatacataa cg 42

<210> SEQ ID NO 125
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 125
gccaacagag atagaaccct tcccagcgat tataccaagc gc 42

<210> SEQ ID NO 126
<211> LENGTH: 42
<212> TYPE: DNA
<213> ORGANISM: Artificial Sequence
<220> FEATURE:

<223> OTHER INFORMATION: Synthetic Polynucleotide

<400> SEQUENCE: 126
tgcgcgaact gatagcccta acgtctttcc agacgttagt aa 42

<210> SEQ ID NO 127
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 127
caaagggcga aaaaccaaca gctgattgcc ctgcgccagg 40

<210> SEQ ID NO 128
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 128
agtccactat taaagaagag agttgcagca agcaacgcgc 40

<210> SEQ ID NO 129
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 129
tagggttgag tgttgtgccc cagcaggcga aaacctgtcg 40

<210> SEQ ID NO 130
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 130
aatcccttat aaatcagttc cgaaatcggc aa 32

<210> SEQ ID NO 131
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 131
gtgagacggg cgtctatca 19

<210> SEQ ID NO 132
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 132
gtggtttttg tttcctgtgt gaaa 24

<210> SEQ ID NO 133
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 133
cgtattggtc accgcctggc cctgacgtgg actccaacgt 40

<210> SEQ ID NO 134
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 134
ggggagagat tccacacaac atac 24

<210> SEQ ID NO 135
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 135
gaatcggccg gtccacgctg gttttccagt ttggaacaag 40

<210> SEQ ID NO 136
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 136
tgccagctgt gtaaagcctg gggt 24

<210> SEQ ID NO 137
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 137
gtcgggaaat cctgtttgat ggtgaaagaa tagcccgaga 40

<210> SEQ ID NO 138
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 138
gttgcgctca ctgcccaact cacattaatt gc 32

<210> SEQ ID NO 139
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 139
gtcatagctc ttttcacca 19

<210> SEQ ID NO 140
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 140
ttgttatccg ctcacagcgg tttg 24

<210> SEQ ID NO 141
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 141
gagccggaag cataaagcat taat 24

<210> SEQ ID NO 142
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 142
gcctaatgag tgagctgctt tcca 24

<210> SEQ ID NO 143
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 143
aaaatacata cataaaggtg gctattacgg ggttggaggt ca 42

<210> SEQ ID NO 144
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 144
tagcaaggcc ggaaacgtca ccgaacaaga cccgttagta ac 42

<210> SEQ ID NO 145
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 145
cagactgtag cgcgttttca taacgaagac gcctggtcgt tc 42

<210> SEQ ID NO 146
<211> LENGTH: 42

<212> TYPE: DNA
<213> ORGANISM: Artificial Sequence
<220> FEATURE:
<223> OTHER INFORMATION: Synthetic Polynucleotide

<400> SEQUENCE: 146
aaccagagcc accaccggaa caccgtaatg ggataggtca cg 42

<210> SEQ ID NO 147
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 147
caccagaacc accaccagag caaaattttt agaaccctca ta 42

<210> SEQ ID NO 148
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 148
ataaatcctc attaaagcca gcaaatatcg cgttttaatt cg 42

<210> SEQ ID NO 149
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 149
caggagtgta ctggtaataa gtaatttcaa ctttaatcat tg 42

<210> SEQ ID NO 150
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 150
ttcggaacct attattctga aaaagacagc atcggaacga gg 42

<210> SEQ ID NO 151
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 151
cagtaccagg cggataagtg ccaccctcag aaccgccacc ct 42

<210> SEQ ID NO 152
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 152
attcatatgg tttaccagcg ctatcacgag tacggtggaa ac 42

<210> SEQ ID NO 153
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 153
agacaccacg gaataagttt atgcagatcc ggtgtcttgt ct 42

<210> SEQ ID NO 154
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 154
atgattaaga ctccttatta ctgctaaact ggaaagcaac ga 42

<210> SEQ ID NO 155
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 155
ccgaggaaac gcaataataa cgttgccagg aggatctgga ac 42

<210> SEQ ID NO 156
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 156
agaaaagtaa gcagatagcc gcagacatca ttgattcagc at 42

<210> SEQ ID NO 157
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 157
aacaatgaaa tagcaatagc ttaaccgtgc atctgccagt tt 42

<210> SEQ ID NO 158
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 158
taacccacaa gaattgagtt attttaacca ataggaacgc ca 42

<210> SEQ ID NO 159
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 159
tgaacaaagt cagagggtaa tgtaatgtgt aggtaaagat tc 42

<210> SEQ ID NO 160
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 160
aaacagggaa gcgcattaga cgcaaggcaa agaattagca aa 42

<210> SEQ ID NO 161
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 161
tcaaaaatga aaatagcagc cggaagcaaa ctccaacagg tc 42

<210> SEQ ID NO 162
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 162
tatttatccc aatccaaata aaaatgcttt aaacagttca ga 42

<210> SEQ ID NO 163
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 163
ttccagagcc taatttgcca gaagaactgg ctcattatac ca 42

<210> SEQ ID NO 164
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 164
ctacaatttt atcctgaatc tgagtaatct tgacaagaac cg 42

<210> SEQ ID NO 165
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 165
tttgaagcct taaatcaaga tttgaggact aaagactttt tc 42

<210> SEQ ID NO 166
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 166
gaacgcgagg cgttttagcg aagcttgata ccgatagttg cg 42

<210> SEQ ID NO 167
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 167
ccttgaaaac atagcgatag cgagttagag tctgagcaaa aa 42

<210> SEQ ID NO 168
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 168
agtcaatagt gaatttatca agtatctgca tatgatgtct ga 42

<210> SEQ ID NO 169
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 169
cctttttaac ctccggctta gtgagtatta cgaaggtgtt at 42

<210> SEQ ID NO 170
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 170
taaatgctga tgcaaatcca acgaagtgag cgaaattaac tc 42

<210> SEQ ID NO 171
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 171
aaaacttttt caaatatatt ttcatgcgta ttaaccaaca gt 42

<210> SEQ ID NO 172
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 172
ctaaatttaa tggtttgaaa tgcctcagga agatcgcact cc 42

<210> SEQ ID NO 173
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 173
gcgttaaata agaataaaca ctttgttaaa attcgcatta aa 42

<210> SEQ ID NO 174
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 174
aagcctgttt agtatcatat ggacagtcaa atcaccatca at 42

<210> SEQ ID NO 175
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 175
tataaagcca acgctcaaca gtctactaat agtagtagca tt 42

<210> SEQ ID NO 176
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 176
catatttaac aacgccaaca tttgctcctt ttgataagag gt 42

<210> SEQ ID NO 177
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 177
tcgagccagt aataagagaa tcaatactgc ggaatcgtca ta 42

<210> SEQ ID NO 178
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 178
aagtaattct gtccagacga catctacgtt aataaaacga ac 42

<210> SEQ ID NO 179

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 179
ctaatgcaga acgcgcctgt tcggtgtaca gaccaggcgc at 42

<210> SEQ ID NO 180
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 180
gaacaagaaa aataatatcc cgggtaaaat acgtaatgcc ac 42

<210> SEQ ID NO 181
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 181
gaaaccaatc aataatcggc tgtatcggtt tatcagcttg ct 42

<210> SEQ ID NO 182
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 182
aacgggtatt aaaccaagta cgagtttcgt caccagtaca aa 42

<210> SEQ ID NO 183
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 183
attaattaca tttaacaatt tgcactcgcg ggatttatt tt 42

<210> SEQ ID NO 184
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 184
ctgagcaaaa gaagatgatg agaaacgaca tacattgcaa gg 42

<210> SEQ ID NO 185
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 185
agttacaaaa tcgcgcagag gagagtgaga tcggttttgt aa 42

<210> SEQ ID NO 186
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 186
gggagaaaca ataacggatt ctgttgagct tgaaacagca aa 42

<210> SEQ ID NO 187
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 187
tttaacgtca gatgaatata cagagcaggc aatgcatgac ga 42

<210> SEQ ID NO 188
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 188
tgcacgtaaa acagaaataa aaaaacgacg gccagtgcca ag 42

<210> SEQ ID NO 189
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 189
ctgaataatg gaagggttag atctggtgcc ggaaaccagg ca 42

<210> SEQ ID NO 190
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 190
tggcaattca tcaatataat cgaagattgt ataagcaaat at 42

<210> SEQ ID NO 191
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 191
agaaggagcg gaattatcat ctgataaatt aatgccggag ag 42

<210> SEQ ID NO 192
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 192
agtttgagta acattatcat ttatattttc atttggggcg cg 42

<210> SEQ ID NO 193
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 193
aactcgtatt aaatcctttg cgcttaattg ctgaatataa tg 42

<210> SEQ ID NO 194
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 194
atttgaggat ttagaagtat tgccagaggg ggtaatagta aa 42

<210> SEQ ID NO 195
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 195
agcactaaca actaatagat tggtagaaag attcatcagt tg 42

<210> SEQ ID NO 196
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 196
agttgaaagg aattgaggaa gtaagggaac cgaactgacc aa 42

<210> SEQ ID NO 197
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 197
tatcaaaccc tcaatcaata tcgaaagagg caaaagaata ca 42

<210> SEQ ID NO 198
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 198
agcaaatgaa aaatctaaag ctgaaaatct ccaaaaaaaa gg 42

<210> SEQ ID NO 199
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 199
tgacggggaa agccggcgaa ccttactgtt tctttacata aa 42

<210> SEQ ID NO 200
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 200
gtcacgctgc gcgtaaccac cccaggagaa cgaggatatt gc 42

<210> SEQ ID NO 201
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 201
taacgtgctt tcctcgttag attaagttgg gtaacgccag gg 42

<210> SEQ ID NO 202
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 202
atcctgagaa gtgtttttat acatatgtac cccggttgat aa 42

<210> SEQ ID NO 203
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 203
tctttgatta gtaataacat caccattaga tacatttcgc aa 42

<210> SEQ ID NO 204
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 204
gccagccatt gcaacaggaa aataaaaacc aaaatagcga ga 42

<210> SEQ ID NO 205
<211> LENGTH: 42
<212> TYPE: DNA
<213> ORGANISM: Artificial Sequence
<220> FEATURE:

<223> OTHER INFORMATION: Synthetic Polynucleotide

<400> SEQUENCE: 205
agattcacca gtcacacgac cctccatgtt acttagccgg aa 42

<210> SEQ ID NO 206
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 206
acgtggcaca gacaatattt taaggaacaa ctaaaggaat tg 42

<210> SEQ ID NO 207
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 207
atctgaactc gctacggcgg ggggagcccc cgatttagag ctcggtcca 49

<210> SEQ ID NO 208
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 208
cattgctgat accgtttagc taacaaacat caagaaaaca aaatggtgg 49

<210> SEQ ID NO 209
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 209
gatacttgcc ctctctgtac ataattaatt ttcccttaga ataatagcc 49

<210> SEQ ID NO 210
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 210
gattgggcgt tatcaatgtt gttttgtcac aatcaataga aaagagtcc 49

<210> SEQ ID NO 211
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 211
tctaatgaag acaaatcccc acgtcaccga cttgagccat ttgaaaaac 49

<210> SEQ ID NO 212
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 212
aaacatcggg ttgagtatta tgtggcgaga aaggaaggga aggaaaaac 49

<210> SEQ ID NO 213
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 213
cgctggcatt cgcatcaaag gcgaattatt catttcaatt acagagtcc 49

<210> SEQ ID NO 214
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 214
agtttataaa tgagtatcaa tttagattaa gacgctgaga agaatagcc 49

<210> SEQ ID NO 215
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 215
tatcgacatc attacgcatc gcaacatata aaagaaacgc aaatggtgg 49

<210> SEQ ID NO 216
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 216
ccatgcagac atcacgaagg tcaccagtag caccattacc atcggtcca 49

<210> SEQ ID NO 217
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 217
aagataacgc ttgtgaaaat gagggcgctg gcaagtgtag cgcggtcca 49

<210> SEQ ID NO 218
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 218
gctaacagta gggaaactgc ggcctgattg ctttgaatac caatggtgg 49

<210> SEQ ID NO 219
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 219
atgggttcag gatgcaggtg aaatcatagg tctgagagac taaatagcc 49

<210> SEQ ID NO 220
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 220
ctcggatggg agtaagcgta tgcagtatgt tagcaaacgt agagagtcc 49

<210> SEQ ID NO 221
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 221
agagtttctg cggcagttaa tcaatgaaac catcgatagc aggaaaaac 49

<210> SEQ ID NO 222
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 222
gcaatacatc aaacgccgcg aacacccgcc gcgcttaatg cggaaaaac 49

<210> SEQ ID NO 223
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 223
tcaggcactg cgtgaagcgg cagtaacagt accttttaca tcagagtcc 49

<210> SEQ ID NO 224
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 224
atcaaaactc aacgagcagc ggttgggtta tataactata tgaatagcc 49

<210> SEQ ID NO 225
<211> LENGTH: 49

<212> TYPE: DNA
<213> ORGANISM: Artificial Sequence
<220> FEATURE:
<223> OTHER INFORMATION: Synthetic Polynucleotide

<400> SEQUENCE: 225
agggttgtcg gacttgtgca aggaataccc aaaagaactg gcatggtgg 49

<210> SEQ ID NO 226
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 226
agtccgtgaa gacggaaacc aaatcaagtt tgcctttagc gtcggtcca 49

<210> SEQ ID NO 227
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 227
ctggggattt gacgcagacc tggttgcttt gacgagcacg tacggtcca 49

<210> SEQ ID NO 228
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 228
ttttcccagt cacgacgttg tgaaattgcg tagattttca ggatggtgg 49

<210> SEQ ID NO 229
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 229
ttatcagtaa acagagaggt ttcgcaagac aaagaacgcg agaatagcc 49

<210> SEQ ID NO 230
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 230
tcagggatta atgaaagatg gaacaaagtt accagaagga aaagagtcc 49

<210> SEQ ID NO 231
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 231
agtgtggcga tccgatagat gcggcatttt cggtcatagc ccgaaaaac 49

<210> SEQ ID NO 232
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 232
gggggatgtg ctgcaaggcg aatcagagcg ggagctaaac aggaaaaac 49

<210> SEQ ID NO 233
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 233
agccagcttt ccggcaccgc tacctaccat atcaaaatta ttagagtcc 49

<210> SEQ ID NO 234
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 234
ctttattatt cgcattcacc ctagttaatt tcatcttctg acaatagcc 49

<210> SEQ ID NO 235
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 235
ttggtgtaga tgggcgcatc gatcttaccg aagccctttt taatggtgg 49

<210> SEQ ID NO 236
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 236
cagaaataga agaattacag ctttcataat caaaatcacc ggcggtcca 49

<210> SEQ ID NO 237
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 237
aagcgccatt cgccattcag gagacaggaa cggtacgcca gacggtcca 49

<210> SEQ ID NO 238
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 238
tcagaaaagc cccaaaaaca gctgattgtt tggattatac ttatggtgg 49

<210> SEQ ID NO 239
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 239
gaggggacga cgacagtatc gaccgaccgt gtgataaata agaatagcc 49

<210> SEQ ID NO 240
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 240
tttttgttaa atcagctcat tagcccaata ataagagcaa gaagagtcc 49

<210> SEQ ID NO 241
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 241
gtgggaacaa acggcggatt gcgcctccct cagagccgcc acgaaaaac 49

<210> SEQ ID NO 242
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 242
cgaacgagta gatttagttt gacttgcctg agtagaagaa ctgaaaaac 49

<210> SEQ ID NO 243
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 243
catttttgcg gatggcttag accgaacgtt attaatttta aaagagtcc 49

<210> SEQ ID NO 244
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 244
agctgaaaag gtggcatcaa ttagggctta attgagaatc gcaatagcc 49

<210> SEQ ID NO 245
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 245
agcttcaaag cgaaccagac ctttacagag agaataacat aaatggtgg 49

<210> SEQ ID NO 246
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 246
attaagcaat aaagcctcag aggccttgat attcacaaac aacggtcca 49

<210> SEQ ID NO 247
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 247
ctgtagctca acatgtttta aaatatccag aacaatatta cccggtcca 49

<210> SEQ ID NO 248
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 248
ggcttttgca aaagaagttt tagactttac aaacaattcg acatggtgg 49

<210> SEQ ID NO 249
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 249
aggattagag agtaccttta agtaatttag gcagaggcat ttaatagcc 49

<210> SEQ ID NO 250
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 250
aatattcatt gaatccccct cgaaacgatt ttttgtttaa cgagagtcc 49

<210> SEQ ID NO 251
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 251
aagaggaagc ccgaaagact taatggaaag cgcagtctct gagaaaaac 49

<210> SEQ ID NO 252
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 252
accctcgttt accagacgac gaacgctcat ggaaatacct acgaaaaac 49

<210> SEQ ID NO 253
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 253
taacggaaca acattattac aagagccgtc aatagataat acagagtcc 49

<210> SEQ ID NO 254
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 254
atgtttagac tggatagcgt cataaagtac cgacaaaagg taaatagcc 49

<210> SEQ ID NO 255
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 255
tgaattacct tatgcgattt tttacaaaat aaacagccat atatggtgg 49

<210> SEQ ID NO 256
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 256
aaacgagaat gaccataaat ccatacatgg cttttgatga tacggtcca 49

<210> SEQ ID NO 257
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 257
agatttagga ataccacatt caaatggatt atttacattg gccggtcca 49

<210> SEQ ID NO 258

<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 258
cgaggcgcag acggtcaatc agttatctaa aatatcttta ggatggtgg 49

<210> SEQ ID NO 259
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 259
gtcaggacgt tgggaagaaa agacaataaa caacatgttc agaatagcc 49

<210> SEQ ID NO 260
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 260
aggctggctg accttcatca ataccaacgc taacgagcgt ctagagtcc 49

<210> SEQ ID NO 261
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 261
taaattgggc ttgagatggt tttttaacgg ggtcagtgcc ttgaaaaac 49

<210> SEQ ID NO 262
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 262
tgtgtcgaaa tccgcgacct gagtaataaa agggacattc tggaaaaac 49

<210> SEQ ID NO 263
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 263
tacgaaggca ccaacctaaa actggtcagt tggcaaatca acagagtcc 49

<210> SEQ ID NO 264
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 264

```
ctttgaaaga ggacagatga atatcaacaa tagataagtc ctaatagcc                49


<210> SEQ ID NO 265
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 265

gtagcaacgg ctacagaggc ttagttgcta ttttgcaccc agatggtgg                49


<210> SEQ ID NO 266
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 266

gatattcatt acccaaatca acagttaatg ccccctgcct atcggtcca                49


<210> SEQ ID NO 267
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 267

ctaaaacact catctttgac cctgacctga aagcgtaaga atcggtcca                49


<210> SEQ ID NO 268
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 268

cgaataataa ttttttcacg tatcaccttg ctgaacctca aaatggtgg                49


<210> SEQ ID NO 269
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 269

atgaggaagt ttccattaaa catcctaatt tacgagcatg taaatagcc                49


<210> SEQ ID NO 270
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 270

ttcgaggtga atttcttaaa cacctcccga cttgcgggag gtagagtcc                49


<210> SEQ ID NO 271
<211> LENGTH: 49
<212> TYPE: DNA
```

<213> ORGANISM: Artificial Sequence
<220> FEATURE:
<223> OTHER INFORMATION: Synthetic Polynucleotide

<400> SEQUENCE: 271
ggatcgtcac cctcagcagc gacatgaaag tattaagagg ctgaaaaac 49

<210> SEQ ID NO 272
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 272
tttcagcgga gtgagaatag atgaatggct attagtcttt aagaaaaac 49

<210> SEQ ID NO 273
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 273
ctacaacgcc tgtagcattc cagtgccacg ctgagagcca gcagagtcc 49

<210> SEQ ID NO 274
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 274
ctccaaaagg agcctttaat tgtctttcct tatcattcca agaatagcc 49

<210> SEQ ID NO 275
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 275
cagagccacc accctcattt taaggcttat ccggtattct aaatggtgg 49

<210> SEQ ID NO 276
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 276
ccgacaatga caacaaccat ctaggattag cggggttttg ctcggtcca 49

<210> SEQ ID NO 277
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 277
atctgaactc gctacggcgg ggggagcccc cgatttagag ctcggtccac gc 52

<210> SEQ ID NO 278
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 278
cattgctgat accgtttagc taacaaacat caagaaaaca aaatggtggt tc 52

<210> SEQ ID NO 279
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 279
gatacttgcc ctctctgtac ataattaatt ttcccttaga ataatagccc ga 52

<210> SEQ ID NO 280
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 280
gattgggcgt tatcaatgtt gttttgtcac aatcaataga aaagagtcca ct 52

<210> SEQ ID NO 281
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 281
tctaatgaag acaaatcccc acgtcaccga cttgagccat ttgaaaaacc gt 52

<210> SEQ ID NO 282
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 282
aaacatcggg ttgagtatta tgtggcgaga aaggaaggga aggaaaaacc gt 52

<210> SEQ ID NO 283
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 283
cgctggcatt cgcatcaaag gcgaattatt catttcaatt acagagtcca ct 52

<210> SEQ ID NO 284
<211> LENGTH: 52
<212> TYPE: DNA
<213> ORGANISM: Artificial Sequence
<220> FEATURE:

<223> OTHER INFORMATION: Synthetic Polynucleotide

<400> SEQUENCE: 284
agtttataaa tgagtatcaa tttagattaa gacgctgaga agaatagccc ga 52

<210> SEQ ID NO 285
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 285
tatcgacatc attacgcatc gcaacatata aaagaaacgc aaatggtggt tc 52

<210> SEQ ID NO 286
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 286
ccatgcagac atcacgaagg tcaccagtag caccattacc atcggtccac gc 52

<210> SEQ ID NO 287
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 287
aagataacgc ttgtgaaaat gagggcgctg gcaagtgtag cgcggtccac gc 52

<210> SEQ ID NO 288
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 288
gctaacagta gggaaactgc ggcctgattg ctttgaatac caatggtggt tc 52

<210> SEQ ID NO 289
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 289
atgggttcag gatgcaggtg aaatcatagg tctgagagac taaatagccc ga 52

<210> SEQ ID NO 290
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 290
ctcggatggg agtaagcgta tgcagtatgt tagcaaacgt agagagtcca ct 52

<210> SEQ ID NO 291
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 291
agagtttctg cggcagttaa tcaatgaaac catcgatagc aggaaaaacc gt 52

<210> SEQ ID NO 292
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 292
gcaatacatc aaacgccgcg aacacccgcc gcgcttaatg cggaaaaacc gt 52

<210> SEQ ID NO 293
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 293
tcaggcactg cgtgaagcgg cagtaacagt accttttaca tcagagtcca ct 52

<210> SEQ ID NO 294
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 294
atcaaaactc aacgagcagc ggttgggtta tataactata tgaatagccc ga 52

<210> SEQ ID NO 295
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 295
agggttgtcg gacttgtgca aggaataccc aaaagaactg gcatggtggt tc 52

<210> SEQ ID NO 296
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 296
agtccgtgaa gacggaaacc aaatcaagtt tgcctttagc gtcggtccac gc 52

<210> SEQ ID NO 297
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 297
ctggggattt gacgcagacc tggttgcttt gacgagcacg tacggtccac gc 52

<210> SEQ ID NO 298
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 298
ttttcccagt cacgacgttg tgaaattgcg tagattttca ggatggtggt tc 52

<210> SEQ ID NO 299
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 299
ttatcagtaa acagagaggt ttcgcaagac aaagaacgcg agaatagccc ga 52

<210> SEQ ID NO 300
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 300
tcagggatta atgaaagatg gaacaaagtt accagaagga aaagagtcca ct 52

<210> SEQ ID NO 301
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 301
agtgtggcga tccgatagat gcggcatttt cggtcatagc ccgaaaaacc gt 52

<210> SEQ ID NO 302
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 302
gggggatgtg ctgcaaggcg aatcagagcg ggagctaaac aggaaaaacc gt 52

<210> SEQ ID NO 303
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 303
agccagcttt ccggcaccgc tacctaccat atcaaaatta ttagagtcca ct 52

<210> SEQ ID NO 304
<211> LENGTH: 52

<212> TYPE: DNA
<213> ORGANISM: Artificial Sequence
<220> FEATURE:
<223> OTHER INFORMATION: Synthetic Polynucleotide

<400> SEQUENCE: 304
ctttattatt cgcattcacc ctagttaatt tcatcttctg acaatagccc ga 52

<210> SEQ ID NO 305
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 305
ttggtgtaga tgggcgcatc gatcttaccg aagccctttt taatggtggt tc 52

<210> SEQ ID NO 306
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 306
cagaaataga agaattacag ctttcataat caaaatcacc ggcggtccac gc 52

<210> SEQ ID NO 307
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 307
aagcgccatt cgccattcag gagacaggaa cggtacgcca gacggtccac gc 52

<210> SEQ ID NO 308
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 308
tcagaaaagc cccaaaaaca gctgattgtt tggattatac ttatggtggt tc 52

<210> SEQ ID NO 309
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 309
gaggggacga cgacagtatc gaccgaccgt gtgataaata agaatagccc ga 52

<210> SEQ ID NO 310
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 310
tttttgttaa atcagctcat tagcccaata ataagagcaa gaagagtcca ct 52

<210> SEQ ID NO 311
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 311
gtgggaacaa acggcggatt gcgcctccct cagagccgcc acgaaaaacc gt 52

<210> SEQ ID NO 312
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 312
cgaacgagta gatttagttt gacttgcctg agtagaagaa ctgaaaaacc gt 52

<210> SEQ ID NO 313
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 313
catttttgcg gatggcttag accgaacgtt attaatttta aaagagtcca ct 52

<210> SEQ ID NO 314
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 314
agctgaaaag gtggcatcaa ttagggctta attgagaatc gcaatagccc ga 52

<210> SEQ ID NO 315
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 315
agcttcaaag cgaaccagac ctttacagag agaataacat aaatggtggt tc 52

<210> SEQ ID NO 316
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 316
attaagcaat aaagcctcag aggccttgat attcacaaac aacggtccac gc 52

<210> SEQ ID NO 317
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 317
ctgtagctca acatgtttta aaatatccag aacaatatta cccggtccac gc 52

<210> SEQ ID NO 318
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 318
ggcttttgca aaagaagttt tagactttac aaacaattcg acatggtggt tc 52

<210> SEQ ID NO 319
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 319
aggattagag agtaccttta agtaatttag gcagaggcat ttaatagccc ga 52

<210> SEQ ID NO 320
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 320
aatattcatt gaatccccct cgaaacgatt ttttgtttaa cgagagtcca ct 52

<210> SEQ ID NO 321
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 321
aagaggaagc ccgaaagact taatggaaag cgcagtctct gagaaaaacc gt 52

<210> SEQ ID NO 322
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 322
accctcgttt accagacgac gaacgctcat ggaaatacct acgaaaaacc gt 52

<210> SEQ ID NO 323
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 323
taacggaaca acattattac aagagccgtc aatagataat acagagtcca ct 52

<210> SEQ ID NO 324
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 324
atgtttagac tggatagcgt cataaagtac cgacaaaagg taaatagccc ga 52

<210> SEQ ID NO 325
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 325
tgaattacct tatgcgattt tttacaaaat aaacagccat atatggtggt tc 52

<210> SEQ ID NO 326
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 326
aaacgagaat gaccataaat ccatacatgg cttttgatga tacggtccac gc 52

<210> SEQ ID NO 327
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 327
agatttagga ataccacatt caaatggatt atttacattg gccggtccac gc 52

<210> SEQ ID NO 328
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 328
cgaggcgcag acggtcaatc agttatctaa aatatcttta ggatggtggt tc 52

<210> SEQ ID NO 329
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 329
gtcaggacgt tgggaagaaa agacaataaa caacatgttc agaatagccc ga 52

<210> SEQ ID NO 330
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 330
aggctggctg accttcatca ataccaacgc taacgagcgt ctagagtcca ct 52

<210> SEQ ID NO 331
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 331
taaattgggc ttgagatggt tttttaacgg ggtcagtgcc ttgaaaaacc gt 52

<210> SEQ ID NO 332
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 332
tgtgtcgaaa tccgcgacct gagtaataaa agggacattc tggaaaaacc gt 52

<210> SEQ ID NO 333
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 333
tacgaaggca ccaacctaaa actggtcagt tggcaaatca acagagtcca ct 52

<210> SEQ ID NO 334
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 334
ctttgaaaga ggacagatga atatcaacaa tagataagtc ctaatagccc ga 52

<210> SEQ ID NO 335
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 335
gtagcaacgg ctacagaggc ttagttgcta ttttgcaccc agatggtggt tc 52

<210> SEQ ID NO 336
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 336
gatattcatt acccaaatca acagttaatg ccccctgcct atcggtccac gc 52

<210> SEQ ID NO 337

<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 337
ctaaaacact catctttgac cctgacctga aagcgtaaga atcggtccac gc 52

<210> SEQ ID NO 338
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 338
cgaataataa ttttttcacg tatcaccttg ctgaacctca aaatggtggt tc 52

<210> SEQ ID NO 339
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 339
atgaggaagt ttccattaaa catcctaatt tacgagcatg taaatagccc ga 52

<210> SEQ ID NO 340
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 340
ttcgaggtga atttcttaaa cacctcccga cttgcgggag gtagagtcca ct 52

<210> SEQ ID NO 341
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 341
ggatcgtcac cctcagcagc gacatgaaag tattaagagg ctgaaaaacc gt 52

<210> SEQ ID NO 342
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 342
tttcagcgga gtgagaatag atgaatggct attagtcttt aagaaaaacc gt 52

<210> SEQ ID NO 343
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 343
ctacaacgcc tgtagcattc cagtgccacg ctgagagcca gcagagtcca ct 52

<210> SEQ ID NO 344
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 344
ctccaaaagg agcctttaat tgtctttcct tatcattcca agaatagccc ga 52

<210> SEQ ID NO 345
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 345
cagagccacc accctcattt taaggcttat ccggtattct aaatggtggt tc 52

<210> SEQ ID NO 346
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 346
ccgacaatga caacaaccat ctaggattag cggggttttg ctcggtccac gc 52

<210> SEQ ID NO 347
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 347
tcatcaacat taaaagaacg cgagaaaatt gttaaatcag accgtgcat 49

<210> SEQ ID NO 348
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 348
taatcgtaaa actaatcttc tgacctaaag ctatttttga ta 42

<210> SEQ ID NO 349
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 349
atatatttta aatggataaa taaggcgtaa aaacattatg tc 42

<210> SEQ ID NO 350
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 350
gcgagctgaa aaggttacta gaaaaagcac gagtagattt ct 42

<210> SEQ ID NO 351
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 351
ggtcattttt gcggttctta ccagtatatt caaagcgaac cc 42

<210> SEQ ID NO 352
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 352
agaaaacgag aatgtgagaa tcgccatatt tagactggat ag 42

<210> SEQ ID NO 353
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 353
acgccaaaag gaatagaggc attttcgacg gaacaacatt ag 42

<210> SEQ ID NO 354
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 354
tagtaaattg ggctacaaaa ggtaaagtat tcattaccca ag 42

<210> SEQ ID NO 355
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 355
gaacgaggcg cagaacatgt tcagctaaac aaagtacaac ca 42

<210> SEQ ID NO 356
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 356
ttcatgagga agttgataag tcctgaactc gtcaccctca tt 42

<210> SEQ ID NO 357
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 357
gctttcgagg tgaacgagca tgtagaaaat aataattttt tg 42

<210> SEQ ID NO 358
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 358
tagcgtaacg atcttcattc caagaacgcc catgtaccgt aa 42

<210> SEQ ID NO 359
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 359
aagtatagcc cggaagaaca agcaagccac tcctcaagag ca 42

<210> SEQ ID NO 360
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 360
atacaggagt gtacccgcgc ccaatagcaa tcctcattaa tc 42

<210> SEQ ID NO 361
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 361
caccctcaga accgggtatt ctaagaacta ttagcgtttg ac 42

<210> SEQ ID NO 362
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 362
cattagcaag gccgtgcggg aggttttgtt aaaggtgaat tt 42

<210> SEQ ID NO 363
<211> LENGTH: 42
<212> TYPE: DNA
<213> ORGANISM: Artificial Sequence
<220> FEATURE:

<223> OTHER INFORMATION: Synthetic Polynucleotide

<400> SEQUENCE: 363
caaagacacc acggttgcac ccagctacat taagactcct gg 42

<210> SEQ ID NO 364
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 364
agaaacaatg aaatacgagc gtctttccga attaactgaa aa 42

<210> SEQ ID NO 365
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 365
gaacaaacgg cggattgaca ataattcg 28

<210> SEQ ID NO 366
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 366
cgtctggcct tcctgtcccg gttgataatc agaagagtct gg 42

<210> SEQ ID NO 367
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 367
agcaaacaag agaatcaggt aaagattcaa aagtttcaac gc 42

<210> SEQ ID NO 368
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 368
aaggataaaa atttttagta gtagcattaa catcaataac ct 42

<210> SEQ ID NO 369
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 369
gtttagctat attttcctga atataatgct gtatagagag ta 42

<210> SEQ ID NO 370
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 370
cctttaattg ctccttgtct ttaccctgac tattcattga at 42

<210> SEQ ID NO 371
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 371
ccccctcaaa tgctttaaca ctatcataac ccttaggaat ac 42

<210> SEQ ID NO 372
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 372
cacattcaac taatgccttt aatcattgtg aattaaggct tg 42

<210> SEQ ID NO 373
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 373
ccctgacgag aaacaccgaa ctgaccaact ttgcgaaatc cg 42

<210> SEQ ID NO 374
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 374
cgacctgctc catgttacgt aatgccacta cgaaacggct ac 42

<210> SEQ ID NO 375
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 375
agaggctttg aggactccga tagttgcgcc gacaaaggag cc 42

<210> SEQ ID NO 376
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 376
tttaattgta tcggttagac gttagtaaat gaaacgcctg ta 42

<210> SEQ ID NO 377
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 377
gcattccaca gacagccagg aggtttagta ccgccaggcg ga 42

<210> SEQ ID NO 378
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 378
taagtgccgt cgagagggtc agtgccttga gtaccgttcc ag 42

<210> SEQ ID NO 379
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 379
taagcgtcat acatggcctc agagccgcca ccagagccac ca 42

<210> SEQ ID NO 380
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 380
ccggaaccgc ctccctcatc gatagcagca ccgttagagc ca 42

<210> SEQ ID NO 381
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 381
gcaaaatcac cagtagaatc aatagaaaat tcaacataca ta 42

<210> SEQ ID NO 382
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 382
aaggtggcaa catataaagc cctttttaag aaaagaattg agttaagcc 49

<210> SEQ ID NO 383
<211> LENGTH: 42

<212> TYPE: DNA
<213> ORGANISM: Artificial Sequence
<220> FEATURE:
<223> OTHER INFORMATION: Synthetic Polynucleotide

<400> SEQUENCE: 383
acaggaagat tgaataggaa cgccatcaaa cgtaatggga ta 42

<210> SEQ ID NO 384
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 384
agatgggcgc atcgtactca ttttttaacc tataa 35

<210> SEQ ID NO 385
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 385
gcaaatattt aaattgtaaa cgtgagatct acaaaggaat ca 42

<210> SEQ ID NO 386
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 386
ccatcaatat gatattcaac cgtaccctgt aatacttaag aa 42

<210> SEQ ID NO 387
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 387
ttagcaaaat taagcaataa agcagtttga ccattagcta aa 42

<210> SEQ ID NO 388
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 388
gtacggtgtc tggaagtttc attcagaccg gaagcaacat ca 42

<210> SEQ ID NO 389
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 389
aaaagattaa gaggaagccc gaaagcgtcc aatactgcaa aa 42

<210> SEQ ID NO 390
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 390
tagcgagagg cttttgcaaa agaattacag gtagaaagct ca 42

<210> SEQ ID NO 391
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 391
ttataccagt caggacgttg ggaaatcaac gtaacaaaga cc 42

<210> SEQ ID NO 392
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 392
aggcgcatag gctggctgac cttggagatt tgtatcagca aa 42

<210> SEQ ID NO 393
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 393
agaatacact aaaacactca tctgcagcga aagacagata ac 42

<210> SEQ ID NO 394
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 394
cgatatattc ggtcgctgag gcttcacgtt gaaaatccaa ct 42

<210> SEQ ID NO 395
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 395
ttcaacagtt tcagcggagt gagaacactg agtttcggaa cc 42

<210> SEQ ID NO 396
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 396
gccaccctca gagccaccac cctaaggatt aggattagcc cc 42

<210> SEQ ID NO 397
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 397
ctgcctattt cggaacctat tatagccaga atggaaagca tt 42

<210> SEQ ID NO 398
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 398
gacaggaggt tgaggcaggt cagccatctt ttcataattg cc 42

<210> SEQ ID NO 399
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 399
tttagcgtca gactgtagcg cgttatcacc gtcaccgaaa gg 42

<210> SEQ ID NO 400
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 400
gcgacattca accgattgag ggatattacg cagtatgtac ca 42

<210> SEQ ID NO 401
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 401
gaaggaaacc gaggaaacgc aatcaccctg aacaaagtca gataatatc 49

<210> SEQ ID NO 402
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 402
atattttgtt aaaattcgca ttaaatttct ttttcaaata ta 42

<210> SEQ ID NO 403
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 403
tagctgataa attaatgccg gagagggtat ttaatggttt ga 42

<210> SEQ ID NO 404
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 404
cagagcataa agctaaatcg gttgtaccta aataagaata aa 42

<210> SEQ ID NO 405
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 405
atataacagt tgattcccaa ttctgcgact gtttagtatc at 42

<210> SEQ ID NO 406
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 406
acttcaaata tcgcgtttta attcgagcaa gccaacgctc aa 42

<210> SEQ ID NO 407
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 407
ttttgccaga gggggtaata gtaaaatgtt taacaacgcc aa 42

<210> SEQ ID NO 408
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 408
aaaaatctac gttaataaaa cgaactaagc cagtaataag ag 42

<210> SEQ ID NO 409
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 409
tcaagagtaa tcttgacaag aaccggataa ttctgtccag ac 42

<210> SEQ ID NO 410
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 410
gacccccagc gattatacca agcgcgaatg cagaacgcgc ct 42

<210> SEQ ID NO 411
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 411
cagggagtta aaggccgctt ttgcgggaaa gaaaaataat at 42

<210> SEQ ID NO 412
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 412
tagaaaggaa caactaaagg aattgcgacc aatcaataat cg 42

<210> SEQ ID NO 413
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 413
ttttcaggga tagcaagccc aataggaagg tattaaacca ag 42

<210> SEQ ID NO 414
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 414
tgaaacatga aagtattaag aggctgaggt ttttattttc at 42

<210> SEQ ID NO 415
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 415
gattggcctt gatattcaca aacaaataaa gcaaatcaga ta 42

<210> SEQ ID NO 416

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 416
tcatcggcat tttcggtcat agccccctgc gaggcgtttt ag 42

<210> SEQ ID NO 417
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 417
gaaggtaaat attgacggaa attattcaaa gccttaaatc aa 42

<210> SEQ ID NO 418
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 418
taacggaata cccaaaagaa ctggcatgaa ttttatcctg aa 42

<210> SEQ ID NO 419
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 419
cgcattagac gggaagagcc t 21

<210> SEQ ID NO 420
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 420
aagacaatgt gagcgagtaa caacccgt 28

<210> SEQ ID NO 421
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 421
ttttagttaa tttcgcatgt caatcatatg tacagccagc tt 42

<210> SEQ ID NO 422
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 422
aataccgacc gtgtcaatgc ctgagtaatg tgtgatgaac gg 42

<210> SEQ ID NO 423
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 423
caccggaatc ataatggcat caattctact aatagaaccc tc 42

<210> SEQ ID NO 424
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 424
atgcgttata caaaatggct tagagcttaa ttgatttggg gc 42

<210> SEQ ID NO 425
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 425
cagtagggct taataccata aatcaaaaat cagttgataa ga 42

<210> SEQ ID NO 426
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 426
catgtaattt aggctacgag gcatagtaag agcaaacagt tc 42

<210> SEQ ID NO 427
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 427
aatataaagt accgtgagat ggtttaattt caaagataca ta 42

<210> SEQ ID NO 428
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 428
gacgacaata aacacggtca atcataaggg aaccagaacg ag 42

<210> SEQ ID NO 429
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 429
gtttatcaac aatatccatt aaacgggtaa aatacttagc cg 42

<210> SEQ ID NO 430
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 430
cccatcctaa tttatttctt aaacagcttg ataaaagact tt 42

<210> SEQ ID NO 431
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 431
gctgtctttc cttaaaagtt ttgtcgtctt tcctatcagc tt 42

<210> SEQ ID NO 432
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 432
taccgcactc atcgataggt gtatcaccgt actcctcata gt 42

<210> SEQ ID NO 433
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 433
cgtaggaatc attatggtaa taagttttaa cggggttgat at 42

<210> SEQ ID NO 434
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 434
tagaaggctt atccccaccc tcagagccac caccttttga tg 42

<210> SEQ ID NO 435
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 435
cgaacctccc gactgaaacg tcaccaatga aaccagagcc gc 42

<210> SEQ ID NO 436
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 436
gattagttgc tattaataag tttattttgt caccaccatt ac 42

<210> SEQ ID NO 437
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 437
tcttaccaac gctaagcaat agctatctta ccgaaagaaa cg 42

<210> SEQ ID NO 438
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 438
cggagacagt cactatcagg tcattgcctg aaagccccaa aa 42

<210> SEQ ID NO 439
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 439
acaggcaagg cattgcggga gaagccttta ggtgagaaag gc 42

<210> SEQ ID NO 440
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 440
ttaaatatgc aaatacattt cgcaaatggt ccaataaatc at 42

<210> SEQ ID NO 441
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 441
caaagcggat tgactccaac aggtcaggat gctcaacatg tt 42

<210> SEQ ID NO 442
<211> LENGTH: 42
<212> TYPE: DNA
<213> ORGANISM: Artificial Sequence
<220> FEATURE:

<223> OTHER INFORMATION: Synthetic Polynucleotide

<400> SEQUENCE: 442
gacgataaaa accggaatcg tcataaatat tatagtcaga ag 42

<210> SEQ ID NO 443
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 443
ttttaagaac tggattcatc agttgagatt cgtttaccag ac 42

<210> SEQ ID NO 444
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 444
tgaacggtgt acagctgctc attcagtgaa taccttatgc ga 42

<210> SEQ ID NO 445
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 445
aaaacgaaag agtcgcctga taaattgtgt aaagaggaca ga 42

<210> SEQ ID NO 446
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 446
catcgcccac gccatcggaa cgagggtagc aggcaccaac ct 42

<210> SEQ ID NO 447
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 447
gattttgcta aatccaaaaa aaaggctcca aatgacaaca ac 42

<210> SEQ ID NO 448
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 448
ccgccaccct catcaccagt acaaactaca ttttctgtat gg 42

<210> SEQ ID NO 449
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 449
taaacagtta atgcggggtt ttgctcagta ccaccctcag aa 42

<210> SEQ ID NO 450
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 450
gagccgccgc cagcgcagtc tctgaattta acagtgcccg ta 42

<210> SEQ ID NO 451
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 451
acagaatcaa gttcaaaatc accggaacca gaaccaccac ca 42

<210> SEQ ID NO 452
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 452
gcgccaaaga caacttgagc catttgggaa taatcagtag cg 42

<210> SEQ ID NO 453
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 453
ccgaacaaag tttagcaaac gtagaaaatt atggtttacc a 41

<210> SEQ ID NO 454
<211> LENGTH: 29
<212> TYPE: DNA
<213> ORGANISM: Artificial Sequence
<220> FEATURE:
<223> OTHER INFORMATION: Synthetic Polynucleotide

<400> SEQUENCE: 454
agagagataa cccacaagta agcagatag 29

<210> SEQ ID NO 455
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 455
agaagatgaa attaactaaa atatatttga aaaagttttc tcgcgttctt tgtcttgcga 60
ttg 63

<210> SEQ ID NO 456
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 456
atttatcaca cggtcggtat ttcaaaccat taaatttagg tc 42

<210> SEQ ID NO 457
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 457
ctagtaatta tgattccggt gtttattctt atttaacgcc tt 42

<210> SEQ ID NO 458
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 458
gtaagaattt gtataacgca tatgatacta aacaggcttt tt 42

<210> SEQ ID NO 459
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 459
attctcaatt aagccctact gttgagcgtt ggctttatac tg 42

<210> SEQ ID NO 460
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 460
tgcctctgcc taaattacat gttggcgttg ttaaatatgg cg 42

<210> SEQ ID NO 461
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 461
cttttgtcgg tactttatat tctcttatta ctggctcgaa aa 42

<210> SEQ ID NO 462
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 462
aacatgttgt ttattgtcgt cgtctggaca gaattacttt ac 42

<210> SEQ ID NO 463
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 463
acttatctat tgttgataaa caggcgcgtt ctgcattagc tg 42

<210> SEQ ID NO 464
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 464
atgctcgtaa attaggatgg gatattattt ttcttgttca gg 42

<210> SEQ ID NO 465
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 465
ggaatgataa ggaaagacag ccgattattg attggtttct ac 42

<210> SEQ ID NO 466
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 466
ttgttctcga tgagtgcggt acttggttta atacccgttc tt 42

<210> SEQ ID NO 467
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 467
ggcgcggtaa tgattcctac gatgaaaata aaaacggctt gc 42

<210> SEQ ID NO 468
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 468
gaataccgga taagccttct atatctgatt tgcttgctat tg 42

<210> SEQ ID NO 469
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 469
tcccgcaagt cgggaggttc gctaaaacgc ctcgcgttct ta 42

<210> SEQ ID NO 470
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 470
ggtgcaaaat agcaactaat cttgatttaa ggcttcaaaa cc 42

<210> SEQ ID NO 471
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 471
gcaaattagg ctctggaaag acgctcgtta gcgttggtaa gattcaggat aaaattgtag 60
ctg 63

<210> SEQ ID NO 472
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 472
attctcaatt agcgtggacc gttgagcgtt ggctttatac tg 42

<210> SEQ ID NO 473
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 473
tgcctctgcc tgaaccacca tttggcgttg ttaaatatgg cg 42

<210> SEQ ID NO 474
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 474
cttttgtcgg ttcgggctat tctcttatta ctggctcgaa aa 42

<210> SEQ ID NO 475
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 475
aacatgttgt tagtggactc tgtctggaca gaattacttt ac 42

<210> SEQ ID NO 476
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 476
acttatctat tacggttttt caggcgcgtt ctgcattagc tg 42

<210> SEQ ID NO 477
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 477
taataccata aatcaaaaat cagttgataa ga 32

<210> SEQ ID NO 478
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 478
aggctacgag gcatagtaag agcaaacagt tc 32

<210> SEQ ID NO 479
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 479
accgtgagat ggtttaattt caaagataca ta 32

<210> SEQ ID NO 480
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 480
aacacggtca atcataaggg aaccagaacg ag 32

<210> SEQ ID NO 481
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 481
aatatccatt aaacgggtaa aatacttagc cg 32

<210> SEQ ID NO 482
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 482
aacggcatct ccgtgagcct cctcacagag cctggggtgc ct 42

<210> SEQ ID NO 483
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 483
ggcagcaccc atcccttaca ctggtgtggt tgcgctcact gc 42

<210> SEQ ID NO 484
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 484
aaatcccgtg gtctggtcag cagcaacccc agctgcatta at 42

<210> SEQ ID NO 485
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 485
gagccgccaa gcagttgggc ggttgtgttt tgcgtattgg gc 42

<210> SEQ ID NO 486
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 486
ggcaccgcta aaacgacggc cagtgccaag acgggcaaca gc 42

<210> SEQ ID NO 487
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 487
cgcgtctggg cctcaggaag atcgcactag agttgcagca ag 42

<210> SEQ ID NO 488
<211> LENGTH: 42

<212> TYPE: DNA
<213> ORGANISM: Artificial Sequence
<220> FEATURE:
<223> OTHER INFORMATION: Synthetic Polynucleotide

<400> SEQUENCE: 488
ggagcaaact tttaaccaat aggaacgcga aaatcctgtt tg 42

<210> SEQ ID NO 489
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 489
gcaaggatat acaaaggcta tcaggtcatt ataaatcaaa ag 42

<210> SEQ ID NO 490
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 490
ctgtttagct aatacttttg cgggagaatc cagtttggaa ca 42

<210> SEQ ID NO 491
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 491
tacctttaaa ccattagata catttcgcca acgtcaaagg gc 42

<210> SEQ ID NO 492
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 492
atccccctcg gaagcaaact ccaacaggac tacgtgaacc at 42

<210> SEQ ID NO 493
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 493
accacattcc aatactgcgg aatcgtcagt gccgtaaagc ac 42

<210> SEQ ID NO 494
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 494
tgccctgacg gtagaaagat tcatcagtat ttagagcttg ac 42

<210> SEQ ID NO 495
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 495
cgcgacctgc gtaacaaagc tgctcattgg aagggaagaa ag 42

<210> SEQ ID NO 496
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 496
acagaggctt tgtatcatcg cctgataaaa gtgtagcggt ca 42

<210> SEQ ID NO 497
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 497
cctttaatta aagacagcat cggaacgagc ttaatgcgcc gc 42

<210> SEQ ID NO 498
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 498
tagcattcct gaaaatctcc aaaaaaaacg agcacgtata ac 42

<210> SEQ ID NO 499
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 499
gataagtgcg agtttcgtca ccagtacaag ctaaacagga gg 42

<210> SEQ ID NO 500
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 500
agtaagcgtt aggattagcg ggttttggt acgccagaat cc 42

<210> SEQ ID NO 501
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 501
caccggaaca atggaaagcg cagtctctca ccgagtaaaa ga 42

<210> SEQ ID NO 502
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 502
cagcaaaatt ttcataatca aaatcaccta gcaatacttc tt 42

<210> SEQ ID NO 503
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 503
taaaggtggc gtcaccgact tgagccatta gaagaactca aa 42

<210> SEQ ID NO 504
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 504
attgagttag cagtatgtta gcaaacgtca atattaccgc ca 42

<210> SEQ ID NO 505
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 505
atttgccagt gagcgctaat atcagagaaa atacctacat tt 42

<210> SEQ ID NO 506
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 506
tttcatcgtt accaacgcta acgagcgttt acattggcag at 42

<210> SEQ ID NO 507
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 507
ccagacgacc gcactcatcg agaacaaggg acattctggc ca 42

<210> SEQ ID NO 508
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 508
aataaacaca taaagtaccg acaaaagggc gtaagaatac gt 42

<210> SEQ ID NO 509
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 509
atttatcaaa ccgaccgtgt gataaatata gtctttaatg cg 42

<210> SEQ ID NO 510
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 510
agatgatgat tagattaaga cgctgagata aaaataccga ac 42

<210> SEQ ID NO 511
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 511
agggttagac gaattattca tttcaatttg aggcggtcag ta 42

<210> SEQ ID NO 512
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 512
agaagtattc tgattgtttg gattatacga gagccagcag ca 42

<210> SEQ ID NO 513
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 513
tcatggtcat agccgtgcct gttcttcgcg agatgccggg tt 42

<210> SEQ ID NO 514
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 514
acctgcagcc agctctttgc tcgtcataaa gtcggtggtg cc 42

<210> SEQ ID NO 515
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 515
atcccacgca accaacgtca gcgtggtgct aaaaaaagcc gc 42

<210> SEQ ID NO 516
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 516
acaggcggcc ttttctgctc atttgccgcc cgggaacgga ta 42

<210> SEQ ID NO 517
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 517
acctcaccgg aaacccagtc acgacgttgt tctggtgccg ga 42

<210> SEQ ID NO 518
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 518
aaccaggcaa agcggacgac gacagtatcg ccttcctgta gc 42

<210> SEQ ID NO 519
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 519
cagctttcat caatgttaaa tcagctcatt aagagaatcg at 42

<210> SEQ ID NO 520
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 520
gaacggtaat cgtgctattt ttgagagatc aaaattttta ga 42

<210> SEQ ID NO 521

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 521
accctcatat attaaaacat tatgaccctg tatattttca tt 42

<210> SEQ ID NO 522
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 522
tggggcgcga gctcgagtag atttagtttg ttgctccttt tg 42

<210> SEQ ID NO 523
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 523
ataagaggtc atttcaaagc gaaccagacc aaatgcttta aa 42

<210> SEQ ID NO 524
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 524
cagttcagaa aacttagact ggatagcgtc aactaatgca ga 42

<210> SEQ ID NO 525
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 525
tacataacgc caaggaacaa cattattaca gagaaacacc ag 42

<210> SEQ ID NO 526
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 526
aacgagtagt aaattcatta cccaaatcaa ctccatgtta ct 42

<210> SEQ ID NO 527
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 527
tagccggaac gagcaaagta caacggagat ttgaggacta aa 42

<210> SEQ ID NO 528
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 528
gactttttca tgacgtcacc ctcagcagcg gtatcggttt at 42

<210> SEQ ID NO 529
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 529
cagcttgctt tcgtaataat tttttcacgt acagacagcc ct 42

<210> SEQ ID NO 530
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 530
catagttagc gtaccatgta ccgtaacact cgtcgagagg gt 42

<210> SEQ ID NO 531
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 531
tgatataagt atactcctca agagaaggat catacatggc tt 42

<210> SEQ ID NO 532
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 532
ttgatgatac aggatcctca ttaaagccag cgcctccctc ag 42

<210> SEQ ID NO 533
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 533
agccgccacc ctcattagcg tttgccatct caccagtagc ac 42

<210> SEQ ID NO 534
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 534
cattaccatt agctaaaggt gaattatcac caacatataa aa 42

<210> SEQ ID NO 535
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 535
gaaacgcaaa gacttaagac tccttattac agcccaataa ta 42

<210> SEQ ID NO 536
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 536
agagcaagaa acacaaagtc agagggtaat ttacaaaata aa 42

<210> SEQ ID NO 537
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 537
cagccatatt attaatttta tcctgaatct aggaatcatt ac 42

<210> SEQ ID NO 538
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 538
cgcgcccaat agcggtatta aaccaagtac gacaataaac aa 42

<210> SEQ ID NO 539
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 539
catgttcagc taagccagta ataagagaat cggaatcata at 42

<210> SEQ ID NO 540
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 540
tactagaaaa agcatttaat ggtttgaaat aatcataggt ct 42

<210> SEQ ID NO 541
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 541
gagagactac cttgaaaaca tagcgatagc aacaaacatc aa 42

<210> SEQ ID NO 542
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 542
gaaaacaaaa ttaacaaaat cgcgcagagg acctaccata tc 42

<210> SEQ ID NO 543
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 543
aaaattattt gcaaattcat caatataatc agactttaca aacaat 46

<210> SEQ ID NO 544
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 544
tcgacaactc taacaactaa tcgtcaatag ataatgaacc tcaaatatc 49

<210> SEQ ID NO 545
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 545
tctgccagca cgtgtttcct gtgtgccgct cac 33

<210> SEQ ID NO 546
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 546
tgggtaaagg ttggtgccgg tgccccctgc ataccggggg tt 42

<210> SEQ ID NO 547
<211> LENGTH: 42
<212> TYPE: DNA
<213> ORGANISM: Artificial Sequence
<220> FEATURE:

<223> OTHER INFORMATION: Synthetic Polynucleotide

<400> SEQUENCE: 547
ccggacttgt agagcttacg gctggaggtg tgcggctggt aa 42

<210> SEQ ID NO 548
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 548
caaacttaaa ttagtgatga agggtaaagt taacggaacg tg 42

<210> SEQ ID NO 549
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 549
cgccagggtt ttcaatcggc gaaacgtaca gaaacagcgg at 42

<210> SEQ ID NO 550
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 550
gccagtttga gggccattcg ccattcaggc taagttgggt aa 42

<210> SEQ ID NO 551
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 551
gcattaaatt ttcattaaat gtgagcgagt aaccgtgcat ct 42

<210> SEQ ID NO 552
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 552
ccggagaggg taaaaactag catgtcaatc ttgttaaaat tc 42

<210> SEQ ID NO 553
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 553
tcggttgtac cattaaatgc aatgcctgag gataaattaa tg 42

<210> SEQ ID NO 554
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 554
caattctgcg aagaaaaggt ggcatcaatt cataaagcta aa 42

<210> SEQ ID NO 555
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 555
ttaattcgag cttttgcgga tggcttagag acagttgatt cc 42

<210> SEQ ID NO 556
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 556
atagtaaaat gtgagaatga ccataaatca aaatatcgcg tt 42

<210> SEQ ID NO 557
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 557
aaacgaacta acaaggaatt acgaggcata ccagaggggg ta 42

<210> SEQ ID NO 558
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 558
aagaaccgga tattgggctt gagatggttt tctacgttaa ta 42

<210> SEQ ID NO 559
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 559
ccaagcgcga aagcgcagac ggtcaatcat agtaatcttg ac 42

<210> SEQ ID NO 560
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 560
cttttgcggg atggaagttt ccattaaacg ccagcgatta ta 42

<210> SEQ ID NO 561
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 561
aggaattgcg aaaggtgaat ttcttaaaca agttaaaggc cg 42

<210> SEQ ID NO 562
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 562
cccaatagga acacgatcta aagttttgtc aggaacaact aa 42

<210> SEQ ID NO 563
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 563
aagaggctga gagcccggaa taggtgtatc agggatagca ag 42

<210> SEQ ID NO 564
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 564
acaaacaaat aaagtgtact ggtaataagt catgaaagta tt 42

<210> SEQ ID NO 565
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 565
catagccccc ttagaaccgc caccctcaga gccttgatat tc 42

<210> SEQ ID NO 566
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 566
gaaattattc ataaggccgg aaacgtcacc ggcattttcg gt 42

<210> SEQ ID NO 567
<211> LENGTH: 42

<212> TYPE: DNA
<213> ORGANISM: Artificial Sequence
<220> FEATURE:
<223> OTHER INFORMATION: Synthetic Polynucleotide

<400> SEQUENCE: 567
gaactggcat gaaccacgga ataagtttat taaatattga cg 42

<210> SEQ ID NO 568
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 568
gaacaccctg aaatgaaata gcaatagcta gaatacccaa aa 42

<210> SEQ ID NO 569
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 569
gcacccagct actatcccaa tccaaataag ggagaattaa ct 42

<210> SEQ ID NO 570
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 570
attccaagaa cgaagcaaat cagatataga agttgctatt tt 42

<210> SEQ ID NO 571
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 571
aggcattttc gatgcagaac gcgcctgttt tctttcctta tc 42

<210> SEQ ID NO 572
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 572
cttctgacct aactgtttag tatcatatgc taatttaggc ag 42

<210> SEQ ID NO 573
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 573
cttagaatcc tttttaacct ccggcttagg agttaatttc at 42

<210> SEQ ID NO 574
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 574
gaataccaag ttattacatt taacaatttc aattaatttt cc 42

<210> SEQ ID NO 575
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 575
tcagatgatg gccgtaaaac agaaataaag cctgattgct tt 42

<210> SEQ ID NO 576
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 576
tctttaggag cacgtattaa atcctttgcc tattcctgat ta 42

<210> SEQ ID NO 577
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 577
aattccacac aagggccgtt ttcacggtca tcagacgatc ca 42

<210> SEQ ID NO 578
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 578
gcgcagtgtc acccgggtca ctgttgccct ccagcatcag cg 42

<210> SEQ ID NO 579
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 579
gggtcattgc aggccagagc acatcctcat aaacgatgct ga 42

<210> SEQ ID NO 580
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 580
ttgccgttcc ggacggaaaa agagacgcag cgccatgttt ac 42

<210> SEQ ID NO 581
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 581
cagtcccgga atatgtgctg caaggcgatt gcgcaactgt tg 42

<210> SEQ ID NO 582
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 582
ggaagggcga tcgtagatgg gcgcatcgta acaacccgtc gg 42

<210> SEQ ID NO 583
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 583
attctccgtg ggttgtaaac gttaatatta tatgtacccc gg 42

<210> SEQ ID NO 584
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 584
ttgataatca gaattcaacc gttctagctt aatgtgtagg ta 42

<210> SEQ ID NO 585
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 585
aagattcaaa aggcaataaa gcctcagagc tactaatagt ag 42

<210> SEQ ID NO 586
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 586
tagcattaac ataagtttca ttccatatac ttaattgctg aa 42

<210> SEQ ID NO 587
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 587
tataatgctg tagaagcccg aaagacttca aaatcaggtc tt 42

<210> SEQ ID NO 588
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 588
taccctgact atttgcaaaa gaagttttgg taagagcaac ac 42

<210> SEQ ID NO 589
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 589
tatcataacc ctgacgttgg gaagaaaaaa atttcaactt ta 42

<210> SEQ ID NO 590
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 590
atcattgtga atggctgacc ttcatcaaga agggaaccga ac 42

<210> SEQ ID NO 591
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 591
tgaccaactt tgacactcat ctttgacccg gtaaaatacg ta 42

<210> SEQ ID NO 592
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 592
atgccactac gacgctgagg cttgcagggg cttgataccg at 42

<210> SEQ ID NO 593
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 593
agttgcgccg acgcggagtg agaatagaag tctttccaga cg 42

<210> SEQ ID NO 594
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 594
ttagtaaatg aaccaccacc ctcattttca ccgtactcag ga 42

<210> SEQ ID NO 595
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 595
ggtttagtac cgaacctatt attctgaaat ttaacggggt ca 42

<210> SEQ ID NO 596
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 596
gtgccttgag taggcaggtc agacgattgg ccaccaccct ca 42

<210> SEQ ID NO 597
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 597
gagccgccac catgtagcgc gttttcatca atgaaaccat cg 42

<210> SEQ ID NO 598
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 598
atagcagcac cggattgagg gagggaaggt ttgtcacaat ca 42

<210> SEQ ID NO 599
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 599
atagaaaatt cagaaacgca ataataacgt cttaccgaag cc 42

<210> SEQ ID NO 600

<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 600
ctttttaaga aagggaagcg cattagacga aacgattttt tg 42

<210> SEQ ID NO 601
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 601
tttaacgtca aaagccttaa atcaagatta ggcttatccg gt 42

<210> SEQ ID NO 602
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 602
attctaagaa cgcaatcaat aatcggctga tcaacaatag at 42

<210> SEQ ID NO 603
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 603
aagtcctgaa cattaacaac gccaacatgg ttatacaaat tc 42

<210> SEQ ID NO 604
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 604
ttaccagtat aatttttcaa atatattttt tgggttatat aa 42

<210> SEQ ID NO 605
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 605
ctatatgtaa attgtaaatc gtcgctatta tttgaattac ct 42

<210> SEQ ID NO 606
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 606
tttttaatgg aaaaacaata acggattcga aattgcgtag at 42

<210> SEQ ID NO 607
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 607
tttcaggttt aagagcggaa ttatcatcac gaacgttatt aa 42

<210> SEQ ID NO 608
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 608
ttttaaaagt ttaaaggaat tgagtaaaat a 31

<210> SEQ ID NO 609
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 609
cggaagcata aagtgtaatt gaggatcccc gg 32

<210> SEQ ID NO 610
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 610
gtgcactctg tggtctcaca ttaattgctt cagcaaatcg tt 42

<210> SEQ ID NO 611
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 611
cactcaatcc gccgggaaac ctgtcgtggc aagaatgcca ac 42

<210> SEQ ID NO 612
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 612
tccgtttttt cgtcgcgggg agaggcggac atcgacataa aa 42

<210> SEQ ID NO 613
<211> LENGTH: 42
<212> TYPE: DNA

<213> ORGANISM: Artificial Sequence
<220> FEATURE:
<223> OTHER INFORMATION: Synthetic Polynucleotide

<400> SEQUENCE: 613
atagactttc tccgtctttt caccagtgag ctttcagagg tg 42

<210> SEQ ID NO 614
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 614
ctcttcgcta ttaccgcctg gccctgagcc agccagcttt cc 42

<210> SEQ ID NO 615
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 615
cggattgacc gtaattgccc cagcaggcca tcaaaaataa tt 42

<210> SEQ ID NO 616
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 616
aaaacaggaa gattatcggc aaaatccctt gcctgagagt ct 42

<210> SEQ ID NO 617
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 617
ggccggagac agtcgggttg agtgttgtgc ctttatttca ac 42

<210> SEQ ID NO 618
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 618
catacaggca aggcaagaac gtggactcaa atggtcaata ac 42

<210> SEQ ID NO 619
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 619
gttttaaata tgcacagggc gatggccctc aggattagag ag 42

<210> SEQ ID NO 620
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 620
aagcaaagcg gattttttg gggtcgagta aatattcatt ga 42

<210> SEQ ID NO 621
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 621
gacgacgata aaaaaaaggg agccccgtg agatttagga at 42

<210> SEQ ID NO 622
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 622
cgattttaag aactaacgtg gcgagaaaca gtgaataagg ct 42

<210> SEQ ID NO 623
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 623
agatgaacgg tgtagctagg gcgctggcat tgtgtcgaaa tc 42

<210> SEQ ID NO 624
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 624
cctaaaacga aagaaccaca cccgccgcgg gtagcaacgg ct 42

<210> SEQ ID NO 625
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 625
aaccatcgcc cacgtatggt tgctttgagg ctccaaaagg ag 42

<210> SEQ ID NO 626
<211> LENGTH: 42
<212> TYPE: DNA
<213> ORGANISM: Artificial Sequence
<220> FEATURE:

<223> OTHER INFORMATION: Synthetic Polynucleotide

<400> SEQUENCE: 626
tgggattttg ctaaagaatc agagcgggaa ctacaacgcc tg 42

<210> SEQ ID NO 627
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 627
gaaccgccac cctctttaga caggaacgct cagtaccagg cg 42

<210> SEQ ID NO 628
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 628
gtataaacag ttaaataatc agtgaggcga atttaccgtt cc 42

<210> SEQ ID NO 629
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 629
ccagagccgc cgcccaaatt aaccgttggg aaccagagcc ac 42

<210> SEQ ID NO 630
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 630
gcgacagaat caagatcact tgcctgagtt gggaattaga gc 42

<210> SEQ ID NO 631
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 631
ccagcgccaa agacggtaat atccagaaag aaaatacata ca 42

<210> SEQ ID NO 632
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 632
atagccgaac aaagaaaaac gctcatggga taacccacaa ga 42

<210> SEQ ID NO 633
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 633
agcagccttt acagctgaaa tggattatct ttccagagcc ta 42

<210> SEQ ID NO 634
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 634
ttagcgaacc tcccaccagt aataaaagca agccgttttt at 42

<210> SEQ ID NO 635
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 635
atatcccatc ctaacttctg acctgaaata aagtaattct gt 42

<210> SEQ ID NO 636
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 636
tcaacagtag ggctttttga atggctatag gcgttaaata ag 42

<210> SEQ ID NO 637
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 637
aatccaatcg caagtaaaac atcgccatag agtcaatagt ga 42

<210> SEQ ID NO 638
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 638
aaatcaatat atgtagataa aacagaggac ctgagcaaaa ga 42

<210> SEQ ID NO 639
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 639
aatatacagt aacaaacagt gccacgcttt ctgaataatg ga 42

<210> SEQ ID NO 640
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 640
tatcattttg cggaagcatc accttgctac atttgaggat tt 42

<210> SEQ ID NO 641
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 641
aatgagtgag ctaagctgcg gccagaatgc ggccatacga gc 42

<210> SEQ ID NO 642
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 642
ccgctttcca gtcgggcgcg gttgcggtat gagtgcgcgc ct 42

<210> SEQ ID NO 643
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 643
gaatcggcca acgctcgtcg ctggcagcct ccggcgcttt cg 42

<210> SEQ ID NO 644
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 644
gccagggtgg tttttggtga agggatagct ctccaaacgc gg 42

<210> SEQ ID NO 645
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 645
tgattgccct tcacgccagc tggcgaaagg gggttgtgag ag 42

<210> SEQ ID NO 646
<211> LENGTH: 42

<212> TYPE: DNA
<213> ORGANISM: Artificial Sequence
<220> FEATURE:
<223> OTHER INFORMATION: Synthetic Polynucleotide

<400> SEQUENCE: 646
cggtccacgc tggttgggat aggtcacgtt ggtggtgcgg gc 42

<210> SEQ ID NO 647
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 647
atggtggttc cgaagtataa gcaaatattt aaaaacaaac gg 42

<210> SEQ ID NO 648
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 648
aatagcccga gataaaatca ccatcaatat gataaagccc ca 42

<210> SEQ ID NO 649
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 649
agagtccact attaaaagaa ttagcaaaat taaggtgaga aa 42

<210> SEQ ID NO 650
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 650
gaaaaaccgt ctatactaaa gtacggtgtc tggccaataa at 42

<210> SEQ ID NO 651
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 651
cacccaaatc aagtgcatca aaaagattaa gaggctcaac at 42

<210> SEQ ID NO 652
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 652
taaatcggaa ccctccaaaa tagcgagagg ctttatagtc ag 42

<210> SEQ ID NO 653
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 653
ggggaaagcc ggcgggctca ttataccagt cagcgtttac ca 42

<210> SEQ ID NO 654
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 654
cgaaaggagc gggccagacc aggcgcatag gcttacctta tg 42

<210> SEQ ID NO 655
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 655
cgctgcgcgt aaccggcaaa agaatacact aaaaaagagg ac 42

<210> SEQ ID NO 656
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 656
tacagggcgc gtaccataac cgatatattc ggtaggcacc aa 42

<210> SEQ ID NO 657
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 657
gtgctttcct cgttacaact ttcaacagtt tcaaatgaca ac 42

<210> SEQ ID NO 658
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 658
ccgattaaag ggatagaacc gccaccctca gagttttctg ta 42

<210> SEQ ID NO 659
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 659
tgagaagtgt tttttgcccc ctgcctattt cggccaccct ca 42

<210> SEQ ID NO 660
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 660
gtctgtccat cacgagcatt gacaggaggt tgaacagtgc cc 42

<210> SEQ ID NO 661
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 661
tgattagtaa taactttgcc tttagcgtca gacgaaccac ca 42

<210> SEQ ID NO 662
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 662
ctatcggcct tgctaaaagg gcgacattca acctaatcag ta 42

<210> SEQ ID NO 663
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 663
gccattgcaa caggttacca gaaggaaacc gagtatggtt ta 42

<210> SEQ ID NO 664
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 664
tgacgctcaa tcgtagagaa taacataaaa acaagtaagc ag 42

<210> SEQ ID NO 665
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 665
tcaccagtca cacggacttg cgggaggttt tgaaatgaaa at 42

<210> SEQ ID NO 666
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 666
acagagatag aacctttacg agcatgtaga aaccgaggcg tt 42

<210> SEQ ID NO 667
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 667
ggcacagaca atattaattg agaatcgcca tatagaaaaa ta 42

<210> SEQ ID NO 668
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 668
cgaactgata gcccacaaag aacgcgagaa aacagccaac gc 42

<210> SEQ ID NO 669
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 669
gaaccaccag cagagagtga ataaccttgc ttcgctgatg ca 42

<210> SEQ ID NO 670
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 670
ttaacaccgc ctgcgtacct tttacatcgg gagacagtac at 42

<210> SEQ ID NO 671
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 671
aatgaaaaat ctaaacaaag aaaccaccag aagcgtcaga tg 42

<210> SEQ ID NO 672
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 672
aaaccctcaa tcaagttggc aaatcaacag ttggagtaac at 42

<210> SEQ ID NO 673
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 673
cgctggttgg gataggtcac gttggtggtg cgggc 35

<210> SEQ ID NO 674
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 674
ttccgaagta taagcaaata tttaaaaaca aacgg 35

<210> SEQ ID NO 675
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 675
cgagataaaa tcaccatcaa tatgataaag cccca 35

<210> SEQ ID NO 676
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 676
actattaaaa gaattagcaa aattaaggtg agaaa 35

<210> SEQ ID NO 677
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 677
cgtctatact aaagtacggt gtctggccaa taaat 35

<210> SEQ ID NO 678
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 678
tggttgggat aggtcacgtt ggtggtgcgg gc 32

<210> SEQ ID NO 679

<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 679
cgaagtataa gcaaatattt aaaaacaaac gg 32

<210> SEQ ID NO 680
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 680
gataaaatca ccatcaatat gataaagccc ca 32

<210> SEQ ID NO 681
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 681
attaaaagaa ttagcaaaat taaggtgaga aa 32

<210> SEQ ID NO 682
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 682
ctatactaaa gtacggtgtc tggccaataa at 32

<210> SEQ ID NO 683
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 683
tgcaatttaa ttcttttagc atttcaatat ttgtagattt gagaatttcg tttttttatt 60
ca 62

<210> SEQ ID NO 684
<211> LENGTH: 84
<212> TYPE: DNA
<213> ORGANISM: Artificial Sequence
<220> FEATURE:
<223> OTHER INFORMATION: Synthetic Polynucleotide

<400> SEQUENCE: 684
tggttctgga gttttactcg ggacacttca gcgtaatatc ggaagcaggc actttgaaac 60
ctataagtcc tgactattaa taac 84

<210> SEQ ID NO 685
<211> LENGTH: 40
<212> TYPE: DNA
<213> ORGANISM: Artificial Sequence

```
<220> FEATURE:
<223> OTHER INFORMATION: Synthetic Polynucleotide

<400> SEQUENCE: 685

ggctcccttt agggttccga tgatcctcaa ctgtgaggag                              40


<210> SEQ ID NO 686
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 686

ctcctcacag ttgaggatca tcggaaccct aaagggagcc                              40


<210> SEQ ID NO 687
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (9)..(17)
<223> OTHER INFORMATION: n is a, c, g, or t

<400> SEQUENCE: 687

gcctggggnn nnnnnnntga gtgagc                                             26


<210> SEQ ID NO 688
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (11)..(19)
<223> OTHER INFORMATION: n is a, c, g, or t

<400> SEQUENCE: 688

agctcactca nnnnnnnnnc cccaggc                                            27
```